United States Patent
Hu et al.

(10) Patent No.: US 12,018,078 B2
(45) Date of Patent: Jun. 25, 2024

(54) SEMA4D ANTIBODY, PREPARATION METHOD THEREFOR AND USE THEREOF

(71) Applicant: JIANGSU HUAIYU PHARMACEUTICAL CO., LTD., Jiangsu (CN)

(72) Inventors: Yingying Hu, Shanghai (CN); Xiaodan Cao, Shanghai (CN); Zihan Jin, Shanghai (CN); Lina Wang, Shanghai (CN); Yuandong Wang, Shanghai (CN); Xiaohui Shao, Shanghai (CN); Shaoping Hu, Shanghai (CN); Mingming Pan, Shanghai (CN); Yan Liu, Shanghai (CN); Wei Shao, Shanghai (CN); Yanyan Li, Shanghai (CN); Xiaoxuan Lan, Shanghai (CN); Ying Gu, Shanghai (CN); Siran Zhu, Shanghai (CN); Lile Liu, Shanghai (CN); Qing Duan, Shanghai (CN)

(73) Assignee: JIANGSU HUAIYU PHARMACEUTICAL CO., LTD., Jiangsu (CN)

( * ) Notice: Subject to any disclaimer, the term of this patent is extended or adjusted under 35 U.S.C. 154(b) by 580 days.

(21) Appl. No.: 17/260,022

(22) PCT Filed: Jul. 15, 2019

(86) PCT No.: PCT/CN2019/096050
§ 371 (c)(1),
(2) Date: Feb. 16, 2021

(87) PCT Pub. No.: WO2020/011275
PCT Pub. Date: Jan. 16, 2020

(65) Prior Publication Data
US 2022/0073608 A1 Mar. 10, 2022

(30) Foreign Application Priority Data
Jul. 13, 2018 (CN) .......................... 201810768301.7

(51) Int. Cl.
*C07K 16/28* (2006.01)
*A61K 39/00* (2006.01)
(Continued)

(52) U.S. Cl.
CPC .......... *C07K 16/2803* (2013.01); *A61P 35/00* (2018.01); *G01N 33/6854* (2013.01);
(Continued)

(58) Field of Classification Search
CPC .......... C07K 16/2803; C07K 2317/565; C07K 2317/76; C07K 2317/92; A61P 35/00; G01N 33/6854; A61K 2039/505
See application file for complete search history.

(56) References Cited

U.S. PATENT DOCUMENTS 9,221,902 B2 * 12/2015 Smider .................. C40B 40/08
2017/0355756 A1 * 12/2017 Julien .................... A61P 25/00

FOREIGN PATENT DOCUMENTS

| CN | 103608030 A | 2/2014 | |
| WO | WO-2008068048 A2 * | 6/2008 | ............. A61P 31/10 |
| WO | 2013/148854 A1 | 10/2013 | |

OTHER PUBLICATIONS

Chen et al., Enhancement and destruction of antibody function by somatic mutation: unequal occurrence is controlled by V gene combinatorial associations. EMBO J. Jun. 15, 1995;14(12):2784-94. (Year: 1995).*

(Continued)

*Primary Examiner* — Aurora M Fontainhas
*Assistant Examiner* — Selam Berhane
(74) *Attorney, Agent, or Firm* — NKL Law; Allen Xue

(57) ABSTRACT

Provided are a murine or fully human monoclonal antibody targeting SEMA4D and a preparation method therefor,
(Continued)

wherein the antibody binds to the SEMA4D antigen and has activities such as combating tumors.

9 Claims, 22 Drawing Sheets

Specification includes a Sequence Listing.

(51) Int. Cl.
*A61P 35/00* (2006.01)
*G01N 33/68* (2006.01)

(52) U.S. Cl.
CPC .. *A61K 2039/505* (2013.01); *C07K 2317/565* (2013.01); *C07K 2317/76* (2013.01); *C07K 2317/92* (2013.01)

(56) References Cited

OTHER PUBLICATIONS

Koenig et al., Mutational landscape of antibody variable domains reveals a switch modulating the interdomain conformational dynamics and antigen binding. PNAS Jan. 24, 2017 114 (4) E486-E495; first published Jan. 5, 2017; (Year: 2017).*
Kussie, Paul H., "A Single Engineered Amino Acid Substitution Changes Antibody Fine Specificity", 1994, Journal of Immunology 152(1): pp. 146-152. (Year: 1994).*
Edwards et al., The remarkable flexibility of the human antibody repertoire; isolation of over one thousand different antibodies to a single protein, BLyS. J Mol Biol. Nov. 14, 2003;334(1):103-18. (Year: 2003).*

* cited by examiner

SEQUENCE LISTING

<160> NUMBER OF SEQ ID NOS: 453

<210> SEQ ID NO 1
<211> LENGTH: 118
<212> TYPE: PRT
<213> ORGANISM: Artificial sequence
<220> FEATURE:
<223> OTHER INFORMATION: synthesized

<400> SEQUENCE: 1

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met Tyr Trp Val Arg Gln Ala Pro Glu Lys Gly Leu Glu Gly Val
        35                  40                  45

Ala Tyr Ile Ser Ser Gly Ser Ser Thr Ile Tyr Ser Val Asp Lys Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Thr Trp Leu Pro Gly Asn Ala Met Asp Tyr Trp Gly Gln Gly Thr
            100                 105                 110

Ser Val Thr Val Ser Ser
        115

<210> SEQ ID NO 2
<211> LENGTH: 5
<212> TYPE: PRT
<213> ORGANISM: Artificial sequence
<220> FEATURE:
<223> OTHER INFORMATION: synthesized

<400> SEQUENCE: 2

Asp Tyr Gly Met Tyr
1               5

<210> SEQ ID NO 3
<211> LENGTH: 17
<212> TYPE: PRT
<213> ORGANISM: Artificial sequence
<220> FEATURE:
<223> OTHER INFORMATION: synthesized

<400> SEQUENCE: 3

Tyr Ile Ser Ser Gly Ser Ser Thr Ile Tyr Ser Val Asp Lys Val Lys
1               5                   10                  15

Gly

<210> SEQ ID NO 4
<211> LENGTH: 9
<212> TYPE: PRT
<213> ORGANISM: Artificial sequence
<220> FEATURE:
<223> OTHER INFORMATION: synthesized

<400> SEQUENCE: 4

Trp Leu Pro Gly Asn Ala Met Asp Tyr
1               5

<210> SEQ ID NO 5

```
<211> LENGTH: 107
<212> TYPE: PRT
<213> ORGANISM: Artificial sequence
<220> FEATURE:
<223> OTHER INFORMATION: synthesized

<400> SEQUENCE: 5

Asp Ile Leu Leu Thr Gln Ser Pro Ala Ile Leu Ser Val Ser Pro Gly
1               5                   10                  15
Gln Arg Val Ser Phe Ser Cys Arg Ala Ser Gln Ser Ile Gly Thr Ser
            20                  25                  30
Ile His Trp Tyr Gln Gln Arg Thr Asn Gly Ser Pro Arg Leu Leu Ile
        35                  40                  45
Lys Tyr Ala Ser Glu Ser Ile Ser Gly Ile Pro Ser Arg Phe Ser Gly
    50                  55                  60
Ser Gly Ser Gly Thr Asp Phe Thr Leu Ser Ile Asn Ser Val Glu Ser
65                  70                  75                  80
Glu Asp Ile Ala Asp Tyr Tyr Cys Gln Gln Ser Ile Arg Trp Pro Tyr
                85                  90                  95
Thr Phe Gly Gly Gly Thr Lys Leu Glu Ile Lys
            100                 105

<210> SEQ ID NO 6
<211> LENGTH: 11
<212> TYPE: PRT
<213> ORGANISM: Artificial sequence
<220> FEATURE:
<223> OTHER INFORMATION: synthesized

<400> SEQUENCE: 6

Arg Ala Ser Gln Ser Ile Gly Thr Ser Ile His
1               5                   10

<210> SEQ ID NO 7
<211> LENGTH: 7
<212> TYPE: PRT
<213> ORGANISM: Artificial sequence
<220> FEATURE:
<223> OTHER INFORMATION: synthesized

<400> SEQUENCE: 7

Tyr Ala Ser Glu Ser Ile Ser
1               5

<210> SEQ ID NO 8
<211> LENGTH: 9
<212> TYPE: PRT
<213> ORGANISM: Artificial sequence
<220> FEATURE:
<223> OTHER INFORMATION: synthesized

<400> SEQUENCE: 8

Gln Gln Ser Ile Arg Trp Pro Tyr Thr
1               5

<210> SEQ ID NO 9
<211> LENGTH: 118
<212> TYPE: PRT
<213> ORGANISM: Artificial sequence
<220> FEATURE:
<223> OTHER INFORMATION: synthesized

<400> SEQUENCE: 9

Gln Val Gln Leu Gln Gln Ser Gly Ala Glu Leu Val Lys Pro Gly Ala
```

```
                1               5                  10                  15
            Ser Val Lys Leu Ser Cys Lys Ala Thr Gly Tyr Thr Phe Thr Gly Tyr
                            20                  25                  30

Trp Ile Glu Trp Val Lys Gln Arg Pro Gly His Gly Leu Glu Trp Ile
                        35                  40                  45

Gly Glu Ile Leu Pro Gly Ser Gly Ser Thr Lys Tyr Asn Glu Lys Phe
                    50                  55                  60

Lys Asp Arg Ala Thr Phe Thr Glu Asp Thr Ser Ser Asn Thr Ala Tyr
            65                  70                  75                  80

Met Gln Leu Ser Ser Leu Thr Thr Glu Asp Ser Ala Ile Tyr Tyr Cys
                            85                  90                  95

Ala Arg Gly Gly Leu Asp Ser Phe Phe Asp Tyr Trp Gly Gln Gly Thr
                        100                 105                 110

Thr Leu Thr Val Ser Ser
                    115

<210> SEQ ID NO 10
<211> LENGTH: 5
<212> TYPE: PRT
<213> ORGANISM: Artificial sequence
<220> FEATURE:
<223> OTHER INFORMATION: synthesized

<400> SEQUENCE: 10

Gly Tyr Trp Ile Glu
1               5

<210> SEQ ID NO 11
<211> LENGTH: 17
<212> TYPE: PRT
<213> ORGANISM: Artificial sequence
<220> FEATURE:
<223> OTHER INFORMATION: synthesized

<400> SEQUENCE: 11

Glu Ile Leu Pro Gly Ser Gly Ser Thr Lys Tyr Asn Glu Lys Phe Lys
1               5                   10                  15

Asp

<210> SEQ ID NO 12
<211> LENGTH: 9
<212> TYPE: PRT
<213> ORGANISM: Artificial sequence
<220> FEATURE:
<223> OTHER INFORMATION: synthesized

<400> SEQUENCE: 12

Gly Gly Leu Asp Ser Phe Phe Asp Tyr
1               5

<210> SEQ ID NO 13
<211> LENGTH: 112
<212> TYPE: PRT
<213> ORGANISM: Artificial sequence
<220> FEATURE:
<223> OTHER INFORMATION: synthesized

<400> SEQUENCE: 13

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ile Ile Val His Ser
                20                  25                  30
```

```
Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser Tyr Val Pro Trp Thr Phe Gly Gly Gly Thr Lys Leu Glu Ile Lys
            100                 105                 110
```

<210> SEQ ID NO 14
<211> LENGTH: 16
<212> TYPE: PRT
<213> ORGANISM: Artificial sequence
<220> FEATURE:
<223> OTHER INFORMATION: synthesized

<400> SEQUENCE: 14

```
Arg Ser Ser Gln Ile Ile Val His Ser Asn Gly Asn Thr Tyr Leu Glu
1               5                   10                  15
```

<210> SEQ ID NO 15
<211> LENGTH: 7
<212> TYPE: PRT
<213> ORGANISM: Artificial sequence
<220> FEATURE:
<223> OTHER INFORMATION: synthesized

<400> SEQUENCE: 15

```
Lys Val Ser Asn Arg Phe Ser
1               5
```

<210> SEQ ID NO 16
<211> LENGTH: 9
<212> TYPE: PRT
<213> ORGANISM: Artificial sequence
<220> FEATURE:
<223> OTHER INFORMATION: synthesized

<400> SEQUENCE: 16

```
Phe Gln Gly Ser Tyr Val Pro Trp Thr
1               5
```

<210> SEQ ID NO 17
<211> LENGTH: 117
<212> TYPE: PRT
<213> ORGANISM: Artificial sequence
<220> FEATURE:
<223> OTHER INFORMATION: synthesized

<400> SEQUENCE: 17

```
Glu Val Gln Leu Gln Gln Ser Val Ala Glu Leu Val Arg Pro Gly Ala
1               5                   10                  15

Thr Val Lys Leu Ser Cys Thr Thr Ser Gly Phe Asn Ile Gln Asn Thr
            20                  25                  30

Tyr Met His Trp Val Lys Gln Arg Pro Glu Gln Gly Leu Glu Trp Ile
            35                  40                  45

Gly Arg Ile Asp Pro Ala Ser Gly Asn Thr Ile Tyr Ala Pro Lys Phe
 50                  55                  60

Gln Gly Arg Ala Thr Ile Thr Ala Asp Thr Ser Ser Asn Thr Ala Tyr
65                  70                  75                  80
```

```
Leu Gln Leu Ser Ser Leu Thr Ser Glu Asp Thr Ala Ile Tyr Tyr Cys
                85                  90                  95

Ala Arg Met Asp Gly Tyr Tyr Asp Pro Tyr Trp Gly Gln Gly Thr Leu
            100                 105                 110

Val Thr Val Ser Ala
        115

<210> SEQ ID NO 18
<211> LENGTH: 5
<212> TYPE: PRT
<213> ORGANISM: Artificial sequence
<220> FEATURE:
<223> OTHER INFORMATION: synthesized

<400> SEQUENCE: 18

Asn Thr Tyr Met His
1               5

<210> SEQ ID NO 19
<211> LENGTH: 17
<212> TYPE: PRT
<213> ORGANISM: Artificial sequence
<220> FEATURE:
<223> OTHER INFORMATION: synthesized

<400> SEQUENCE: 19

Arg Ile Asp Pro Ala Ser Gly Asn Thr Ile Tyr Ala Pro Lys Phe Gln
1               5                   10                  15

Gly

<210> SEQ ID NO 20
<211> LENGTH: 8
<212> TYPE: PRT
<213> ORGANISM: Artificial sequence
<220> FEATURE:
<223> OTHER INFORMATION: synthesized

<400> SEQUENCE: 20

Met Asp Gly Tyr Tyr Asp Pro Tyr
1               5

<210> SEQ ID NO 21
<211> LENGTH: 107
<212> TYPE: PRT
<213> ORGANISM: Artificial sequence
<220> FEATURE:
<223> OTHER INFORMATION: synthesized

<400> SEQUENCE: 21

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Thr Gly Thr Ser
            20                  25                  30

Ile His Trp Tyr Gln Gln Arg Thr Asn Gly Ser Pro Arg Leu Leu Ile
        35                  40                  45

Lys Tyr Thr Ser Glu Ser Ile Ser Gly Ile Pro Ser Arg Phe Ser Gly
    50                  55                  60

Ser Gly Ser Gly Thr Asp Phe Thr Leu Thr Ile Asn Ser Val Glu Ser
65                  70                  75                  80

Glu Asp Ile Gly Asp Tyr Tyr Cys Arg Gln Ser Ile Ser Arg Pro Phe
                85                  90                  95
```

```
Thr Phe Gly Ser Gly Thr Lys Leu Glu Met Lys
            100                 105
```

<210> SEQ ID NO 22
<211> LENGTH: 11
<212> TYPE: PRT
<213> ORGANISM: Artificial sequence
<220> FEATURE:
<223> OTHER INFORMATION: synthesized

<400> SEQUENCE: 22

```
Arg Ala Ser Gln Ser Thr Gly Thr Ser Ile His
1               5                   10
```

<210> SEQ ID NO 23
<211> LENGTH: 7
<212> TYPE: PRT
<213> ORGANISM: Artificial sequence
<220> FEATURE:
<223> OTHER INFORMATION: synthesized

<400> SEQUENCE: 23

```
Tyr Thr Ser Glu Ser Ile Ser
1               5
```

<210> SEQ ID NO 24
<211> LENGTH: 9
<212> TYPE: PRT
<213> ORGANISM: Artificial sequence
<220> FEATURE:
<223> OTHER INFORMATION: synthesized

<400> SEQUENCE: 24

```
Arg Gln Ser Ile Ser Arg Pro Phe Thr
1               5
```

<210> SEQ ID NO 25
<211> LENGTH: 121
<212> TYPE: PRT
<213> ORGANISM: Artificial sequence
<220> FEATURE:
<223> OTHER INFORMATION: synthesized

<400> SEQUENCE: 25

```
Glu Val Lys Leu Val Glu Ser Gly Gly Leu Val Gln Pro Gly Gly
1               5                   10                  15

Ser Leu Ser Leu Ser Cys Ala Ala Ser Gly Phe Thr Phe Thr Asp Tyr
            20                  25                  30

Tyr Met Ser Trp Val Arg Gln Pro Pro Gly Lys Ala Leu Glu Trp Leu
            35                  40                  45

Gly Phe Ile Arg Asn Lys Ala Asn Gly Tyr Thr Thr Glu Cys Ser Ala
        50                  55                  60

Ser Val Lys Gly Arg Phe Thr Ile Ser Arg Asp Asn Ser Gln Asn Ile
65                  70                  75                  80

Leu Tyr Leu Gln Met Asn Ala Leu Arg Ala Glu Asp Ser Ala Thr Tyr
                85                  90                  95

Tyr Cys Ala Thr Tyr Gly Arg Leu Gly Tyr Thr Met Asp Tyr Trp Gly
            100                 105                 110

Gln Gly Thr Ser Val Thr Val Ser Ser
            115                 120
```

<210> SEQ ID NO 26
<211> LENGTH: 5

-continued

<210> SEQ ID NO 26
... (header as shown)
<212> TYPE: PRT
<213> ORGANISM: Artificial sequence
<220> FEATURE:
<223> OTHER INFORMATION: synthesized

<400> SEQUENCE: 26

Asp Tyr Tyr Met Ser
1               5

<210> SEQ ID NO 27
<211> LENGTH: 19
<212> TYPE: PRT
<213> ORGANISM: Artificial sequence
<220> FEATURE:
<223> OTHER INFORMATION: synthesized

<400> SEQUENCE: 27

Phe Ile Arg Asn Lys Ala Asn Gly Tyr Thr Thr Glu Cys Ser Ala Ser
1               5                   10                  15

Val Lys Gly

<210> SEQ ID NO 28
<211> LENGTH: 10
<212> TYPE: PRT
<213> ORGANISM: Artificial sequence
<220> FEATURE:
<223> OTHER INFORMATION: synthesized

<400> SEQUENCE: 28

Tyr Gly Arg Leu Gly Tyr Thr Met Asp Tyr
1               5                   10

<210> SEQ ID NO 29
<211> LENGTH: 112
<212> TYPE: PRT
<213> ORGANISM: Artificial sequence
<220> FEATURE:
<223> OTHER INFORMATION: synthesized

<400> SEQUENCE: 29

Asp Val Leu Met Thr Gln Thr Pro Leu Ser Leu Pro Val Ser Leu Gly
1               5                   10                  15

Asp Gln Ala Ser Ile Ser Cys Arg Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 30
<211> LENGTH: 16
<212> TYPE: PRT
<213> ORGANISM: Artificial sequence
<220> FEATURE:
<223> OTHER INFORMATION: synthesized

<400> SEQUENCE: 30

-continued

Arg Ser Ser Gln Ser Ile Val His Ser Asn Gly Asn Thr Tyr Leu Glu
1               5                   10                  15

<210> SEQ ID NO 31
<211> LENGTH: 7
<212> TYPE: PRT
<213> ORGANISM: Artificial sequence
<220> FEATURE:
<223> OTHER INFORMATION: synthesized

<400> SEQUENCE: 31

Lys Val Ser Asn Arg Phe Ser
1               5

<210> SEQ ID NO 32
<211> LENGTH: 9
<212> TYPE: PRT
<213> ORGANISM: Artificial sequence
<220> FEATURE:
<223> OTHER INFORMATION: synthesized

<400> SEQUENCE: 32

Phe Gln Gly Ser His Val Pro Trp Thr
1               5

<210> SEQ ID NO 33
<211> LENGTH: 118
<212> TYPE: PRT
<213> ORGANISM: Artificial sequence
<220> FEATURE:
<223> OTHER INFORMATION: synthesized

<400> SEQUENCE: 33

Gln Val Gln Leu Gln Gln Pro Gly Ala Glu Leu Val Arg Pro Gly Ser
1               5                   10                  15

Ser Val Lys Leu Ser Cys Lys Ala Ser Gly His Thr Leu Thr Gly Phe
                20                  25                  30

Trp Met His Trp Val Arg Gln Arg Pro Ile Pro Gly Leu Glu Trp Ile
            35                  40                  45

Gly Asn Ile Asp Pro Ser Asp Ser Glu Thr His Tyr Asn Gln Lys Phe
        50                  55                  60

Glu Asp Lys Ala Thr Leu Thr Val Asp Lys Ser Ser Asn Thr Ala Tyr
65                  70                  75                  80

Met Leu Leu Ser Ser Leu Thr Ser Glu Asp Ser Ala Val Tyr Tyr Cys
                85                  90                  95

Ala Arg Glu Gly Gly Thr Gly Tyr Phe Asp Val Trp Gly Thr Gly Thr
            100                 105                 110

Thr Val Thr Val Ser Ser
        115

<210> SEQ ID NO 34
<211> LENGTH: 5
<212> TYPE: PRT
<213> ORGANISM: Artificial sequence
<220> FEATURE:
<223> OTHER INFORMATION: synthesized

<400> SEQUENCE: 34

Gly Phe Trp Met His
1               5

<210> SEQ ID NO 35
<211> LENGTH: 17

```
<212> TYPE: PRT
<213> ORGANISM: Artificial sequence
<220> FEATURE:
<223> OTHER INFORMATION: synthesized

<400> SEQUENCE: 35

Asn Ile Asp Pro Ser Asp Ser Glu Thr His Tyr Asn Gln Lys Phe Glu
1               5                   10                  15

Asp

<210> SEQ ID NO 36
<211> LENGTH: 9
<212> TYPE: PRT
<213> ORGANISM: Artificial sequence
<220> FEATURE:
<223> OTHER INFORMATION: synthesized

<400> SEQUENCE: 36

Glu Gly Gly Thr Gly Tyr Phe Asp Val
1               5

<210> SEQ ID NO 37
<211> LENGTH: 110
<212> TYPE: PRT
<213> ORGANISM: Artificial sequence
<220> FEATURE:
<223> OTHER INFORMATION: synthesized

<400> SEQUENCE: 37

Glu Phe Val Leu Thr Gln Ser Pro Thr Thr Leu Ala Ala Ser Pro Gly
1               5                   10                  15

Glu Lys Ile Thr Ile Thr Cys Ser Ala Ser Ser Ser Ile Ser Ser Asn
                20                  25                  30

Tyr Leu His Trp Tyr Gln Gln Lys Pro Gly Phe Ser Pro Lys Leu Leu
            35                  40                  45

Ile Tyr Arg Thr Ser Asn Leu Ala Ser Gly Val Pro Ala Arg Phe Ser
        50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Lys Gly Ser Ser Ile Pro
                85                  90                  95

Arg Met Tyr Thr Phe Gly Gly Gly Thr Lys Leu Glu Ile Lys
            100                 105                 110

<210> SEQ ID NO 38
<211> LENGTH: 12
<212> TYPE: PRT
<213> ORGANISM: Artificial sequence
<220> FEATURE:
<223> OTHER INFORMATION: synthesized

<400> SEQUENCE: 38

Ser Ala Ser Ser Ser Ile Ser Ser Asn Tyr Leu His
1               5                   10

<210> SEQ ID NO 39
<211> LENGTH: 7
<212> TYPE: PRT
<213> ORGANISM: Artificial sequence
<220> FEATURE:
<223> OTHER INFORMATION: synthesized

<400> SEQUENCE: 39
```

```
Arg Thr Ser Asn Leu Ala Ser
1               5

<210> SEQ ID NO 40
<211> LENGTH: 11
<212> TYPE: PRT
<213> ORGANISM: Artificial sequence
<220> FEATURE:
<223> OTHER INFORMATION: synthesized

<400> SEQUENCE: 40

Gln Lys Gly Ser Ser Ile Pro Arg Met Tyr Thr
1               5                   10

<210> SEQ ID NO 41
<211> LENGTH: 120
<212> TYPE: PRT
<213> ORGANISM: Artificial sequence
<220> FEATURE:
<223> OTHER INFORMATION: synthesized

<400> SEQUENCE: 41

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Asn
                20                  25                  30

Tyr Tyr Trp Asn Trp Ile Arg Gln Phe Pro Gly Asn Lys Leu Glu Trp
            35                  40                  45

Met Gly Tyr Ile Ser Tyr Asp Gly Ser Asn Asp Tyr Asn Pro Ser Leu
        50                  55                  60

Lys Asn Arg Ile Ser Ile Thr Arg Asp Thr Ser Lys Asn Gln Phe Phe
65                  70                  75                  80

Leu Arg Leu Asn Ser Val Thr Thr Glu Asp Thr Ala Thr Tyr Phe Cys
                85                  90                  95

Ala Arg Val Thr Ser Gly Tyr Leu Tyr Tyr Phe Asp Asn Trp Gly Gln
            100                 105                 110

Gly Thr Thr Leu Thr Val Ser Ser
        115                 120

<210> SEQ ID NO 42
<211> LENGTH: 6
<212> TYPE: PRT
<213> ORGANISM: Artificial sequence
<220> FEATURE:
<223> OTHER INFORMATION: synthesized

<400> SEQUENCE: 42

Ser Asn Tyr Tyr Trp Asn
1               5

<210> SEQ ID NO 43
<211> LENGTH: 16
<212> TYPE: PRT
<213> ORGANISM: Artificial sequence
<220> FEATURE:
<223> OTHER INFORMATION: synthesized

<400> SEQUENCE: 43

Tyr Ile Ser Tyr Asp Gly Ser Asn Asp Tyr Asn Pro Ser Leu Lys Asn
1               5                   10                  15

<210> SEQ ID NO 44
<211> LENGTH: 11
```

```
<212> TYPE: PRT
<213> ORGANISM: Artificial sequence
<220> FEATURE:
<223> OTHER INFORMATION: synthesized

<400> SEQUENCE: 44

Val Thr Ser Gly Tyr Leu Tyr Tyr Phe Asp Asn
1               5                   10

<210> SEQ ID NO 45
<211> LENGTH: 105
<212> TYPE: PRT
<213> ORGANISM: Artificial sequence
<220> FEATURE:
<223> OTHER INFORMATION: synthesized

<400> SEQUENCE: 45

Glu Ile Val Leu Thr Gln Ser Pro Ala Ile Thr Ala Ala Ser Leu Gly
1               5                   10                  15

Gln Lys Val Thr Ile Thr Cys Ser Ala Ser Ser Val Ser Tyr Met
            20                  25                  30

His Trp Tyr Gln Gln Arg Ser Gly Thr Ser Pro Lys Pro Trp Ile Tyr
        35                  40                  45

Glu Ile Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Ile Tyr Tyr Cys Gln Gln Trp Asn Phe Pro Leu Thr Phe
                85                  90                  95

Gly Ala Gly Thr Lys Leu Glu Leu Lys
            100                 105

<210> SEQ ID NO 46
<211> LENGTH: 10
<212> TYPE: PRT
<213> ORGANISM: Artificial sequence
<220> FEATURE:
<223> OTHER INFORMATION: synthesized

<400> SEQUENCE: 46

Ser Ala Ser Ser Ser Val Ser Tyr Met His
1               5                   10

<210> SEQ ID NO 47
<211> LENGTH: 7
<212> TYPE: PRT
<213> ORGANISM: Artificial sequence
<220> FEATURE:
<223> OTHER INFORMATION: synthesized

<400> SEQUENCE: 47

Glu Ile Ser Lys Leu Ala Ser
1               5

<210> SEQ ID NO 48
<211> LENGTH: 8
<212> TYPE: PRT
<213> ORGANISM: Artificial sequence
<220> FEATURE:
<223> OTHER INFORMATION: synthesized

<400> SEQUENCE: 48

Gln Gln Trp Asn Phe Pro Leu Thr
1               5
```

-continued

```
<210> SEQ ID NO 49
<211> LENGTH: 122
<212> TYPE: PRT
<213> ORGANISM: Artificial sequence
<220> FEATURE:
<223> OTHER INFORMATION: synthesized

<400> SEQUENCE: 49

Asp Val Lys Leu Val Glu Ser Gly Glu Asp Leu Val Lys Pro Gly Gly
1               5                   10                  15

Ser Leu Lys Val Ser Cys Ala Ala Ser Gly Phe Thr Phe Arg Asp Tyr
            20                  25                  30

Ala Met Ser Trp Val Arg Gln Thr Pro Glu Lys Arg Leu Glu Trp Val
        35                  40                  45

Ala Tyr Ile Ser Ser Gly Gly Asp Tyr Ile Tyr Tyr Ala Asp Ser Val
    50                  55                  60

Lys Gly Arg Phe Thr Ile Ser Arg Asp Asn Ala Arg Asn Thr Leu Tyr
65                  70                  75                  80

Leu Gln Met Thr Ser Leu Arg Ser Glu Asp Thr Ala Met Tyr Phe Cys
                85                  90                  95

Thr Arg Asp Pro Ser Phe Tyr Gly Arg Gly Tyr Tyr Phe Asp Tyr Trp
            100                 105                 110

Gly Gln Gly Thr Ser Leu Thr Val Ser Ser
        115                 120

<210> SEQ ID NO 50
<211> LENGTH: 5
<212> TYPE: PRT
<213> ORGANISM: Artificial sequence
<220> FEATURE:
<223> OTHER INFORMATION: synthesized

<400> SEQUENCE: 50

Asp Tyr Ala Met Ser
1               5

<210> SEQ ID NO 51
<211> LENGTH: 17
<212> TYPE: PRT
<213> ORGANISM: Artificial sequence
<220> FEATURE:
<223> OTHER INFORMATION: synthesized

<400> SEQUENCE: 51

Tyr Ile Ser Ser Gly Gly Asp Tyr Ile Tyr Tyr Ala Asp Ser Val Lys
1               5                   10                  15

Gly

<210> SEQ ID NO 52
<211> LENGTH: 13
<212> TYPE: PRT
<213> ORGANISM: Artificial sequence
<220> FEATURE:
<223> OTHER INFORMATION: synthesized

<400> SEQUENCE: 52

Asp Pro Ser Phe Tyr Gly Arg Gly Tyr Tyr Phe Asp Tyr
1               5                   10

<210> SEQ ID NO 53
<211> LENGTH: 106
```

-continued

```
<212> TYPE: PRT
<213> ORGANISM: Artificial sequence
<220> FEATURE:
<223> OTHER INFORMATION: synthesized

<400> SEQUENCE: 53

Asp Ile Val Met Thr Gln Ser His Lys Phe Met Ser Ala Ser Val Gly
1               5                   10                  15

Asp Arg Val Ser Ile Thr Cys Lys Ala Ser Gln Asp Val Gly Ala Thr
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Asn Asn Val Gln Ser
65                  70                  75                  80

Glu Asp Leu Ala Asp Tyr Phe Cys Gln Gln Tyr Ser Asn Tyr Pro Thr
                85                  90                  95

Phe Gly Gly Gly Thr Lys Leu Glu Ile Lys
            100                 105

<210> SEQ ID NO 54
<211> LENGTH: 11
<212> TYPE: PRT
<213> ORGANISM: Artificial sequence
<220> FEATURE:
<223> OTHER INFORMATION: synthesized

<400> SEQUENCE: 54

Lys Ala Ser Gln Asp Val Gly Ala Thr Val Ala
1               5                   10

<210> SEQ ID NO 55
<211> LENGTH: 7
<212> TYPE: PRT
<213> ORGANISM: Artificial sequence
<220> FEATURE:
<223> OTHER INFORMATION: synthesized

<400> SEQUENCE: 55

Trp Ala Ser Thr Arg His Thr
1               5

<210> SEQ ID NO 56
<211> LENGTH: 8
<212> TYPE: PRT
<213> ORGANISM: Artificial sequence
<220> FEATURE:
<223> OTHER INFORMATION: synthesized

<400> SEQUENCE: 56

Gln Gln Tyr Ser Asn Tyr Pro Thr
1               5

<210> SEQ ID NO 57
<211> LENGTH: 116
<212> TYPE: PRT
<213> ORGANISM: Artificial sequence
<220> FEATURE:
<223> OTHER INFORMATION: synthesized

<400> SEQUENCE: 57

Glu Val Gln Leu Gln Gln Ser Val Ala Glu Leu Val Arg Pro Gly Ala
1               5                   10                  15
```

```
Ser Val Lys Leu Ser Cys Thr Val Ser Gly Phe Asn Ile Lys Asn Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asp Thr Lys Tyr Asp Pro Lys Phe
 50                  55                  60

Gln Ala Lys Ala Thr Val Thr Ala Asp Thr Ser Ser Asn Thr Ala Tyr
 65                  70                  75                  80

Leu His Leu Ser Ser Leu Thr Ser Glu Asp Thr Ala Ile Tyr Tyr Cys
                85                  90                  95

Val Glu Asp Asp Tyr Gly Leu Gly Ser Trp Gly Gln Gly Thr Thr Leu
            100                 105                 110

Thr Val Ser Ser
        115

<210> SEQ ID NO 58
<211> LENGTH: 5
<212> TYPE: PRT
<213> ORGANISM: Artificial sequence
<220> FEATURE:
<223> OTHER INFORMATION: synthesized

<400> SEQUENCE: 58

Asn Thr Tyr Met His
1               5

<210> SEQ ID NO 59
<211> LENGTH: 17
<212> TYPE: PRT
<213> ORGANISM: Artificial sequence
<220> FEATURE:
<223> OTHER INFORMATION: synthesized

<400> SEQUENCE: 59

Arg Ile Asp Pro Ala Asn Gly Asp Thr Lys Tyr Asp Pro Lys Phe Gln
1               5                   10                  15

Ala

<210> SEQ ID NO 60
<211> LENGTH: 7
<212> TYPE: PRT
<213> ORGANISM: Artificial sequence
<220> FEATURE:
<223> OTHER INFORMATION: synthesized

<400> SEQUENCE: 60

Asp Asp Tyr Gly Leu Gly Ser
1               5

<210> SEQ ID NO 61
<211> LENGTH: 107
<212> TYPE: PRT
<213> ORGANISM: Artificial sequence
<220> FEATURE:
<223> OTHER INFORMATION: synthesized

<400> SEQUENCE: 61

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Ser Asn
            20                  25                  30
```

```
Val Ala Trp Tyr Gln Gln Lys Pro Gly Gln Ser Pro Lys Ser Leu Ile
        35                  40                  45

Tyr Ala Thr Ser His Arg Tyr Ser Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Glu Tyr Phe Cys Gln His Tyr Asn Asn Tyr Pro Tyr
                 85                  90                  95

Thr Phe Gly Gly Gly Thr Lys Leu Glu Ile Lys
            100                 105
```

<210> SEQ ID NO 62
<211> LENGTH: 11
<212> TYPE: PRT
<213> ORGANISM: Artificial sequence
<220> FEATURE:
<223> OTHER INFORMATION: synthesized

<400> SEQUENCE: 62

```
Lys Ala Ser Gln Asn Val Gly Ser Asn Val Ala
 1               5                  10
```

<210> SEQ ID NO 63
<211> LENGTH: 7
<212> TYPE: PRT
<213> ORGANISM: Artificial sequence
<220> FEATURE:
<223> OTHER INFORMATION: synthesized

<400> SEQUENCE: 63

```
Ala Thr Ser His Arg Tyr Ser
 1               5
```

<210> SEQ ID NO 64
<211> LENGTH: 9
<212> TYPE: PRT
<213> ORGANISM: Artificial sequence
<220> FEATURE:
<223> OTHER INFORMATION: synthesized

<400> SEQUENCE: 64

```
Gln His Tyr Asn Asn Tyr Pro Tyr Thr
 1               5
```

<210> SEQ ID NO 65
<211> LENGTH: 119
<212> TYPE: PRT
<213> ORGANISM: Artificial sequence
<220> FEATURE:
<223> OTHER INFORMATION: synthesized

<400> SEQUENCE: 65

```
Glu Val Gln Leu Gln Gln Ser Gly Pro Val Leu Val Lys Pro Gly Ala
 1               5                  10                  15

Ser Val Lys Ile Ser Cys Lys Ala Ser Gly Tyr Thr Phe Thr Asp Tyr
                 20                  25                  30

Tyr Met Asn Trp Val Lys Gln Ser His Gly Lys Ser Leu Glu Trp Ile
             35                  40                  45

Gly Asp Ile Asn Pro Asp Asn Gly Phe Thr Tyr Asn Gln Lys Phe
     50                  55                  60

Lys Gly Lys Ala Thr Leu Thr Val Asp Arg Ser Ser Thr Ala Tyr
 65                  70                  75                  80
```

Met Glu Phe Arg Ser Leu Thr Ser Glu Asp Ser Ala Val Tyr Tyr Cys
                85                  90                  95

Ala Arg Asp Gly Ser Ser Ala Tyr Gly Met Asp Tyr Trp Gly Gln Gly
            100                 105                 110

Thr Ser Val Thr Val Ser Ser
        115

<210> SEQ ID NO 66
<211> LENGTH: 5
<212> TYPE: PRT
<213> ORGANISM: Artificial sequence
<220> FEATURE:
<223> OTHER INFORMATION: synthesized

<400> SEQUENCE: 66

Asp Tyr Tyr Met Asn
1               5

<210> SEQ ID NO 67
<211> LENGTH: 17
<212> TYPE: PRT
<213> ORGANISM: Artificial sequence
<220> FEATURE:
<223> OTHER INFORMATION: synthesized

<400> SEQUENCE: 67

Asp Ile Asn Pro Asp Asn Gly Phe Thr Ser Tyr Asn Gln Lys Phe Lys
1               5                   10                  15

Gly

<210> SEQ ID NO 68
<211> LENGTH: 10
<212> TYPE: PRT
<213> ORGANISM: Artificial sequence
<220> FEATURE:
<223> OTHER INFORMATION: synthesized

<400> SEQUENCE: 68

Asp Gly Ser Ser Ala Tyr Gly Met Asp Tyr
1               5                   10

<210> SEQ ID NO 69
<211> LENGTH: 111
<212> TYPE: PRT
<213> ORGANISM: Artificial sequence
<220> FEATURE:
<223> OTHER INFORMATION: synthesized

<400> SEQUENCE: 69

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Ser Ile His
            20                  25                  30

Gly Thr His Leu Met His Trp Tyr Gln Gln Lys Pro Gly Gln Pro Pro
        35                  40                  45

Lys Leu Leu Ile Tyr Ala Ala Ser Asn Leu Glu Ser Gly Val Pro Ala
    50                  55                  60

Arg Phe Ser Gly Ser Gly Ser Glu Thr Asp Phe Thr Leu Asn Ile His
65                  70                  75                  80

Thr Val Glu Glu Glu Asp Ala Ala Thr Tyr Phe Cys Gln Gln Ser Ile
                85                  90                  95

Glu Glu Pro Arg Thr Phe Gly Gly Gly Thr Lys Val Glu Ile Lys

-continued

<210> SEQ ID NO 70
<211> LENGTH: 15
<212> TYPE: PRT
<213> ORGANISM: Artificial sequence
<220> FEATURE:
<223> OTHER INFORMATION: synthesized

<400> SEQUENCE: 70

Arg Ala Ser Glu Ser Val Ser Ile His Gly Thr His Leu Met His
1               5                   10                  15

<210> SEQ ID NO 71
<211> LENGTH: 7
<212> TYPE: PRT
<213> ORGANISM: Artificial sequence
<220> FEATURE:
<223> OTHER INFORMATION: synthesized

<400> SEQUENCE: 71

Ala Ala Ser Asn Leu Glu Ser
1               5

<210> SEQ ID NO 72
<211> LENGTH: 9
<212> TYPE: PRT
<213> ORGANISM: Artificial sequence
<220> FEATURE:
<223> OTHER INFORMATION: synthesized

<400> SEQUENCE: 72

Gln Gln Ser Ile Glu Glu Pro Arg Thr
1               5

<210> SEQ ID NO 73
<211> LENGTH: 118
<212> TYPE: PRT
<213> ORGANISM: Artificial sequence
<220> FEATURE:
<223> OTHER INFORMATION: synthesized

<400> SEQUENCE: 73

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
                20                  25                  30

Tyr Met His Trp Val Lys Gln Ser His Gly Asn Ile Leu Asp Trp Ile
            35                  40                  45

Gly Tyr Ile Tyr Pro Tyr Asn Gly Val Ser Thr Tyr Asn Gln Arg Phe
        50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Lys Gly Ala Ser Gly Tyr Asp Gly Asp Tyr Trp Gly Gln Gly Thr
                100                 105                 110

Thr Leu Thr Val Ser Ser
            115

<210> SEQ ID NO 74
<211> LENGTH: 5
<212> TYPE: PRT

```
<213> ORGANISM: Artificial sequence
<220> FEATURE:
<223> OTHER INFORMATION: synthesized

<400> SEQUENCE: 74

Gly Tyr Tyr Met His
1               5

<210> SEQ ID NO 75
<211> LENGTH: 17
<212> TYPE: PRT
<213> ORGANISM: Artificial sequence
<220> FEATURE:
<223> OTHER INFORMATION: synthesized

<400> SEQUENCE: 75

Tyr Ile Tyr Pro Tyr Asn Gly Val Ser Thr Tyr Asn Gln Arg Phe Lys
1               5                   10                  15

Gly

<210> SEQ ID NO 76
<211> LENGTH: 9
<212> TYPE: PRT
<213> ORGANISM: Artificial sequence
<220> FEATURE:
<223> OTHER INFORMATION: synthesized

<400> SEQUENCE: 76

Gly Ala Ser Gly Tyr Asp Gly Asp Tyr
1               5

<210> SEQ ID NO 77
<211> LENGTH: 106
<212> TYPE: PRT
<213> ORGANISM: Artificial sequence
<220> FEATURE:
<223> OTHER INFORMATION: synthesized

<400> SEQUENCE: 77

Gln Ile Val Leu Thr Gln Ser Pro Ala Ile Met Ser Ala Ser Pro Gly
1               5                   10                  15

Glu Lys Val Thr Ile Thr Cys Ser Ala Thr Ser Val Val Ser Tyr Met
                20                  25                  30

His Trp Phe Gln Gln Lys Pro Gly Thr Ser Pro Lys Leu Trp Ile Tyr
            35                  40                  45

Leu Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Pro Thr
                85                  90                  95

Phe Gly Gly Gly Thr Lys Leu Glu Ile Lys
            100                 105

<210> SEQ ID NO 78
<211> LENGTH: 10
<212> TYPE: PRT
<213> ORGANISM: Artificial sequence
<220> FEATURE:
<223> OTHER INFORMATION: synthesized

<400> SEQUENCE: 78

Ser Ala Thr Ser Val Val Ser Tyr Met His
1               5                   10
```

1               5                    10

<210> SEQ ID NO 79
<211> LENGTH: 7
<212> TYPE: PRT
<213> ORGANISM: Artificial sequence
<220> FEATURE:
<223> OTHER INFORMATION: synthesized

<400> SEQUENCE: 79

Leu Thr Ser Asn Leu Ala Ser
1               5

<210> SEQ ID NO 80
<211> LENGTH: 9
<212> TYPE: PRT
<213> ORGANISM: Artificial sequence
<220> FEATURE:
<223> OTHER INFORMATION: synthesized

<400> SEQUENCE: 80

Gln Gln Arg Ser Ser Tyr Pro Pro Thr
1               5

<210> SEQ ID NO 81
<211> LENGTH: 118
<212> TYPE: PRT
<213> ORGANISM: Artificial sequence
<220> FEATURE:
<223> OTHER INFORMATION: synthesized

<400> SEQUENCE: 81

Gln Val Gln Leu Gln Gln Ser Gly Ala Glu Leu Met Lys Pro Gly Ala
1               5                   10                  15

Ser Val Lys Leu Ser Cys Lys Ala Thr Gly Tyr Thr Phe Thr Gly Tyr
            20                  25                  30

Trp Ile Glu Trp Val Lys Gln Arg Pro Gly His Gly Phe Glu Trp Ile
        35                  40                  45

Gly Glu Ile Leu Pro Gly Ser Gly Thr Thr Lys Tyr Asn Lys Lys Phe
    50                  55                  60

Gln Gly Lys Ala Thr Ile Thr Ala Asp Thr Ser Ser Asn Thr Ala Tyr
65                  70                  75                  80

Ile Gln Leu Ser Ser Leu Thr Thr Glu Asp Ser Ala Met Tyr Tyr Cys
                85                  90                  95

Ala Arg Gly Gly Gln Asp His Phe Phe Ala Asp Trp Gly Gln Gly Thr
            100                 105                 110

Thr Leu Thr Val Ser Ser
        115

<210> SEQ ID NO 82
<211> LENGTH: 5
<212> TYPE: PRT
<213> ORGANISM: Artificial sequence
<220> FEATURE:
<223> OTHER INFORMATION: synthesized

<400> SEQUENCE: 82

Gly Tyr Trp Ile Glu
1               5

<210> SEQ ID NO 83
<211> LENGTH: 17
<212> TYPE: PRT

<213> ORGANISM: Artificial sequence
<220> FEATURE:
<223> OTHER INFORMATION: synthesized

<400> SEQUENCE: 83

Glu Ile Leu Pro Gly Ser Gly Thr Thr Lys Tyr Asn Lys Lys Phe Gln
1               5                   10                  15
Gly

<210> SEQ ID NO 84
<211> LENGTH: 9
<212> TYPE: PRT
<213> ORGANISM: Artificial sequence
<220> FEATURE:
<223> OTHER INFORMATION: synthesized

<400> SEQUENCE: 84

Gly Gly Gln Asp His Phe Phe Ala Asp
1               5

<210> SEQ ID NO 85
<211> LENGTH: 112
<212> TYPE: PRT
<213> ORGANISM: Artificial sequence
<220> FEATURE:
<223> OTHER INFORMATION: synthesized

<400> SEQUENCE: 85

Asp Ile Leu Met Thr Gln Ser Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Asn Gly Asp Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser Tyr Val Pro Trp Thr Phe Gly Gly Gly Thr Arg Leu Glu Ile Lys
            100                 105                 110

<210> SEQ ID NO 86
<211> LENGTH: 16
<212> TYPE: PRT
<213> ORGANISM: Artificial sequence
<220> FEATURE:
<223> OTHER INFORMATION: synthesized

<400> SEQUENCE: 86

Arg Ser Ser Gln Thr Ile Val His Ser Asn Gly Asp Thr Tyr Leu Glu
1               5                   10                  15

<210> SEQ ID NO 87
<211> LENGTH: 7
<212> TYPE: PRT
<213> ORGANISM: Artificial sequence
<220> FEATURE:
<223> OTHER INFORMATION: synthesized

<400> SEQUENCE: 87

Lys Val Ser Asn Arg Phe Ser

```
1               5

<210> SEQ ID NO 88
<211> LENGTH: 9
<212> TYPE: PRT
<213> ORGANISM: Artificial sequence
<220> FEATURE:
<223> OTHER INFORMATION: synthesized

<400> SEQUENCE: 88

Phe Gln Gly Ser Tyr Val Pro Trp Thr
1               5

<210> SEQ ID NO 89
<211> LENGTH: 121
<212> TYPE: PRT
<213> ORGANISM: Artificial sequence
<220> FEATURE:
<223> OTHER INFORMATION: synthesized

<400> SEQUENCE: 89

Glu Val Lys Leu Glu Glu Ser Gly Gly Gly Leu Val Gln Pro Gly Gly
1               5                   10                  15

Ser Leu Ser Leu Ser Cys Ala Ala Ser Gly Phe Thr Phe Thr Asp Tyr
            20                  25                  30

Tyr Met Ser Trp Val Arg Gln Pro Pro Gly Lys Ala Pro Glu Trp Leu
        35                  40                  45

Gly Phe Ile Arg Asn Arg Ala Tyr Gly Tyr Thr Thr Glu Tyr Ser Ala
    50                  55                  60

Ser Val Lys Gly Arg Phe Thr Phe Ser Arg Asp Asn Ser Gln Ser Ile
65                  70                  75                  80

Leu Phe Leu His Met Asn Ala Leu Arg Pro Glu Asp Ser Ala Thr Tyr
                85                  90                  95

Tyr Cys Ala Arg Tyr Pro Leu Leu Gly Tyr Ala Leu Asp Tyr Trp Gly
            100                 105                 110

Gln Gly Thr Ser Val Thr Val Ser Ser
        115                 120

<210> SEQ ID NO 90
<211> LENGTH: 5
<212> TYPE: PRT
<213> ORGANISM: Artificial sequence
<220> FEATURE:
<223> OTHER INFORMATION: synthesized

<400> SEQUENCE: 90

Asp Tyr Tyr Met Ser
1               5

<210> SEQ ID NO 91
<211> LENGTH: 19
<212> TYPE: PRT
<213> ORGANISM: Artificial sequence
<220> FEATURE:
<223> OTHER INFORMATION: synthesized

<400> SEQUENCE: 91

Phe Ile Arg Asn Arg Ala Tyr Gly Tyr Thr Thr Glu Tyr Ser Ala Ser
1               5                   10                  15

Val Lys Gly

<210> SEQ ID NO 92
```

```
<211> LENGTH: 10
<212> TYPE: PRT
<213> ORGANISM: Artificial sequence
<220> FEATURE:
<223> OTHER INFORMATION: synthesized

<400> SEQUENCE: 92

Tyr Pro Leu Leu Gly Tyr Ala Leu Asp Tyr
1               5                   10

<210> SEQ ID NO 93
<211> LENGTH: 112
<212> TYPE: PRT
<213> ORGANISM: Artificial sequence
<220> FEATURE:
<223> OTHER INFORMATION: synthesized

<400> SEQUENCE: 93

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Val
                85                  90                  95

Ser His Val Pro Trp Thr Phe Gly Gly Gly Thr Lys Leu Glu Ile Lys
            100                 105                 110

<210> SEQ ID NO 94
<211> LENGTH: 16
<212> TYPE: PRT
<213> ORGANISM: Artificial sequence
<220> FEATURE:
<223> OTHER INFORMATION: synthesized

<400> SEQUENCE: 94

Arg Ser Ser Gln Ser Ile Val His Ser Asn Gly Asn Thr Tyr Leu Glu
1               5                   10                  15

<210> SEQ ID NO 95
<211> LENGTH: 7
<212> TYPE: PRT
<213> ORGANISM: Artificial sequence
<220> FEATURE:
<223> OTHER INFORMATION: synthesized

<400> SEQUENCE: 95

Lys Val Ser Asn Arg Phe Ser
1               5

<210> SEQ ID NO 96
<211> LENGTH: 9
<212> TYPE: PRT
<213> ORGANISM: Artificial sequence
<220> FEATURE:
<223> OTHER INFORMATION: synthesized

<400> SEQUENCE: 96

Phe Gln Val Ser His Val Pro Trp Thr
```

```
<210> SEQ ID NO 97
<211> LENGTH: 117
<212> TYPE: PRT
<213> ORGANISM: Artificial sequence
<220> FEATURE:
<223> OTHER INFORMATION: synthesized

<400> SEQUENCE: 97

Glu Val Gln Leu Gln Gln Ser Gly Ala Glu Leu Val Arg Pro Gly Ala
1               5                   10                  15
Ser Val Lys Leu Ser Cys Thr Ala Ser Gly Phe Asn Ile Lys Asp Asp
            20                  25                  30
Tyr Ile His Trp Val Lys Gln Arg Pro Glu Gln Gly Leu Glu Trp Ile
        35                  40                  45
Gly Trp Ile Asp Pro Ala Asn Gly His Ile Glu Tyr Ala Ser Asn Phe
    50                  55                  60
Gln Ala Lys Ala Thr Ile Thr Ala Asp Thr Ser Ser Asn Thr Ala Tyr
65                  70                  75                  80
Leu Gln Leu Ser Ser Leu Thr Ser Glu Asp Thr Ala Val Tyr Tyr Cys
                85                  90                  95
Thr Thr Gly Asp Tyr Asp Gly Phe Thr Tyr Trp Gly Gln Gly Thr Leu
            100                 105                 110
Val Thr Val Ser Thr
        115

<210> SEQ ID NO 98
<211> LENGTH: 5
<212> TYPE: PRT
<213> ORGANISM: Artificial sequence
<220> FEATURE:
<223> OTHER INFORMATION: synthesized

<400> SEQUENCE: 98

Asp Asp Tyr Ile His
1               5

<210> SEQ ID NO 99
<211> LENGTH: 17
<212> TYPE: PRT
<213> ORGANISM: Artificial sequence
<220> FEATURE:
<223> OTHER INFORMATION: synthesized

<400> SEQUENCE: 99

Trp Ile Asp Pro Ala Asn Gly His Ile Glu Tyr Ala Ser Asn Phe Gln
1               5                   10                  15
Ala

<210> SEQ ID NO 100
<211> LENGTH: 8
<212> TYPE: PRT
<213> ORGANISM: Artificial sequence
<220> FEATURE:
<223> OTHER INFORMATION: synthesized

<400> SEQUENCE: 100

Gly Asp Tyr Asp Gly Phe Thr Tyr
1               5

<210> SEQ ID NO 101
```

<211> LENGTH: 106
<212> TYPE: PRT
<213> ORGANISM: Artificial sequence
<220> FEATURE:
<223> OTHER INFORMATION: synthesized

<400> SEQUENCE: 101

Gln Ile Val Leu Thr Gln Ser Pro Ala Ile Met Ser Ala Ser Pro Gly
1               5                   10                  15

Glu Lys Val Thr Ile Ser Cys Ser Ala Arg Ser Ser Val Ser Tyr Met
            20                  25                  30

Tyr Trp Tyr Gln Gln Lys Pro Gly Ser Ser Pro Lys Pro Trp Ile Tyr
        35                  40                  45

Arg Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln His Tyr His Thr Tyr Pro Tyr Thr
                85                  90                  95

Phe Gly Gly Gly Thr Lys Leu Glu Ile Lys
            100                 105

<210> SEQ ID NO 102
<211> LENGTH: 10
<212> TYPE: PRT
<213> ORGANISM: Artificial sequence
<220> FEATURE:
<223> OTHER INFORMATION: synthesized

<400> SEQUENCE: 102

Ser Ala Arg Ser Ser Val Ser Tyr Met Tyr
1               5                   10

<210> SEQ ID NO 103
<211> LENGTH: 7
<212> TYPE: PRT
<213> ORGANISM: Artificial sequence
<220> FEATURE:
<223> OTHER INFORMATION: synthesized

<400> SEQUENCE: 103

Arg Thr Ser Asn Leu Ala Ser
1               5

<210> SEQ ID NO 104
<211> LENGTH: 9
<212> TYPE: PRT
<213> ORGANISM: Artificial sequence
<220> FEATURE:
<223> OTHER INFORMATION: synthesized

<400> SEQUENCE: 104

Gln His Tyr His Thr Tyr Pro Tyr Thr
1               5

<210> SEQ ID NO 105
<211> LENGTH: 117
<212> TYPE: PRT
<213> ORGANISM: Artificial sequence
<220> FEATURE:
<223> OTHER INFORMATION: synthesized

<400> SEQUENCE: 105

Glu Val Gln Leu Gln Gln Ser Gly Ala Glu Leu Val Arg Pro Gly Ala

```
                1               5                  10                 15
Ser Val Lys Leu Ser Cys Thr Ala Ser Gly Phe Asn Ile Lys Asp Glu
                20                 25                 30

Tyr Ile His Trp Val Lys Gln Arg Pro Glu Gln Gly Leu Glu Trp Ile
            35                 40                 45

Gly Trp Ile Asp Pro Ala Asn Gly His Thr Glu Tyr Ala Ser Arg Phe
        50                 55                 60

Gln Ala Lys Ala Thr Ile Thr Ala Asp Thr Ser Ser Asn Thr Ala Tyr
65                 70                 75                 80

Leu Gln Leu Ser Ser Leu Thr Ser Glu Asp Thr Ala Val Tyr Tyr Cys
                85                 90                 95

Thr Thr Gly Asp Tyr Asp Gly Phe Ala Tyr Trp Gly Gln Gly Thr Leu
                100                105                110

Val Thr Val Ser Thr
            115
```

<210> SEQ ID NO 106
<211> LENGTH: 5
<212> TYPE: PRT
<213> ORGANISM: Artificial sequence
<220> FEATURE:
<223> OTHER INFORMATION: synthesized

<400> SEQUENCE: 106

```
Asp Glu Tyr Ile His
1               5
```

<210> SEQ ID NO 107
<211> LENGTH: 17
<212> TYPE: PRT
<213> ORGANISM: Artificial sequence
<220> FEATURE:
<223> OTHER INFORMATION: synthesized

<400> SEQUENCE: 107

```
Trp Ile Asp Pro Ala Asn Gly His Thr Glu Tyr Ala Ser Arg Phe Gln
1               5                  10                 15

Ala
```

<210> SEQ ID NO 108
<211> LENGTH: 8
<212> TYPE: PRT
<213> ORGANISM: Artificial sequence
<220> FEATURE:
<223> OTHER INFORMATION: synthesized

<400> SEQUENCE: 108

```
Gly Asp Tyr Asp Gly Phe Ala Tyr
1               5
```

<210> SEQ ID NO 109
<211> LENGTH: 106
<212> TYPE: PRT
<213> ORGANISM: Artificial sequence
<220> FEATURE:
<223> OTHER INFORMATION: synthesized

<400> SEQUENCE: 109

```
Gln Ile Val Leu Thr Gln Ser Pro Ala Ile Met Ser Ala Ser Pro Gly
1               5                  10                 15

Glu Lys Val Thr Ile Ser Cys Ser Ala Arg Ser Ser Val Ser Tyr Met
            20                 25                 30
```

Tyr Trp Tyr Gln Gln Lys Pro Gly Ser Ser Pro Lys Pro Trp Ile Tyr
            35                  40                  45

Arg Thr Ser Asn Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln His Tyr His Thr Tyr Pro Tyr Thr
                85                  90                  95

Phe Gly Gly Gly Thr Lys Leu Glu Ile Lys
            100                 105

<210> SEQ ID NO 110
<211> LENGTH: 10
<212> TYPE: PRT
<213> ORGANISM: Artificial sequence
<220> FEATURE:
<223> OTHER INFORMATION: synthesized

<400> SEQUENCE: 110

Ser Ala Arg Ser Ser Val Ser Tyr Met Tyr
1               5                   10

<210> SEQ ID NO 111
<211> LENGTH: 7
<212> TYPE: PRT
<213> ORGANISM: Artificial sequence
<220> FEATURE:
<223> OTHER INFORMATION: synthesized

<400> SEQUENCE: 111

Arg Thr Ser Asn Leu Ala Ser
1               5

<210> SEQ ID NO 112
<211> LENGTH: 9
<212> TYPE: PRT
<213> ORGANISM: Artificial sequence
<220> FEATURE:
<223> OTHER INFORMATION: synthesized

<400> SEQUENCE: 112

Gln His Tyr His Thr Tyr Pro Tyr Thr
1               5

<210> SEQ ID NO 113
<211> LENGTH: 119
<212> TYPE: PRT
<213> ORGANISM: Artificial sequence
<220> FEATURE:
<223> OTHER INFORMATION: synthesized

<400> SEQUENCE: 113

Gln Val Gln Leu Gln Gln Pro Gly Ala Glu Val Val Lys Pro Gly Ala
1               5                   10                  15

Ser Val Lys Leu Ser Cys Lys Ala Ser Gly Tyr Thr Val Thr Ser Tyr
            20                  25                  30

Trp Met His Trp Val Lys Gln Arg Pro Gly Gln Gly Leu Glu Trp Ile
            35                  40                  45

Gly Met Ile His Pro Asn Gly Ile Ser Thr Asn Tyr Asn Glu Lys Phe
        50                  55                  60

Lys Ser Lys Ala Thr Leu Thr Gly Asp Lys Ser Ser Ser Thr Ala Tyr
65                  70                  75                  80

Met Gln Leu Ser Ser Leu Thr Ser Glu Asp Ser Ala Val Tyr Phe Cys
            85                  90                  95

Ala Arg Gly Gly Asp Ser Asp Tyr Tyr Phe Asp Tyr Trp Gly Gln Gly
            100                 105                 110

Thr Thr Leu Thr Val Ser Ser
        115

<210> SEQ ID NO 114
<211> LENGTH: 5
<212> TYPE: PRT
<213> ORGANISM: Artificial sequence
<220> FEATURE:
<223> OTHER INFORMATION: synthesized

<400> SEQUENCE: 114

Ser Tyr Trp Met His
1               5

<210> SEQ ID NO 115
<211> LENGTH: 17
<212> TYPE: PRT
<213> ORGANISM: Artificial sequence
<220> FEATURE:
<223> OTHER INFORMATION: synthesized

<400> SEQUENCE: 115

Met Ile His Pro Asn Gly Ile Ser Thr Asn Tyr Asn Glu Lys Phe Lys
1               5                   10                  15

Ser

<210> SEQ ID NO 116
<211> LENGTH: 10
<212> TYPE: PRT
<213> ORGANISM: Artificial sequence
<220> FEATURE:
<223> OTHER INFORMATION: synthesized

<400> SEQUENCE: 116

Gly Gly Asp Ser Asp Tyr Tyr Phe Asp Tyr
1               5                   10

<210> SEQ ID NO 117
<211> LENGTH: 106
<212> TYPE: PRT
<213> ORGANISM: Artificial sequence
<220> FEATURE:
<223> OTHER INFORMATION: synthesized

<400> SEQUENCE: 117

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Gly Ser Ser Pro Arg Leu Trp Ile Tyr
            35                  40                  45

Asp Thr Ser Asn Leu Val Ser Gly Val Pro Ala Arg Phe Ser Gly Ser
        50                  55                  60

Arg Ser Gly Thr Ser Tyr Ser Leu Thr Leu Ser Ser Met Glu Ala Glu
65                  70                  75                  80

Asp Ala Ala Thr Tyr Tyr Cys Gln Gln Tyr Ser Gly Tyr Pro Tyr Thr
            85                  90                  95

Phe Gly Gly Gly Thr Lys Leu Glu Ile Lys
            100                 105

<210> SEQ ID NO 118
<211> LENGTH: 10
<212> TYPE: PRT
<213> ORGANISM: Artificial sequence
<220> FEATURE:
<223> OTHER INFORMATION: synthesized

<400> SEQUENCE: 118

Ser Ala Ser Ser Ser Val Ser Tyr Met Tyr
1               5                   10

<210> SEQ ID NO 119
<211> LENGTH: 7
<212> TYPE: PRT
<213> ORGANISM: Artificial sequence
<220> FEATURE:
<223> OTHER INFORMATION: synthesized

<400> SEQUENCE: 119

Asp Thr Ser Asn Leu Val Ser
1               5

<210> SEQ ID NO 120
<211> LENGTH: 9
<212> TYPE: PRT
<213> ORGANISM: Artificial sequence
<220> FEATURE:
<223> OTHER INFORMATION: synthesized

<400> SEQUENCE: 120

Gln Gln Tyr Ser Gly Tyr Pro Tyr Thr
1               5

<210> SEQ ID NO 121
<211> LENGTH: 122
<212> TYPE: PRT
<213> ORGANISM: Artificial sequence
<220> FEATURE:
<223> OTHER INFORMATION: synthesized

<400> SEQUENCE: 121

Glu Phe Gln Leu Gln Gln Ser Gly Pro Glu Val Val Lys Pro Gly Ala
1               5                   10                  15

Ser Val Lys Ile Ser Cys Lys Ala Ser Gly Tyr Ser Phe Thr Asp Tyr
            20                  25                  30

Asn Met Asn Trp Met Lys Gln Ser Lys Gly Lys Ser Leu Glu Trp Ile
        35                  40                  45

Gly Val Ile Asn Pro Asn Tyr Gly Thr Thr Tyr Asn Gln Asn Phe
    50                  55                  60

Lys Gly Lys Ala Thr Leu Thr Val Asp Gln Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Asp Met Tyr Tyr Val Tyr Ala Tyr Tyr Thr Met Asp Tyr Trp
            100                 105                 110

Gly Gln Gly Thr Ser Val Thr Val Ser Ser
            115                 120

<210> SEQ ID NO 122
<211> LENGTH: 5

```
<212> TYPE: PRT
<213> ORGANISM: Artificial sequence
<220> FEATURE:
<223> OTHER INFORMATION: synthesized

<400> SEQUENCE: 122

Asp Tyr Asn Met Asn
1               5

<210> SEQ ID NO 123
<211> LENGTH: 17
<212> TYPE: PRT
<213> ORGANISM: Artificial sequence
<220> FEATURE:
<223> OTHER INFORMATION: synthesized

<400> SEQUENCE: 123

Val Ile Asn Pro Asn Tyr Gly Thr Thr Thr Tyr Asn Gln Asn Phe Lys
1               5                   10                  15

Gly

<210> SEQ ID NO 124
<211> LENGTH: 13
<212> TYPE: PRT
<213> ORGANISM: Artificial sequence
<220> FEATURE:
<223> OTHER INFORMATION: synthesized

<400> SEQUENCE: 124

Asp Met Tyr Tyr Val Tyr Ala Tyr Tyr Thr Met Asp Tyr
1               5                   10

<210> SEQ ID NO 125
<211> LENGTH: 112
<212> TYPE: PRT
<213> ORGANISM: Artificial sequence
<220> FEATURE:
<223> OTHER INFORMATION: synthesized

<400> SEQUENCE: 125

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly His Thr Tyr Leu His Trp Tyr Leu Gln Arg Pro Gly Gln Ser
            35                  40                  45

Pro Thr Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Gly
                85                  90                  95

Thr His Val Pro Trp Thr Phe Gly Gly Gly Thr Lys Leu Glu Ile Lys
            100                 105                 110

<210> SEQ ID NO 126
<211> LENGTH: 16
<212> TYPE: PRT
<213> ORGANISM: Artificial sequence
<220> FEATURE:
<223> OTHER INFORMATION: synthesized

<400> SEQUENCE: 126
```

```
Arg Ser Ser Gln Ser Leu Val His Ser Asn Gly His Thr Tyr Leu His
1               5                   10                  15
```

<210> SEQ ID NO 127
<211> LENGTH: 7
<212> TYPE: PRT
<213> ORGANISM: Artificial sequence
<220> FEATURE:
<223> OTHER INFORMATION: synthesized

<400> SEQUENCE: 127

```
Lys Val Ser Asn Arg Phe Ser
1               5
```

<210> SEQ ID NO 128
<211> LENGTH: 9
<212> TYPE: PRT
<213> ORGANISM: Artificial sequence
<220> FEATURE:
<223> OTHER INFORMATION: synthesized

<400> SEQUENCE: 128

```
Ser Gln Gly Thr His Val Pro Trp Thr
1               5
```

<210> SEQ ID NO 129
<211> LENGTH: 123
<212> TYPE: PRT
<213> ORGANISM: Artificial sequence
<220> FEATURE:
<223> OTHER INFORMATION: synthesized

<400> SEQUENCE: 129

```
Glu Val Gln Leu Gln Gln Ser Gly Pro Val Leu Val Lys Pro Gly Ala
1               5                   10                  15

Ser Val Lys Met Ser Cys Lys Ala Ser Gly Tyr Thr Phe Thr Asp Tyr
                20                  25                  30

Tyr Met Asn Trp Val Lys Gln Ser His Gly Lys Ser Leu Glu Trp Ile
            35                  40                  45

Gly Leu Ile Asn Pro Tyr Ser Gly Gly Ser Thr Phe Asn Gln Lys Phe
        50                  55                  60

Lys Ala Lys Ala Thr Leu Thr Val Asp Lys Ser Ser Ser Ala Tyr
65                  70                  75                  80

Met Asp Leu Asn Ser Leu Thr Ser Glu Asp Ser Ala Val Tyr Tyr Cys
                85                  90                  95

Ala Arg Val Gly Asp Gly Tyr Tyr Gly Val Thr His Gly Met Asp Tyr
            100                 105                 110

Trp Gly Gln Gly Thr Ser Val Thr Val Ser Ser
        115                 120
```

<210> SEQ ID NO 130
<211> LENGTH: 5
<212> TYPE: PRT
<213> ORGANISM: Artificial sequence
<220> FEATURE:
<223> OTHER INFORMATION: synthesized

<400> SEQUENCE: 130

```
Asp Tyr Tyr Met Asn
1               5
```

<210> SEQ ID NO 131
<211> LENGTH: 17

```
<212> TYPE: PRT
<213> ORGANISM: Artificial sequence
<220> FEATURE:
<223> OTHER INFORMATION: synthesized

<400> SEQUENCE: 131

Leu Ile Asn Pro Tyr Ser Gly Gly Ser Thr Phe Asn Gln Lys Phe Lys
1               5                   10                  15

Ala

<210> SEQ ID NO 132
<211> LENGTH: 14
<212> TYPE: PRT
<213> ORGANISM: Artificial sequence
<220> FEATURE:
<223> OTHER INFORMATION: synthesized

<400> SEQUENCE: 132

Val Gly Asp Gly Tyr Tyr Gly Val Thr His Gly Met Asp Tyr
1               5                   10

<210> SEQ ID NO 133
<211> LENGTH: 107
<212> TYPE: PRT
<213> ORGANISM: Artificial sequence
<220> FEATURE:
<223> OTHER INFORMATION: synthesized

<400> SEQUENCE: 133

Asp Ile Val Met Thr Pro Ser Gln Lys Phe Met Ser Thr Thr Val Gly
1               5                   10                  15

Asp Arg Val Ser Ile Thr Cys Lys Ala Ser Gln Asn Val Gly Thr Ala
                20                  25                  30

Val Ala Trp Tyr Gln Gln Lys Pro Gly Gln Ser Pro Thr Ile Leu Ile
            35                  40                  45

Tyr Ser Ala Ser Asn Arg Tyr Thr Gly Val Pro Asp Arg Phe Thr Gly
        50                  55                  60

Ser Gly Ser Gly Thr Asp Phe Thr Leu Thr Ile Ser Asn Met Lys Ser
65                  70                  75                  80

Glu Asp Leu Ala Asp Tyr Phe Cys Gln Gln Tyr Tyr Ile Tyr Pro Phe
                85                  90                  95

Thr Phe Ala Ala Gly Thr Lys Leu Glu Leu Lys
            100                 105

<210> SEQ ID NO 134
<211> LENGTH: 11
<212> TYPE: PRT
<213> ORGANISM: Artificial sequence
<220> FEATURE:
<223> OTHER INFORMATION: synthesized

<400> SEQUENCE: 134

Lys Ala Ser Gln Asn Val Gly Thr Ala Val Ala
1               5                   10

<210> SEQ ID NO 135
<211> LENGTH: 7
<212> TYPE: PRT
<213> ORGANISM: Artificial sequence
<220> FEATURE:
<223> OTHER INFORMATION: synthesized

<400> SEQUENCE: 135
```

```
Ser Ala Ser Asn Arg Tyr Thr
1               5
```

<210> SEQ ID NO 136
<211> LENGTH: 9
<212> TYPE: PRT
<213> ORGANISM: Artificial sequence
<220> FEATURE:
<223> OTHER INFORMATION: synthesized

<400> SEQUENCE: 136

```
Gln Gln Tyr Tyr Ile Tyr Pro Phe Thr
1               5
```

<210> SEQ ID NO 137
<211> LENGTH: 122
<212> TYPE: PRT
<213> ORGANISM: Artificial sequence
<220> FEATURE:
<223> OTHER INFORMATION: synthesized

<400> SEQUENCE: 137

```
Glu Phe Gln Leu Gln Gln Ser Gly Pro Glu Val Val Lys Pro Gly Ala
1               5                   10                  15

Ser Val Lys Ile Ser Cys Lys Ala Ser Gly Tyr Ser Phe Thr Asp Tyr
                20                  25                  30

Asn Met Asn Trp Met Lys Gln Ser Lys Gly Lys Ser Leu Glu Trp Ile
            35                  40                  45

Gly Val Ile Ser Pro Asp Tyr Gly Thr Thr Thr Tyr Asn Gln Asn Phe
        50                  55                  60

Lys Asp Lys Ala Thr Leu Thr Val Asp Gln Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Lys Asp Met Tyr Tyr Val Tyr Ala Tyr Tyr Thr Met Asp Tyr Trp
                100                 105                 110

Gly His Gly Thr Ser Val Thr Val Ser Ser
            115                 120
```

<210> SEQ ID NO 138
<211> LENGTH: 5
<212> TYPE: PRT
<213> ORGANISM: Artificial sequence
<220> FEATURE:
<223> OTHER INFORMATION: synthesized

<400> SEQUENCE: 138

```
Asp Tyr Asn Met Asn
1               5
```

<210> SEQ ID NO 139
<211> LENGTH: 17
<212> TYPE: PRT
<213> ORGANISM: Artificial sequence
<220> FEATURE:
<223> OTHER INFORMATION: synthesized

<400> SEQUENCE: 139

```
Val Ile Ser Pro Asp Tyr Gly Thr Thr Thr Tyr Asn Gln Asn Phe Lys
1               5                   10                  15

Asp
```

```
<210> SEQ ID NO 140
<211> LENGTH: 13
<212> TYPE: PRT
<213> ORGANISM: Artificial sequence
<220> FEATURE:
<223> OTHER INFORMATION: synthesized

<400> SEQUENCE: 140

Asp Met Tyr Tyr Val Tyr Ala Tyr Tyr Thr Met Asp Tyr
1               5                  10

<210> SEQ ID NO 141
<211> LENGTH: 112
<212> TYPE: PRT
<213> ORGANISM: Artificial sequence
<220> FEATURE:
<223> OTHER INFORMATION: synthesized

<400> SEQUENCE: 141

Asp Val Val Met Thr Gln Thr Pro Leu Ser Leu Pro Val Ser Leu Gly
1               5                  10                  15

Asp Gln Ala Ser Ile Ser Cys Arg Ser Ser Gln Ser Leu Val His Ser
            20                  25                  30

Asn Gly His Thr Tyr Leu His Trp Tyr Leu Gln Arg Pro Gly Gln Ser
        35                  40                  45

Pro Thr Leu Leu Ile Tyr Lys Val Ser Asn Arg Phe Ser Gly Val Pro
    50                  55                  60

Asp Arg Val Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Gly
                85                  90                  95

Thr His Val Pro Arg Thr Phe Gly Gly Gly Thr Lys Leu Glu Ile Lys
            100                 105                 110

<210> SEQ ID NO 142
<211> LENGTH: 16
<212> TYPE: PRT
<213> ORGANISM: Artificial sequence
<220> FEATURE:
<223> OTHER INFORMATION: synthesized

<400> SEQUENCE: 142

Arg Ser Ser Gln Ser Leu Val His Ser Asn Gly His Thr Tyr Leu His
1               5                  10                  15

<210> SEQ ID NO 143
<211> LENGTH: 7
<212> TYPE: PRT
<213> ORGANISM: Artificial sequence
<220> FEATURE:
<223> OTHER INFORMATION: synthesized

<400> SEQUENCE: 143

Lys Val Ser Asn Arg Phe Ser
1               5

<210> SEQ ID NO 144
<211> LENGTH: 9
<212> TYPE: PRT
<213> ORGANISM: Artificial sequence
<220> FEATURE:
<223> OTHER INFORMATION: synthesized

<400> SEQUENCE: 144
```

Ser Gln Gly Thr His Val Pro Arg Thr
1               5

<210> SEQ ID NO 145
<211> LENGTH: 123
<212> TYPE: PRT
<213> ORGANISM: Artificial sequence
<220> FEATURE:
<223> OTHER INFORMATION: synthesized

<400> SEQUENCE: 145

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Asp Tyr
            20                  25                  30

Gly Ile Ser Trp Val Lys Gln Arg Thr Gly Gln Gly Leu Glu Trp Ile
        35                  40                  45

Gly Glu Ile Tyr Leu Arg Asn Asp Asn Ser Tyr Tyr Asn Glu Lys Phe
    50                  55                  60

Lys Gly Lys Ala Thr Leu Thr Ala Asp Lys Ser Ser Asn Thr Ala Tyr
65                  70                  75                  80

Met Glu Leu Arg Ser Leu Thr Ser Glu Asp Ser Ala Val Tyr Phe Cys
                85                  90                  95

Ala Arg Trp Gly Asp His Gly Asn Asn Tyr Glu Asp Ala Met Asp Tyr
            100                 105                 110

Trp Gly Gln Gly Thr Ser Val Thr Val Ser Ser
        115                 120

<210> SEQ ID NO 146
<211> LENGTH: 5
<212> TYPE: PRT
<213> ORGANISM: Artificial sequence
<220> FEATURE:
<223> OTHER INFORMATION: synthesized

<400> SEQUENCE: 146

Asp Tyr Gly Ile Ser
1               5

<210> SEQ ID NO 147
<211> LENGTH: 17
<212> TYPE: PRT
<213> ORGANISM: Artificial sequence
<220> FEATURE:
<223> OTHER INFORMATION: synthesized

<400> SEQUENCE: 147

Glu Ile Tyr Leu Arg Asn Asp Asn Ser Tyr Tyr Asn Glu Lys Phe Lys
1               5                   10                  15

Gly

<210> SEQ ID NO 148
<211> LENGTH: 14
<212> TYPE: PRT
<213> ORGANISM: Artificial sequence
<220> FEATURE:
<223> OTHER INFORMATION: synthesized

<400> SEQUENCE: 148

Trp Gly Asp His Gly Asn Asn Tyr Glu Asp Ala Met Asp Tyr
1               5                   10

-continued

```
<210> SEQ ID NO 149
<211> LENGTH: 111
<212> TYPE: PRT
<213> ORGANISM: Artificial sequence
<220> FEATURE:
<223> OTHER INFORMATION: synthesized

<400> SEQUENCE: 149
```

Asp Ile Val Leu Thr Gln Ser Pro Ala Ser Leu Ala Met Ser Leu Gly
1               5                   10                  15

Lys Arg Ala Thr Ile Ser Cys Arg Ala Ser Glu Ser Val Ser Ile Ile
            20                  25                  30

Gly Ser Asn Leu Ile His Trp Tyr Gln Gln Lys Pro Gly Gln Pro Pro
        35                  40                  45

Lys Leu Leu Ile Tyr His Ala Ser Asn Leu Glu Thr Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Ile Tyr Tyr Cys Leu Gln Ser Arg
                85                  90                  95

Lys Val Pro Tyr Thr Phe Gly Gly Gly Thr Lys Leu Glu Ile Lys
            100                 105                 110

```
<210> SEQ ID NO 150
<211> LENGTH: 15
<212> TYPE: PRT
<213> ORGANISM: Artificial sequence
<220> FEATURE:
<223> OTHER INFORMATION: synthesized

<400> SEQUENCE: 150
```

Arg Ala Ser Glu Ser Val Ser Ile Ile Gly Ser Asn Leu Ile His
1               5                   10                  15

```
<210> SEQ ID NO 151
<211> LENGTH: 7
<212> TYPE: PRT
<213> ORGANISM: Artificial sequence
<220> FEATURE:
<223> OTHER INFORMATION: synthesized

<400> SEQUENCE: 151
```

His Ala Ser Asn Leu Glu Thr
1               5

```
<210> SEQ ID NO 152
<211> LENGTH: 9
<212> TYPE: PRT
<213> ORGANISM: Artificial sequence
<220> FEATURE:
<223> OTHER INFORMATION: synthesized

<400> SEQUENCE: 152
```

Leu Gln Ser Arg Lys Val Pro Tyr Thr
1               5

```
<210> SEQ ID NO 153
<211> LENGTH: 117
<212> TYPE: PRT
<213> ORGANISM: Artificial sequence
<220> FEATURE:
<223> OTHER INFORMATION: synthesized

<400> SEQUENCE: 153
```

```
Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Glu
            20                  25                  30

Tyr Ile His Trp Val Lys Gln Arg Pro Glu Gln Gly Leu Glu Trp Ile
        35                  40                  45

Gly Trp Ile Asp Pro Ala Asn Gly His Thr Glu Tyr Ala Ser Arg Phe
    50                  55                  60

Gln Ala Lys Ala Thr Ile Thr Ala Asp Thr Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Thr Gly Asp Tyr Asp Gly Phe Val Tyr Trp Gly Gln Gly Thr Leu
            100                 105                 110

Val Thr Val Ser Thr
            115
```

<210> SEQ ID NO 154
<211> LENGTH: 5
<212> TYPE: PRT
<213> ORGANISM: Artificial sequence
<220> FEATURE:
<223> OTHER INFORMATION: synthesized

<400> SEQUENCE: 154

```
Asp Glu Tyr Ile His
1               5
```

<210> SEQ ID NO 155
<211> LENGTH: 17
<212> TYPE: PRT
<213> ORGANISM: Artificial sequence
<220> FEATURE:
<223> OTHER INFORMATION: synthesized

<400> SEQUENCE: 155

```
Trp Ile Asp Pro Ala Asn Gly His Thr Glu Tyr Ala Ser Arg Phe Gln
1               5                   10                  15

Ala
```

<210> SEQ ID NO 156
<211> LENGTH: 8
<212> TYPE: PRT
<213> ORGANISM: Artificial sequence
<220> FEATURE:
<223> OTHER INFORMATION: synthesized

<400> SEQUENCE: 156

```
Gly Asp Tyr Asp Gly Phe Val Tyr
1               5
```

<210> SEQ ID NO 157
<211> LENGTH: 106
<212> TYPE: PRT
<213> ORGANISM: Artificial sequence
<220> FEATURE:
<223> OTHER INFORMATION: synthesized

<400> SEQUENCE: 157

```
Gln Ile Val Leu Thr Gln Ser Pro Ala Ile Met Ser Ala Ser Pro Gly
1               5                   10                  15

Glu Lys Val Thr Ile Phe Cys Ser Ala Arg Ser Ser Val Ser Tyr Met
```

```
                 20                  25                  30
Tyr Trp Tyr Gln Gln Lys Pro Gly Ser Ser Lys Pro Trp Ile Tyr
             35                  40                  45

Arg Thr Ser Asn Leu Ala Ser Gly Val Pro Ala Arg Phe Ser Gly Ser
         50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln His Tyr His Thr Tyr Pro Tyr Thr
                 85                  90                  95

Phe Gly Gly Gly Thr Lys Leu Glu Ile Lys
                100                 105

<210> SEQ ID NO 158
<211> LENGTH: 10
<212> TYPE: PRT
<213> ORGANISM: Artificial sequence
<220> FEATURE:
<223> OTHER INFORMATION: synthesized

<400> SEQUENCE: 158

Ser Ala Arg Ser Ser Val Ser Tyr Met Tyr
1               5                  10

<210> SEQ ID NO 159
<211> LENGTH: 7
<212> TYPE: PRT
<213> ORGANISM: Artificial sequence
<220> FEATURE:
<223> OTHER INFORMATION: synthesized

<400> SEQUENCE: 159

Arg Thr Ser Asn Leu Ala Ser
1               5

<210> SEQ ID NO 160
<211> LENGTH: 9
<212> TYPE: PRT
<213> ORGANISM: Artificial sequence
<220> FEATURE:
<223> OTHER INFORMATION: synthesized

<400> SEQUENCE: 160

Gln His Tyr His Thr Tyr Pro Tyr Thr
1               5

<210> SEQ ID NO 161
<211> LENGTH: 117
<212> TYPE: PRT
<213> ORGANISM: Artificial sequence
<220> FEATURE:
<223> OTHER INFORMATION: synthesized

<400> SEQUENCE: 161

Gln Val Gln Leu Lys Glu Ser Gly Pro Gly Leu Val Ala Pro Ser Gln
1               5                  10                  15

Ser Leu Ser Ile Thr Cys Thr Val Ser Gly Phe Ser Leu Ser Ser Tyr
             20                  25                  30

Gly Val Asp Trp Val Arg Gln Pro Pro Gly Lys Asp Leu Glu Trp Leu
             35                  40                  45

Gly Val Ile Trp Gly Gly Gly Thr Thr Ile Tyr Asn Ser Ala Leu Met
         50                  55                  60

Ser Arg Leu Asn Ile Thr Lys Asp Asn Ser Lys Asn Gln Val Phe Leu
```

```
                65                  70                  75                  80
Lys Met Asn Ser Leu Gln Ser Asp Asp Thr Ala Met Tyr Tyr Cys Ala
                        85                  90                  95

Lys Arg Gly Tyr Tyr Gly Tyr Phe Asp Tyr Trp Gly Gln Gly Thr Thr
                100                 105                 110

Leu Thr Val Ser Ser
        115

<210> SEQ ID NO 162
<211> LENGTH: 5
<212> TYPE: PRT
<213> ORGANISM: Artificial sequence
<220> FEATURE:
<223> OTHER INFORMATION: synthesized

<400> SEQUENCE: 162

Ser Tyr Gly Val Asp
1               5

<210> SEQ ID NO 163
<211> LENGTH: 16
<212> TYPE: PRT
<213> ORGANISM: Artificial sequence
<220> FEATURE:
<223> OTHER INFORMATION: synthesized

<400> SEQUENCE: 163

Val Ile Trp Gly Gly Gly Thr Thr Ile Tyr Asn Ser Ala Leu Met Ser
1               5                   10                  15

<210> SEQ ID NO 164
<211> LENGTH: 9
<212> TYPE: PRT
<213> ORGANISM: Artificial sequence
<220> FEATURE:
<223> OTHER INFORMATION: synthesized

<400> SEQUENCE: 164

Arg Gly Tyr Tyr Gly Tyr Phe Asp Tyr
1               5

<210> SEQ ID NO 165
<211> LENGTH: 106
<212> TYPE: PRT
<213> ORGANISM: Artificial sequence
<220> FEATURE:
<223> OTHER INFORMATION: synthesized

<400> SEQUENCE: 165

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

Tyr Trp Tyr His Gln Lys Pro Gly Ser Ser Pro Arg Leu Leu Ile Tyr
            35                  40                  45

Asp Thr Ser Asn Leu Ala Phe Gly Val Pro Val Arg Phe Ser Gly Arg
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Leu Thr
                85                  90                  95

Phe Gly Ala Gly Thr Lys Leu Glu Leu Lys
                100                 105
```

<210> SEQ ID NO 166
<211> LENGTH: 10
<212> TYPE: PRT
<213> ORGANISM: Artificial sequence
<220> FEATURE:
<223> OTHER INFORMATION: synthesized

<400> SEQUENCE: 166

Ser Ala Ser Ser Ser Val Ser Tyr Met Tyr
1               5                   10

<210> SEQ ID NO 167
<211> LENGTH: 7
<212> TYPE: PRT
<213> ORGANISM: Artificial sequence
<220> FEATURE:
<223> OTHER INFORMATION: synthesized

<400> SEQUENCE: 167

Asp Thr Ser Asn Leu Ala Phe
1               5

<210> SEQ ID NO 168
<211> LENGTH: 9
<212> TYPE: PRT
<213> ORGANISM: Artificial sequence
<220> FEATURE:
<223> OTHER INFORMATION: synthesized

<400> SEQUENCE: 168

Gln Gln Trp Ser Ser Tyr Pro Leu Thr
1               5

<210> SEQ ID NO 169
<211> LENGTH: 118
<212> TYPE: PRT
<213> ORGANISM: Artificial sequence
<220> FEATURE:
<223> OTHER INFORMATION: synthesized

<400> SEQUENCE: 169

Glu Val Lys Leu Val Glu Ser Gly Gly Gly Leu Val Gln Pro Gly Ser
1               5                   10                  15

Ser Met Lys Leu Ser Cys Thr Ala Ser Gly Phe Thr Phe Ser Asp Tyr
                20                  25                  30

Tyr Met Ala Trp Val Arg Gln Val Pro Asp Lys Gly Leu Glu Trp Val
            35                  40                  45

Ala Asn Ile Asn Tyr Asp Gly Asn Asn Pro Tyr Tyr Val Asp Ser Leu
    50                  55                  60

Lys Ser Arg Phe Ile Ile Ser Arg Asp Asn Ala Lys Asn Ile Leu Tyr
65                  70                  75                  80

Leu Gln Met Ser Ser Leu Lys Ser Glu Asp Thr Ala Thr Tyr Tyr Cys
                85                  90                  95

Ala Arg Asp Ile Ser Pro Gly Tyr Phe Asp His Trp Gly Gln Gly Thr
            100                 105                 110

Thr Leu Thr Val Ser Ser
        115

<210> SEQ ID NO 170
<211> LENGTH: 5
<212> TYPE: PRT

```
<213> ORGANISM: Artificial sequence
<220> FEATURE:
<223> OTHER INFORMATION: synthesized

<400> SEQUENCE: 170

Asp Tyr Tyr Met Ala
1               5

<210> SEQ ID NO 171
<211> LENGTH: 17
<212> TYPE: PRT
<213> ORGANISM: Artificial sequence
<220> FEATURE:
<223> OTHER INFORMATION: synthesized

<400> SEQUENCE: 171

Asn Ile Asn Tyr Asp Gly Asn Asn Pro Tyr Tyr Val Asp Ser Leu Lys
1               5                   10                  15

Ser

<210> SEQ ID NO 172
<211> LENGTH: 9
<212> TYPE: PRT
<213> ORGANISM: Artificial sequence
<220> FEATURE:
<223> OTHER INFORMATION: synthesized

<400> SEQUENCE: 172

Asp Ile Ser Pro Gly Tyr Phe Asp His
1               5

<210> SEQ ID NO 173
<211> LENGTH: 111
<212> TYPE: PRT
<213> ORGANISM: Artificial sequence
<220> FEATURE:
<223> OTHER INFORMATION: synthesized

<400> SEQUENCE: 173

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Ser Ile His
                20                  25                  30

Gly Thr His Leu Met His Trp Tyr Gln Gln Lys Pro Gly Gln Pro Pro
            35                  40                  45

Lys Leu Leu Ile Tyr Ala Ala Ser Asn Leu Glu Ser Gly Val Pro Ala
        50                  55                  60

Arg Phe Ser Gly Ser Gly Ser Glu Thr Asp Phe Thr Leu Asn Ile His
65                  70                  75                  80

Pro Val Glu Glu Glu Asp Ala Ala Ile Tyr Phe Cys Gln Gln Ser Ile
                85                  90                  95

Glu Asp Pro His Thr Phe Gly Gly Gly Thr Lys Leu Glu Ile Lys
                100                 105                 110

<210> SEQ ID NO 174
<211> LENGTH: 15
<212> TYPE: PRT
<213> ORGANISM: Artificial sequence
<220> FEATURE:
<223> OTHER INFORMATION: synthesized

<400> SEQUENCE: 174

Arg Ala Ser Glu Ser Val Ser Ile His Gly Thr His Leu Met His
1               5                   10                  15
```

<210> SEQ ID NO 175
<211> LENGTH: 7
<212> TYPE: PRT
<213> ORGANISM: Artificial sequence
<220> FEATURE:
<223> OTHER INFORMATION: synthesized

<400> SEQUENCE: 175

Ala Ala Ser Asn Leu Glu Ser
1               5

<210> SEQ ID NO 176
<211> LENGTH: 9
<212> TYPE: PRT
<213> ORGANISM: Artificial sequence
<220> FEATURE:
<223> OTHER INFORMATION: synthesized

<400> SEQUENCE: 176

Gln Gln Ser Ile Glu Asp Pro His Thr
1               5

<210> SEQ ID NO 177
<211> LENGTH: 118
<212> TYPE: PRT
<213> ORGANISM: Artificial sequence
<220> FEATURE:
<223> OTHER INFORMATION: synthesized

<400> SEQUENCE: 177

Glu Val Lys Leu Val Glu Ser Gly Gly Gly Leu Val Gln Pro Gly Ser
1               5                   10                  15

Ser Met Lys Leu Ser Cys Thr Ala Ser Gly Phe Thr Phe Ser Asp Tyr
            20                  25                  30

Tyr Met Ala Trp Val Arg Gln Val Pro Asp Lys Gly Leu Glu Trp Val
        35                  40                  45

Ala Asn Ile Asn Tyr Asp Gly Asn Asn Pro Tyr Tyr Val Asp Ser Leu
    50                  55                  60

Lys Thr Arg Phe Ile Ile Ser Arg Asp Asn Ala Lys Asn Ile Leu Tyr
65                  70                  75                  80

Leu Gln Met Ser Ser Leu Lys Ser Glu Asp Thr Ala Thr Tyr Tyr Cys
                85                  90                  95

Ala Arg Asp Ile Ser Pro Gly Tyr Phe Asp His Trp Gly Gln Gly Thr
            100                 105                 110

Thr Leu Thr Val Ser Ser
        115

<210> SEQ ID NO 178
<211> LENGTH: 5
<212> TYPE: PRT
<213> ORGANISM: Artificial sequence
<220> FEATURE:
<223> OTHER INFORMATION: synthesized

<400> SEQUENCE: 178

Asp Tyr Tyr Met Ala
1               5

<210> SEQ ID NO 179
<211> LENGTH: 17
<212> TYPE: PRT

```
<213> ORGANISM: Artificial sequence
<220> FEATURE:
<223> OTHER INFORMATION: synthesized

<400> SEQUENCE: 179

Asn Ile Asn Tyr Asp Gly Asn Asn Pro Tyr Tyr Val Asp Ser Leu Lys
1               5                   10                  15

Thr

<210> SEQ ID NO 180
<211> LENGTH: 9
<212> TYPE: PRT
<213> ORGANISM: Artificial sequence
<220> FEATURE:
<223> OTHER INFORMATION: synthesized

<400> SEQUENCE: 180

Asp Ile Ser Pro Gly Tyr Phe Asp His
1               5

<210> SEQ ID NO 181
<211> LENGTH: 111
<212> TYPE: PRT
<213> ORGANISM: Artificial sequence
<220> FEATURE:
<223> OTHER INFORMATION: synthesized

<400> SEQUENCE: 181

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Ser Ile His
            20                  25                  30

Gly Thr His Leu Met His Trp Tyr Gln Gln Lys Pro Gly Gln Pro Pro
        35                  40                  45

Lys Leu Leu Ile Tyr Ala Ala Ser Asn Leu Glu Ser Gly Val Pro Ala
    50                  55                  60

Arg Phe Ser Gly Ser Gly Ser Glu Thr Asp Phe Thr Leu Asn Ile His
65                  70                  75                  80

Pro Val Glu Glu Glu Asp Ala Ala Ile Tyr Phe Cys Gln Gln Ser Ile
                85                  90                  95

Glu Asp Pro His Thr Phe Gly Gly Gly Thr Lys Leu Glu Ile Lys
            100                 105                 110

<210> SEQ ID NO 182
<211> LENGTH: 15
<212> TYPE: PRT
<213> ORGANISM: Artificial sequence
<220> FEATURE:
<223> OTHER INFORMATION: synthesized

<400> SEQUENCE: 182

Arg Ala Ser Glu Ser Val Ser Ile His Gly Thr His Leu Met His
1               5                   10                  15

<210> SEQ ID NO 183
<211> LENGTH: 7
<212> TYPE: PRT
<213> ORGANISM: Artificial sequence
<220> FEATURE:
<223> OTHER INFORMATION: synthesized

<400> SEQUENCE: 183

Ala Ala Ser Asn Leu Glu Ser
```

```
1               5
```

<210> SEQ ID NO 184
<211> LENGTH: 9
<212> TYPE: PRT
<213> ORGANISM: Artificial sequence
<220> FEATURE:
<223> OTHER INFORMATION: synthesized

<400> SEQUENCE: 184

```
Gln Gln Ser Ile Glu Asp Pro His Thr
1               5
```

<210> SEQ ID NO 185
<211> LENGTH: 117
<212> TYPE: PRT
<213> ORGANISM: Artificial sequence
<220> FEATURE:
<223> OTHER INFORMATION: synthesized

<400> SEQUENCE: 185

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ile Ser Tyr
            20                  25                  30

Gly Val Asp Trp Val Arg Gln Pro Pro Gly Lys Gly Leu Glu Trp Leu
        35                  40                  45

Gly Val Ile Trp Gly Val Gly Ile Thr Lys Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Lys Arg Gly Tyr Tyr Gly Tyr Phe Asp Tyr Trp Gly Gln Gly Thr Thr
            100                 105                 110

Leu Thr Val Ser Ser
        115
```

<210> SEQ ID NO 186
<211> LENGTH: 5
<212> TYPE: PRT
<213> ORGANISM: Artificial sequence
<220> FEATURE:
<223> OTHER INFORMATION: synthesized

<400> SEQUENCE: 186

```
Ser Tyr Gly Val Asp
1               5
```

<210> SEQ ID NO 187
<211> LENGTH: 16
<212> TYPE: PRT
<213> ORGANISM: Artificial sequence
<220> FEATURE:
<223> OTHER INFORMATION: synthesized

<400> SEQUENCE: 187

```
Val Ile Trp Gly Val Gly Ile Thr Lys Tyr Asn Ser Ala Leu Met Ser
1               5                   10                  15
```

<210> SEQ ID NO 188
<211> LENGTH: 9
<212> TYPE: PRT

```
<213> ORGANISM: Artificial sequence
<220> FEATURE:
<223> OTHER INFORMATION: synthesized

<400> SEQUENCE: 188

Arg Gly Tyr Tyr Gly Tyr Phe Asp Tyr
1               5

<210> SEQ ID NO 189
<211> LENGTH: 106
<212> TYPE: PRT
<213> ORGANISM: Artificial sequence
<220> FEATURE:
<223> OTHER INFORMATION: synthesized

<400> SEQUENCE: 189

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

Tyr Trp Tyr Gln Gln Lys Pro Gly Ala Ser Pro Arg Leu Leu Ile Tyr
            35                  40                  45

Asp Thr Ser Asn Leu Ala Ser Gly Val Pro Val Arg Phe Ser Gly Ser
        50                  55                  60

Gly Ser Gly Thr Ser Tyr Ser Leu Thr Ile Ser Gln Met Glu Thr Glu
65                  70                  75                  80

Asp Ala Ala Thr Tyr Tyr Cys Gln Gln Trp Ser Ser Tyr Pro Leu Thr
                85                  90                  95

Phe Gly Ala Gly Thr Lys Leu Glu Leu Lys
            100                 105

<210> SEQ ID NO 190
<211> LENGTH: 10
<212> TYPE: PRT
<213> ORGANISM: Artificial sequence
<220> FEATURE:
<223> OTHER INFORMATION: synthesized

<400> SEQUENCE: 190

Ser Ala Ser Ser Ser Val Ser Tyr Met Tyr
1               5                   10

<210> SEQ ID NO 191
<211> LENGTH: 7
<212> TYPE: PRT
<213> ORGANISM: Artificial sequence
<220> FEATURE:
<223> OTHER INFORMATION: synthesized

<400> SEQUENCE: 191

Asp Thr Ser Asn Leu Ala Ser
1               5

<210> SEQ ID NO 192
<211> LENGTH: 9
<212> TYPE: PRT
<213> ORGANISM: Artificial sequence
<220> FEATURE:
<223> OTHER INFORMATION: synthesized

<400> SEQUENCE: 192

Gln Gln Trp Ser Ser Tyr Pro Leu Thr
1               5
```

```
<210> SEQ ID NO 193
<211> LENGTH: 122
<212> TYPE: PRT
<213> ORGANISM: Artificial sequence
<220> FEATURE:
<223> OTHER INFORMATION: synthesized

<400> SEQUENCE: 193

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val Asp Trp Val Arg Gln Pro Pro Gly Lys Gly Leu Glu Trp Leu
        35                  40                  45

Gly Val Ile Trp Gly Gly Gly Asn Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Lys Ser Pro Asp Phe Val Ser Ser Tyr Ser Tyr Ala Met Asp Tyr Trp
            100                 105                 110

Gly Gln Gly Thr Ser Val Thr Val Ser Ser
        115                 120

<210> SEQ ID NO 194
<211> LENGTH: 5
<212> TYPE: PRT
<213> ORGANISM: Artificial sequence
<220> FEATURE:
<223> OTHER INFORMATION: synthesized

<400> SEQUENCE: 194

Ser Tyr Gly Val Asp
1               5

<210> SEQ ID NO 195
<211> LENGTH: 16
<212> TYPE: PRT
<213> ORGANISM: Artificial sequence
<220> FEATURE:
<223> OTHER INFORMATION: synthesized

<400> SEQUENCE: 195

Val Ile Trp Gly Gly Gly Asn Thr Asn Tyr Asn Ser Ala Leu Met Ser
1               5                   10                  15

<210> SEQ ID NO 196
<211> LENGTH: 14
<212> TYPE: PRT
<213> ORGANISM: Artificial sequence
<220> FEATURE:
<223> OTHER INFORMATION: synthesized

<400> SEQUENCE: 196

Ser Pro Asp Phe Val Ser Ser Tyr Ser Tyr Ala Met Asp Tyr
1               5                   10

<210> SEQ ID NO 197
<211> LENGTH: 112
<212> TYPE: PRT
<213> ORGANISM: Artificial sequence
<220> FEATURE:
```

<223> OTHER INFORMATION: synthesized

<400> SEQUENCE: 197

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Arg Ile Val His Ser
            20                  25                  30

Asn Gly Asn Thr Tyr Leu Gln Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ser
                85                  90                  95

Ser Tyr Val Pro Pro Thr Phe Gly Gly Gly Thr Lys Leu Glu Ile Lys
            100                 105                 110

<210> SEQ ID NO 198
<211> LENGTH: 16
<212> TYPE: PRT
<213> ORGANISM: Artificial sequence
<220> FEATURE:
<223> OTHER INFORMATION: synthesized

<400> SEQUENCE: 198

Arg Ser Ser Gln Arg Ile Val His Ser Asn Gly Asn Thr Tyr Leu Gln
1               5                   10                  15

<210> SEQ ID NO 199
<211> LENGTH: 7
<212> TYPE: PRT
<213> ORGANISM: Artificial sequence
<220> FEATURE:
<223> OTHER INFORMATION: synthesized

<400> SEQUENCE: 199

Lys Val Ser Asn Arg Phe Ser
1               5

<210> SEQ ID NO 200
<211> LENGTH: 9
<212> TYPE: PRT
<213> ORGANISM: Artificial sequence
<220> FEATURE:
<223> OTHER INFORMATION: synthesized

<400> SEQUENCE: 200

Phe Gln Ser Ser Tyr Val Pro Pro Thr
1               5

<210> SEQ ID NO 201
<211> LENGTH: 117
<212> TYPE: PRT
<213> ORGANISM: Artificial sequence
<220> FEATURE:
<223> OTHER INFORMATION: synthesized

<400> SEQUENCE: 201

Gln Val His Leu Lys Glu Ser Gly Pro Gly Leu Val Ala Pro Ser Gln
1               5                   10                  15

Asn Leu Ser Ile Thr Cys Thr Val Ser Gly Phe Ser Leu Thr Ser Tyr
            20                  25                  30

```
Gly Val Asp Trp Val Arg Gln Pro Pro Gly Lys Gly Leu Glu Trp Leu
        35                  40                  45
Gly Val Thr Trp Gly Gly Gly Asn Thr Lys Tyr Asn Ser Ala Leu Met
    50                  55                  60
Ser Arg Leu His Ile Ser Lys Asp Asn Ser Lys Ser Gln Val Phe Leu
65                  70                  75                  80
Lys Met Asn Ser Leu Gln Thr Asp Asp Thr Ala Val Tyr Tyr Cys Ala
                85                  90                  95
Lys Arg Gly Tyr Tyr Gly Tyr Phe Asp Tyr Trp Gly Gln Gly Ala Thr
                100                 105                 110
Leu Thr Val Ser Ser
        115
```

<210> SEQ ID NO 202
<211> LENGTH: 5
<212> TYPE: PRT
<213> ORGANISM: Artificial sequence
<220> FEATURE:
<223> OTHER INFORMATION: synthesized

<400> SEQUENCE: 202

```
Ser Tyr Gly Val Asp
1               5
```

<210> SEQ ID NO 203
<211> LENGTH: 16
<212> TYPE: PRT
<213> ORGANISM: Artificial sequence
<220> FEATURE:
<223> OTHER INFORMATION: synthesized

<400> SEQUENCE: 203

```
Val Thr Trp Gly Gly Gly Asn Thr Lys Tyr Asn Ser Ala Leu Met Ser
1               5                   10                  15
```

<210> SEQ ID NO 204
<211> LENGTH: 9
<212> TYPE: PRT
<213> ORGANISM: Artificial sequence
<220> FEATURE:
<223> OTHER INFORMATION: synthesized

<400> SEQUENCE: 204

```
Arg Gly Tyr Tyr Gly Tyr Phe Asp Tyr
1               5
```

<210> SEQ ID NO 205
<211> LENGTH: 106
<212> TYPE: PRT
<213> ORGANISM: Artificial sequence
<220> FEATURE:
<223> OTHER INFORMATION: synthesized

<400> SEQUENCE: 205

```
Gln Ile Val Leu Thr Gln Ser Pro Ala Ile Met Ser Ala Ser Pro Gly
1               5                   10                  15
Glu Lys Val Thr Met Thr Cys Ser Ala Ser Ser Ser Val Ser Tyr Met
            20                  25                  30
Tyr Trp Tyr Gln Gln Lys Pro Gly Ser Ser Pro Arg Leu Leu Ile Tyr
        35                  40                  45
Asp Thr Ser Asn Leu Ala Ser Gly Val Pro Val Arg Phe Gly Gly Ser
    50                  55                  60
```

```
Gly Ser Gly Thr Ser Tyr Ser Leu Thr Ile Phe Arg Met Glu Ala Glu
 65                  70                  75                  80

Asp Ala Ala Thr Tyr Tyr Cys Gln Gln Trp Ser Ser Tyr Pro Leu Thr
                 85                  90                  95

Phe Gly Ala Gly Thr Lys Leu Glu Leu Lys
            100                 105
```

<210> SEQ ID NO 206
<211> LENGTH: 10
<212> TYPE: PRT
<213> ORGANISM: Artificial sequence
<220> FEATURE:
<223> OTHER INFORMATION: synthesized

<400> SEQUENCE: 206

```
Ser Ala Ser Ser Ser Val Ser Tyr Met Tyr
 1               5                  10
```

<210> SEQ ID NO 207
<211> LENGTH: 7
<212> TYPE: PRT
<213> ORGANISM: Artificial sequence
<220> FEATURE:
<223> OTHER INFORMATION: synthesized

<400> SEQUENCE: 207

```
Asp Thr Ser Asn Leu Ala Ser
 1               5
```

<210> SEQ ID NO 208
<211> LENGTH: 9
<212> TYPE: PRT
<213> ORGANISM: Artificial sequence
<220> FEATURE:
<223> OTHER INFORMATION: synthesized

<400> SEQUENCE: 208

```
Gln Gln Trp Ser Ser Tyr Pro Leu Thr
 1               5
```

<210> SEQ ID NO 209
<211> LENGTH: 122
<212> TYPE: PRT
<213> ORGANISM: Artificial sequence
<220> FEATURE:
<223> OTHER INFORMATION: synthesized

<400> SEQUENCE: 209

```
Gln Val Gln Leu Lys Glu Ser Gly Pro Gly Leu Val Ala Pro Ser Gln
 1               5                  10                  15

Ser Leu Ser Ile Thr Cys Thr Val Ser Gly Phe Ser Leu Thr Ser Tyr
                 20                  25                  30

Gly Val Asp Trp Val Arg Gln Pro Pro Gly Lys Gly Leu Glu Trp Leu
             35                  40                  45

Gly Val Ile Trp Gly Gly Ser Thr Asn Tyr Asn Ser Ala Leu Met Ser
         50                  55                  60

Ser Arg Leu Ser Ile Ser Lys Asp Asn Ser Lys Ser Gln Ile Phe Leu
 65                  70                  75                  80

Lys Met Asn Ser Leu Gln Thr Asp Asp Thr Ala Met Tyr Tyr Cys Ala
                 85                  90                  95

Lys Ser Pro Asp Phe Val Ser Ser Tyr Ser Tyr Ala Met Asp Tyr Trp
            100                 105                 110
```

Gly Gln Gly Thr Ser Val Thr Val Ser Ser
         115                 120

<210> SEQ ID NO 210
<211> LENGTH: 5
<212> TYPE: PRT
<213> ORGANISM: Artificial sequence
<220> FEATURE:
<223> OTHER INFORMATION: synthesized

<400> SEQUENCE: 210

Ser Tyr Gly Val Asp
1               5

<210> SEQ ID NO 211
<211> LENGTH: 16
<212> TYPE: PRT
<213> ORGANISM: Artificial sequence
<220> FEATURE:
<223> OTHER INFORMATION: synthesized

<400> SEQUENCE: 211

Val Ile Trp Gly Gly Gly Ser Thr Asn Tyr Asn Ser Ala Leu Met Ser
1               5                   10                  15

<210> SEQ ID NO 212
<211> LENGTH: 14
<212> TYPE: PRT
<213> ORGANISM: Artificial sequence
<220> FEATURE:
<223> OTHER INFORMATION: synthesized

<400> SEQUENCE: 212

Ser Pro Asp Phe Val Ser Ser Tyr Ser Tyr Ala Met Asp Tyr
1               5                   10

<210> SEQ ID NO 213
<211> LENGTH: 112
<212> TYPE: PRT
<213> ORGANISM: Artificial sequence
<220> FEATURE:
<223> OTHER INFORMATION: synthesized

<400> SEQUENCE: 213

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Arg Ile Val His Ser
            20                  25                  30

Asn Gly Asn Thr Tyr Leu Gln Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ser
                85                  90                  95

Ser Tyr Val Pro Pro Thr Phe Gly Gly Gly Thr Lys Leu Glu Ile Lys
            100                 105                 110

<210> SEQ ID NO 214
<211> LENGTH: 16
<212> TYPE: PRT
<213> ORGANISM: Artificial sequence
<220> FEATURE:
<223> OTHER INFORMATION: synthesized

<400> SEQUENCE: 214

Arg Ser Ser Gln Arg Ile Val His Ser Asn Gly Asn Thr Tyr Leu Gln
1               5                   10                  15

<210> SEQ ID NO 215
<211> LENGTH: 7
<212> TYPE: PRT
<213> ORGANISM: Artificial sequence
<220> FEATURE:
<223> OTHER INFORMATION: synthesized

<400> SEQUENCE: 215

Lys Val Ser Asn Arg Phe Ser
1               5

<210> SEQ ID NO 216
<211> LENGTH: 9
<212> TYPE: PRT
<213> ORGANISM: Artificial sequence
<220> FEATURE:
<223> OTHER INFORMATION: synthesized

<400> SEQUENCE: 216

Phe Gln Ser Ser Tyr Val Pro Pro Thr
1               5

<210> SEQ ID NO 217
<211> LENGTH: 122
<212> TYPE: PRT
<213> ORGANISM: Artificial sequence
<220> FEATURE:
<223> OTHER INFORMATION: synthesized

<400> SEQUENCE: 217

Glu Val Gln Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Asp Ile Asn Pro Asn Asn Gly Gly Thr Ile Tyr Asn Gln Lys Phe
    50                  55                  60

Lys Gly Lys Ala Thr Leu Thr Val Asp Lys Ser Ala Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Ser Ser Ile Tyr Tyr Asp Tyr Asp Gly Phe Ala Tyr Trp
            100                 105                 110

Gly Gln Gly Thr Leu Val Thr Val Ser Ala
        115                 120

<210> SEQ ID NO 218
<211> LENGTH: 5
<212> TYPE: PRT
<213> ORGANISM: Artificial sequence
<220> FEATURE:
<223> OTHER INFORMATION: synthesized

<400> SEQUENCE: 218

Asp Tyr Asn Met Asp

```
<210> SEQ ID NO 219
<211> LENGTH: 17
<212> TYPE: PRT
<213> ORGANISM: Artificial sequence
<220> FEATURE:
<223> OTHER INFORMATION: synthesized

<400> SEQUENCE: 219

Asp Ile Asn Pro Asn Asn Gly Gly Thr Ile Tyr Asn Gln Lys Phe Lys
1               5                   10                  15
Gly

<210> SEQ ID NO 220
<211> LENGTH: 13
<212> TYPE: PRT
<213> ORGANISM: Artificial sequence
<220> FEATURE:
<223> OTHER INFORMATION: synthesized

<400> SEQUENCE: 220

Ser Ser Ile Tyr Tyr Asp Tyr Asp Gly Gly Phe Ala Tyr
1               5                   10

<210> SEQ ID NO 221
<211> LENGTH: 107
<212> TYPE: PRT
<213> ORGANISM: Artificial sequence
<220> FEATURE:
<223> OTHER INFORMATION: synthesized

<400> SEQUENCE: 221

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
                20                  25                  30

Leu Ala Trp Tyr Gln Gln Lys Gln Gly Lys Ser Pro Gln Leu Leu Val
            35                  40                  45

Tyr Asn Ala Lys Thr Leu Ala Asp Gly Val Pro Ser Arg Phe Ser Gly
50                  55                  60

Ser Gly Ser Gly Thr Gln Tyr Ser Leu Lys Ile Asn Ser Leu Gln Pro
65                  70                  75                  80

Glu Asp Phe Gly Thr Tyr Tyr Cys Gln His Phe Trp Ser Ile Pro Phe
                85                  90                  95

Thr Phe Gly Ser Gly Thr Lys Leu Glu Ile Lys
            100                 105

<210> SEQ ID NO 222
<211> LENGTH: 11
<212> TYPE: PRT
<213> ORGANISM: Artificial sequence
<220> FEATURE:
<223> OTHER INFORMATION: synthesized

<400> SEQUENCE: 222

Arg Ala Ser Gly Asn Ile His Asn Tyr Leu Ala
1               5                   10

<210> SEQ ID NO 223
<211> LENGTH: 7
<212> TYPE: PRT
<213> ORGANISM: Artificial sequence
```

```
<220> FEATURE:
<223> OTHER INFORMATION: synthesized

<400> SEQUENCE: 223

Asn Ala Lys Thr Leu Ala Asp
1               5

<210> SEQ ID NO 224
<211> LENGTH: 9
<212> TYPE: PRT
<213> ORGANISM: Artificial sequence
<220> FEATURE:
<223> OTHER INFORMATION: synthesized

<400> SEQUENCE: 224

Gln His Phe Trp Ser Ile Pro Phe Thr
1               5

<210> SEQ ID NO 225
<211> LENGTH: 115
<212> TYPE: PRT
<213> ORGANISM: Artificial sequence
<220> FEATURE:
<223> OTHER INFORMATION: synthesized

<400> SEQUENCE: 225

Gln Ile Gln Leu Gln Gln Ser Gly Ala Glu Leu Val Lys Pro Gly Thr
1               5                   10                  15

Ser Val Gln Ile Ser Cys Lys Ala Ser Glu Tyr Asp Phe Ser Arg Tyr
            20                  25                  30

Trp Met Asn Trp Val Lys His Arg Pro Gly Glu Gly Leu Glu Trp Ile
        35                  40                  45

Gly Gln Ile Tyr Pro Gly Asp Gly Asp Ile Asn Tyr Asn Gly Lys Phe
    50                  55                  60

Glu Ala Lys Ala Thr Leu Thr Ala Asp Lys Ser Ser Ser Thr Ala Phe
65                  70                  75                  80

Met Gln Leu Ser Gly Leu Thr Ser Glu Asp Ser Ala Val Tyr Phe Cys
                85                  90                  95

Ala Arg Gly Ile Ala Met Asp Tyr Trp Gly Gln Gly Thr Ser Val Thr
            100                 105                 110

Val Ser Ser
        115

<210> SEQ ID NO 226
<211> LENGTH: 5
<212> TYPE: PRT
<213> ORGANISM: Artificial sequence
<220> FEATURE:
<223> OTHER INFORMATION: synthesized

<400> SEQUENCE: 226

Arg Tyr Trp Met Asn
1               5

<210> SEQ ID NO 227
<211> LENGTH: 17
<212> TYPE: PRT
<213> ORGANISM: Artificial sequence
<220> FEATURE:
<223> OTHER INFORMATION: synthesized

<400> SEQUENCE: 227

Gln Ile Tyr Pro Gly Asp Gly Asp Ile Asn Tyr Asn Gly Lys Phe Glu
```

-continued

```
1               5                  10                 15
Ala

<210> SEQ ID NO 228
<211> LENGTH: 6
<212> TYPE: PRT
<213> ORGANISM: Artificial sequence
<220> FEATURE:
<223> OTHER INFORMATION: synthesized

<400> SEQUENCE: 228

Gly Ile Ala Met Asp Tyr
1               5

<210> SEQ ID NO 229
<211> LENGTH: 107
<212> TYPE: PRT
<213> ORGANISM: Artificial sequence
<220> FEATURE:
<223> OTHER INFORMATION: synthesized

<400> SEQUENCE: 229

Asp Ile Gln Met Thr Gln Ser Thr Ser Ser Leu Thr Ala Ser Leu Gly
1               5                  10                 15

Asp Arg Val Thr Ile Ser Cys Arg Ala Ser Gln Asp Val Ser Asn Tyr
                20                  25                 30

Leu Asn Trp His Gln Gln Lys Pro Asp Gly Thr Val Lys Leu Leu Ile
            35                  40                 45

Tyr Tyr Thr Ser Arg Leu Gln Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 230
<211> LENGTH: 11
<212> TYPE: PRT
<213> ORGANISM: Artificial sequence
<220> FEATURE:
<223> OTHER INFORMATION: synthesized

<400> SEQUENCE: 230

Arg Ala Ser Gln Asp Val Ser Asn Tyr Leu Asn
1               5                  10

<210> SEQ ID NO 231
<211> LENGTH: 7
<212> TYPE: PRT
<213> ORGANISM: Artificial sequence
<220> FEATURE:
<223> OTHER INFORMATION: synthesized

<400> SEQUENCE: 231

Tyr Thr Ser Arg Leu Gln Ser
1               5

<210> SEQ ID NO 232
<211> LENGTH: 9
<212> TYPE: PRT
<213> ORGANISM: Artificial sequence
```

```
<220> FEATURE:
<223> OTHER INFORMATION: synthesized

<400> SEQUENCE: 232

Gln Gln Gly Asn Thr Leu Pro Trp Thr
1               5

<210> SEQ ID NO 233
<211> LENGTH: 120
<212> TYPE: PRT
<213> ORGANISM: Artificial sequence
<220> FEATURE:
<223> OTHER INFORMATION: synthesized

<400> SEQUENCE: 233

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Thr Ile Ser Gly Gly Gly Asp Tyr Thr His Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ser Glu Asp Thr Ala Leu Tyr Tyr Cys
                85                  90                  95

Ala Arg Gln Gly Phe Ser Thr Val Val Thr Thr Gly Asp Trp Gly Gln
            100                 105                 110

Gly Thr Thr Leu Thr Val Ser Ser
        115                 120

<210> SEQ ID NO 234
<211> LENGTH: 5
<212> TYPE: PRT
<213> ORGANISM: Artificial sequence
<220> FEATURE:
<223> OTHER INFORMATION: synthesized

<400> SEQUENCE: 234

Ser Tyr Thr Met Ser
1               5

<210> SEQ ID NO 235
<211> LENGTH: 17
<212> TYPE: PRT
<213> ORGANISM: Artificial sequence
<220> FEATURE:
<223> OTHER INFORMATION: synthesized

<400> SEQUENCE: 235

Thr Ile Ser Gly Gly Gly Asp Tyr Thr His Tyr Ala Asp Ser Val Lys
1               5                   10                  15

Gly

<210> SEQ ID NO 236
<211> LENGTH: 11
<212> TYPE: PRT
<213> ORGANISM: Artificial sequence
<220> FEATURE:
<223> OTHER INFORMATION: synthesized

<400> SEQUENCE: 236
```

-continued

```
Gln Gly Phe Ser Thr Val Val Thr Gly Asp
1               5                   10

<210> SEQ ID NO 237
<211> LENGTH: 107
<212> TYPE: PRT
<213> ORGANISM: Artificial sequence
<220> FEATURE:
<223> OTHER INFORMATION: synthesized

<400> SEQUENCE: 237

Asp Ile Val Met Thr Gln Ser Gln Lys Phe Met Ser Thr Thr Val Gly
1               5                   10                  15

Asp Arg Val Ser Ile Thr Cys Lys Ala Ser Gln Ser Val Gly Ala Ala
            20                  25                  30

Val Ala Trp Tyr Gln Gln Lys Pro Gly Gln Ser Pro Lys Leu Leu Ile
        35                  40                  45

Tyr Ser Ala Ser Thr Arg Tyr Thr Gly Val Pro Asp Arg Phe Thr Gly
    50                  55                  60

Ser Gly Ser Gly Thr Asp Phe Thr Leu Asn Ile Arg Arg Met Gln Ser
65                  70                  75                  80

Glu Asp Leu Ala Glu Tyr Phe Cys Gln Gln Tyr Arg Ser Tyr Pro Leu
                85                  90                  95

Thr Phe Gly Ser Gly Thr Lys Leu Glu Ile Lys
            100                 105

<210> SEQ ID NO 238
<211> LENGTH: 11
<212> TYPE: PRT
<213> ORGANISM: Artificial sequence
<220> FEATURE:
<223> OTHER INFORMATION: synthesized

<400> SEQUENCE: 238

Lys Ala Ser Gln Ser Val Gly Ala Ala Val Ala
1               5                   10

<210> SEQ ID NO 239
<211> LENGTH: 7
<212> TYPE: PRT
<213> ORGANISM: Artificial sequence
<220> FEATURE:
<223> OTHER INFORMATION: synthesized

<400> SEQUENCE: 239

Ser Ala Ser Thr Arg Tyr Thr
1               5

<210> SEQ ID NO 240
<211> LENGTH: 9
<212> TYPE: PRT
<213> ORGANISM: Artificial sequence
<220> FEATURE:
<223> OTHER INFORMATION: synthesized

<400> SEQUENCE: 240

Gln Gln Tyr Arg Ser Tyr Pro Leu Thr
1               5

<210> SEQ ID NO 241
<211> LENGTH: 118
<212> TYPE: PRT
<213> ORGANISM: Artificial sequence
```

```
<220> FEATURE:
<223> OTHER INFORMATION: synthesized

<400> SEQUENCE: 241

Gln Val Gln Met Gln Gln Ser Gly Ala Glu Leu Met Lys Pro Gly Ala
1               5                   10                  15

Ser Val Lys Leu Ser Cys Lys Ala Asn Gly Tyr Thr Phe Ser Gly Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Asp Ser Pro Lys Tyr Ser Ala Lys Phe
    50                  55                  60

Lys Gly Lys Ala Thr Ile Thr Ala Asp Thr Ser Ser Asn Thr Ala Tyr
65                  70                  75                  80

Met Gln Leu Ser Ser Leu Thr Thr Glu Asp Ser Ala Ile Tyr Tyr Cys
                85                  90                  95

Ala Lys Gly Gly Asn Thr Ser Phe Phe Asp Phe Trp Gly Gln Gly Thr
            100                 105                 110

Thr Leu Thr Val Ser Ser
            115

<210> SEQ ID NO 242
<211> LENGTH: 5
<212> TYPE: PRT
<213> ORGANISM: Artificial sequence
<220> FEATURE:
<223> OTHER INFORMATION: synthesized

<400> SEQUENCE: 242

Gly Tyr Trp Ile Glu
1               5

<210> SEQ ID NO 243
<211> LENGTH: 17
<212> TYPE: PRT
<213> ORGANISM: Artificial sequence
<220> FEATURE:
<223> OTHER INFORMATION: synthesized

<400> SEQUENCE: 243

Glu Ile Leu Pro Gly Ser Asp Ser Pro Lys Tyr Ser Ala Lys Phe Lys
1               5                   10                  15

Gly

<210> SEQ ID NO 244
<211> LENGTH: 9
<212> TYPE: PRT
<213> ORGANISM: Artificial sequence
<220> FEATURE:
<223> OTHER INFORMATION: synthesized

<400> SEQUENCE: 244

Gly Gly Asn Thr Ser Phe Phe Asp Phe
1               5

<210> SEQ ID NO 245
<211> LENGTH: 112
<212> TYPE: PRT
<213> ORGANISM: Artificial sequence
<220> FEATURE:
<223> OTHER INFORMATION: synthesized

<400> SEQUENCE: 245
```

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Arg Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Thr Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Leu Gly Val Tyr Tyr Cys Phe Gln Gly
            85                  90                  95

Ser Phe Val Pro Trp Thr Phe Gly Gly Gly Thr Lys Leu Glu Ile Lys
            100                 105                 110
```

<210> SEQ ID NO 246
<211> LENGTH: 16
<212> TYPE: PRT
<213> ORGANISM: Artificial sequence
<220> FEATURE:
<223> OTHER INFORMATION: synthesized

<400> SEQUENCE: 246

```
Arg Ser Ser Gln Arg Ile Val His Ser Asn Gly Asn Thr Tyr Leu Glu
1               5                   10                  15
```

<210> SEQ ID NO 247
<211> LENGTH: 7
<212> TYPE: PRT
<213> ORGANISM: Artificial sequence
<220> FEATURE:
<223> OTHER INFORMATION: synthesized

<400> SEQUENCE: 247

```
Lys Val Ser Thr Arg Phe Ser
1               5
```

<210> SEQ ID NO 248
<211> LENGTH: 9
<212> TYPE: PRT
<213> ORGANISM: Artificial sequence
<220> FEATURE:
<223> OTHER INFORMATION: synthesized

<400> SEQUENCE: 248

```
Phe Gln Gly Ser Phe Val Pro Trp Thr
1               5
```

<210> SEQ ID NO 249
<211> LENGTH: 120
<212> TYPE: PRT
<213> ORGANISM: Artificial sequence
<220> FEATURE:
<223> OTHER INFORMATION: synthesized

<400> SEQUENCE: 249

```
Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
            35                  40                  45
```

```
Ala Thr Ile Ser Gly Gly Gly Asp Tyr Thr His Tyr Pro Asp Ser Val
 50                  55                  60

Lys Gly Arg Phe Thr Ile Ser Arg Asp Asn Ala Lys Asp Thr Leu Tyr
 65                  70                  75                  80

Leu Gln Met Asn Ser Leu Arg Ser Glu Asp Thr Ala Leu Tyr Tyr Cys
                 85                  90                  95

Ala Arg Gln Gly Phe Ser Thr Val Val Met Thr Gly Asp Trp Gly Gln
            100                 105                 110

Gly Thr Thr Leu Thr Val Ser Ser
            115                 120

<210> SEQ ID NO 250
<211> LENGTH: 5
<212> TYPE: PRT
<213> ORGANISM: Artificial sequence
<220> FEATURE:
<223> OTHER INFORMATION: synthesized

<400> SEQUENCE: 250

Ser Tyr Thr Met Ser
1               5

<210> SEQ ID NO 251
<211> LENGTH: 17
<212> TYPE: PRT
<213> ORGANISM: Artificial sequence
<220> FEATURE:
<223> OTHER INFORMATION: synthesized

<400> SEQUENCE: 251

Thr Ile Ser Gly Gly Gly Asp Tyr Thr His Tyr Pro Asp Ser Val Lys
1               5                   10                  15

Gly

<210> SEQ ID NO 252
<211> LENGTH: 11
<212> TYPE: PRT
<213> ORGANISM: Artificial sequence
<220> FEATURE:
<223> OTHER INFORMATION: synthesized

<400> SEQUENCE: 252

Gln Gly Phe Ser Thr Val Val Met Thr Gly Asp
1               5                   10

<210> SEQ ID NO 253
<211> LENGTH: 107
<212> TYPE: PRT
<213> ORGANISM: Artificial sequence
<220> FEATURE:
<223> OTHER INFORMATION: synthesized

<400> SEQUENCE: 253

Asp Ile Val Met Thr Gln Ser Gln Lys Phe Met Ser Thr Thr Val Gly
1               5                   10                  15

Asp Arg Val Ser Ile Thr Cys Lys Ala Ser Gln Ser Val Gly Thr Ala
            20                  25                  30

Val Ala Trp Tyr Gln Gln Lys Pro Gly Gln Ser Pro Asn Leu Leu Ile
        35                  40                  45

Tyr Ser Ala Ser Thr Arg Tyr Thr Gly Val Pro Asp Arg Phe Thr Gly
    50                  55                  60
```

-continued

Ser Gly Ser Gly Thr Asp Phe Thr Leu Asn Ile Arg Asn Met Gln Ser
65                  70                  75                  80

Glu Asp Leu Ala Glu Tyr Phe Cys Gln Gln Tyr Arg Ser Tyr Pro Leu
                85                  90                  95

Thr Phe Gly Ser Gly Thr Lys Leu Glu Ile Lys
            100                 105

<210> SEQ ID NO 254
<211> LENGTH: 11
<212> TYPE: PRT
<213> ORGANISM: Artificial sequence
<220> FEATURE:
<223> OTHER INFORMATION: synthesized

<400> SEQUENCE: 254

Lys Ala Ser Gln Ser Val Gly Thr Ala Val Ala
1               5                   10

<210> SEQ ID NO 255
<211> LENGTH: 7
<212> TYPE: PRT
<213> ORGANISM: Artificial sequence
<220> FEATURE:
<223> OTHER INFORMATION: synthesized

<400> SEQUENCE: 255

Ser Ala Ser Thr Arg Tyr Thr
1               5

<210> SEQ ID NO 256
<211> LENGTH: 9
<212> TYPE: PRT
<213> ORGANISM: Artificial sequence
<220> FEATURE:
<223> OTHER INFORMATION: synthesized

<400> SEQUENCE: 256

Gln Gln Tyr Arg Ser Tyr Pro Leu Thr
1               5

<210> SEQ ID NO 257
<211> LENGTH: 120
<212> TYPE: PRT
<213> ORGANISM: Artificial sequence
<220> FEATURE:
<223> OTHER INFORMATION: synthesized

<400> SEQUENCE: 257

Glu Val Met Leu Val Glu Ser Gly Gly Gly Leu Val Lys Pro Gly Gly
1               5                   10                  15

Ser Leu Lys Leu Ser Cys Glu Ala Ser Gly Phe Thr Phe Asn Thr Tyr
            20                  25                  30

Thr Met Ser Trp Ile Arg Gln Thr Pro Glu Lys Arg Leu Glu Trp Val
        35                  40                  45

Ala Thr Ile Asn Gly Gly Gly Thr Asn Ala Tyr Tyr Leu Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Ala Arg Gln Gly Phe Thr Thr Val Pro Thr Gly Asp Trp Gly Gln
            100                 105                 110

Gly Thr Thr Leu Thr Val Ser Ser
            115                 120

<210> SEQ ID NO 258
<211> LENGTH: 5
<212> TYPE: PRT
<213> ORGANISM: Artificial sequence
<220> FEATURE:
<223> OTHER INFORMATION: synthesized

<400> SEQUENCE: 258

Thr Tyr Thr Met Ser
1               5

<210> SEQ ID NO 259
<211> LENGTH: 17
<212> TYPE: PRT
<213> ORGANISM: Artificial sequence
<220> FEATURE:
<223> OTHER INFORMATION: synthesized

<400> SEQUENCE: 259

Thr Ile Asn Gly Gly Gly Thr Asn Ala Tyr Tyr Leu Asp Ser Val Lys
1               5                   10                  15

Gly

<210> SEQ ID NO 260
<211> LENGTH: 11
<212> TYPE: PRT
<213> ORGANISM: Artificial sequence
<220> FEATURE:
<223> OTHER INFORMATION: synthesized

<400> SEQUENCE: 260

Gln Gly Phe Thr Thr Val Val Pro Thr Gly Asp
1               5                   10

<210> SEQ ID NO 261
<211> LENGTH: 107
<212> TYPE: PRT
<213> ORGANISM: Artificial sequence
<220> FEATURE:
<223> OTHER INFORMATION: synthesized

<400> SEQUENCE: 261

Asp Ile Val Met Thr Gln Ser Gln Lys Phe Met Ser Thr Ile Gly
1               5                   10                  15

Asp Arg Val Ser Ile Thr Cys Lys Ala Ser Gln Ser Val Gly Ala Ala
                20                  25                  30

Ile Ala Trp Tyr Gln Gln Lys Pro Gly Gln Ser Pro Lys Leu Leu Ile
            35                  40                  45

Tyr Ser Ala Ser Ser Arg Tyr Thr Gly Val Pro Asn Arg Phe Thr Gly
        50                  55                  60

Ser Gly Ser Gly Thr Asp Phe Thr Leu Thr Ile Asp Asn Val Gln Ser
65                  70                  75                  80

Glu Asp Leu Ser Asp Tyr Val Cys Gln Gln Tyr Arg Ser Tyr Pro Leu
                85                  90                  95

Thr Phe Gly Ser Gly Thr Lys Leu Glu Val Arg
            100                 105

<210> SEQ ID NO 262
<211> LENGTH: 11
<212> TYPE: PRT

<213> ORGANISM: Artificial sequence
<220> FEATURE:
<223> OTHER INFORMATION: synthesized

<400> SEQUENCE: 262

Lys Ala Ser Gln Ser Val Gly Ala Ala Ile Ala
1               5                   10

<210> SEQ ID NO 263
<211> LENGTH: 7
<212> TYPE: PRT
<213> ORGANISM: Artificial sequence
<220> FEATURE:
<223> OTHER INFORMATION: synthesized

<400> SEQUENCE: 263

Ser Ala Ser Ser Arg Tyr Thr
1               5

<210> SEQ ID NO 264
<211> LENGTH: 9
<212> TYPE: PRT
<213> ORGANISM: Artificial sequence
<220> FEATURE:
<223> OTHER INFORMATION: synthesized

<400> SEQUENCE: 264

Gln Gln Tyr Arg Ser Tyr Pro Leu Thr
1               5

<210> SEQ ID NO 265
<211> LENGTH: 115
<212> TYPE: PRT
<213> ORGANISM: Artificial sequence
<220> FEATURE:
<223> OTHER INFORMATION: synthesized

<400> SEQUENCE: 265

Gln Ile Gln Leu Gln Gln Ser Gly Ala Glu Leu Val Lys Ser Gly Thr
1               5                   10                  15

Ser Val Lys Ile Ser Cys Lys Ala Ser Glu Tyr Asp Phe Ser Arg Tyr
                20                  25                  30

Trp Met Asn Trp Val Lys His Arg Pro Gly Glu Gly Leu Glu Trp Ile
            35                  40                  45

Gly Gln Ile Tyr Pro Gly Asp Gly Asp Ile Asn Tyr Asn Gly Lys Phe
        50                  55                  60

Glu Ala Lys Ala Thr Leu Thr Ala Asp Lys Ser Ser Ser Thr Ala Phe
65                  70                  75                  80

Met Gln Leu Ser Gly Leu Thr Ser Glu Asp Ser Ala Val Tyr Phe Cys
                85                  90                  95

Ala Arg Gly Ile Ala Met Asp Phe Trp Gly Gln Gly Thr Ser Val Thr
                100                 105                 110

Val Ser Ser
        115

<210> SEQ ID NO 266
<211> LENGTH: 5
<212> TYPE: PRT
<213> ORGANISM: Artificial sequence
<220> FEATURE:
<223> OTHER INFORMATION: synthesized

<400> SEQUENCE: 266

Arg Tyr Trp Met Asn
1               5

<210> SEQ ID NO 267
<211> LENGTH: 17
<212> TYPE: PRT
<213> ORGANISM: Artificial sequence
<220> FEATURE:
<223> OTHER INFORMATION: synthesized

<400> SEQUENCE: 267

Gln Ile Tyr Pro Gly Asp Gly Asp Ile Asn Tyr Asn Gly Lys Phe Glu
1               5                   10                  15

Ala

<210> SEQ ID NO 268
<211> LENGTH: 6
<212> TYPE: PRT
<213> ORGANISM: Artificial sequence
<220> FEATURE:
<223> OTHER INFORMATION: synthesized

<400> SEQUENCE: 268

Gly Ile Ala Met Asp Phe
1               5

<210> SEQ ID NO 269
<211> LENGTH: 107
<212> TYPE: PRT
<213> ORGANISM: Artificial sequence
<220> FEATURE:
<223> OTHER INFORMATION: synthesized

<400> SEQUENCE: 269

Asp Ile Gln Met Thr Gln Ser Thr Ser Ser Leu Thr Ala Ser Leu Gly
1               5                   10                  15

Asp Arg Val Thr Ile Ser Cys Arg Ala Ser Gln Asp Val Ser Asn Tyr
            20                  25                  30

Leu Asn Trp His Gln Gln Lys Pro Asp Gly Thr Val Lys Leu Leu Ile
        35                  40                  45

Tyr Tyr Thr Ser Arg Leu Gln Ser Gly Val Pro Ser Arg Phe Ser Gly
    50                  55                  60

Ser Gly Ser Gly Thr Asp Tyr Ser Leu Thr Ile Thr Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Ile
            100                 105

<210> SEQ ID NO 270
<211> LENGTH: 11
<212> TYPE: PRT
<213> ORGANISM: Artificial sequence
<220> FEATURE:
<223> OTHER INFORMATION: synthesized

<400> SEQUENCE: 270

Arg Ala Ser Gln Asp Val Ser Asn Tyr Leu Asn
1               5                   10

<210> SEQ ID NO 271
<211> LENGTH: 7
<212> TYPE: PRT

```
<213> ORGANISM: Artificial sequence
<220> FEATURE:
<223> OTHER INFORMATION: synthesized

<400> SEQUENCE: 271

Tyr Thr Ser Arg Leu Gln Ser
1               5

<210> SEQ ID NO 272
<211> LENGTH: 9
<212> TYPE: PRT
<213> ORGANISM: Artificial sequence
<220> FEATURE:
<223> OTHER INFORMATION: synthesized

<400> SEQUENCE: 272

Gln Gln Gly Asn Thr Leu Pro Trp Thr
1               5

<210> SEQ ID NO 273
<211> LENGTH: 120
<212> TYPE: PRT
<213> ORGANISM: Artificial sequence
<220> FEATURE:
<223> OTHER INFORMATION: synthesized

<400> SEQUENCE: 273

Gln Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Asp Ile Asn Trp Val Lys Gln Arg Pro Gly Gln Gly Leu Glu Trp Ile
        35                  40                  45

Gly Trp Ile Tyr Pro Gly Asp Gly Ser Thr Lys Ser Lys Glu Lys Phe
    50                  55                  60

Arg Gly Lys Ala Thr Leu Thr Val Asp Thr Ser Ser Ser Thr Ala Tyr
65                  70                  75                  80

Met Glu Leu His Ser Leu Thr Ser Glu Asp Ser Ala Val Tyr Leu Cys
                85                  90                  95

Ala Arg Asp Tyr Gly Thr Pro Tyr Tyr Ala Met Asp Tyr Trp Gly Gln
            100                 105                 110

Gly Thr Ser Val Thr Val Ser Ser
        115                 120

<210> SEQ ID NO 274
<211> LENGTH: 5
<212> TYPE: PRT
<213> ORGANISM: Artificial sequence
<220> FEATURE:
<223> OTHER INFORMATION: synthesized

<400> SEQUENCE: 274

Asn Tyr Asp Ile Asn
1               5

<210> SEQ ID NO 275
<211> LENGTH: 17
<212> TYPE: PRT
<213> ORGANISM: Artificial sequence
<220> FEATURE:
<223> OTHER INFORMATION: synthesized

<400> SEQUENCE: 275
```

Trp Ile Tyr Pro Gly Asp Gly Ser Thr Lys Ser Lys Glu Lys Phe Arg
1               5                   10                  15

Gly

<210> SEQ ID NO 276
<211> LENGTH: 11
<212> TYPE: PRT
<213> ORGANISM: Artificial sequence
<220> FEATURE:
<223> OTHER INFORMATION: synthesized

<400> SEQUENCE: 276

Asp Tyr Gly Thr Pro Tyr Tyr Ala Met Asp Tyr
1               5                   10

<210> SEQ ID NO 277
<211> LENGTH: 112
<212> TYPE: PRT
<213> ORGANISM: Artificial sequence
<220> FEATURE:
<223> OTHER INFORMATION: synthesized

<400> SEQUENCE: 277

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Ile Gln Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser Phe Val Pro Trp Thr Phe Gly Gly Gly Thr Asn Leu Glu Ile Lys
            100                 105                 110

<210> SEQ ID NO 278
<211> LENGTH: 16
<212> TYPE: PRT
<213> ORGANISM: Artificial sequence
<220> FEATURE:
<223> OTHER INFORMATION: synthesized

<400> SEQUENCE: 278

Arg Ser Ser Gln Ser Ile Ile Gln Ser Asn Gly Asn Thr Tyr Leu Glu
1               5                   10                  15

<210> SEQ ID NO 279
<211> LENGTH: 7
<212> TYPE: PRT
<213> ORGANISM: Artificial sequence
<220> FEATURE:
<223> OTHER INFORMATION: synthesized

<400> SEQUENCE: 279

Lys Val Ser Asn Arg Phe Ser
1               5

<210> SEQ ID NO 280
<211> LENGTH: 9
<212> TYPE: PRT

<213> ORGANISM: Artificial sequence
<220> FEATURE:
<223> OTHER INFORMATION: synthesized

<400> SEQUENCE: 280

Phe Gln Gly Ser Phe Val Pro Trp Thr
1               5

<210> SEQ ID NO 281
<211> LENGTH: 123
<212> TYPE: PRT
<213> ORGANISM: Artificial sequence
<220> FEATURE:
<223> OTHER INFORMATION: synthesized

<400> SEQUENCE: 281

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Asn Asn Asp
            20                  25                  30

Gly Met Ser Trp Val Arg Gln Thr Pro Asp Lys Arg Leu Glu Trp Val
        35                  40                  45

Ala Ser Ile Ser Ser Asp Gly Ser Tyr Ser Phe Tyr Pro Asp Asn Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Ser Gln Arg Gly Tyr Tyr Gly Asn Ser Leu Ala Trp Phe Ala Tyr
            100                 105                 110

Trp Gly Gln Gly Thr Leu Val Thr Val Ser Ala
        115                 120

<210> SEQ ID NO 282
<211> LENGTH: 5
<212> TYPE: PRT
<213> ORGANISM: Artificial sequence
<220> FEATURE:
<223> OTHER INFORMATION: synthesized

<400> SEQUENCE: 282

Asn Asp Gly Met Ser
1               5

<210> SEQ ID NO 283
<211> LENGTH: 17
<212> TYPE: PRT
<213> ORGANISM: Artificial sequence
<220> FEATURE:
<223> OTHER INFORMATION: synthesized

<400> SEQUENCE: 283

Ser Ile Ser Ser Asp Gly Ser Tyr Ser Phe Tyr Pro Asp Asn Val Lys
1               5                   10                  15

Gly

<210> SEQ ID NO 284
<211> LENGTH: 14
<212> TYPE: PRT
<213> ORGANISM: Artificial sequence
<220> FEATURE:
<223> OTHER INFORMATION: synthesized

<400> SEQUENCE: 284

Gln Arg Gly Tyr Tyr Gly Asn Ser Leu Ala Trp Phe Ala Tyr
1               5                   10

<210> SEQ ID NO 285
<211> LENGTH: 107
<212> TYPE: PRT
<213> ORGANISM: Artificial sequence
<220> FEATURE:
<223> OTHER INFORMATION: synthesized

<400> SEQUENCE: 285

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Met Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Phe Cys Gln Gln Ser Lys Thr Trp Pro Leu
                85                  90                  95

Thr Phe Gly Ala Gly Thr Thr Leu Glu Leu Lys
            100                 105

<210> SEQ ID NO 286
<211> LENGTH: 11
<212> TYPE: PRT
<213> ORGANISM: Artificial sequence
<220> FEATURE:
<223> OTHER INFORMATION: synthesized

<400> SEQUENCE: 286

Arg Ala Ser Gln Ser Ile Gly Thr Ser Ile His
1               5                   10

<210> SEQ ID NO 287
<211> LENGTH: 7
<212> TYPE: PRT
<213> ORGANISM: Artificial sequence
<220> FEATURE:
<223> OTHER INFORMATION: synthesized

<400> SEQUENCE: 287

Tyr Ala Ser Glu Ser Met Ser
1               5

<210> SEQ ID NO 288
<211> LENGTH: 9
<212> TYPE: PRT
<213> ORGANISM: Artificial sequence
<220> FEATURE:
<223> OTHER INFORMATION: synthesized

<400> SEQUENCE: 288

Gln Gln Ser Lys Thr Trp Pro Leu Thr
1               5

<210> SEQ ID NO 289
<211> LENGTH: 118
<212> TYPE: PRT

<213> ORGANISM: Artificial sequence
<220> FEATURE:
<223> OTHER INFORMATION: synthesized

<400> SEQUENCE: 289

```
Glu Val His Leu Val Glu Ser Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Glu Lys Gly Leu Asp Trp Val
        35                  40                  45

Ala Tyr Ile Ser Ser Gly Gly Thr Thr Ile Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Thr Leu Gly Ser Asp Asp Thr Ala Met Tyr Ser Cys
                85                  90                  95

Ala Arg Thr Arg Pro Gly Asp Ala Met Asp Tyr Trp Gly Gln Gly Thr
                100                 105                 110

Ser Val Thr Val Ser Ser
        115
```

<210> SEQ ID NO 290
<211> LENGTH: 5
<212> TYPE: PRT
<213> ORGANISM: Artificial sequence
<220> FEATURE:
<223> OTHER INFORMATION: synthesized

<400> SEQUENCE: 290

```
Asp Tyr Gly Met His
1               5
```

<210> SEQ ID NO 291
<211> LENGTH: 17
<212> TYPE: PRT
<213> ORGANISM: Artificial sequence
<220> FEATURE:
<223> OTHER INFORMATION: synthesized

<400> SEQUENCE: 291

```
Tyr Ile Ser Ser Gly Gly Thr Thr Ile Tyr Ala Asp Thr Val Lys
1               5                   10                  15

Gly
```

<210> SEQ ID NO 292
<211> LENGTH: 9
<212> TYPE: PRT
<213> ORGANISM: Artificial sequence
<220> FEATURE:
<223> OTHER INFORMATION: synthesized

<400> SEQUENCE: 292

```
Thr Arg Pro Gly Asp Ala Met Asp Tyr
1               5
```

<210> SEQ ID NO 293
<211> LENGTH: 107
<212> TYPE: PRT
<213> ORGANISM: Artificial sequence
<220> FEATURE:
<223> OTHER INFORMATION: synthesized

<400> SEQUENCE: 293

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ala Gly Thr Ser
            20                  25                  30

Ile His Trp Tyr Gln Gln Arg Thr Asn Gly Ser Pro Arg Leu Leu Ile
        35                  40                  45

Lys Tyr Thr Ser Glu Ser Ile Ser Gly Ile Pro Ser Arg Phe Ser Gly
50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Leu Arg Trp Pro Phe
                85                  90                  95

Thr Phe Gly Ser Gly Thr Arg Leu Glu Ile Lys
            100                 105

<210> SEQ ID NO 294
<211> LENGTH: 11
<212> TYPE: PRT
<213> ORGANISM: Artificial sequence
<220> FEATURE:
<223> OTHER INFORMATION: synthesized

<400> SEQUENCE: 294

Arg Ala Ser Gln Ser Ala Gly Thr Ser Ile His
1               5                   10

<210> SEQ ID NO 295
<211> LENGTH: 7
<212> TYPE: PRT
<213> ORGANISM: Artificial sequence
<220> FEATURE:
<223> OTHER INFORMATION: synthesized

<400> SEQUENCE: 295

Tyr Thr Ser Glu Ser Ile Ser
1               5

<210> SEQ ID NO 296
<211> LENGTH: 9
<212> TYPE: PRT
<213> ORGANISM: Artificial sequence
<220> FEATURE:
<223> OTHER INFORMATION: synthesized

<400> SEQUENCE: 296

Gln Gln Ser Leu Arg Trp Pro Phe Thr
1               5

<210> SEQ ID NO 297
<211> LENGTH: 118
<212> TYPE: PRT
<213> ORGANISM: Artificial sequence
<220> FEATURE:
<223> OTHER INFORMATION: synthesized

<400> SEQUENCE: 297

Gln Val Gln Leu Gln Gln Pro Glu Ala Glu Leu Val Lys Pro Gly Ala
1               5                   10                  15

Ser Val Lys Met Ser Cys Lys Ala Ser Gly Tyr Thr Phe Pro Arg Tyr
            20                  25                  30

Trp Ile Thr Trp Met Arg Gln Arg Pro Gly Gln Gly Leu Glu Trp Ile

```
                35                  40                  45
Gly Asp Ile Phe Pro Ser Ser Glu Tyr Thr His Tyr Asn Glu Lys Phe
    50                  55                  60

Arg Arg Lys Ala Thr Leu Thr Val Asp Thr Ser Ser Ile Ala Tyr
 65                  70                  75                  80

Ile Gln Leu Ser Ser Leu Thr Ser Glu Asp Ser Ala Val Tyr Tyr Cys
                85                  90                  95

Ala Arg Gly Glu Tyr Asp Ala Trp Phe Ala Tyr Trp Gly Gln Gly Thr
            100                 105                 110

Leu Val Thr Val Ser Ala
        115

<210> SEQ ID NO 298
<211> LENGTH: 5
<212> TYPE: PRT
<213> ORGANISM: Artificial sequence
<220> FEATURE:
<223> OTHER INFORMATION: synthesized

<400> SEQUENCE: 298

Arg Tyr Trp Ile Thr
1               5

<210> SEQ ID NO 299
<211> LENGTH: 17
<212> TYPE: PRT
<213> ORGANISM: Artificial sequence
<220> FEATURE:
<223> OTHER INFORMATION: synthesized

<400> SEQUENCE: 299

Asp Ile Phe Pro Ser Ser Glu Tyr Thr His Tyr Asn Glu Lys Phe Arg
1               5                   10                  15

Arg

<210> SEQ ID NO 300
<211> LENGTH: 9
<212> TYPE: PRT
<213> ORGANISM: Artificial sequence
<220> FEATURE:
<223> OTHER INFORMATION: synthesized

<400> SEQUENCE: 300

Gly Glu Tyr Asp Ala Trp Phe Ala Tyr
1               5

<210> SEQ ID NO 301
<211> LENGTH: 107
<212> TYPE: PRT
<213> ORGANISM: Artificial sequence
<220> FEATURE:
<223> OTHER INFORMATION: synthesized

<400> SEQUENCE: 301

Asp Ile Gln Met Thr Gln Thr Thr Ser Ser Leu Ser Val Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu Asp Ser Gly Val Pro Ser Arg Phe Ser Gly
    50                  55                  60
```

Ser Gly Ser Gly Thr Asp Tyr Ser Leu Thr Ile Ser Asn Leu Glu Gln
65                  70                  75                  80

Glu Asp Leu Ala Thr Tyr Phe Cys Gln Gln Gly Asn Thr Leu Pro Pro
                85                  90                  95

Thr Phe Gly Gly Gly Thr Lys Leu Glu Ile Arg
            100                 105

<210> SEQ ID NO 302
<211> LENGTH: 11
<212> TYPE: PRT
<213> ORGANISM: Artificial sequence
<220> FEATURE:
<223> OTHER INFORMATION: synthesized

<400> SEQUENCE: 302

Arg Ala Ser Gln Asp Ile Ser Asn Tyr Leu Asn
1               5                   10

<210> SEQ ID NO 303
<211> LENGTH: 7
<212> TYPE: PRT
<213> ORGANISM: Artificial sequence
<220> FEATURE:
<223> OTHER INFORMATION: synthesized

<400> SEQUENCE: 303

Tyr Thr Ser Arg Leu Asp Ser
1               5

<210> SEQ ID NO 304
<211> LENGTH: 9
<212> TYPE: PRT
<213> ORGANISM: Artificial sequence
<220> FEATURE:
<223> OTHER INFORMATION: synthesized

<400> SEQUENCE: 304

Gln Gln Gly Asn Thr Leu Pro Pro Thr
1               5

<210> SEQ ID NO 305
<211> LENGTH: 117
<212> TYPE: PRT
<213> ORGANISM: Artificial sequence
<220> FEATURE:
<223> OTHER INFORMATION: synthesized

<400> SEQUENCE: 305

Glu Val Gln Leu Gln Gln Ser Gly Ala Glu Leu Val Arg Pro Gly Ala
1               5                   10                  15

Ser Val Lys Leu Ser Cys Thr Thr Ser Gly Phe Asn Ile Lys Asp Glu
                20                  25                  30

His Met Tyr Trp Val Lys Gln Arg Pro Glu Gln Gly Leu Glu Trp Ile
            35                  40                  45

Ala Trp Ile Asp Pro Glu Asn Asp Asn Thr Glu Tyr Ala Ser Lys Phe
    50                  55                  60

Gln Gly Lys Ala Thr Ile Thr Ala Asp Thr Ser Ser Asn Thr Val Tyr
65                  70                  75                  80

Leu Gln Leu Ser Asn Leu Thr Ser Glu Asp Thr Ala Val Tyr Phe Cys
                85                  90                  95

Thr Thr Gly Asp Tyr Asp Gly Phe Thr Tyr Trp Gly Gln Gly Thr Leu
            100                 105                 110

Val Thr Val Ser Ala
        115

<210> SEQ ID NO 306
<211> LENGTH: 5
<212> TYPE: PRT
<213> ORGANISM: Artificial sequence
<220> FEATURE:
<223> OTHER INFORMATION: synthesized

<400> SEQUENCE: 306

Asp Glu His Met Tyr
1               5

<210> SEQ ID NO 307
<211> LENGTH: 17
<212> TYPE: PRT
<213> ORGANISM: Artificial sequence
<220> FEATURE:
<223> OTHER INFORMATION: synthesized

<400> SEQUENCE: 307

Trp Ile Asp Pro Glu Asn Asp Asn Thr Glu Tyr Ala Ser Lys Phe Gln
1               5                   10                  15

Gly

<210> SEQ ID NO 308
<211> LENGTH: 8
<212> TYPE: PRT
<213> ORGANISM: Artificial sequence
<220> FEATURE:
<223> OTHER INFORMATION: synthesized

<400> SEQUENCE: 308

Gly Asp Tyr Asp Gly Phe Thr Tyr
1               5

<210> SEQ ID NO 309
<211> LENGTH: 108
<212> TYPE: PRT
<213> ORGANISM: Artificial sequence
<220> FEATURE:
<223> OTHER INFORMATION: synthesized

<400> SEQUENCE: 309

Glu Ile Val Leu Thr Gln Ser Pro Thr Thr Met Ala Ala Ser Pro Gly
1               5                   10                  15

Glu Lys Ile Thr Ile Thr Cys Ser Ala Ser Ser Ser Ile Ser Ser Asn
            20                  25                  30

Phe Leu His Trp Phe Gln Gln Lys Pro Arg Phe Ser Pro Lys Leu Leu
        35                  40                  45

Ile Tyr Arg Thr Ser Asn Leu Ala Ser Gly Val Pro Ala Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Phe Met Pro
                85                  90                  95

Phe Thr Phe Gly Thr Gly Thr Lys Leu Glu Leu Lys
            100                 105

<210> SEQ ID NO 310
<211> LENGTH: 12

```
<212> TYPE: PRT
<213> ORGANISM: Artificial sequence
<220> FEATURE:
<223> OTHER INFORMATION: synthesized

<400> SEQUENCE: 310

Ser Ala Ser Ser Ser Ile Ser Ser Asn Phe Leu His
1               5                   10

<210> SEQ ID NO 311
<211> LENGTH: 7
<212> TYPE: PRT
<213> ORGANISM: Artificial sequence
<220> FEATURE:
<223> OTHER INFORMATION: synthesized

<400> SEQUENCE: 311

Arg Thr Ser Asn Leu Ala Ser
1               5

<210> SEQ ID NO 312
<211> LENGTH: 9
<212> TYPE: PRT
<213> ORGANISM: Artificial sequence
<220> FEATURE:
<223> OTHER INFORMATION: synthesized

<400> SEQUENCE: 312

Gln Gln Gly Ser Phe Met Pro Phe Thr
1               5

<210> SEQ ID NO 313
<211> LENGTH: 121
<212> TYPE: PRT
<213> ORGANISM: Artificial sequence
<220> FEATURE:
<223> OTHER INFORMATION: synthesized

<400> SEQUENCE: 313

Glu Val Lys Leu Val Glu Ser Gly Gly Gly Leu Val Gln Pro Gly Gly
1               5                   10                  15

Ser Leu Ser Leu Ser Cys Val Thr Ser Gly Phe Thr Phe Thr Asp Tyr
            20                  25                  30

Tyr Met Ser Trp Val Arg Gln Ser Pro Gly Lys Ala Leu Glu Trp Leu
        35                  40                  45

Gly Phe Ile Arg Asn Lys Ala Tyr Gly Asp Thr Thr Glu Tyr Ser Glu
    50                  55                  60

Ser Val Lys Gly Arg Phe Thr Ile Ser Arg Asp Asn Ser Gln Ser Ile
65                  70                  75                  80

Leu Tyr Leu His Met Asn Ala Leu Arg Ala Glu Asp Ser Ala Thr Tyr
                85                  90                  95

Tyr Cys Ala Arg Tyr Pro Arg Thr Gly Tyr Ala Leu Asp Tyr Trp Gly
            100                 105                 110

Gln Gly Thr Ser Val Thr Val Ser Ser
        115                 120

<210> SEQ ID NO 314
<211> LENGTH: 5
<212> TYPE: PRT
<213> ORGANISM: Artificial sequence
<220> FEATURE:
<223> OTHER INFORMATION: synthesized

<400> SEQUENCE: 314
```

-continued

```
Asp Tyr Tyr Met Ser
1               5

<210> SEQ ID NO 315
<211> LENGTH: 19
<212> TYPE: PRT
<213> ORGANISM: Artificial sequence
<220> FEATURE:
<223> OTHER INFORMATION: synthesized

<400> SEQUENCE: 315

Phe Ile Arg Asn Lys Ala Tyr Gly Asp Thr Thr Glu Tyr Ser Glu Ser
1               5                   10                  15

Val Lys Gly

<210> SEQ ID NO 316
<211> LENGTH: 10
<212> TYPE: PRT
<213> ORGANISM: Artificial sequence
<220> FEATURE:
<223> OTHER INFORMATION: synthesized

<400> SEQUENCE: 316

Tyr Pro Arg Thr Gly Tyr Ala Leu Asp Tyr
1               5                   10

<210> SEQ ID NO 317
<211> LENGTH: 112
<212> TYPE: PRT
<213> ORGANISM: Artificial sequence
<220> FEATURE:
<223> OTHER INFORMATION: synthesized

<400> SEQUENCE: 317

Asp Val Phe Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Pro Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Tyr Cys Phe Gln Val
                85                  90                  95

Ser His Val Pro Tyr Thr Phe Gly Gly Gly Thr Lys Leu Glu Ile Lys
            100                 105                 110

<210> SEQ ID NO 318
<211> LENGTH: 16
<212> TYPE: PRT
<213> ORGANISM: Artificial sequence
<220> FEATURE:
<223> OTHER INFORMATION: synthesized

<400> SEQUENCE: 318

Arg Ser Ser Gln Ser Ile Val His Ser Asn Gly Asn Thr Tyr Leu Glu
1               5                   10                  15

<210> SEQ ID NO 319
<211> LENGTH: 7
```

```
<212> TYPE: PRT
<213> ORGANISM: Artificial sequence
<220> FEATURE:
<223> OTHER INFORMATION: synthesized

<400> SEQUENCE: 319

Lys Val Ser Asn Arg Phe Pro
1               5

<210> SEQ ID NO 320
<211> LENGTH: 9
<212> TYPE: PRT
<213> ORGANISM: Artificial sequence
<220> FEATURE:
<223> OTHER INFORMATION: synthesized

<400> SEQUENCE: 320

Phe Gln Val Ser His Val Pro Tyr Thr
1               5

<210> SEQ ID NO 321
<211> LENGTH: 122
<212> TYPE: PRT
<213> ORGANISM: Artificial sequence
<220> FEATURE:
<223> OTHER INFORMATION: synthesized

<400> SEQUENCE: 321

Gln Val Thr Leu Lys Glu Ser Gly Pro Thr Leu Val Lys Pro Thr Gln
1               5                   10                  15

Thr Leu Thr Leu Ala Cys Ser Phe Ser Gly Phe Ser Leu Thr Thr Thr
            20                  25                  30

Gly Val Ala Val Thr Trp Ile Arg Gln Pro Pro Gly Lys Ala Leu Glu
        35                  40                  45

Trp Leu Ala Leu Ile Asp Trp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Ala Ser Gly Asp Ser Gly Gly Tyr Phe Ala Asp Trp
            100                 105                 110

Gly Gln Gly Thr Leu Val Thr Val Ser Ser
        115                 120

<210> SEQ ID NO 322
<211> LENGTH: 7
<212> TYPE: PRT
<213> ORGANISM: Artificial sequence
<220> FEATURE:
<223> OTHER INFORMATION: synthesized

<400> SEQUENCE: 322

Thr Thr Gly Val Ala Val Thr
1               5

<210> SEQ ID NO 323
<211> LENGTH: 16
<212> TYPE: PRT
<213> ORGANISM: Artificial sequence
<220> FEATURE:
<223> OTHER INFORMATION: synthesized

<400> SEQUENCE: 323
```

```
Leu Ile Asp Trp Asp Asp Asp Lys Tyr Tyr Ser Thr Ser Leu Lys Thr
1               5                   10                  15

<210> SEQ ID NO 324
<211> LENGTH: 12
<212> TYPE: PRT
<213> ORGANISM: Artificial sequence
<220> FEATURE:
<223> OTHER INFORMATION: synthesized

<400> SEQUENCE: 324

Ile Ala Ser Gly Asp Ser Gly Gly Tyr Phe Ala Asp
1               5                   10

<210> SEQ ID NO 325
<211> LENGTH: 108
<212> TYPE: PRT
<213> ORGANISM: Artificial sequence
<220> FEATURE:
<223> OTHER INFORMATION: synthesized

<400> SEQUENCE: 325

Ser Ser Glu Leu Thr Gln Ala Pro Ser Val Ser Val Ser Pro Gly Gln
1               5                   10                  15

Thr Ala Ser Ile Thr Cys Ser Gly Asp Lys Leu Asp Asp Lys Tyr Val
            20                  25                  30

Tyr Trp Tyr Gln Gln Lys Pro Gly Gln Pro Val Leu Val Ile Tyr
        35                  40                  45

Arg Asp Asn Lys Arg Pro Ser Gly Ile Pro Glu Arg Phe Ser Gly Ser
    50                  55                  60

Asn Ser Gly Asn Thr Ala Thr Leu Thr Ile Ser Ala Thr Gln Ala Leu
65                  70                  75                  80

Asp Glu Ala Asp Tyr Tyr Cys Gln Ala Trp Glu Ser Ser Asp Gln
                85                  90                  95

Tyr Val Phe Gly Thr Gly Thr Lys Val Thr Val Leu
            100                 105

<210> SEQ ID NO 326
<211> LENGTH: 11
<212> TYPE: PRT
<213> ORGANISM: Artificial sequence
<220> FEATURE:
<223> OTHER INFORMATION: synthesized

<400> SEQUENCE: 326

Ser Gly Asp Lys Leu Asp Asp Lys Tyr Val Tyr
1               5                   10

<210> SEQ ID NO 327
<211> LENGTH: 7
<212> TYPE: PRT
<213> ORGANISM: Artificial sequence
<220> FEATURE:
<223> OTHER INFORMATION: synthesized

<400> SEQUENCE: 327

Arg Asp Asn Lys Arg Pro Ser
1               5

<210> SEQ ID NO 328
<211> LENGTH: 11
<212> TYPE: PRT
<213> ORGANISM: Artificial sequence
```

<220> FEATURE:
<223> OTHER INFORMATION: synthesized

<400> SEQUENCE: 328

Gln Ala Trp Glu Ser Ser Asp Gln Tyr Val
1               5                   10

<210> SEQ ID NO 329
<211> LENGTH: 122
<212> TYPE: PRT
<213> ORGANISM: Artificial sequence
<220> FEATURE:
<223> OTHER INFORMATION: synthesized

<400> SEQUENCE: 329

Gln Val Gln Leu Gln Glu Ser Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Thr Arg Tyr Tyr Gly Ser Gly Ser Trp Ser Leu Phe Asp Tyr Trp
            100                 105                 110

Gly Gln Gly Thr Leu Val Thr Val Ser Ser
        115                 120

<210> SEQ ID NO 330
<211> LENGTH: 5
<212> TYPE: PRT
<213> ORGANISM: Artificial sequence
<220> FEATURE:
<223> OTHER INFORMATION: synthesized

<400> SEQUENCE: 330

Gly Tyr Tyr Trp Ser
1               5

<210> SEQ ID NO 331
<211> LENGTH: 16
<212> TYPE: PRT
<213> ORGANISM: Artificial sequence
<220> FEATURE:
<223> OTHER INFORMATION: synthesized

<400> SEQUENCE: 331

Glu Ile Asn His Ser Gly Ser Thr Asn Tyr Asn Pro Ser Leu Lys Ser
1               5                   10                  15

<210> SEQ ID NO 332
<211> LENGTH: 14
<212> TYPE: PRT
<213> ORGANISM: Artificial sequence
<220> FEATURE:
<223> OTHER INFORMATION: synthesized

<400> SEQUENCE: 332

Thr Arg Tyr Tyr Gly Ser Gly Ser Trp Ser Leu Phe Asp Tyr

<210> SEQ ID NO 333
<211> LENGTH: 110
<212> TYPE: PRT
<213> ORGANISM: Artificial sequence
<220> FEATURE:
<223> OTHER INFORMATION: synthesized

<400> SEQUENCE: 333

Gln Pro Val Leu Thr Gln Pro Pro Ser Ala Ser Gly Ala Pro Gly Gln
1               5                   10                  15
Thr Val Thr Ile Ser Cys Ser Gly Gly Asn Ser Asn Val Gly Thr Asn
            20                  25                  30
Thr Val Asn Trp Tyr Gln Gln Leu Pro Gly Thr Ala Pro Lys Leu Leu
        35                  40                  45
Ile Tyr Tyr Asp Asp Leu Leu Ala Ser Gly Val Ser Asp Arg Phe Ser
    50                  55                  60
Gly Ser Lys Ser Gly Thr Ser Ala Ser Leu Ala Ile Ser Gly Leu Gln
65                  70                  75                  80
Ala Glu Glu Ala Asp Tyr Tyr Cys Ala Ala Trp Asp Asp Thr Leu
                85                  90                  95
Asn Gly Trp Val Phe Gly Gly Gly Thr Lys Leu Thr Val Leu
            100                 105                 110

<210> SEQ ID NO 334
<211> LENGTH: 13
<212> TYPE: PRT
<213> ORGANISM: Artificial sequence
<220> FEATURE:
<223> OTHER INFORMATION: synthesized

<400> SEQUENCE: 334

Ser Gly Gly Asn Ser Asn Val Gly Thr Asn Thr Val Asn
1               5                   10

<210> SEQ ID NO 335
<211> LENGTH: 7
<212> TYPE: PRT
<213> ORGANISM: Artificial sequence
<220> FEATURE:
<223> OTHER INFORMATION: synthesized

<400> SEQUENCE: 335

Tyr Asp Asp Leu Leu Ala Ser
1               5

<210> SEQ ID NO 336
<211> LENGTH: 11
<212> TYPE: PRT
<213> ORGANISM: Artificial sequence
<220> FEATURE:
<223> OTHER INFORMATION: synthesized

<400> SEQUENCE: 336

Ala Ala Trp Asp Asp Thr Leu Asn Gly Trp Val
1               5                   10

<210> SEQ ID NO 337
<211> LENGTH: 354
<212> TYPE: DNA
<213> ORGANISM: Artificial sequence
<220> FEATURE:
<223> OTHER INFORMATION: synthesized

<400> SEQUENCE: 337

| gaggtgcagc tggtggagtc tgggggaggc ttagtgaagc ctggagggtc cctgaaactc | 60 |
| tcctgtgcag cctctggatt cactttcagt gactatggaa tgtactgggt tcgtcaggct | 120 |
| ccagagaagg ggctggaggg ggttgcatac attagtagtg gcagtagtac catctactct | 180 |
| gtagacaaag tgaagggccg attcaccatc tccagagaca atgccaagaa caccctgttc | 240 |
| ctgcaaatga ccagtctgag gtctgaggac acggccatgt attactgtgc aacgtggcta | 300 |
| ccgggaaatg ctatggacta ctggggtcaa ggaacctcag tcaccgtctc ctca | 354 |

<210> SEQ ID NO 338
<211> LENGTH: 321
<212> TYPE: DNA
<213> ORGANISM: Artificial sequence
<220> FEATURE:
<223> OTHER INFORMATION: synthesized

<400> SEQUENCE: 338

| gacatcttgc tgactcagtc tccagccatc ctgtctgtga gtccaggaca aagagtcagt | 60 |
| ttctcctgca gggccagtca gagcattggc acaagcatac actggtatca gcaaagaaca | 120 |
| aatggttctc caaggcttct cataaagtat gcttctgagt ctatctctgg gatcccttcc | 180 |
| aggtttagtg gcagtggatc aggacagat tttactctta gcatcaacag tgtggagtct | 240 |
| gaagatattg cagattatta ctgtcaacaa agtattaggt ggccgtacac attcggaggg | 300 |
| gggaccaagc tggaaataaa a | 321 |

<210> SEQ ID NO 339
<211> LENGTH: 354
<212> TYPE: DNA
<213> ORGANISM: Artificial sequence
<220> FEATURE:
<223> OTHER INFORMATION: synthesized

<400> SEQUENCE: 339

| caggttcagc tccagcagtc tggagctgag ctggtgaagc ctggggcctc agtgaagctt | 60 |
| tcctgcaagg ctactggcta cacattcact ggctactgga tagagtgggt aaagcagagg | 120 |
| cctggacatg gccttgagtg gattggagag atttttacctg gaagtggtag tactaagtac | 180 |
| aatgagaagt tcaaggacag gccacattc actgaagata tcctccaa cacagcctac | 240 |
| atgcaactca gcagcctgac aactgaggac tctgccatct attactgtgc aagagggggg | 300 |
| ttggacagtt tctttgacta ctggggccaa ggcaccactc tcacagtctc ctca | 354 |

<210> SEQ ID NO 340
<211> LENGTH: 336
<212> TYPE: DNA
<213> ORGANISM: Artificial sequence
<220> FEATURE:
<223> OTHER INFORMATION: synthesized

<400> SEQUENCE: 340

| gatgttttga tgacccaaac tccactctcc ctgcctgtca gtcttggaga tcaagcctcc | 60 |
| atctcttgca gatctagtca gatcattgta catagtaatg aaacaccta tttagaatgg | 120 |
| tacctgcaga aaccaggcca gtctccaaag ctcctgatct acaaggtttc aaccgatttt | 180 |
| tctggggtcc cagacaggtt cagtggcagt ggatcaggga cagatttcac actcaagatc | 240 |
| agcagagtgg aggctgagga tctgggagtt tattactgct ttcaaggttc atatgttccg | 300 | tggacgttcg gtggaggcac caaactggaa atcaaa         336

<210> SEQ ID NO 341
<211> LENGTH: 351
<212> TYPE: DNA
<213> ORGANISM: Artificial sequence
<220> FEATURE:
<223> OTHER INFORMATION: synthesized

<400> SEQUENCE: 341
gaggttcagc tgcagcagtc tgtggcagag cttgtgaggc caggggccac agtgaagttg    60
tcctgcacaa cttctggctt caacattcaa aacacctata tgcactgggt gaagcagagg   120
cctgaacagg gcctggagtg gattggaagg attgatcctg cgagtggtaa tactatatat   180
gccccgaagt tccagggcag ggccactatt actgcagaca catcctccaa cacagcctac   240
ctgcagctca gcagcctgac atctgaggac actgccatct attactgtgc tagaatggat   300
ggttactacg atccttactg gggccaaggg actctggtca ctgtctctgc a            351

<210> SEQ ID NO 342
<211> LENGTH: 321
<212> TYPE: DNA
<213> ORGANISM: Artificial sequence
<220> FEATURE:
<223> OTHER INFORMATION: synthesized

<400> SEQUENCE: 342
gacatcttgc tgactcagtc tccagccatc ctgtctgtga gtccaggaga aagagtcagt    60
ttctcctgca gggccagtca gagcactggc acaagcatac actggtatca gcaaagaaca   120
aatggttctc caaggcttct cataaagtat acttctgagt ctatttctgg gatcccttcc   180
aggtttagtg gcagtggatc aggacagat tttactctta ccatcaacag tgtggagtct   240
gaagatattg gagattatta ctgtcgacaa agtattagca ggccattcac gttcggctcg   300
gggacaaagt tggaaatgaa a                                              321

<210> SEQ ID NO 343
<211> LENGTH: 363
<212> TYPE: DNA
<213> ORGANISM: Artificial sequence
<220> FEATURE:
<223> OTHER INFORMATION: synthesized

<400> SEQUENCE: 343
gaggtgaagc tggtggagtc tgaggaggc ttggtacagc ctgggggttc tctgagtctc     60
tcctgtgcag cttctggatt caccttcact gattactaca tgagctgggt ccgccagcct   120
ccagggaagg cacttgagtg gttgggtttt attagaaaca aagctaatgg ttacacaaca   180
gagtgcagtg catctgtgaa gggtcgattc accatctcca gagataattc caaaacatc    240 ctctatcttc aaatgaatgc cctgagagct gaggacagtg ccacttatta ctgtgcaaca   300
tatgggagat tgggatatac tatggactac tggggtcaag gaacctcagt caccgtctcc   360
tca                                                                  363

<210> SEQ ID NO 344
<211> LENGTH: 336
<212> TYPE: DNA
<213> ORGANISM: Artificial sequence
<220> FEATURE:
<223> OTHER INFORMATION: synthesized

<400> SEQUENCE: 344

```
gatgttttga tgacccaaac tccactctcc ctgcctgtca gtcttggaga tcaagcctcc      60
atctcttgca gatctagtca gagcattgta catagtaatg gaaacaccta tttagaatgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240
aacagagtgg aggctgagga tctgggagtt tattactgct ttcaaggttc acatgttccg     300
tggacgttcg gtggaggcac caagctggaa atcaaa                               336
```

<210> SEQ ID NO 345  
<211> LENGTH: 354  
<212> TYPE: DNA  
<213> ORGANISM: Artificial sequence  
<220> FEATURE:  
<223> OTHER INFORMATION: synthesized

<400> SEQUENCE: 345

```
caggtccaac tgcagcagcc tggggctgag ctggtgaggc ctgggtcttc agtgaagctg      60
tcctgcaagg cttctggcca caccctcacc gggttctgga tgcattgggt gaggcagagg     120
cctataccag gccttgaatg gattggtaac attgacccct ctgatagtga aactcactac     180
aatcaaaagt tcgaggacaa ggccacattg actgtagaca aatcctccaa cacagcctac     240
atgctactca gcagcctgac atctgaggac tctgcggtct attactgtgc aagagagggg     300
gggaccgggt acttcgatgt ctggggcaca gggaccacgg tcaccgtctc ctca           354
```

<210> SEQ ID NO 346  
<211> LENGTH: 330  
<212> TYPE: DNA  
<213> ORGANISM: Artificial sequence  
<220> FEATURE:  
<223> OTHER INFORMATION: synthesized

<400> SEQUENCE: 346

```
gaatttgtgc tcacccagtc tccaaccacc ctggctgcat ctcccgggga aagatcact      60 atcacctgca gtgccagctc aagtataagt tccaattact tgcattggta tcagcagaag    120
ccaggattct cccctaaact cttgatttat aggacatcca atctggcttc tggagtccca    180
gctcgcttca gtggcagtgg gtctgggacc tcttactctc tcacaattgg caccatggag    240
gctgaagatg ttgccactta ctactgccag aagggtagta gtataccacg catgtacacg    300
ttcggagggg ggaccaagct ggaaataaaa                                      330
```

<210> SEQ ID NO 347  
<211> LENGTH: 360  
<212> TYPE: DNA  
<213> ORGANISM: Artificial sequence  
<220> FEATURE:  
<223> OTHER INFORMATION: synthesized

<400> SEQUENCE: 347

```
gatgtacagc ttcaggagtc aggacctggc ctcgtgaaac cttctcagtc tctgtctctc      60
acctgctctg tcactggcta ctccatcacc agtaattatt actggaactg gatccggcag     120
tttccaggaa acaaactgga gtggatgggc tacataagct acgatggtag caatgactac     180
aacccatctc tcaaaaatcg aatctccatc actcgtgaca catctaagaa ccagttttc     240 ctgaggttga attctgtgac tactgaggac acagccacat atttctgtgc aagagtgacc     300
tcaggctacc tgtactactt tgacaactgg ggccaaggca ccactctcac agtctcctca     360
```

<210> SEQ ID NO 348
<211> LENGTH: 315
<212> TYPE: DNA
<213> ORGANISM: Artificial sequence
<220> FEATURE:
<223> OTHER INFORMATION: synthesized

<400> SEQUENCE: 348

```
gaaattgtgc tcactcagtc tccagccatc acagctgcat ctctggggca aaaggtcacc      60
atcacctgca gtgccagttc aagtgtaagt tacatgcact ggtaccagca gaggtcaggc     120
acctccccca aaccatggat ttatgaaata tccaaactgg cttctggagt cccagctcgc     180
ttcagtggca gtgggtctgg gacctcttac tctctcacaa tcagcagcat ggaggctgaa     240
gatgctgcca tttattactg ccagcagtgg aattttccgc tcacgttcgg tgctgggacc     300
aagctggagc tgaaa                                                     315
```

<210> SEQ ID NO 349
<211> LENGTH: 366
<212> TYPE: DNA
<213> ORGANISM: Artificial sequence
<220> FEATURE:
<223> OTHER INFORMATION: synthesized

<400> SEQUENCE: 349

```
gacgtgaagc tggtggagtc tggggaagac ttagtgaagc ctggagggtc cctgaaagtc      60
tcctgtgcag cctctggatt cactttccgt gactatgcca tgtcttgggt tcgccagact     120
ccagagaaga ggctggagtg ggtcgcatac attagtagtg gtggtgatta tatctactat     180
gcagactctg tgaagggccg attcaccata tccagagaca atgccaggaa caccctatac     240
ctacaaatga ccagtctgag gtctgaggac acagccatgt atttctgtac aagagatccc     300
tccttctacg gcagaggata ttattttgac tattggggcc aaggcaccag tctcacagtc     360
tcctca                                                                366
```

<210> SEQ ID NO 350
<211> LENGTH: 318
<212> TYPE: DNA
<213> ORGANISM: Artificial sequence
<220> FEATURE:
<223> OTHER INFORMATION: synthesized

<400> SEQUENCE: 350

```
gacattgtga tgacccagtc tcacaaattc atgtccgcat cagtaggaga cagggtcagc      60
atcacctgca aggccagtca ggatgtgggt gctactgtag cctggtatca acagaaacca     120
gggcaatctc ctaaactact gatttactgg gcatccaccc ggcacactgg agtccctgat     180
cgcttcacag gcagtggatc tgggacagat ttcactctca ccattaacaa tgtgcagtct     240
gaagacttgg cagattattt ctgtcagcaa tatagcaact atccgacgtt cggtggaggc     300
accaagctgg aaatcaaa                                                  318
```

<210> SEQ ID NO 351
<211> LENGTH: 348
<212> TYPE: DNA
<213> ORGANISM: Artificial sequence
<220> FEATURE:
<223> OTHER INFORMATION: synthesized

<400> SEQUENCE: 351

```
gaggttcagc tgcagcagtc tgtggcagag cttgtgaggc caggggcctc agtcaagttg      60
```

```
tcctgcacag tttctggctt caacattaaa aacacctata tgcactgggt gaagcagagg    120
cctgaacagg gcctggaatg gattggaagg attgatcctg cgaatggtga tactaaatat    180
gacccgaagt tccaggccaa ggccactgta actgcagaca catcctccaa cacagcctac    240
ctgcatctca gtagcctgac atctgaggac actgccatct attactgtgt agaggatgat    300
tacggccttg ggtcctgggg ccaaggcacc actctcacag tttcctca                 348
```

<210> SEQ ID NO 352
<211> LENGTH: 321
<212> TYPE: DNA
<213> ORGANISM: Artificial sequence
<220> FEATURE:
<223> OTHER INFORMATION: synthesized

<400> SEQUENCE: 352

```
gacattgtga tgacccagtc tcaaaaattc atgtccacat cagttggaga cagggtcagc     60
gtcacctgca aggccagtca gaatgtgggt tctaatgtag cctggtatca acagaaacct    120
gggcaatctc ctaaatcact gatttacgcg acatctcacc gctacagtgg agtccctgat    180
cgcttcacag gcagtggatc tgggacagat ttcactctca ccatcagcaa tgtgcagtct    240
gaagacttgg cagagtattt ctgtcagcat tataacaact atccgtacac gttcggaggg    300
gggaccaagc tggaaataaa a                                              321
```

<210> SEQ ID NO 353
<211> LENGTH: 357
<212> TYPE: DNA
<213> ORGANISM: Artificial sequence
<220> FEATURE:
<223> OTHER INFORMATION: synthesized

<400> SEQUENCE: 353

```
gaggtccagc tgcaacaatc tggacctgta ctggtgaagc ctggggcttc agtgaagata     60
tcctgtaagg cttctggata cacgttcact gactactaca tgaactgggt gaagcagagc    120
catggaaaga gccttgagtg gattggagat attaatcctg acaatggttt tactagttac    180
aaccagaagt tcaagggcaa ggccacattg actgttgaca ggtcctccag cacagcctac    240
atggagttcc gcagcctgac atctgaggac tctgcagtct attactgtgc cagagacggt    300
agtagcgcct atggtatgga ctattggggt caaggaacct cagtcaccgt ctcctcc       357
```

<210> SEQ ID NO 354
<211> LENGTH: 333
<212> TYPE: DNA
<213> ORGANISM: Artificial sequence
<220> FEATURE:
<223> OTHER INFORMATION: synthesized

<400> SEQUENCE: 354

```
gacattgtgc tgacccagtc tccagcttct ttggctgtgt ctctagggca gagggccacc     60
atctcctgca gagccagtga aagtgtcagt attcatggta ctcatttaat gcactggtac    120
caacagaaac caggacagcc acccaaactc ctcatctatg ctgcatccaa cctagaatct    180
ggagtccctg ccaggttcag tggcagtggg tctgagacag acttcaccct caacatccat    240
actgtggagg aggaggatgc tgcaacctat ttctgtcagc aaagtattga ggaacctcgg    300
acgttcggtg gaggcaccaa ggtggaaatc aaa                                 333
```

<210> SEQ ID NO 355

```
<211> LENGTH: 354
<212> TYPE: DNA
<213> ORGANISM: Artificial sequence
<220> FEATURE:
<223> OTHER INFORMATION: synthesized

<400> SEQUENCE: 355
gaggttcaac tgcagcagtc tggacctgag ctggtgaagc ctggggcttc agtgaagata      60
tcctgcaagg cttctggtta ctcattcact ggctactaca tgcactgggt gaagcagagc     120
catggaaata tcctcgattg gattggatat atttatcctt acaatggtgt ttctacctac     180
aaccagagat tcaagggcaa ggccacattg actgtagaca gtcctctag cacagcctac      240 atggagctcc gcagcctgac atctgaggac tctgcagtct attactgtgc aaaggggget     300 agtggttacg acggtgacta ctggggccaa ggcaccactc tcacagtctc ctca           354

<210> SEQ ID NO 356
<211> LENGTH: 318
<212> TYPE: DNA
<213> ORGANISM: Artificial sequence
<220> FEATURE:
<223> OTHER INFORMATION: synthesized

<400> SEQUENCE: 356
caaattgttc tcacccagtc tccagcaatc atgtctgcat ctccagggga aaggtcacc       60 ataacctgca gtgccacctc agttgtaagt tacatgcact ggttccagca gaagccaggc     120
acttctccca aactctggat ttatctcaca tccaacctgg cttctggagt ccctgctcgc     180
ttcagtggca gtggatctgg gacctcttac tctctcacaa tcagccgaat ggaggctgaa     240
gatgctgcca cttattactg ccagcaaagg agtagttacc cacccacgtt cggagggggg     300
accaagctgg aaataaaa                                                    318

<210> SEQ ID NO 357
<211> LENGTH: 354
<212> TYPE: DNA
<213> ORGANISM: Artificial sequence
<220> FEATURE:
<223> OTHER INFORMATION: synthesized

<400> SEQUENCE: 357
caggttcagc tgcagcagtc tggagctgag ctgatgaagc ctggggcctc agtgaagctt      60
tcctgcaagg caactggcta cacattcact ggctactgga tagagtgggt aaagcagagg     120
cctggacatg gctttgagtg gattggagag atttttacctg gaagtggtac cactaaatac    180
aataagaagt tccagggcaa ggccacaatc actgcagata catcctccaa cacagcctac     240
atacaactca gtagcctgac aactgaggac tctgccatgt attactgtgc aagaggggga    300
caggaccact tctttgccga ctggggccaa ggcaccactc tcacagtctc ctca          354

<210> SEQ ID NO 358
<211> LENGTH: 336
<212> TYPE: DNA
<213> ORGANISM: Artificial sequence
<220> FEATURE:
<223> OTHER INFORMATION: synthesized

<400> SEQUENCE: 358
gatattttga tgacccaaag tccactctcc ctgcctgtca gtcttggaga tcaagcctcc      60
atctcttgca gatcaagtca gaccattgta catagtaatg gagacaccta tttagaatgg     120
tacctgcaga aaccaggcca gtctccaaag ctcctgatct acaaagtttc caaccgattt     180
```

| | | |
|---|---|---|
| tctggggtcc cagacaggtt cagtggcagt ggttcaggga cagatttcac actcaagatc | 240 |
| agcagagtgg aggctgagga tctgggaatt tattactgct ttcaaggttc atatgttccg | 300 |
| tggacgttcg gtggaggcac caggctggaa atcaaa | 336 |

<210> SEQ ID NO 359
<211> LENGTH: 363
<212> TYPE: DNA
<213> ORGANISM: Artificial sequence
<220> FEATURE:
<223> OTHER INFORMATION: synthesized

<400> SEQUENCE: 359

| | |
|---|---|
| gaggtgaagc tggaggagtc tggaggaggc ttggtacagc cggggggttc tctgagtctc | 60 |
| tcctgtgcag cttctggatt caccttcact gactactaca tgagctgggt ccgccagcct | 120 |
| ccagggaagg cacctgagtg gttgggtttt attagaaaca gagcttatgg ttacacaaca | 180 |
| gagtacagtg catctgtgaa gggtcggttc accttctcca gagataattc caaagcatc | 240 |
| ctctttcttc atatgaatgc cctgagacct gaggacagtg ccacttatta ctgtgcaaga | 300 |
| tatcctttat tagggtatgc tttggactac tggggtcaag gaacctcagt caccgtctcc | 360 |
| tca | 363 |

<210> SEQ ID NO 360
<211> LENGTH: 336
<212> TYPE: DNA
<213> ORGANISM: Artificial sequence
<220> FEATURE:
<223> OTHER INFORMATION: synthesized

<400> SEQUENCE: 360

| | |
|---|---|
| gatgtcttga tgacccaaac tccactctcc ctgcctgtca gtcttggaga tcaagcctcc | 60 |
| atctcttgca gatctagtca gagtattgta catagtaatg gaaacaccta tttagaatgg | 120 |
| tacctgcaga aaccaggcca gtctccaaag ctcctgatct acaaagtttc caaccgattt | 180 |
| tctggggtcc cagacaggtt cagtggcagt ggatcaggga cagatttcac actcaagatc | 240 |
| agcagagtgg aggctgagga tctgggaatt tattactgct ttcaagtttc acatgttccg | 300 |
| tggacgttcg gtggaggcac caagctggaa atcaaa | 336 |

<210> SEQ ID NO 361
<211> LENGTH: 351
<212> TYPE: DNA
<213> ORGANISM: Artificial sequence
<220> FEATURE:
<223> OTHER INFORMATION: synthesized

<400> SEQUENCE: 361

| | |
|---|---|
| gaggttcagc tgcagcagtc tggggctgag cttgtgaggc caggggcctc agtcaagttg | 60 |
| tcctgcacag cttctggctt taacattaaa gacgactata cactgggt gaagcagagg | 120 |
| cctgaacagg gcctggagtg gattggatgg attgatcctg cgaatggtca tattgaatat | 180 |
| gcctcgaact tccaggccaa ggccactatt acagcagaca catcctccaa cacagcctac | 240 |
| ctgcagctca gcagcctgac atctgaggac actgccgtct attactgtac tacggggat | 300 |
| tacgacgggt ttacttactg gggccaaggg actctggtca ctgtctctac a | 351 |

<210> SEQ ID NO 362
<211> LENGTH: 318
<212> TYPE: DNA

<213> ORGANISM: Artificial sequence
<220> FEATURE:
<223> OTHER INFORMATION: synthesized

<400> SEQUENCE: 362

```
caaattgttc tcacccagtc tccagcaatc atgtctgcat ctccagggga gaaggtcacc    60
atatcctgca gtgccaggtc aagtgtaagt tacatgtatt ggtaccagca gaagccagga   120
tcctccccca aaccctggat ttatcgaaca tccaacctgg cttctggagt ccctgctcgc   180
ttcagtggca gtgggtctgg gacctcttac tctctcacaa tcagcagcat ggaggctgaa   240
gatgctgcca cttattactg ccagcactat catacttacc cgtacacgtt cggggggggg   300
accaagctgg aaataaaa                                                  318
```

<210> SEQ ID NO 363
<211> LENGTH: 351
<212> TYPE: DNA
<213> ORGANISM: Artificial sequence
<220> FEATURE:
<223> OTHER INFORMATION: synthesized

<400> SEQUENCE: 363

```
gaggttcagc tgcagcagtc tggggctgag cttgtgaggc caggggcctc agtcaagttg    60
tcctgcacag cttctggctt aacattaaa gacgaatata tacactgggt gaaacagagg   120
cctgaacagg gcctggagtg gattggctgg attgatcctg cgaatggtca tactgaatat   180
gcctcgaggt tccaggccaa ggccactata acagcagaca catcctccaa cacagcctac   240
ttgcagctca gcagcctgac atctgaggac actgccgtct attactgtac tacggggat    300
tacgacgggt ttgcttactg gggccaaggg actctggtca ctgtctctac a            351
```

<210> SEQ ID NO 364
<211> LENGTH: 318
<212> TYPE: DNA
<213> ORGANISM: Artificial sequence
<220> FEATURE:
<223> OTHER INFORMATION: synthesized

<400> SEQUENCE: 364

```
caaattgttc tcacccagtc tccagcaatc atgtctgcat ctccagggga gaaggtcacc    60
atatcctgca gtgccaggtc aagtgtaagt tacatgtatt ggtaccagca gaagccagga   120
tcctccccca aaccctggat ttatcgcaca tccaacctgg cttctggagt ccctgctcgc   180
ttcagtggca gtgggtctgg gacctcttac tctctcacaa tcagcagcat ggaggctgaa   240
gatgctgcca cttattactg ccagcattat catacttacc cgtacacgtt cggaggggg   300
accaagctgg aaataaag                                                  318
```

<210> SEQ ID NO 365
<211> LENGTH: 357
<212> TYPE: DNA
<213> ORGANISM: Artificial sequence
<220> FEATURE:
<223> OTHER INFORMATION: synthesized

<400> SEQUENCE: 365

```
caggtccaac tgcagcagcc tggggctgag gtggtaaagc ctggggcttc agtgaagttg    60
tcctgcaagg cttctggcta cactgtcacc agctactgga tgcactgggt gaagcagagg   120
cctggacaag gccttgagtg gattggaatg attcatccta atggtattag tactaactac   180
aatgagaagt tcaagagcaa ggccacactg actggagaca aatcctccag cacagcctac   240
```

-continued

```
atgcaactca gcagcctgac atctgaggac tctgcggtct atttctgtgc aagagggggg    300
gatagtgact actactttga ctactggggc caaggcacca ctctcacagt ctcctca       357

<210> SEQ ID NO 366
<211> LENGTH: 318
<212> TYPE: DNA
<213> ORGANISM: Artificial sequence
<220> FEATURE:
<223> OTHER INFORMATION: synthesized

<400> SEQUENCE: 366
caaattgttc tcacccagtc tccagcaatc atgtctgcat ctccagggga aaaggtcacc    60
atgacctgca gtgccagctc aagtgtaagt tacatgtact ggtaccagca gaagccaggc   120
tcctccccca gactctggat ttatgacaca tccaacctgg tttctggagt ccctgctcgc   180
ttcagtggca gtaggtctgg gacctcttat tctctcacac tcagcagcat ggaggctgaa   240
gatgctgcca cttattactg ccagcagtac agtggttacc catacacgtt cggagggggg   300
accaagctgg aaataaaa                                                 318

<210> SEQ ID NO 367
<211> LENGTH: 366
<212> TYPE: DNA
<213> ORGANISM: Artificial sequence
<220> FEATURE:
<223> OTHER INFORMATION: synthesized

<400> SEQUENCE: 367
gagttccagc tgcagcagtc tggacctgag gtggtgaagc ctggcgcttc agtgaagata    60
tcctgcaagg cttctggtta ctcattcact gactacaaca tgaactggat gaagcagagc   120
aaaggaaaga gtcttgagtg gattggagta atcaatccta actatggcac tactacttac   180
aatcagaact tcaagggcaa ggccacattg actgtagacc aatcttccag cacagcctac   240
atgcagctca acagcctgac atctgaagac tctgcagtct attactgtgc aagagacatg   300
tactatgttt acgcttacta ctactatgga tactggggtc aaggaaccct cagtcaccgtc   360 tcctca                                                              366

<210> SEQ ID NO 368
<211> LENGTH: 336
<212> TYPE: DNA
<213> ORGANISM: Artificial sequence
<220> FEATURE:
<223> OTHER INFORMATION: synthesized

<400> SEQUENCE: 368
gatgttgtga tgacccaaac tccactctcc ctgcctgtca gtcttggaga tcaagcctcc    60
atctcttgca gatctagtca gagccttgta cacagtaatg gacacaccta tttacattgg   120
tacctgcaga ggccaggcca gtctccaacg ctcctgatct acaaagtttc caaccgattt   180
tctggggtcc cagacaggtt cagtggcagt ggatccggga cagatttcac actcaagatc   240
agcagagtgg aggctgagga tctgggagtt tatttctgct ctcaaggtac acatgttccg   300
tggacgttcg gtggaggcac caagctggaa atcaaa                             336

<210> SEQ ID NO 369
<211> LENGTH: 369
<212> TYPE: DNA
<213> ORGANISM: Artificial sequence
<220> FEATURE:
```

<223> OTHER INFORMATION: synthesized

<400> SEQUENCE: 369

| gaggtccagc tgcaacagtc tggacctgtg ctggtgaagc ctggggcttc agtgaagatg | 60 |
| tcctgtaagg cttctggata cacattcact gactattata tgaactgggt gaagcagagc | 120 |
| catggaaaga gccttgagtg gattggactt attaatcctt acagcggtgg tagtaccttc | 180 |
| aaccagaagt tcaaggccaa ggccacattg actgtcgaca gtcctccag ttcagcctac | 240 |
| atggacctca acagcctgac atctgaagac tctgcagtct attactgtgc aagagttgga | 300 |
| gatggttact acggggttac ccatggtatg gactattggg gtcaaggaac ctcagtcacc | 360 |
| gtctcctca | 369 |

<210> SEQ ID NO 370
<211> LENGTH: 321
<212> TYPE: DNA
<213> ORGANISM: Artificial sequence
<220> FEATURE:
<223> OTHER INFORMATION: synthesized

<400> SEQUENCE: 370

| gacattgtga tgacccegte tcaaaaattc atgtccacaa cagtaggaga cagggtcagc | 60 |
| atcacctgca aggccagtca aatgtgggt actgctgtag cctggtatca acagaaacca | 120 |
| ggacaatctc ccacaatact gatttactca gcatccaatc ggtatactgg agtccctgat | 180 |
| cgcttcacag gcagtggatc ggggacagat ttcactctca ccattagcaa tatgaagtct | 240 |
| gaagacctgg cagattattt ctgtcagcaa tactacatct atccgttcac gttcgctgct | 300 |
| gggaccaagc tggaactgaa a | 321 |

<210> SEQ ID NO 371
<211> LENGTH: 366
<212> TYPE: DNA
<213> ORGANISM: Artificial sequence
<220> FEATURE:
<223> OTHER INFORMATION: synthesized

<400> SEQUENCE: 371

| gagttccagc tgcagcagtc tggacctgag gtggtgaagc ctggcgcttc agtgaagata | 60 |
| tcctgcaagg cttctggtta ctcattcact gactacaaca tgaactggat gaaacagagc | 120 |
| aaaggaaaga gtcttgagtg gattggagta atcagtcctg actatggcac tactacttac | 180 |
| aatcagaact tcaaagacaa ggccacattg actgtggacc aatcttccag cacagcctac | 240 |
| atgcagctca acagcctgac atctgaagac tctgcagtct attactgtgc aaaagacatg | 300 |
| tactatgttt acgcttacta tactatggac tactggggtc acggaacctc agtcaccgtc | 360 |
| tcctca | 366 |

<210> SEQ ID NO 372
<211> LENGTH: 336
<212> TYPE: DNA
<213> ORGANISM: Artificial sequence
<220> FEATURE:
<223> OTHER INFORMATION: synthesized

<400> SEQUENCE: 372

| gatgttgtga tgacccaaac tccactctcc ctgcctgtca gtcttggaga tcaagcctcc | 60 |
| atctcttgca gatctagtca gagccttgta cacagtaatg gacacaccta tttacattgg | 120 |
| tacctgcaga ggccaggcca gtctccaacg ctcctgatct acaaagtatc caaccgattt | 180 |

<210> SEQ ID NO 373
<211> LENGTH: 369
<212> TYPE: DNA
<213> ORGANISM: Artificial sequence
<220> FEATURE:
<223> OTHER INFORMATION: synthesized

<400> SEQUENCE: 373

```
tctggggtcc cagacagggt cagtggcagt ggatccggga cagatttcac actcaagatc    240
agcagagtgg aggctgagga tctgggagtt tatttctgtt ctcaaggtac acatgttccg    300
aggacgttcg gtggaggcac caagctggaa atcaaa                              336
```

<210> SEQ ID NO 373
<211> LENGTH: 369
<212> TYPE: DNA
<213> ORGANISM: Artificial sequence
<220> FEATURE:
<223> OTHER INFORMATION: synthesized

<400> SEQUENCE: 373

```
caggttcagc tgcagcagtc tggagctgaa ctggcgaggc ctggggcttc agtgaagctg     60
tcctgcaagg cttctggcta caccttcaca gactatggta taagctgggt gaagcagaga    120
actggacagg gccttgagtg gattggagag atttatctta gaatgataa tagttactac    180
aatgaaaagt tcaagggcaa ggccacactg actgcagata aatcctccaa cacagcgtac    240
atggagctcc gcagtctgac atctgaggac tctgcggtct atttctgtgc gagatggggg    300
gaccatggta acaactacga ggatgctatg gactactggg gtcaaggaac ctcagtcacc    360
gtctcctca                                                            369
```

<210> SEQ ID NO 374
<211> LENGTH: 333
<212> TYPE: DNA
<213> ORGANISM: Artificial sequence
<220> FEATURE:
<223> OTHER INFORMATION: synthesized

<400> SEQUENCE: 374

```
gacattgtgc tgacccaatc tccagcttct ttggctatgt ctctagggaa gagggccacc     60
atctcctgca gagccagcga aagtgtcagt attattggtt ctaatttaat acactggtac    120
caacagaaac caggacagcc acccaaactc ctcatctatc atgcatccaa tctagaaact    180
ggagtccctg ccaggttcag tggcagtggg tctagaacag acttcaccct caccattgat    240
cctgtggagg aagatgatgt tgcaatctat tactgtctac aaagtaggaa ggttccgtac    300
acgttcggag gggggaccaa gctggaaata aaa                                 333
```

<210> SEQ ID NO 375
<211> LENGTH: 351
<212> TYPE: DNA
<213> ORGANISM: Artificial sequence
<220> FEATURE:
<223> OTHER INFORMATION: synthesized

<400> SEQUENCE: 375

```
gaggttcagc tgcagcagtc tggggctgag cttgtgaggc caggggcctc agtcaagttg     60
tcctgcacag cttctggctt taacattaaa gacgaatata cactgggt gaaacagagg      120
cctgaacagg gcctggagtg gattggctgg attgatcctg cgaatggtca tactgaatat    180
gcctcgaggt tccaggccaa ggccactata acagcagaca catcctccaa cacagcctac    240
ttgcagctca gcagcctgac atctgaggac actgccgtct attactgtac acggggggat    300
tacgacgggt tgtttattg gggccaaggg actctggtca ctgtctctac a              351
```

<210> SEQ ID NO 376
<211> LENGTH: 318
<212> TYPE: DNA

```
<213> ORGANISM: Artificial sequence
<220> FEATURE:
<223> OTHER INFORMATION: synthesized

<400> SEQUENCE: 376
caaattgtcc tcacccagtc gccagcaatc atgtctgcat ctccagggga gaaggtcacc      60
atattctgca gtgccaggtc aagtgtaagt tacatgtatt ggtaccaaca gaagccagga     120
tcctccccca aaccctggat ttatcgcaca tccaacctgg cttctggagt ccctgctcgc     180
ttcagtggca gtgggtctgg gacctcttac tctctcacaa tcagcagcat ggaggctgaa     240
gatgctgcca cttattactg ccagcattat catacttacc cgtacacgtt cggaggggggg     300 accaagctgg aaataaaa                                                   318

<210> SEQ ID NO 377
<211> LENGTH: 351
<212> TYPE: DNA
<213> ORGANISM: Artificial sequence
<220> FEATURE:
<223> OTHER INFORMATION: synthesized

<400> SEQUENCE: 377
caggtgcagc tgaaggagtc aggacctggc ctggtggcgc cctcacagag cctgtccatc      60
acttgcactg tctctggggtt ttcattatcc agctatggtg tagactgggt tcgccagcct    120
ccaggaaaag atctggaatg gctgggagta atatggggtg gtggaaccac aatttataat     180
tcagctctca tgtccagact gaacatcacc aaagacaact ccaagaacca agttttccta    240
aaaatgaaca gtctgcaaag tgatgacaca gccatgtact actgtgccaa gcggggatac    300
tatggttact ttgactactg gggccaaggc accactctca cagtctcctc a             351

<210> SEQ ID NO 378
<211> LENGTH: 318
<212> TYPE: DNA
<213> ORGANISM: Artificial sequence
<220> FEATURE:
<223> OTHER INFORMATION: synthesized

<400> SEQUENCE: 378
caaattgttc tcacccagtc tccagcaatc atgtctgctt ctccagggga gaaggtcacc      60
atgacctgca gtgccagctc aagtgtaagt tacatgtact ggtaccacca gaagccagga    120
tcctccccca gactcctgat ttatgacaca tccaatctgg cttttggagt ccctgttcgc    180
ttcagtggca gggggtctgg gacctcttac tctctcacaa tcagccgcat ggaggctgaa    240
gatgctgcca cttattactg ccagcagtgg agtagttacc cgctcacgtt cggagctggg    300
accaagctgg agctgaaa                                                  318

<210> SEQ ID NO 379
<211> LENGTH: 354
<212> TYPE: DNA
<213> ORGANISM: Artificial sequence
<220> FEATURE:
<223> OTHER INFORMATION: synthesized

<400> SEQUENCE: 379
gaagtgaagc tggtggagtc tgggggaggc ttagtgcagc ctggaagttc catgaaactc      60
tcctgcacag cctctggatt cactttcagt gactattaca tggcttgggt ccgccaggtt    120
ccagataagg gtctagaatg ggttgcaaac attaattatg atgggaataa ccctactat     180 gtggactcct tgaagagccg tttcatcatc tcgagagaca atgcaaagaa cattctatac    240
```
ctgcaaatga gcagtctgaa gtctgaggac acagccacgt attactgtgc aagagatatt    300
tctccggggt actttgacca ctggggccaa ggcaccactc tcacagtctc ctca           354

<210> SEQ ID NO 380
<211> LENGTH: 333
<212> TYPE: DNA
<213> ORGANISM: Artificial sequence
<220> FEATURE:
<223> OTHER INFORMATION: synthesized

<400> SEQUENCE: 380
gacattgtgc tgacccaatc tccagcttct ttggctgtgt ctctagggca gagggccacc    60
atctcctgca gagccagtga aagtgtcagt attcatggta ctcatttaat gcactggtac    120
caacagaaac caggacagcc acccaaactc ctcatctatg ctgcatccaa cctagaatct    180
ggagtccctg ccaggttcag tggcagtggg tctgagacag acttcaccct caacatccat    240
cctgtggagg aggaggatgc tgcaatctat ttctgtcagc aaagtattga ggatcctcac    300
acgttcggag gggggaccaa gctggaaata aaa                                 333

<210> SEQ ID NO 381
<211> LENGTH: 354
<212> TYPE: DNA
<213> ORGANISM: Artificial sequence
<220> FEATURE:
<223> OTHER INFORMATION: synthesized

<400> SEQUENCE: 381
gaagtgaagc tggtggagtc tggggaggc ttagtgcagc ctggaagttc catgaaactc     60
tcctgcacag cctctggatt cactttcagt gactattaca tggcttgggt ccgccaggtt    120
ccagataagg gtctagaatg ggttgcaaac attaattatg atgggaataa tccctactat    180
gtggactcct tgaagacccg tttcatcatc tcgagagaca tgcaaagaa cattctatac    240 ctgcaaatga gcagtctgaa gtctgaggac acagccacgt attactgtgc aagagatatt    300
tctccggggt attttgacca ctggggccaa ggcaccactc tcacagtctc ctca           354

<210> SEQ ID NO 382
<211> LENGTH: 333
<212> TYPE: DNA
<213> ORGANISM: Artificial sequence
<220> FEATURE:
<223> OTHER INFORMATION: synthesized

<400> SEQUENCE: 382
gacattgtgc tgacccaatc tccagcttct ttggctgtgt ctctagggca gagggccacc    60
atctcctgca gagccagtga aagtgtcagt attcatggta ctcatttaat gcactggtac    120
caacagaaac caggacagcc acccaaactc ctcatctatg ctgcatccaa cctagaatct    180
ggagtccctg ccaggttcag tggcagtggg tctgagacag acttcaccct caacatccat    240
cctgtggagg aggaggatgc tgcaatctat ttctgtcagc aaagtattga ggatcctcac    300
acgttcggag gggggaccaa gctggaaata aaa                                 333

<210> SEQ ID NO 383
<211> LENGTH: 351
<212> TYPE: DNA
<213> ORGANISM: Artificial sequence
<220> FEATURE:
<223> OTHER INFORMATION: synthesized

<400> SEQUENCE: 383

```
caagtgcagc tgaaggagtc aggacctggc ctggtggcgc cctcacagag cctgtccatc    60
acttgcactg tctctgggtt ttcattaatc agctatggtg tagactgggt tcgccagcct   120
ccaggaaagg gtctggagtg gctgggagtt atatggggtt ttggaatcac aaaatataat   180
tcagctctca tgtccagact gagtatcagc aaagacaact ccaagagcca agttttctta   240
aaaatgaaca gtctgcaaac tgatgacaca gccatgtact actgtgccaa acggggatac   300
tatggttatt ttgactactg gggccagggc actactctca cagtctcctc a            351
```

<210> SEQ ID NO 384
<211> LENGTH: 318
<212> TYPE: DNA
<213> ORGANISM: Artificial sequence
<220> FEATURE:
<223> OTHER INFORMATION: synthesized

<400> SEQUENCE: 384

```
caaattgttc tcacccagtc tccagctatc atgtctgcat ctccagggga gaaggtcacc    60
atgacctgca gtgccagctc aagtgtaagt tacatgtact ggtaccagca gaagccagga   120
gcctccccca gactcctgat ttatgacaca tccaacctgg cttctggagt ccctgttcgt   180
ttcagtggca gtgggtctgg gacctcttac tctctcacaa tcagccaaat ggagactgaa   240
gatgctgcca cgtattactg ccagcagtgg agtagttacc cgctcacgtt cggtgctggg   300
accaagctgg agctgaaa                                                 318
```

<210> SEQ ID NO 385
<211> LENGTH: 366
<212> TYPE: DNA
<213> ORGANISM: Artificial sequence
<220> FEATURE:
<223> OTHER INFORMATION: synthesized

<400> SEQUENCE: 385

```
caggtgcaac tgaaggagtc aggacctggc ctggtggcgc cctcacagag cctgtccatc    60
acttgcactg tctctgggtt ttcattaacc agctatggtg tagactgggt tcgccagcct   120
ccaggaaagg gtctggagtg gctgggagta atatggggtg gtggaaacac aaattataat   180
tcagctctca tgtccagact gagcatcagc aaagacaact ccaagagcca agttttctta   240
aaaatgaaca gtctacaaac tgatgacaca gccatgtact actgtgccaa atcccccgac   300
ttcgttagta gctattccta tgctatggac tactggggtc aaggaacctc cgtcaccgtc   360
tcctca                                                              366
```

<210> SEQ ID NO 386
<211> LENGTH: 336
<212> TYPE: DNA
<213> ORGANISM: Artificial sequence
<220> FEATURE:
<223> OTHER INFORMATION: synthesized

<400> SEQUENCE: 386

```
gatgttttga tgacccaaac tccactctcc ctgcctgtca gtcttggaga tcaagcctcc    60
atctcttgca gatctagtca gagaattgta catagtaatg gaaacaccta tttacaatgg   120
tacctgcaga aaccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tattactgct ttcaaagttc atatgttcct   300
```
ccgacgttcg gtggaggcac caagctggaa atcaaa                                 336

<210> SEQ ID NO 387
<211> LENGTH: 351
<212> TYPE: DNA
<213> ORGANISM: Artificial sequence
<220> FEATURE:
<223> OTHER INFORMATION: synthesized

<400> SEQUENCE: 387
caggtacacc tgaaggagtc aggacctggc ctggtggcgc cctcacagaa cctgtccatc        60
acttgcactg tctctgggtt ttcattaacc agctatggtg tggactgggt ccgccagcct       120
ccaggaaagg gtctggagtg gctgggagta acatggggtg gtggaaatac aaaatataat       180
tcagctctca tgtccagact gcacatcagc aaagacaact ccaagagcca agttttctta       240
aaaatgaaca gtctgcaaac tgatgacaca gccgtatact actgtgccaa acggggtac       300 tatggttact ttgactactg gggccaaggc gccactctca cagtctcctc a                351

<210> SEQ ID NO 388
<211> LENGTH: 318
<212> TYPE: DNA
<213> ORGANISM: Artificial sequence
<220> FEATURE:
<223> OTHER INFORMATION: synthesized

<400> SEQUENCE: 388
caaattgttc tcacccagtc tccagcaatc atgtctgcat ctccagggga gaaggtcacc        60
atgacctgca gtgccagctc aagtgtaagt tacatgtact ggtaccagca gaagcccgga       120
tcctccccca gactcctgat ttatgacaca tccaacctgg cttctggagt ccctgttcgc       180
ttcggtggca gtggatctgg gacctcttac tctctcacaa tcttccgaat ggaggctgaa       240
gatgctgcca cttattactg ccagcagtgg agtagttacc cgctcacgtt cggtgctggg       300
accaagctgg agctgaaa                                                      318

<210> SEQ ID NO 389
<211> LENGTH: 366
<212> TYPE: DNA
<213> ORGANISM: Artificial sequence
<220> FEATURE:
<223> OTHER INFORMATION: synthesized

<400> SEQUENCE: 389
caggtgcaac tgaaggagtc aggacctggc ctggtggcgc cctcacagag cctgtccatc        60
acttgcactg tctctgggtt ttcattaacc agctatggtg tagactgggt tcgccagcct       120
ccaggaaagg gtctggagtg gctgggagta atatggggtg gtggaagcac aaattataat       180
tcagctctca tgtccagact gagcatcagc aaagacaact ccaagagcca aattttctta       240
aaaatgaaca gtctgcaaac tgatgacaca gccatgtact actgtgccaa atcccccgac       300
ttcgttagta gctattccta tgctatggac tactggggtc aaggaacctc cgtcaccgtc       360
tcctca                                                                    366

<210> SEQ ID NO 390
<211> LENGTH: 336
<212> TYPE: DNA
<213> ORGANISM: Artificial sequence
<220> FEATURE:
<223> OTHER INFORMATION: synthesized

<400> SEQUENCE: 390

```
gatgttttga tgacccaaac tccactctcc ctgcctgtca gtcttggaga tcaagcctcc    60
atctcttgca gatctagtca gagaattgta catagtaatg gaaacaccta tttacaatgg   120
tacctgcaga aaccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tattactgct ttcaaagttc atatgttcct   300
ccgacgttcg gtggaggcac caagctggaa atcaaa                             336
```

<210> SEQ ID NO 391
<211> LENGTH: 366
<212> TYPE: DNA
<213> ORGANISM: Artificial sequence
<220> FEATURE:
<223> OTHER INFORMATION: synthesized

<400> SEQUENCE: 391

```
gaggtccagc tgcaacagtc tggacctgag ctggtgaagc ctggggcttc agtgaagata    60
ccctgcaagg cttctggata cacattcact gactacaaca tggactgggt gaagcagagc   120
catggaaaga gccttgagtg gattggagat attaatccta caatggtgg tactatctac    180
aaccagaagt tcaagggcaa ggccacattg actgtagaca gtccgccag cacagcctac    240
atggagctcc gcagcctgac atctgaggac actgcagtct attactgtgc aagatcctca   300
atctactatg attacgacgg agggtttgct tactggggcc aagggactct ggtcactgtc   360
tctgca                                                              366
```

<210> SEQ ID NO 392
<211> LENGTH: 321
<212> TYPE: DNA
<213> ORGANISM: Artificial sequence
<220> FEATURE:
<223> OTHER INFORMATION: synthesized

<400> SEQUENCE: 392

```
gacatccaga tgactcagtc tccagcctcc ctatctgcat ctgtgggaga aactgtcacc    60
atcacatgtc gagcaagtgg gaatattcac aattatttag catggtatca gcagaaacag   120
ggaaaatctc ctcagctcct ggtctataat gcaaaaacct tagcagatgg tgtgccatca   180
aggttcagtg gcagtggatc aggaacacaa tattctctca gatcaacag cctgcagcct   240
gaagattttg ggacttatta ctgtcaacat ttttggagta ttccattcac gttcggctcg   300
gggacaaagt tggaaataaa a                                             321
```

<210> SEQ ID NO 393
<211> LENGTH: 345
<212> TYPE: DNA
<213> ORGANISM: Artificial sequence
<220> FEATURE:
<223> OTHER INFORMATION: synthesized

<400> SEQUENCE: 393

```
cagattcagc tgcagcagtc tggggctgag ctggtgaagc ctgggacctc agtgcagatt    60
tcctgcaaag cttctgaata cgatttcagt cgctactgga tgaactgggt gaaacacagg   120
cctggagagg gtcttgaatg gattggacag atttatcctg agatggtga cattaattac   180
aacgaaaagt tcgaggccaa ggccacactg actgcagaca atcctccag cacagccttc   240
atgcagctca gcggcctgac ctctgaggac tctgcggtct atttctgtgc aagagggatt   300
```

```
gctatggact actggggtca gggaacctca gtcaccgtct cctca          345
```

<210> SEQ ID NO 394
<211> LENGTH: 321
<212> TYPE: DNA
<213> ORGANISM: Artificial sequence
<220> FEATURE:
<223> OTHER INFORMATION: synthesized

<400> SEQUENCE: 394

```
gatatccaga tgacacagag tacatcctcc ctgactgcct ctctgggaga cagagtcacc    60
atcagttgca gggcaagtca ggacgttagt aattatctaa actggcatca gcagaaacca   120
gatggaactg ttaaactcct gatctactac acatcaagat tacagtcagg agtcccatca   180
aggttcagtg gcagtgggtc tggaacagat tattctctca ccattagcaa cctgaacaa   240
gaagatattg ccacttactt ttgccaacag ggtaatacgc ttccgtggac gttcggtgga   300
ggcaccaagc tggaaatcaa a                                             321
```

<210> SEQ ID NO 395
<211> LENGTH: 360
<212> TYPE: DNA
<213> ORGANISM: Artificial sequence
<220> FEATURE:
<223> OTHER INFORMATION: synthesized

<400> SEQUENCE: 395

```
gaagtgatgc tggtggagtc tgggggaggc ttagtgaagc ctggagggtc cctgaaactc    60
tcctgtgcag cctctggatt cactttcagt agctatacca tgtcttgggt tcgccagact   120
ccggagaaga ggctggagtg gtcgcaacc attagtggtg gtggtgatta cacccactat   180
gcagacagtg tgaagggtcg attcaccatc tccagagaca atgccaagaa cacectgtac   240
ctgcaaatga acagtctgag gtctgaggac acggccttat attactgtgc aagacaaggt   300
ttttctacgg tagtaactac gggggactgg ggccaaggca ccactctcac agtctcctca   360
```

<210> SEQ ID NO 396
<211> LENGTH: 321
<212> TYPE: DNA
<213> ORGANISM: Artificial sequence
<220> FEATURE:
<223> OTHER INFORMATION: synthesized

<400> SEQUENCE: 396

```
gacattgtga tgacccagtc tcaaaaattc atgtccacaa cagtaggaga cagggtcagc    60
atcacctgca aggccagtca gagtgtgggt gctgctgtag cctggtatca acagaaacca   120
ggacaatctc ctaaactact gatttattca gcttccactc gttacactgg agtccctgat   180
cgcttcacag gcagtggatc tgggacagat ttcactctca atattaggag aatgcagtct   240
gaagacctgg cagagtattt ctgtcagcaa tataggagct atcctctcac gttcggctcg   300
gggacaaagt tggaaataaa a                                             321
```

<210> SEQ ID NO 397
<211> LENGTH: 354
<212> TYPE: DNA
<213> ORGANISM: Artificial sequence
<220> FEATURE:
<223> OTHER INFORMATION: synthesized

<400> SEQUENCE: 397

| | |
|---|---|
| caggttcaga tgcagcagtc tggagctgaa ctgatgaagc ctggggcctc agtgaaactt | 60 |
| tcctgtaagg ctaatggcta cacattcagt ggctactgga tagagtgggt aaagcagagg | 120 |
| cctggccatg gccttgagtg gattggagag atttttacctg gaagtgatag tcctaagtac | 180 |
| agtgcgaagt tcaagggcaa ggccacaatt actgcagata catcctccaa cacagcctac | 240 |
| atgcaactca gcagcctgac aactgaggac tctgccatct attactgtgc taaggggggt | 300 |
| aatacgtcct tctttgactt ctggggccaa ggcaccactc tcacagtctc ctca | 354 |

<210> SEQ ID NO 398
<211> LENGTH: 336
<212> TYPE: DNA
<213> ORGANISM: Artificial sequence
<220> FEATURE:
<223> OTHER INFORMATION: synthesized

<400> SEQUENCE: 398

| | |
|---|---|
| gatgttttga tgacccaaac tccactctcc ctgcctgtca gtcttggaga tcaagcctcc | 60 |
| atctcttgca gatctagtca gcgcattgta catagtaatg gaaacaccta tttagaatgg | 120 |
| tacctgcaga aaccaggcca gtctccaaag ctcctgatct acaaagtttc cacccgattt | 180 |
| tctggagtcc cagacaggtt cagtggcagt ggatcaggga cagatttcac actcaagatc | 240 |
| agcagagtgg aggctgagga tctggagagtt tattactgct ttcaaggttc atttgttccg | 300 |
| tggacgttcg gtggaggcac caagctggaa attaaa | 336 |

<210> SEQ ID NO 399
<211> LENGTH: 360
<212> TYPE: DNA
<213> ORGANISM: Artificial sequence
<220> FEATURE:
<223> OTHER INFORMATION: synthesized

<400> SEQUENCE: 399

| | |
|---|---|
| gaagtgatgc tggtggagtc tgggggaggc ttagtgaagc ctggagggtc cctgaaactc | 60 |
| tcctgtgcag cctctggatt cactttttagt agttatacca tgtcttgggt tcgccagact | 120 |
| ccggagaaga ggctggagtg ggtcgcaacc attagtggtg gtggtgatta cacccactat | 180 |
| ccagacagtg tgaagggtcg attcaccatc tccagagaca atgccaagga cacccctgtac | 240 |
| ctgcaaatga acagtctgag gtctgaggac acggccttat attactgtgc aagacaaggt | 300 |
| ttttctacgg tagtaatgac gggggactgg ggccaaggca ccactctcac agtttcctca | 360 |

<210> SEQ ID NO 400
<211> LENGTH: 321
<212> TYPE: DNA
<213> ORGANISM: Artificial sequence
<220> FEATURE:
<223> OTHER INFORMATION: synthesized

<400> SEQUENCE: 400

| | |
|---|---|
| gacattgtga tgacccagtc tcaaaaattc atgtccacaa cagtaggaga cagggtcagc | 60 |
| atcacctgca aggccagtca gagtgtgggt actgctgtag cctggtatca acagaaacca | 120 |
| ggacaatctc ctaacctact gatttactca gcttccactc gttacactgg agtccctgat | 180 |
| cgcttcacag gcagtgggtc tgggacagat ttcactctca atattaggaa tatgcagtct | 240 |
| gaagacctgg cagaatattt ctgtcaacaa tataggagct atcctctcac gttcggctcg | 300 |
| gggacaaagt tggaaataaa a | 321 |

<210> SEQ ID NO 401
<211> LENGTH: 360
<212> TYPE: DNA
<213> ORGANISM: Artificial sequence
<220> FEATURE:
<223> OTHER INFORMATION: synthesized

<400> SEQUENCE: 401

```
gaagtgatgc tggtggagtc tgggggaggc ttagtgaagc ctggagggtc cctgaaactc      60
tcctgtgaag cctctggatt cactttcaat acctatacca tgtcttggat tcgccagact     120
ccggagaaga ggctggagtg ggtcgcaacc attaatggtg gtggtactaa tgcctactat     180
ctagacagtg tgaagggtcg attcaccatc tccagagaca tgccaagaa cacccctgtac     240
ctgcaaatga gtagtctgag gtctgaagac acggccttgt attactgtgc acgacaaggt     300
tttactaccg ttgtacctac gggggactgg ggccaaggca ccactctcac agtctcctca     360
```

<210> SEQ ID NO 402
<211> LENGTH: 321
<212> TYPE: DNA
<213> ORGANISM: Artificial sequence
<220> FEATURE:
<223> OTHER INFORMATION: synthesized

<400> SEQUENCE: 402

```
gacattgtga tgacccagtc tcaaaaattc atgtcctcaa caataggaga cagggtcagc      60
atcacctgta aggccagtca gagtgtgggt gctgctattg cctggtatca acagaagcca     120
ggacaatctc ctaagttact gatttactca gcatccagtc ggtacactgg agtccctaat     180
cgcttcacag gcagtggatc tgggacagat ttcactctca ccattgacaa tgtgcagtct     240
gaagacctgt cagattatgt ctgtcagcaa tatcgcagct atcctctcac gttcggctcg     300
gggacaaaat tggaggtgag a                                                321
```

<210> SEQ ID NO 403
<211> LENGTH: 345
<212> TYPE: DNA
<213> ORGANISM: Artificial sequence
<220> FEATURE:
<223> OTHER INFORMATION: synthesized

<400> SEQUENCE: 403

```
cagattcagc tgcagcagtc tggggctgag ctggtgaagt ctgggacctc agtgaagatt      60
tcctgcaaag cttctgaata cgatttcagt cgctactgga tgaactgggt gaaacacagg     120
cctggagagg tcttgaatg gattggacag atttatcctg agatggtga cattaattac      180
aacggaaagt tcgaggccaa ggccacactg actgcagaca atcctccag cacagccttc      240
atgcagctca gcggcctgac ctctgaggac tctgcggtct atttctgtgc aagagggatt     300
gctatggact tctggggtca gggaacctca gtcaccgtct cctca                     345
```

<210> SEQ ID NO 404
<211> LENGTH: 321
<212> TYPE: DNA
<213> ORGANISM: Artificial sequence
<220> FEATURE:
<223> OTHER INFORMATION: synthesized

<400> SEQUENCE: 404

```
gatatccaga tgacacagag tacatcctcc ctgactgcct ctctgggaga cagagtcacc      60
atcagttgca gggcaagtca ggacgttagt aattatctaa actggcatca acagaaacca     120
```

```
gacggaactg ttaaactcct gatctactac acatcaagat tacagtcagg agtcccatca    180
aggttcagtg gcagtgggtc tggaacagat tattctctca ccattaccaa cctggagcaa    240
gaagatattg ccacttactt ttgccaacag gggaatacgc ttccgtggac gttcggtgga    300
ggcaccaagc tggaaatcat a                                              321

<210> SEQ ID NO 405
<211> LENGTH: 360
<212> TYPE: DNA
<213> ORGANISM: Artificial sequence
<220> FEATURE:
<223> OTHER INFORMATION: synthesized

<400> SEQUENCE: 405
caggttcagc tgcagcagtc tggacctgaa ctggtgaagc cggggcttc agtgaagttg      60 tcctgcaagg cttctggcta caccttcaca aactacgata taaactgggt gaagcagagg    120
cctggacagg gacttgagtg gattggatgg atttatcctg agatggtag tactaagtcc     180 aaagagaaat tcagggcaa ggccacattg actgtagata cttcctccag tacagcgtac     240
atggaactgc acagcctgac atctgaggac tctgcggtct atctctgtgc aagagactac    300
ggcaccccct actatgctat ggactactgg ggtcaaggaa cctcagtcac cgtctcctca    360

<210> SEQ ID NO 406
<211> LENGTH: 336
<212> TYPE: DNA
<213> ORGANISM: Artificial sequence
<220> FEATURE:
<223> OTHER INFORMATION: synthesized

<400> SEQUENCE: 406
gatgttttga tgacccaaac tccactctcc ctgcctgtca gtcttggaga tcaagcctcc     60
atctcttgca gatctagtca gagtattata cagagtaatg gaaacaccta tttagagtgg    120
tacctgcaga aaccaggcca gtctccaaag ctcctaatct acaaagtttc caaccgattt    180
tctggggtcc cagacaggtt cagtggcagt ggatcaggga cagatttcac actcaagatc    240
agcagagtgg aggctgagga tctgggagtt tattactgct ttcaaggttc atttgttccg    300
tggacgttcg gtggaggcac caacctggaa atcaaa                               336

<210> SEQ ID NO 407
<211> LENGTH: 369
<212> TYPE: DNA
<213> ORGANISM: Artificial sequence
<220> FEATURE:
<223> OTHER INFORMATION: synthesized

<400> SEQUENCE: 407
gaggtgcagc tggtggagtc tgggggagac ttagtgaagc ctggagggtc cctgaaactc      60
tcctgtgcag cctctggatt cactttcaat aacgatggca tgtcttgggt tcgccagact    120
ccagacaaga ggctgagtg ggtcgcaagc attagtagtg atggtagtta ctccttctat     180
ccagacaatg tgaaggggcg attcaccatc tccagagaca atgccaagaa caccctgtac    240
ctgcaaatga gcagtctgaa gtcagaggac acagccatgt attactgtgc aagtcagagg    300
ggttattatg gtaatagcct cgcctggttt gcttactggg gccaagggac tctggtcact    360
gtctctgca                                                             369

<210> SEQ ID NO 408
<211> LENGTH: 321
```

```
<212> TYPE: DNA
<213> ORGANISM: Artificial sequence
<220> FEATURE:
<223> OTHER INFORMATION: synthesized

<400> SEQUENCE: 408
gacatcttgc tgactcagtc tccagtcatc ctgtctgtga gtccaggaga aagagtcagt    60
ttctcctgca gggccagtca gagcattggc acaagcatac actggtatca gcaaagaaca   120
aatggttctc caaggcttct cataaagtat gcttctgagt ctatgtctgg gatcccttcc   180
aggtttagtg gcagtggctc aggacagat tttactctta gcatcaacag tgtggagtct   240
gaagatattg cagattattt ctgtcaacaa agtaaaacct ggccgctcac gttcggtgct   300
gggaccacgc tggagctgaa a                                            321

<210> SEQ ID NO 409
<211> LENGTH: 354
<212> TYPE: DNA
<213> ORGANISM: Artificial sequence
<220> FEATURE:
<223> OTHER INFORMATION: synthesized

<400> SEQUENCE: 409
gaggtgcact tggtggagtc tgggggaggc ttagtgaagc ctggagggtc cctgaaactc    60
tcctgtgcag cctctggatt cactttcagt gactatggaa tgcactgggt tcgtcaggct   120
ccagagaagg ggctggactg ggttgcatac attagtagtg gcggtactac catctactat   180
gcagacacag tgaagggccg attcaccatc tccagagaca tgccaagaa caccctcttc   240 ctgcaaatga ccactctggg gtctgacgac acggccatgt attcctgtgc aaggacccgt   300
cccggggatg ctatggacta ctggggtcaa ggaacctcag tcaccgtctc ctca        354

<210> SEQ ID NO 410
<211> LENGTH: 321
<212> TYPE: DNA
<213> ORGANISM: Artificial sequence
<220> FEATURE:
<223> OTHER INFORMATION: synthesized

<400> SEQUENCE: 410
gacatcttgc tgactcagtc tccagccatc ctgtctgtga gtccaggaga aagagtcagt    60
ttctcctgca gggccagtca gagcgctggc acaagcatac actggtatca gcaaagaaca   120
aatggttctc caaggcttct catcaagtat acgtctgagt ctatctctgg gatcccttcc   180
aggtttagtg gcagtggatc aggacagac tttactctta gcatcaacag tgtggagtct   240
gaagatattg cagattatta ctgtcaacaa agtcttaggt ggccattcac gttcggctcg   300
gggacaaggt tggaaataaa a                                            321

<210> SEQ ID NO 411
<211> LENGTH: 354
<212> TYPE: DNA
<213> ORGANISM: Artificial sequence
<220> FEATURE:
<223> OTHER INFORMATION: synthesized

<400> SEQUENCE: 411
caggtccaac tgcagcagcc tgaggctgag cttgtgaagc ctggggcttc agtgaagatg    60
tcctgcaagg cctctggcta caccttcccc aggtattgga taacctggat gagacagagg   120
cctggacaag gccttgaatg gattggagat attttttccta gtagtgagta tactcactac   180
```
aatgagaagt tcaggaggaa ggccactctg actgttgaca catcctccag tatagcctac    240
atacaactca gcagcctgac atctgaggac tctgcggtct attattgtgc aagagggaa     300 tatgacgcct ggtttgctta ctggggccaa gggactctgg tcactgtctc tgca          354

<210> SEQ ID NO 412
<211> LENGTH: 321
<212> TYPE: DNA
<213> ORGANISM: Artificial sequence
<220> FEATURE:
<223> OTHER INFORMATION: synthesized

<400> SEQUENCE: 412
gatatccaga tgacacagac cacatcctcc ctgtctgtct ctctgggaga cagagtcacc    60
atcagttgca gggcaagtca ggacattagt aattatttaa attggtatca gcagaaacca   120
gatggaactg ttaaactcct gatctactac acatcaagat tagactcagg agtcccatca   180
aggttcagtg gcagtgggtc tggaacagat tattctctca ccattagcaa cctggagcaa   240
gaagatcttg ccacttactt ttgccaacag ggtaatacgc ttcctccgac gttcggtgga   300
ggcaccaagc tggagatcag a                                             321

<210> SEQ ID NO 413
<211> LENGTH: 351
<212> TYPE: DNA
<213> ORGANISM: Artificial sequence
<220> FEATURE:
<223> OTHER INFORMATION: synthesized

<400> SEQUENCE: 413
gaggttcagc tgcagcagtc tggggctgag cttgtgaggc caggggcctc agtcaagttg    60
tcctgcacaa cttctggctt taacattaaa gacgagcata tgtattgggt gaagcagagg   120
cctgaacagg gcctggagtg gattgcatgg attgatcctg agaatgataa tactgaatat   180
gcctcgaagt tccagggcaa ggccactata acagcagaca catcctccaa cacagtctac   240
ctgcaactca gcaacctgac atctgaggac actgccgtct atttctgtac tacgggagat   300
tacgacgggt ttacttactg gggccaaggg actctggtca ctgtctctgc a            351

<210> SEQ ID NO 414
<211> LENGTH: 324
<212> TYPE: DNA
<213> ORGANISM: Artificial sequence
<220> FEATURE:
<223> OTHER INFORMATION: synthesized

<400> SEQUENCE: 414
gaaattgtgc tcacccagtc tccaaccacc atggctgcat ctcccgggga gaagatcact    60
atcacctgca gtgccagctc aagtataagt tccaatttct tgcattggtt tcagcagaag   120
ccaagattct cccctaaaact cttgatttat aggacatcca atctggcttc tggagtccca   180
gctcgcttca gtggcagtgg gtctgggacc tcttactctc tcacaattgg caccatggag   240
gctgaggatg ttgccactta ctactgccag cagggtagtt ttatgccgtt cacgttcggt   300
actgggacca aactggagct gaaa                                          324

<210> SEQ ID NO 415
<211> LENGTH: 363
<212> TYPE: DNA
<213> ORGANISM: Artificial sequence
<220> FEATURE:
<223> OTHER INFORMATION: synthesized

<400> SEQUENCE: 415

```
gaggtgaaat tggtggagtc tggaggagga ttggtacagc ctgggggttc gctgagtctc      60
tcctgtgtaa cttctggatt caccttcact gattactaca tgagctgggt ccgccagtct     120
ccagggaagg cacttgagtg gttgggtttt attagaaaca agcttatgg tgacacaaca      180 gagtacagtg aatctgtgaa gggtcggttc accatctcca gagataattc caaagcatc     240 ctctatcttc acatgaatgc cctgagagct gaagacagtg ccacttacta ctgcgcaaga    300
tatcctcgga caggctatgc tctggactac tggggtcaag aacctcagt caccgtctcc     360 tca                                                                  363
```

<210> SEQ ID NO 416
<211> LENGTH: 336
<212> TYPE: DNA
<213> ORGANISM: Artificial sequence
<220> FEATURE:
<223> OTHER INFORMATION: synthesized

<400> SEQUENCE: 416

```
gatgttttca tgacccaaac tccactctcc ctgcctgtca gtcttggaga tcaagcctcc      60
atctcttgca gatctagtca gagtattgtc catagtaatg gaaacaccta tttagaatgg    120
tacctgcaga aaccaggcca gtctccaaag ctcctgatct acaaagtttc caaccgattt    180
cctggggtcc cagacaggtt cagtggcagt ggatcaggga cagatttcac actcaagatc    240
aacagagtgg aggctgagga tctgggagtt tattactgct ttcaggtttc acatgttccg    300
tacacgttcg gaggggggac caagctggaa ataaaa                              336
```

<210> SEQ ID NO 417
<211> LENGTH: 366
<212> TYPE: DNA
<213> ORGANISM: Artificial sequence
<220> FEATURE:
<223> OTHER INFORMATION: synthesized

<400> SEQUENCE: 417

```
caggtcacct tgaaggagtc tggtcctacg ctggttaaac ccacacagac cctcacgctg      60
gcctgcagct ctctgggtt ctcactcacc actactgggg tggctgtgac ctggatccgc     120
cagcccccag ggaaggccct ggagtggctt gcactcattg attgggatga tgataaatac    180
tacagcacat ctctgaagac caggctcacc atctccaagg acacctccaa aaaccaggtg    240
gtccttacaa tgaccaacat ggaccctgtg gacacagcca catattactg tgcacgcatc    300
gcgagcggtg attccggagg ttactttgcc gactgggc agggaaccct ggtcaccgtc    360
tcctca                                                               366
```

<210> SEQ ID NO 418
<211> LENGTH: 324
<212> TYPE: DNA
<213> ORGANISM: Artificial sequence
<220> FEATURE:
<223> OTHER INFORMATION: synthesized

<400> SEQUENCE: 418

```
tcttctgagc tgactcaggc accctcagtg tccgtgtctc caggacagac agccagcatc      60
acctgttctg gagataagtt ggacgataaa tatgtttact ggtatcaaca gaagccaggc    120 cagcccccctg tcctggtcat ctatcgtgat aacaagcggc cctctgggat ccctgagaga    180
```

```
ttctctggct ccaactctgg gaacacagcc actctgacca tcagcgcgac ccaggctctg      240
gatgaggccg actattactg tcaggcgtgg gaaagtagta gtgatcagta tgtcttcgga      300
actgggacca aggtcaccgt ccta                                             324
```

<210> SEQ ID NO 419
<211> LENGTH: 366
<212> TYPE: DNA
<213> ORGANISM: Artificial sequence
<220> FEATURE:
<223> OTHER INFORMATION: synthesized

<400> SEQUENCE: 419

```
caggtgcaac tgcaggagtc gggcgcagga ctgttgaagc cttcggagac cctgtccctc       60
acctgcgctg tctatggtgg gtccttcagt ggttactact ggagctggat ccgccagccc      120
ccagggaagg ggctggagtg gattgggaa atcaatcata gtggaagcac caactacaac       180
ccgtccctca agagtcgagt caccatatca gtagacacgt ccaagaacca gttctccctg      240
aagctgagct ctgtgaccgc tgcggacacg gccgtgtatt actgtgcgag aacaagatac      300
tatggttcgg ggagctggtc gcttttttgac tactggggcc agggaaccct ggtcaccgtc     360
tcctca                                                                 366
```

<210> SEQ ID NO 420
<211> LENGTH: 330
<212> TYPE: DNA
<213> ORGANISM: Artificial sequence
<220> FEATURE:
<223> OTHER INFORMATION: synthesized

<400> SEQUENCE: 420

```
cagcctgtgc tgactcagcc accctcagcg tctggggccc ccggacagac agtcaccatc       60
tcttgttctg gaggcaactc caacgtcgga actaatactg tgaattggta tcagcaactc      120
ccaggaacgg ctcccaaact cctcatctat tatgatgatc tactggcctc aggggtctct      180
gaccgattct ctggctccaa gtctggcacc tcagcctccc tggccatcag tggactccag      240
gctgaggagg aggctgatta ttactgtgca gcatgggatg acaccctgaa tggttgggtg      300
ttcggcggag ggaccaagct gactgtccta                                       330
```

<210> SEQ ID NO 421
<211> LENGTH: 713
<212> TYPE: PRT
<213> ORGANISM: Artificial sequence
<220> FEATURE:
<223> OTHER INFORMATION: synthesized

<400> SEQUENCE: 421

Met Ala Phe Ala Pro Ile Pro Arg Ile Thr Trp Glu His Arg Glu Val
1               5                   10                  15

His Leu Val Gln Phe His Glu Pro Asp Ile Tyr Asn Tyr Ser Ala Leu
            20                  25                  30

Leu Leu Ser Glu Asp Lys Asp Thr Leu Tyr Ile Gly Ala Arg Glu Ala
        35                  40                  45

Val Phe Ala Val Asn Ala Leu Asn Ile Ser Glu Lys Gln His Glu Val
    50                  55                  60

Tyr Trp Lys Val Ser Glu Asp Lys Lys Ala Lys Cys Ala Glu Lys Gly
65                  70                  75                  80

Lys Ser Lys Gln Thr Glu Cys Leu Asn Tyr Ile Arg Val Leu Gln Pro
                85                  90                  95

```
Leu Ser Ala Thr Ser Leu Tyr Val Cys Gly Thr Asn Ala Phe Gln Pro
            100                 105                 110

Ala Cys Asp His Leu Asn Leu Thr Ser Phe Lys Phe Leu Gly Lys Asn
        115                 120                 125

Glu Asp Gly Lys Gly Arg Cys Pro Phe Asp Pro Ala His Ser Tyr Thr
    130                 135                 140

Ser Val Met Val Asp Gly Glu Leu Tyr Ser Gly Thr Ser Tyr Asn Phe
145                 150                 155                 160

Leu Gly Ser Glu Pro Ile Ile Ser Arg Asn Ser Ser His Ser Pro Leu
                165                 170                 175

Arg Thr Glu Tyr Ala Ile Pro Trp Leu Asn Glu Pro Ser Phe Val Phe
            180                 185                 190

Ala Asp Val Ile Arg Lys Ser Pro Asp Ser Pro Asp Gly Glu Asp Asp
        195                 200                 205

Arg Val Tyr Phe Phe Phe Thr Glu Val Ser Val Glu Tyr Glu Phe Val
    210                 215                 220

Phe Arg Val Leu Ile Pro Arg Ile Ala Arg Val Cys Lys Gly Asp Gln
225                 230                 235                 240

Gly Gly Leu Arg Thr Leu Gln Lys Lys Trp Thr Ser Phe Leu Lys Ala
                245                 250                 255

Arg Leu Ile Cys Ser Arg Pro Asp Ser Gly Leu Val Phe Asn Val Leu
            260                 265                 270

Arg Asp Val Phe Val Leu Arg Ser Pro Gly Leu Lys Val Pro Val Phe
        275                 280                 285

Tyr Ala Leu Phe Thr Pro Gln Leu Asn Asn Val Gly Leu Ser Ala Val
    290                 295                 300

Cys Ala Tyr Asn Leu Ser Thr Ala Glu Glu Val Phe Ser His Gly Lys
305                 310                 315                 320

Tyr Met Gln Ser Thr Thr Val Glu Gln Ser His Thr Lys Trp Val Arg
                325                 330                 335

Tyr Asn Gly Pro Val Pro Lys Pro Arg Pro Gly Ala Cys Ile Asp Ser
            340                 345                 350

Glu Ala Arg Ala Ala Asn Tyr Thr Ser Ser Leu Asn Leu Pro Asp Lys
        355                 360                 365

Thr Leu Gln Phe Val Lys Asp His Pro Leu Met Asp Asp Ser Val Thr
    370                 375                 380

Pro Ile Asp Asn Arg Pro Arg Leu Ile Lys Lys Asp Val Asn Tyr Thr
385                 390                 395                 400

Gln Ile Val Val Asp Arg Thr Gln Ala Leu Asp Gly Thr Val Tyr Asp
                405                 410                 415

Val Met Phe Val Ser Thr Asp Arg Gly Ala Leu His Lys Ala Ile Ser
            420                 425                 430

Leu Glu His Ala Val His Ile Ile Glu Glu Thr Gln Leu Phe Gln Asp
        435                 440                 445

Phe Glu Pro Val Gln Thr Leu Leu Leu Ser Ser Lys Lys Gly Asn Arg
    450                 455                 460

Phe Val Tyr Ala Gly Ser Asn Ser Gly Val Val Gln Ala Pro Leu Ala
465                 470                 475                 480

Phe Cys Gly Lys His Gly Thr Cys Glu Asp Cys Val Leu Ala Arg Asp
                485                 490                 495

Pro Tyr Cys Ala Trp Ser Pro Thr Ala Thr Cys Val Ala Leu His
            500                 505                 510
```

```
Gln Thr Glu Ser Pro Ser Arg Gly Leu Ile Gln Glu Met Ser Gly Asp
            515                 520                 525

Ala Ser Val Cys Pro Asp Lys Ser Lys Gly Ser Tyr Arg Gln His Phe
        530                 535                 540

Phe Lys His Gly Gly Thr Ala Glu Leu Lys Cys Ser Gln Lys Ser Asn
545                 550                 555                 560

Leu Ala Arg Val Phe Trp Lys Phe Gln Asn Gly Val Leu Lys Ala Glu
                565                 570                 575

Ser Pro Lys Tyr Gly Leu Met Gly Arg Lys Asn Leu Leu Ile Phe Asn
            580                 585                 590

Leu Ser Glu Gly Asp Ser Gly Val Tyr Gln Cys Leu Ser Glu Glu Arg
        595                 600                 605

Val Lys Asn Lys Thr Val Phe Gln Val Val Ala Lys His Val Leu Glu
    610                 615                 620

Val Lys Val Val Pro Lys Pro Val Val Ala Pro Thr Leu Ser Val Val
625                 630                 635                 640

Gln Thr Glu Gly Ser Arg Ile Ala Thr Lys Val Leu Val Ala Ser Thr
                645                 650                 655

Gln Gly Ser Ser Pro Thr Pro Ala Val Gln Ala Thr Ser Ser Gly
            660                 665                 670

Ala Ile Thr Leu Pro Pro Lys Pro Ala Pro Thr Gly Thr Ser Cys Glu
        675                 680                 685

Pro Lys Ile Val Ile Asn Thr Val Pro Gln Leu His Ser Glu Lys Thr
            690                 695                 700

Met Tyr Leu Lys Ser Ser Asp Asn Arg
705                 710

<210> SEQ ID NO 422
<211> LENGTH: 2589
<212> TYPE: DNA
<213> ORGANISM: Artificial sequence
<220> FEATURE:
<223> OTHER INFORMATION: synthesized

<400> SEQUENCE: 422
atgaggatgt gcaccccat  taggggctg  ctcatggccc  ttgcagtgat  gtttgggaca      60
gcgatggcat ttgcacccat accccggatc acctgggagc acagagaggt gcacctggtg     120
cagtttcatg agccagacat ctacaactac tcagccttgc tgctgagcga ggacaaggac     180
accttgtaca taggtgcccg ggaggcggtc ttcgctgtga acgcactcaa catctccgag     240
aagcagcatg aggtgtattg gaaggtctca gaagacaaaa agcaaaaatg tgcagaaaag     300
gggaaatcaa aacagacaga gtgcctcaac tacatccggg tgctgcagcc actcagcgcc     360
acttcccttt acgtgtgtgg gaccaacgca ttccagccgg cctgtgacca cctgaactta     420
acatccttta gtttctggga aaaatgaa  gatggcaaag  aagatgtcc  ctttgaccca     480 gcacacagct acatccgt  catggttgat ggagaacttt attcggggac gtcgtataat     540
tttttgggaa gtgaaccat  catctcccga aattcttccc acagtcctct gaggacagaa     600
tatgcaatcc cttggctgaa cgagcctagt ttcgtgtttg ctgacgtgat ccgaaaagc      660 ccagacagcc ccgacggtga ggatgacagg gtctacttct tcttcacgga ggtgtctgtg     720
gagtatgagt ttgtgttcag ggtgctgatc ccacggatag caagagtgtg caggggggac     780
cagggcggcc tgaggacctt gcagaagaaa tggaccctcct tcctgaaagc ccgactcatc     840
tgctcccggc cagacagcgg cttggtcttc aatgtgctgc gggatgtctt cgtgctcagg     900
```

```
tccccgggcc tgaaggtgcc tgtgttctat gcactcttca ccccacagct gaacaacgtg      960
gggctgtcgg cagtgtgcgc ctacaacctg tccacagccg aggaggtctt ctcccacggg     1020
aagtacatgc agagcaccac agtggagcag tcccacacca agtgggtgcg ctataatggc     1080
ccggtaccca agccgcggcc tggagcgtgc atcgacagcg aggcacgggc cgccaactac     1140
accagctcct tgaatttgcc agacaagacg ctgcagttcg ttaaagacca ccctttgatg     1200
gatgactcgg taaccccaat agacaacagg cccaggttaa tcaagaaaga tgtgaactac     1260
acccagatcg tggtggaccg gacccaggcc ctggatggga ctgtctatga tgtcatgttt     1320
gtcagcacag accggggagc tctgcacaaa gccatcagcc tcgagcacgc tgttcacatc     1380
atcgaggaga cccagctctt ccaggacttt gagccagtcc agaccctgct gctgtcttca     1440
aagaagggca acaggtttgt ctatgctggc tctaactcgg gcgtggtcca ggccccgctg     1500
gccttctgtg ggaagcacgg cacctgcgag gactgtgtgc tggcgcggga cccctactgc     1560
gcctggagcc cgcccacagc gacctgcgtg gctctgcacc agaccgagag ccccagcagg     1620
ggtttgattc aggagatgag cggcgatgct tctgtgtgcc cggataaaag taaggaagt      1680 taccggcagc attttttcaa gcacggtggc acagcggaac tgaaatgctc ccaaaaatcc     1740
aacctggccc gggtctttg gaagttccag aatggcgtgt gaaggccga gagccccaag      1800 tacggtctta tgggcagaaa aaacttgctc atcttcaact tgtcagaagg agacagtggg     1860
gtgtaccagt gcctgtcaga ggagagggtt aagaacaaaa cggtcttcca agtggtcgcc     1920
aagcacgtcc tggaagtgaa ggtggttcca agcccgtag tggcccccac cttgtcagtt     1980
gttcagacag aagtagtag gattgccacc aaagtgttgg tggcatccac ccaagggtct     2040
tctcccccaa ccccagccgt gcaggccacc tcctccgggg ccatcaccct tcctcccaag    2100
cctgcgccca ccggcacatc ctgcgaacca agatcgtca tcaacacggt cccccagctc      2160
cactcggaga aaaccatgta tcttaagtcc agcgacaacc gcctcctcat gtccctcttc     2220
ctcttcttct tgttctctt cctctgcctc tttttctaca actgctataa gggatacctg      2280
cccagacagt gcttgaaatt ccgctcggcc ctactaattg ggaagaagaa gcccaagtca     2340
gatttctgtg accgtgagca gagcctgaag gagacgttag tagagccagg gagcttctcc     2400
cagcagaatg gggagcaccc caagccagcc ctggacaccg gctatgagac cgagcaagac     2460
accatcacca gcaaagtccc cacggatagg gaggactcac agaggatcga cgacctttct     2520
gccagggaca agcccttga cgtcaagtgt gagctgaagt tcgctgactc agacgcagat     2580
ggagactga                                                            2589
```

```
<210> SEQ ID NO 423
<211> LENGTH: 50
<212> TYPE: DNA
<213> ORGANISM: Artificial sequence
<220> FEATURE:
<223> OTHER INFORMATION: synthesized

<400> SEQUENCE: 423
cttgtcgcga ttcttaaggg tgtccagtgc caggtcacct tgaaggagtc                  50

<210> SEQ ID NO 424
<211> LENGTH: 50
<212> TYPE: DNA
<213> ORGANISM: Artificial sequence
<220> FEATURE:
<223> OTHER INFORMATION: synthesized

<400> SEQUENCE: 424
```

-continued agggaacacg gaagggccct tggtgctagc tgaggagacg gtgaccaggg        50

<210> SEQ ID NO 425
<211> LENGTH: 50
<212> TYPE: DNA
<213> ORGANISM: Artificial sequence
<220> FEATURE:
<223> OTHER INFORMATION: synthesized

<400> SEQUENCE: 425
ctcctcctcc actgcacagg gtctctctcc tcttctgagc tgactcaggc        50

<210> SEQ ID NO 426
<211> LENGTH: 50
<212> TYPE: DNA
<213> ORGANISM: Artificial sequence
<220> FEATURE:
<223> OTHER INFORMATION: synthesized

<400> SEQUENCE: 426
agtgaccgag ggggcagcct tgggttgacc taggacggtg accttggtcc        50

<210> SEQ ID NO 427
<211> LENGTH: 50
<212> TYPE: DNA
<213> ORGANISM: Artificial sequence
<220> FEATURE:
<223> OTHER INFORMATION: synthesized

<400> SEQUENCE: 427
cttgtcgcga ttcttaaggg tgtccagtgc caggtgcaac tgcaggagtc        50

<210> SEQ ID NO 428
<211> LENGTH: 50
<212> TYPE: DNA
<213> ORGANISM: Artificial sequence
<220> FEATURE:
<223> OTHER INFORMATION: synthesized

<400> SEQUENCE: 428
ctcctcctcc actgcacagg gtctctctcc cagcctgtgc tgactcagcc        50

<210> SEQ ID NO 429
<211> LENGTH: 50
<212> TYPE: DNA
<213> ORGANISM: Artificial sequence
<220> FEATURE:
<223> OTHER INFORMATION: synthesized

<400> SEQUENCE: 429
agtgaccgag ggggcagcct tgggttgacc taggacagtc agcttggtcc        50

<210> SEQ ID NO 430
<211> LENGTH: 18
<212> TYPE: DNA
<213> ORGANISM: Artificial sequence
<220> FEATURE:
<223> OTHER INFORMATION: synthesized

<400> SEQUENCE: 430 gcccttttg agtttgga        18

<210> SEQ ID NO 431
<211> LENGTH: 18
<212> TYPE: DNA

```
<213> ORGANISM: Artificial sequence
<220> FEATURE:
<223> OTHER INFORMATION: synthesized

<400> SEQUENCE: 431
cactgcattc tagttgtg                                                   18

<210> SEQ ID NO 432
<211> LENGTH: 2589
<212> TYPE: DNA
<213> ORGANISM: Artificial sequence
<220> FEATURE:
<223> OTHER INFORMATION: synthesized

<400> SEQUENCE: 432
atgaggatgt gcatccctat taggggctg ctcatggccc ttgcagtgat gtttgggaca       60
gcgatggctt ttgcacccat accccggatc acctgggagc acagagaggt gcgcctggtg     120
cagtttcacg agccggacat ctacaactac tcagccttgc tgctgagcga ggacaaggac     180
accttgtaca taggcgcccg ggaggcggtc ttcgctgtga acgcactcaa catctccgag     240
aagcagcatg aggtgtattg gaaggtctca gaagacaaaa agcaaaatg tgcagaaaag     300 gggaaatcaa aacagacaga gtgcctcaac tacatccggg tgctgcagcc gctcagcgcc     360
acttcccttt acgtgtgtgg gaccaacgca ttccagccgg cctgtgacca cctgaactta     420
acatccttta gtttctggg gaaaaacgaa gatggcaaag gaagatgtcc ctttgaccca     480
gcgcacagct acacatccgt catggttgat ggagaacttt attcagggac gtcgtataat     540 ttttgggaa gtgaacccat catctcccga aattcttccc acagtcctct gaggacggaa     600
tacgcaatcc cttggctgaa cgagcctagt tttgtgtttg ccgacgtgat tcgaaaaagc     660
ccagacagcc ccgacggcga ggatgacagg gtctacttct tcttcacaga ggtgtctgtg     720
gagtacgagt ttgtgttcag ggtgctgatc ccacggatag caagagtgtg caaggggac     780 cagggcggcc tgaggacctt gcagaagaaa tggacctcct tcctgaaagc ccgactcatc     840 tgctccggc cagacagcag cttggtcttc aatgtgctgc gggacgtctt cgtgctcagg     900
tccccgggcc tgaaggtgcc tgtgttctac gcactcttca ccccacagct gaacaacgtg     960
gggctgtcgg cagtgtgcgc ctacaacctg tccacagccg aggaggtctt ctcccacggg    1020
aaatacatgc agagcgccac ggtggagcag tcccacacca gtgggtgcg ctacaacggc    1080 ccggtcccca gccgcggcc tggagcgtgc atcgacagtg aggcacgggc agccaactac    1140
accagctcct tgaatttgcc agacaagacg ctgcagttcg tcaaagacca cccttttgatg    1200 gatgactcgg tgaccccaat agacaacagg cccaggttaa tcaagaaaga gtgaactac    1260 acccagatcg tggtggaccg gacccaggcc ctggatggga ctgtctatga tgtcatgttt    1320
gtcagcacag accggggagc tctgcacaaa gccatcagcc tcgagcatgc tgttcacatc    1380
atcgaggaga cccagctctt ccaggacttt gagccggtcc agaccctgct gctgtcttca    1440
aagaagggca ggaggttcgt ctatgctggc tctaactcgg gcgtggtcca ggcccctctg    1500
gccttctgtg ggaagcacgg cacctgcgag gactgtgtgc tggctcggga ccctactgc    1560 gcctggagcc cacccacagc gacgtgtgtg gctctgtacc agactgagag ccccagcagg    1620
ggtttggttc aggagatgag cggcgatgct tctgtgtgcc cggataaaag taaggaagt    1680 taccggcagc attttttcaa gcacggtggc acagcggaac tgaaatgctc ccaaaagtcc    1740
aacctggccc gggtgttttg gaagttccag aatggcgtgt tgaaggctga gccccaag    1800 tacggtctta tgggcagaaa aaacttgctc atcttcaact tatcagaagg agacagtggg    1860
```

```
gtgtaccagt gcctgtcaga ggagagggtt aagaacaaga cggtcttcca agtagtcgcc    1920
aagcacgtcc tggaagtgaa ggtggttcca agcccgtgg tggcccccac cttgtcagtt    1980
gttcagacag aaggtagtag gattgccacc aaagtgttgg tggcatccac ccaagggtct    2040
tctcccccga ccccagccgt gcaggccacc tcctccgggg ccatcaccct tcctcccaag    2100
cctgtgccca ccagcacatc ctgtgaacca agattgtca tcaacacggt ccccagctc     2160 cactcggaga aaaccatgta tcttaagtcc agcgataacc gcctcctcat gtccctcttc    2220
ctcttcttct tgttctctt cctctgcctc ttttctaca actgctataa gggatacctg    2280
cccagacagt gcttgaaatt ccgctcggcc ctactaattg gaagaagaa gcccaagtca    2340 gatttctgtg accgtgagca gagcctgaag gagacgttag tagagccagg gagcttctcc    2400
cagcagaatg gggagcaccc caagccagcc ctggacaccg gctatgagac cgagcaagac    2460
accatcacca gcaaagtccc cacggatagg gaggactcac agaggatcga cgacctttct    2520
gccagggaca gcccctttga cgtcaagtgt gagctgaagt tcgctgactc agacgcagat    2580
ggagactga                                                           2589

<210> SEQ ID NO 433
<211> LENGTH: 2586
<212> TYPE: DNA
<213> ORGANISM: Artificial sequence
<220> FEATURE:
<223> OTHER INFORMATION: synthesized

<400> SEQUENCE: 433
atgaggatgt gtgccccgt taggggctg ttcttggccc tggtggtagt gttgagaacc    60
gcggtggcat ttgcacctgt gcctcggctc acctgggaac atggagaggt aggtctggtg    120
cagtttcaca agccaggcat cttaactac tcggccttgc tgatgagtga ggacaaagac    180
actctgtatg taggcgcccg ggaagcagtc tttgcagtga atgcgctgaa catctctgag    240
aagcaacatg aggtatattg gaaggtctct gaagacaaaa aatccaagtg tgcagagaag    300
gggaaatcaa agcagacgga atgcctaaac tacattcgag tactacagcc actaagcagc    360
acttccctct atgtgtgtgg gaccaatgcg ttccagccca cctgtgacca cctgaacttg    420
acatccttca gtttctggg gaaaagtgaa gatggcaaag gaagatgccc cttcgacccc    480
gcccacagct acacatcagt catggttggg ggcgagctct actctgggac gtcctataat    540
ttcttgggca gtgaaccat catctctcga aactcttccc acagtccctt gaggacggag    600
tatgccatcc cgtggctgaa cgagcctagc ttcgtctttg ctgacgtgat ccagaaaagc    660
ccagatggtc cggagggtga agatgacaag gtctacttct tttttacgga ggtatccgtg    720
gagtacgaat tcgtcttcaa gttgatgatc ccgcgagttg ccagggtgtg caagggcgac    780
cagggcggcc tgcggacttt gcaaaaaaag tggacctcct tcctaaaggc caggctgatc    840
tgctccaagc cagacagtgg cctggtcttc aacatacttc aggatgtgtt tgtgctgagg    900
gccccgggcc tcaaggagcc tgtgttctat gcggtcttca ccccacagct gaacaatgtg    960
ggtctgtcag cggtgtgcgc ctacacactg gccacggtgg aggcagtctt ctcccgtgga    1020
aagtacatgc agagtgccac agtggagcag tctcacacca gtgggtgcg ctacaatggc    1080 ccagtgccca ctccccgacc tggagcgtgt atcgacagtg aggcccgggc agccaactac    1140
accagctcct tgaatctccc agacaaaaca ctgcagtttg taaaagacca ccctttgatg    1200
gatgactcag tgacccgat agacaacaga cccaagctga tcaaaaaaga tgtaaactac    1260
```

| | |
|---|---|
| acccagatag tggtagacag gacccaggcc ctggatggga ctttctacga cgtcatgttc | 1320 |
| atcagcacag accggggagc tctgcataaa gcagtcatcc tcacaaaaga ggtgcatgtc | 1380 |
| atcgaggaga cccaactctt ccgggactct gaaccggtcc taactctgct gctatcgtca | 1440 |
| aagaagggga ggaagtttgt ctatgcaggc tccaactctg gagtggtcca agcgccctg | 1500 |
| gcattctgcg aaaagcacgg tagctgtgaa gactgtgtgt tagcacggga cccctactgt | 1560 |
| gcctggagcc cagccatcaa ggcctgtgtt accctgcacc aggaagaggc ctccagcagg | 1620 |
| ggctggattc aggacatgag cggtgacaca tcctcatgcc tggataagag taaagaaagt | 1680 |
| ttcaaccagc atttttcaa gcacggcggc acagcggaac tcaaatgttt ccaaaagtcc | 1740 |
| aacctagccc gggtggtatg gaagttccag aatggcgagt tgaaggccgc aagtcccaag | 1800 |
| tacggctttg tgggcaggaa gcacctgctc atcttcaacc tgtcggacgg agacagcggc | 1860 |
| gtgtaccagt gcctgtcaga ggaaagggtg aggaataaaa cggtctccca gctgctggcc | 1920 |
| aagcacgttc tggaagtgaa gatggtacct cggaccccc cctcacctac ctcagaggat | 1980 |
| gctcagacag aaggtagtaa gatcacatcc aaaatgccgg ttgcatctac ccaggggtcc | 2040 |
| tctcccccta cccggctct gtgggcaacc tcccccagag ccgccaccct acctcccaag | 2100 |
| tcctcctccg gcacatcctg tgaaccaaag atggtcatca acacggtccc ccagctccac | 2160 |
| tcagagaaga cggtgtatct caagtccagt gacaaccgcc tgctcatgtc tctcctcctc | 2220 |
| ttcatctttg tcctcttcct ctgcctcttt tcctacaact gctacaaggg ctacctgccc | 2280 |
| ggacagtgct taaaattccg ctcagccctg ctgcttggaa agaaaacacc caagtcagac | 2340 |
| ttctctgacc tggagcagag tgtgaaggag acactggtcg agcctgggag cttctcccag | 2400 |
| cagaacggcg accaccccaa gccagccctg gatacgggct atgaaacgga gcaggacacc | 2460 |
| atcaccagca aagtccccac ggatcgtgag gactcgcaac ggatcgatga actctctgcc | 2520 |
| cgggacaaac cgtttgatgt caagtgtgaa ctgaagtttg cagattcgga tgctgacggg | 2580 |
| gactga | 2586 |

<210> SEQ ID NO 434
<211> LENGTH: 6408
<212> TYPE: DNA
<213> ORGANISM: Artificial sequence
<220> FEATURE:
<223> OTHER INFORMATION: synthesized

<400> SEQUENCE: 434

| | |
|---|---|
| atgcctgctc tgggcccagc tcttctccag gctctctggg ccgggtgggt cctcacccctc | 60 |
| cagccccttc caccaactgc attcactccc aatggcacgt atctgcagca cctggcaagg | 120 |
| gaccccacct caggcaccct ctacctgggg gctaccaact tcctgttcca gctgagccct | 180 |
| gggctgcagc tggaggccac agtgtccacc ggccctgtgc tagacagcag ggactgcctg | 240 |
| ccacctgtga tgcctgatga gtgccccag gcccagccta ccaacaaccc gaatcagctg | 300 |
| ctcctggtga gccaggggc cctggtggta tgcgggagc tgcaccaggg ggtctgtgaa | 360 |
| cagcggcgcc tggggcagct cgagcagctg ctgctgcggc cagagcggcc tggggacaca | 420 |
| caatatgtgg ctgccaatga tcctgcggtc agcacggtgg ggctggtagc ccagggcttg | 480 |
| gcaggggagc cctcctgtt tgtggggcga ggatacacca gcagggtgt gggggtggc | 540 |
| attccaccca tcacaacccg ggccctgtgg ccgcccgacc ccaagctgc cttctcctat | 600 |
| gaggagacag ccaagctggc agtgggccgc ctctccgagt acagccacca cttcgtgagt | 660 |
| gcctttgcac gtgggggccag cgcctacttc ctgttcctgc ggcgggacct gcaggctcag | 720 |

```
tctagagctt tcgtgccta tgtatctcga gtgtgtctcc gggaccagca ctactactcc    780
tatgtggagt tgcctctggc ctgcgaaggt ggccgctacg ggctgatcca ggctgcagct    840
gtggccacgt ccagggaggt ggcgcatggg gaggtgctct ttgcagcttt ctcctcggct    900
gcacccccca ctgtgggccg gccccatcg cggctgctg gggcatctgg agcctctgcc    960
ctctgtgcct tccccctgga tgaggtggac cggcttgcta atcgcacgcg agatgcctgc   1020
tacacccggg agggtcgtgc tgaggatggg accgaggtgg cctacatcga gtatgatgtc   1080
aattctgact gtgcacagct gccagtggac accctggatg cttatccctg tggctcagac   1140
cacacgccca gccccatggc cagccgggtc ccgctggaag ccacaccaat tctggagtgg   1200
ccagggattc agctaacagc tgtggcagtc accatggaag atggacacac catcgctttc   1260
ctgggtgata tcaagggca gctgcacagg gtctacttgg gcccagggag cgatggccac   1320
ccatactcca cacagagcat ccagcagggg tctgcagtga gcagagacct cacctttgat   1380
gggacctttg agcacctgta tgtcatgacc cagagcacac ttctgaaggt tcctgtggct   1440
tcctgtgctc agcacctgga ctgtgcatct tgccttgctc acagggaccc atactgtggg   1500
tggtgcgtgc tccttggcag gtgcagtcgc cgttctgagt gctcgagggg ccagggccca   1560
gagcagtggc tatggagctt ccagcctgag ctgggctgtc tgcaagtggc agccatgagt   1620
cctgccaaca tcagccgaga ggagacgagg gaggttttcc tatcagtgcc agacctgcca   1680
cccctgtggc caggggagtc atattcctgc cactttgggg aacatcagag tcctgccctg   1740
ctgactggtt ctggtgtgat gtgccccctcc ccagaccta gtgaggcccc agtgctgccg   1800
agaggagccg actacgtatc cgtgagcgtg gagctcagat ttggcgctgt tgtgatcgcc   1860
aaaacttccc tctctttcta tgactgtgtg gcggtcactg aactccgccc atctgcgcag   1920
tgccaggcct gtgtgagcag ccgctggggg tgtaactggt gtgtctggca gcacctgtgc   1980
acccacaagg cctcgtgtga tgctgggccc atggttgcaa gccatcagag cccgcttgtc   2040
tccccagacc ctcctgcaag aggtggaccc agcccctccc cacccacagc ccccaaagcc   2100
ctggccaccc ctgctcctga caccttccc gtggagcctg ggctccctc cacagccaca   2160
gcttcggaca tctcacctgg ggctagtcct tccctgctca gccctgggg gccatgggca   2220
ggttctggct ccatatcttc ccctggctcc acagggtcgc ctctccatga ggagccctcc   2280
cctcccagcc cccaaaatgg acctggaacc gctgtccctg cccccactga cttcagaccc   2340
tcagccacac ctgaggacct cttggcctcc ccgctgtcac cgtcagaggt agcagcagtg   2400
cccccctgcag accctggccc cgaggctctt catcccacag tgcccctgga cctgccccct   2460
gccactgttc ctgccaccac tttcccaggg gccatgggct ccgtgaagcc cgccctggac   2520
tggctcacga gagaaggcgg cgagctgccc gaggcggacg agtggacggg gggtgacgca   2580
cccgccttct ccacttccac cctcctctca ggtgatggag actcagcaga gcttgagggc   2640
cctcccgccc ccctcatcct cccgtccagc ctcgactacc agtatgacac ccccgggctc   2700
tgggagctgg aagaggcgac cttggggggca agctcctgcc cctgtgtgga gagcgttcag   2760
ggctccacgt tgatgccggt ccatgtggag cgggaaatcc ggctgctagg caggaacctg   2820
caccttttcc aggatggccc aggagacaat gagtgtgtga tggagctgga gggcctcgag   2880
gtggtggttg aggcccgggt cgagtgtgag ccacctccag atacccagtg ccatgtcacc   2940
tgccagcagc accagctcag ctatgaggct ctgcagccgg agctccgtgt ggggctgttt   3000
ctgcgtcggg ccggccgtct gcgtgtggac agtgctgagg ggctgcatgt ggtactgtat   3060
```

-continued

```
gactgttccg tgggacatgg agactgcagc cgctgccaaa ctgccatgcc ccagtatggc    3120
tgtgtgtggt gtgaggggga gcgtccacgt tgtgtgaccc gggaggcctg tggtgaggct    3180
gaggctgtgg ccacccagtg cccagcgccc ctcatccact cggtggagcc actgactggg    3240
cctgtagacg gaggcacccg tgtcaccatc aggggctcca acctgggcca gcatgtgcag    3300
gatgtgctgg gcatggtcac ggtggctgga gtgccctgtg ctgtggatgc ccaggagtac    3360
gaggtctcca gcagcctcgt gtgcatcacc ggggccagtg ggaggaggt ggccggcgcc    3420 acagcggtgg aggtgccggg aagaggacgt ggtgtctcag aacacgactt tgcctaccag    3480
gatccgaagg tccattccat cttcccggcc cgcggcccca gagctggggg cacccgtctc    3540
accctgaatg gctccaagct cctgactggg cggctggagg acatccgagt ggtggttgga    3600
gaccagcctt gtcacttgct gccggagcag cagtcagaac aactgcggtg tgagaccagc    3660
ccacgcccca cgcctgccac gctccctgtg gctgtgtggt ttggggccac ggagcggagg    3720
cttcaacgcg gacagttcaa gtataccttg daccccaaca tcacctctgc tggccccacc    3780
aagagcttcc tcagtggagg acgtgagata tgcgtccgtg ccagaatct ggacgtggta    3840 cagacgccaa gaatccgggt gaccgtggtc tcgagaatgc tgcagcccag ccaggggctt    3900
ggacggaggc gtcgcgtggt cccggagacg gcatgttccc ttggaccctc ctgcagtagc    3960
cagcaatttg aggagccgtg ccatgtcaac tcctcccagc tcatcacgtg ccgcacacct    4020
gccctcccag gcctgcctga ggaccctggg gtccgggtgg aatttatcct tgacaacctg    4080
gtctttgact ttgcaacact gaaccccaca cctttctcct atgaggccga ccccaccctg    4140
cagccactca accctgagga ccccaccatg ccattccggc acaagcctgg gagtgtgttc    4200
tccgtggagg gggagaacct ggaccttgca atgtccaagg aggaggtggt ggctatgata    4260
ggggatggcc cctgtgtggt gaagacgctg acgcggcacc acctgtactg cgagcccccc    4320
gtggagcagc ccctgccacg gcaccatgcc ctccgagagg cacctgactc tttgcctgag    4380
ttcacggtgc agatggggaa cttgcgcttc tccctgggtc acgtgcagta tgacggcgag    4440
agccctgggg cttttcctgt ggcagcccag gtgggcttgg gggtgggcac ctctcttctg    4500
gctctgggtg tcatcatcat tgtcctcatg tacaggagga gagcaagca ggccctgagg    4560 gactataaga aggttcagat ccagctggag aatctggaga gcagtgtgcg ggaccgctgc    4620
aagaaggaat tcacagacct catgactgag atgaccgatc tcaccagtga cctcctgggc    4680
agcggcatcc ccttcctcga ctacaaggtg tatgcggaga ggatcttctt ccctgggcac    4740
cgcgagtcgc ccttgcaccg ggacctgggt gtgcctgaga gcagacggcc cactgtggag    4800
caagggctgg ggcagctctc taacctgctc aacagcaagc tcttcctcac caagttcatc    4860
cacacgctgg agagccagcg caccttttca gctcgggacc gtgcctacgt ggcatctctg    4920
ctcaccgtgg cactgcatgg gaagcttgag tatttcactg acatcctccg cactctgctc    4980
agtgacctgg ttgcccagta tgtggccaag aaccccaagc tgatgctgcg caggacagag    5040
actgtggtgg agaagctgct caccaactgg atgtccatct gtctgtatac cttcgtgagg    5100
gactccgtag gggagcctct gtacatgctc tttcgaggga ttaagcacca agtggataag    5160
gggccagtgg acagtgtgac aggcaaggcc aaatacacct tgaacgacaa ccgcctgctc    5220
agagaggatg tggagtaccg tccccctgacc ttgaatgcac tattggctgt ggggcctggg    5280
gcaggagagg cccagggcgt gccgtgaag gtcctagact gtgacaccat ctcccaggca    5340
aaggagaaga tgctggacca gctttataaa ggagtgcctc tcacccagcg gccagaccct    5400
cgcacccttg atgttgagtg gcggtctggg gtggccgggc acctcattct ttctgacgag    5460
```

-continued

```
gatgtcacttctgaggtccagggtctgtggaggcgcctgaacacactgcagcattacaag    5520 gtcccagatggagcaactgtggccctcgtcccctgcctcaccaagcatgtgctccgggaa    5580 aaccaggattatgtccctggagagcggaccccaatgctggaggatgtagatgagggggc    5640 atccggcctggcacctggtgaagccaagtgatgagccggagccgcccagcctcggagg    5700 ggcagccttcggggcggggagcgtgagcgcgccaaggccatccctgagatctacctgacc    5760 cgcctgctgtccatgaagggcaccctgcagaagttcgtggatgacctgttccaggtgatt    5820 ctcagcaccagccgccccgtgccgctcgctgtgaagtactctttgacctgctggatgag    5880 caggcccagcagcatggcatctccgaccagacaccatccacatctggaagaccaacagc    5940 ttgcctctgaggttctggatcaatataataaaaaacccgcagtttgtgttcgacgtgcaa    6000 acatctgataacatggatgcggtgctccttgtcattgcacagaccttcatggacgcctgc    6060 accctggccgaccacaagctgggccgggactccccgatcaacaaacttctgtatgcacgg    6120 gacattccccggtacaagcggatggtggaaaggtactatgcagacatcagacagactgtc    6180 ccagccagcgaccaagagatgaactctgtcctggctgaactgtcctggaactactccgga    6240 gacctcggggcgcgagtggccctgcatgaactctacaagtacatcaacaagtactatgac    6300 cagatcatcactgccctggaggaggatggcacggcccagaagatgcagctgggctatcgg    6360 ctccagcagattgcagctgctgtggaaaacaaggtcacagatctatag    6408
```

```
<210> SEQ ID NO 435
<211> LENGTH: 122
<212> TYPE: PRT
<213> ORGANISM: Artificial sequence
<220> FEATURE:
<223> OTHER INFORMATION: synthesized

<400> SEQUENCE: 435

Gln Val Gln Leu Gln Glu Ser Gly Ala Gly Leu Leu Lys Pro Ser Glu
1               5                  10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Thr Arg Tyr Tyr Gly Ser Gly Ser Trp Ser Leu Phe Asp Tyr Trp
            100                 105                 110

Gly Gln Gly Thr Leu Val Thr Val Ser Ser
        115                 120
```

```
<210> SEQ ID NO 436
<211> LENGTH: 16
<212> TYPE: PRT
<213> ORGANISM: Artificial sequence
<220> FEATURE:
<223> OTHER INFORMATION: synthesized

<400> SEQUENCE: 436

Glu Ile Asp His Ser Gly Ser Thr Asn Tyr Asn Pro Ser Leu Lys Ser
1               5                  10                  15
```

<210> SEQ ID NO 437
<211> LENGTH: 110
<212> TYPE: PRT
<213> ORGANISM: Artificial sequence
<220> FEATURE:
<223> OTHER INFORMATION: synthesized

<400> SEQUENCE: 437

```
Gln Pro Val Leu Thr Gln Pro Pro Ser Ala Ser Gly Ala Pro Gly Gln
1               5                   10                  15

Thr Val Thr Ile Ser Cys Ser Gly Gly Asn Ser Asn Val Gly Thr Asn
            20                  25                  30

Thr Val Asn Trp Tyr Gln Gln Leu Pro Gly Thr Ala Pro Lys Leu Leu
        35                  40                  45

Ile Tyr Tyr Asp Asp Leu Leu Ala Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ala Glu Glu Glu Ala Asp Tyr Tyr Cys Ala Ala Trp Asp Asp Thr Leu
                85                  90                  95

Ser Gly Trp Val Phe Gly Gly Gly Thr Lys Leu Thr Val Leu
            100                 105                 110
```

<210> SEQ ID NO 438
<211> LENGTH: 11
<212> TYPE: PRT
<213> ORGANISM: Artificial sequence
<220> FEATURE:
<223> OTHER INFORMATION: synthesized

<400> SEQUENCE: 438

```
Ala Ala Trp Asp Asp Thr Leu Ser Gly Trp Val
1               5                   10
```

<210> SEQ ID NO 439
<211> LENGTH: 122
<212> TYPE: PRT
<213> ORGANISM: Artificial sequence
<220> FEATURE:
<223> OTHER INFORMATION: synthesized

<400> SEQUENCE: 439

```
Gln Val Gln Leu Gln Glu Ser Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ala Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Thr Arg Tyr Tyr Gly Ser Gly Ser Trp Ser Leu Phe Asp Tyr Trp
            100                 105                 110

Gly Gln Gly Thr Leu Val Thr Val Ser Ser
            115                 120
```

<210> SEQ ID NO 440
<211> LENGTH: 16
<212> TYPE: PRT
<213> ORGANISM: Artificial sequence
<220> FEATURE:
<223> OTHER INFORMATION: synthesized

<400> SEQUENCE: 440

Glu Ile Asn His Ala Gly Ser Thr Asn Tyr Asn Pro Ser Leu Lys Ser
1               5                   10                  15

<210> SEQ ID NO 441
<211> LENGTH: 110
<212> TYPE: PRT
<213> ORGANISM: Artificial sequence
<220> FEATURE:
<223> OTHER INFORMATION: synthesized

<400> SEQUENCE: 441

Gln Pro Val Leu Thr Gln Pro Pro Ser Ala Ser Gly Ala Pro Gly Gln
1               5                   10                  15

Thr Val Thr Ile Ser Cys Ser Gly Gly Asn Ser Asn Val Gly Thr Asn
            20                  25                  30

Thr Val Asn Trp Tyr Gln Gln Leu Pro Gly Thr Ala Pro Lys Leu Leu
        35                  40                  45

Ile Tyr Tyr Asp Asp Leu Leu Ala Ser Gly Val Ser Asp Arg Phe Ser
50                  55                  60

Gly Ser Lys Ser Gly Thr Ser Ala Ser Leu Ala Ile Ser Gly Leu Gln
65                  70                  75                  80

Ala Glu Glu Glu Ala Asp Tyr Tyr Cys Ala Ala Trp Asp Asp Thr Leu
                85                  90                  95

Asn Ala Trp Val Phe Gly Gly Gly Thr Lys Leu Thr Val Leu
            100                 105                 110

<210> SEQ ID NO 442
<211> LENGTH: 11
<212> TYPE: PRT
<213> ORGANISM: Artificial sequence
<220> FEATURE:
<223> OTHER INFORMATION: synthesized

<400> SEQUENCE: 442

Ala Ala Trp Asp Asp Thr Leu Asn Ala Trp Val
1               5                   10

<210> SEQ ID NO 443
<211> LENGTH: 122
<212> TYPE: PRT
<213> ORGANISM: Artificial sequence
<220> FEATURE:
<223> OTHER INFORMATION: synthesized

<400> SEQUENCE: 443

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Thr Thr Thr
            20                  25                  30

Gly Val Ala Val Thr Trp Ile Arg Gln Pro Pro Gly Lys Ala Leu Glu
        35                  40                  45

Trp Leu Ala Leu Ile Asp Trp Asp Asp Asp Lys Tyr Tyr Ser Thr Ser
50                  55                  60

```
Leu Lys Thr Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Ile Ala Ser Gly Asp Ser Gly Gly Tyr Phe Ala Asp Trp
            100                 105                 110

Gly Gln Gly Thr Leu Val Thr Val Ser Ser
            115                 120
```

<210> SEQ ID NO 444
<211> LENGTH: 108
<212> TYPE: PRT
<213> ORGANISM: Artificial sequence
<220> FEATURE:
<223> OTHER INFORMATION: synthesized

<400> SEQUENCE: 444

```
Ser Tyr Glu Leu Thr Gln Pro Pro Ser Val Ser Val Ser Pro Gly Gln
  1               5                  10                  15

Thr Ala Ser Ile Thr Cys Ser Gly Asp Lys Leu Asp Asp Lys Tyr Val
                 20                  25                  30

Tyr Trp Tyr Gln Gln Lys Pro Gly Gln Ser Pro Val Leu Val Ile Tyr
             35                  40                  45

Arg Asp Asn Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Glu Ser Ser Ser Asp Gln
                 85                  90                  95

Tyr Val Phe Gly Thr Gly Thr Lys Val Thr Val Leu
            100                 105
```

<210> SEQ ID NO 445
<211> LENGTH: 110
<212> TYPE: PRT
<213> ORGANISM: Artificial sequence
<220> FEATURE:
<223> OTHER INFORMATION: synthesized

<400> SEQUENCE: 445

```
Gln Pro Val Leu Thr Gln Pro Pro Ser Ala Ser Gly Thr Pro Gly Gln
  1               5                  10                  15

Thr Val Thr Ile Ser Cys Ser Gly Gly Asn Ser Asn Val Gly Thr Asn
                 20                  25                  30

Thr Val Asn Trp Tyr Gln Gln Leu Pro Gly Thr Ala Pro Lys Leu Leu
             35                  40                  45

Ile Tyr Tyr Asp Asp Leu Leu Ala Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Glu Glu Ala Asp Tyr Tyr Cys Ala Ala Trp Asp Asp Thr Leu
                 85                  90                  95

Ser Gly Trp Val Phe Gly Gly Gly Thr Lys Leu Thr Val Leu
            100                 105                 110
```

<210> SEQ ID NO 446
<211> LENGTH: 122
<212> TYPE: PRT
<213> ORGANISM: Artificial sequence
<220> FEATURE:
<223> OTHER INFORMATION: synthesized

<400> SEQUENCE: 446

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Thr Thr Thr
            20                  25                  30

Gly Val Ala Val Thr Trp Ile Arg Gln Pro Pro Gly Lys Ala Leu Glu
        35                  40                  45

Trp Leu Ala Leu Ile Asp Trp Asp Asp Lys Tyr Tyr Ser Thr Ser
50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Ala Ser Gly Asp Ser Gly Gly Tyr Phe Ala Asp Trp
            100                 105                 110

Gly Gln Gly Thr Leu Val Thr Val Ser Ser
        115                 120

<210> SEQ ID NO 447
<211> LENGTH: 7
<212> TYPE: PRT
<213> ORGANISM: Artificial sequence
<220> FEATURE:
<223> OTHER INFORMATION: synthesized

<400> SEQUENCE: 447

Thr Thr Gly Val Ala Val Thr
1               5

<210> SEQ ID NO 448
<211> LENGTH: 16
<212> TYPE: PRT
<213> ORGANISM: Artificial sequence
<220> FEATURE:
<223> OTHER INFORMATION: synthesized

<400> SEQUENCE: 448

Leu Ile Asp Trp Asp Asp Asp Lys Tyr Tyr Ser Thr Ser Leu Lys Thr
1               5                   10                  15

<210> SEQ ID NO 449
<211> LENGTH: 12
<212> TYPE: PRT
<213> ORGANISM: Artificial sequence
<220> FEATURE:
<223> OTHER INFORMATION: synthesized

<400> SEQUENCE: 449

Ile Ala Ser Gly Asp Ser Gly Gly Tyr Phe Ala Asp
1               5                   10

<210> SEQ ID NO 450
<211> LENGTH: 108
<212> TYPE: PRT
<213> ORGANISM: Artificial sequence
<220> FEATURE:
<223> OTHER INFORMATION: synthesized

<400> SEQUENCE: 450

Ser Tyr Glu Leu Thr Gln Pro Pro Ser Val Ser Val Ser Pro Gly Gln

```
1               5                   10                  15
Thr Ala Ser Ile Thr Cys Ser Gly Asp Lys Leu Asp Asp Lys Tyr Val
            20                  25                  30

Tyr Trp Tyr Gln Gln Lys Pro Gly Gln Ser Pro Val Leu Val Ile Tyr
        35                  40                  45

Met Asp Asn Lys Arg Lys Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Glu Ser Ser Ser Asp Gln
                85                  90                  95

Tyr Val Phe Gly Thr Gly Thr Lys Val Thr Val Leu
            100                 105

<210> SEQ ID NO 451
<211> LENGTH: 11
<212> TYPE: PRT
<213> ORGANISM: Artificial sequence
<220> FEATURE:
<223> OTHER INFORMATION: synthesized

<400> SEQUENCE: 451

Ser Gly Asp Lys Leu Asp Asp Lys Tyr Val Tyr
1               5                   10

<210> SEQ ID NO 452
<211> LENGTH: 7
<212> TYPE: PRT
<213> ORGANISM: Artificial sequence
<220> FEATURE:
<223> OTHER INFORMATION: synthesized

<400> SEQUENCE: 452

Met Asp Asn Lys Arg Lys Ser
1               5

<210> SEQ ID NO 453
<211> LENGTH: 11
<212> TYPE: PRT
<213> ORGANISM: Artificial sequence
<220> FEATURE:
<223> OTHER INFORMATION: synthesized

<400> SEQUENCE: 453

Gln Ala Trp Glu Ser Ser Ser Asp Gln Tyr Val
1               5                   10
```

SEMA4D ANTIBODY, PREPARATION METHOD THEREFOR AND USE THEREOF

INCORPORATION OF SEQUENCE LISTING

This application contains a sequence listing in Computer Readable Form (CRF). The CRF file contains the sequence listing entitled "PB4084406-Seq.txt", which was created on Feb. 16, 2021, and is 229,051 bytes in size. The information in the sequence listing is incorporated herein by reference in entirety.

TECHNICAL FIELD

The present invention belongs to the field of antibodies, and specifically relates to an SEMA4D antibody and the preparation method and application thereof.

BACKGROUND

In recent years, tumor immunotherapy has become the focus of tumor therapy. Wherein, therapeutic monoclonal antibodies against immune checkpoints have shown antitumor activity in the treatment of some tumor types such as melanoma, non-small cell lung cancer and so on. Immune checkpoint antibodies against cytotoxic T lymphocyte-associated antigen-4 (CTLA-4) and programmed cell death 1/programmed cell death ligand 1 (PD-1/PD-L1) have been approved by the US FDA.

However, the low response rate of monotherapy is the main problem of existing tumor immunotherapy. In 2014, the US FDA firstly approved the use of PD-1 antibody to treat melanoma. Relevant clinical trial data showed that the objective response rate of patients in the nivolumab trial group was 32%, and the one-year survival rate was 73%. The 6-month survival rate of patients in the Pembrolizumab trial group was 34%-38%. Later, clinical trial data against non-small cell lung cancer showed that the objective response rate of patients using pembrolizumab was only 19.4%, and the objective response rate of patients using PD-L1 antibodies atezolizumab and durvalumab were only 15% and 14%. Up to now, tumor immunity clinical trials for PD-1 or PD-L1 antibodies have involved small cell lung cancer, head and neck cancer, renal cell carcinoma, bladder cancer, ovarian cancer, breast cancer, lymphoma and many other diseases. Except for patients with Hodgkin's lymphoma, the objective response rate of nivolumab and pembrolizumab group exceeded 60%. The rest of the clinical trial data showed that the objective response rate of patients treated with different PD-1 or PD-L1 antibodies was only 10%-26%. Therefore, tumor immunotherapy is an important method to improve the effectiveness of existing treatments and increase patient benefits.

By analyzing the tumor microenvironment of patients who respond to immune checkpoint antibodies, it was found that most responders had a phenotype of T lymphocyte infiltration. Immune checkpoint antibodies kill tumor cells by activating T cells in the patient's own immune system. Therefore, in order to improve the therapeutic effect of most patients without T lymphocytes or even immune cell infiltration phenotype, one of the solutions is to induce immune cell infiltration to enhance the therapeutic effect of tumor immunotherapy.

Axon guidance factor 4D (Semaphorin 4D, SEMA4D), also known as CD100, is a member of the Semaphorins family. Members of this family include secretory and membrane-bound proteins, and can be divided into 8 subtypes, each with a conserved "Sema" domain of about 500 amino acids at the N-terminus. SEMA4D is a transmembrane protein with a molecular weight of 150 kDa. It is expressed as a homodimer on the cell surface. Its extracellular domain can be cleaved by proteases to form an active soluble protein of 240 kDa, which has biological activity. SEMA4D is expressed in many organs, including lymphoid organs such as the spleen and thymus, and other non-lymphoid organs such as brain and heart. SEMA4D has high expression levels on resting T cells, but low expression levels on resting B cells and antigen presenting cells (APCs). The three receptors of SEMA4D have been confirmed, namely Plexin B1, Plexin B2 and CD72. Plexin B1 has the highest affinity with SEMA4D, followed by Plexin B2, and CD72 has the lowest affinity. Studies have shown that membrane-bound or soluble SEMA4D can bind to the receptor Plexin B1, to activate downstream signaling pathways.

SEMA4D is known to be closely related to the development of certain cancers. Increased expression of SEMA4D has been observed in head and neck cancer, colon cancer, prostate cancer, breast cancer, and lung cancer. One of the mechanisms by which SEMA4D participates in cancer development is to induce the activation and migration of vascular endothelial cells and promote tumor growth and metastasis. And the other is that it can inhibit the migration of immune cells.

The existing anti-human SEMA4D antibody screening method of Vaccinex is single, that is, hybridoma technology combined with humanization. The results of in vitro activity experiments suggest that VX15 antibody may promote T cell activity by inhibiting myeloid inhibitory cells, and this effect can only be achieved under high concentration conditions. Meanwhile, in vivo animal experiments showed that the SEMA4D antibody VX15 alone has no obvious effect on inhibiting tumor growth and metastasis. Moreover, in tumor models such as Colon26 and MC38, the combination of VX15 and immune checkpoint PD-1 antibodies cannot effectively inhibit tumor growth. Therefore, the development and application of SEMA4D antibodies in tumor immunotherapy are limited.

SUMMARY OF THE INVENTION

In order to overcome the shortcomings that the current anti-human SEMA4D antibody screening method is single, the in vitro activity experiment effect is poor, and the combination of existing SEMA4D antibodies and the immune checkpoint PD-1 antibodies cannot effectively inhibit the growth of tumors, multiple antibody screening techniques had been used and diverse antibody sequences were obtained in the present invention.

The SEMA4D antibodies that can effectively inhibit tumor growth when combined with multiple immune checkpoint antibodies were obtained in the present invention.

In a first aspect of the present invention, it provides a heavy chain variable region of an antibody, wherein the heavy chain variable region comprises the following three complementary determining regions or CDRs:

VH-CDR1, VH-CDR2, and VH-CDR3 shown, respectively, in SEQ ID NO: 2, 3, and 4;
VH-CDR1, VH-CDR2, and VH-CDR3 shown, respectively, in SEQ ID NO: 10, 11, and 13;
VH-CDR1, VH-CDR2, and VH-CDR3 shown, respectively, in SEQ ID NO: 18, 19, and 20;
VH-CDR1, VH-CDR2, and VH-CDR3 shown, respectively, in SEQ ID NO: 26, 12, and 13;

VH-CDR1, VH-CDR2, and VH-CDR3 shown, respectively, in SEQ ID NO: 34, 35, and 36;
VH-CDR1, VH-CDR2, and VH-CDR3 shown, respectively, in SEQ ID NO: 42, 43, and 44;
VH-CDR1, VH-CDR2, and VH-CDR3 shown, respectively, in SEQ ID NO: 50, 51, and 52;
VH-CDR1, VH-CDR2, and VH-CDR3 shown, respectively, in SEQ ID NO: 58, 59, and 60;
VH-CDR1, VH-CDR2, and VH-CDR3 shown, respectively, in SEQ ID NO: 66, 67, and 68;
VH-CDR1, VH-CDR2, and VH-CDR3 shown, respectively, in SEQ ID NO: 74, 75, and 76;
VH-CDR1, VH-CDR2, and VH-CDR3 shown, respectively, in SEQ ID NO: 82, 83, and 84;
VH-CDR1, VH-CDR2, and VH-CDR3 shown, respectively, in SEQ ID NO: 90, 91, and 92;
VH-CDR1, VH-CDR2, and VH-CDR3 shown, respectively, in SEQ ID NO: 98, 99, and 100;
VH-CDR1, VH-CDR2, and VH-CDR3 shown, respectively, in SEQ ID NO: 106, 107, and 108;
VH-CDR1, VH-CDR2, and VH-CDR3 shown, respectively, in SEQ ID NO: 114, 115, and 116;
VH-CDR1, VH-CDR2, and VH-CDR3 shown, respectively, in SEQ ID NO: 122, 123, and 124;
VH-CDR1, VH-CDR2, and VH-CDR3 shown, respectively, in SEQ ID NO: 130, 131, and 132;
VH-CDR1, VH-CDR2, and VH-CDR3 shown, respectively, in SEQ ID NO: 138, 139, and 140;
VH-CDR1, VH-CDR2, and VH-CDR3 shown, respectively, in SEQ ID NO: 146, 147, and 148;
VH-CDR1, VH-CDR2, and VH-CDR3 shown, respectively, in SEQ ID NO: 154, 155, and 156;
VH-CDR1, VH-CDR2, and VH-CDR3 shown, respectively, in SEQ ID NO: 162, 163, and 164;
VH-CDR1, VH-CDR2, and VH-CDR3 shown, respectively, in SEQ ID NO: 170, 171, and 172;
VH-CDR1, VH-CDR2, and VH-CDR3 shown, respectively, in SEQ ID NO: 178, 179, and 180;
VH-CDR1, VH-CDR2, and VH-CDR3 shown, respectively, in SEQ ID NO: 186, 187, and 188;
VH-CDR1, VH-CDR2, and VH-CDR3 shown, respectively, in SEQ ID NO: 194, 195, and 196;
VH-CDR1, VH-CDR2, and VH-CDR3 shown, respectively, in SEQ ID NO: 202, 203, and 204;
VH-CDR1, VH-CDR2, and VH-CDR3 shown, respectively, in SEQ ID NO: 210, 211, and 212;
VH-CDR1, VH-CDR2, and VH-CDR3 shown, respectively, in SEQ ID NO: 218, 219, and 220;
VH-CDR1, VH-CDR2, and VH-CDR3 shown, respectively, in SEQ ID NO: 226, 227, and 228;
VH-CDR1, VH-CDR2, and VH-CDR3 shown, respectively, in SEQ ID NO: 234, 235, and 236;
VH-CDR1, VH-CDR2, and VH-CDR3 shown, respectively, in SEQ ID NO: 242, 243, and 244;
VH-CDR1, VH-CDR2, and VH-CDR3 shown, respectively, in SEQ ID NO: 250, 251, and 252;
VH-CDR1, VH-CDR2, and VH-CDR3 shown, respectively, in SEQ ID NO: 258, 259, and 260;
VH-CDR1, VH-CDR2, and VH-CDR3 shown, respectively, in SEQ ID NO: 266, 267, and 268;
VH-CDR1, VH-CDR2, and VH-CDR3 shown, respectively, in SEQ ID NO: 274, 275, and 276;
VH-CDR1, VH-CDR2, and VH-CDR3 shown, respectively, in SEQ ID NO: 282, 283, and 284;
VH-CDR1, VH-CDR2, and VH-CDR3 shown, respectively, in SEQ ID NO: 290, 291, and 292;
VH-CDR1, VH-CDR2, and VH-CDR3 shown, respectively, in SEQ ID NO: 298, 299, and 300;
VH-CDR1, VH-CDR2, and VH-CDR3 shown, respectively, in SEQ ID NO: 306, 307, and 308;
VH-CDR1, VH-CDR2, and VH-CDR3 shown, respectively, in SEQ ID NO: 314, 315, and 316;
VH-CDR1, VH-CDR2, and VH-CDR3 shown, respectively, in SEQ ID NO: 322, 323, and 324;
or
VH-CDR1, VH-CDR2, and VH-CDR3 shown, respectively, in SEQ ID NO: 330, 331, and 332.
wherein, any one of the above amino acid sequences also includes a derivative sequence that is optionally with at least one amino acid added, deleted, modified, and/or substituted, and is capable of retaining the binding affinity to SEMA4D.

In another preferred embodiment, the VH-CDR2 has the amino acid sequence shown in SEQ ID NO:436.

In another preferred embodiment, the VH-CDR2 has the amino acid sequence shown in SEQ ID NO:440.

In another preferred embodiment, the heavy chain variable region has the amino acid sequence shown in SEQ ID NO: 1, 9, 17, 25, 33, 41, 49, 57, 65, 73, 81, 89, 97, 105, 113, 121, 129, 137, 145, 153, 161, 169, 177, 185, 193, 201, 209, 217, 225, 233, 241, 249, 257, 265, 273, 281, 289, 297, 305, 313, 321, or 329.

In another preferred embodiment, the substitution is the mutation of aspartic acid N at position 52 to asparagine D, and/or the mutation of serine S at positon 54 to alanine A.

In another preferred embodiment, the heavy chain variable region has the amino acid sequence shown in SEQ ID NO: 435.

In another preferred embodiment, the heavy chain variable region has the amino acid sequence shown in SEQ ID NO: 439.

In another preferred embodiment, the heavy chain variable region has the amino acid sequence shown in SEQ ID NO: 443.

In a second aspect of the present invention, it provides a heavy chain of an antibody, wherein the heavy chain comprises the heavy chain variable region according to the first aspect of the present invention.

In a third aspect of the present invention, it provides a light chain variable region of an antibody, wherein the light chain variable region comprises the following three complementary determining regions or CDRs:
VL-CDR1, VL-CDR2, and VL-CDR3 shown, respectively, in SEQ ID NO: 6, 7, and 8;
VL-CDR1, VL-CDR2, and VL-CDR3 shown, respectively, in SEQ ID NO: 14, 15, and 16;
VL-CDR1, VL-CDR2, and VL-CDR3 shown, respectively, in SEQ ID NO: 22, 23, and 24;
VL-CDR1, VL-CDR2, and VL-CDR3 shown, respectively, in SEQ ID NO: 30, 31, and 32;
VL-CDR1, VL-CDR2, and VL-CDR3 shown, respectively, in SEQ ID NO: 38, 39, and 40;
VL-CDR1, VL-CDR2, and VL-CDR3 shown, respectively, in SEQ ID NO: 46, 47, and 48;
VL-CDR1, VL-CDR2, and VL-CDR3 shown, respectively, in SEQ ID NO: 54, 55, and 56;
VL-CDR1, VL-CDR2, and VL-CDR3 shown, respectively, in SEQ ID NO: 62, 63, and 64;
VL-CDR1, VL-CDR2, and VL-CDR3 shown, respectively, in SEQ ID NO: 70, 71, and 72;
VL-CDR1, VL-CDR2, and VL-CDR3 shown, respectively, in SEQ ID NO: 78, 79, and 80;

VL-CDR1, VL-CDR2, and VL-CDR3 shown, respectively, in SEQ ID NO: 86, 87, and 88;
VL-CDR1, VL-CDR2, and VL-CDR3 shown, respectively, in SEQ ID NO: 94, 95, and 96;
VL-CDR1, VL-CDR2, and VL-CDR3 shown, respectively, in SEQ ID NO: 102, 103, and 104;
VL-CDR1, VL-CDR2, and VL-CDR3 shown, respectively, in SEQ ID NO: 110, 111, and 112;
VL-CDR1, VL-CDR2, and VL-CDR3 shown, respectively, in SEQ ID NO: 118, 119, and 120;
VL-CDR1, VL-CDR2, and VL-CDR3 shown, respectively, in SEQ ID NO: 126, 127, and 128;
VL-CDR1, VL-CDR2, and VL-CDR3 shown, respectively, in SEQ ID NO: 134, 135, and 136;
VL-CDR1, VL-CDR2, and VL-CDR3 shown, respectively, in SEQ ID NO: 142, 143, and 144;
VL-CDR1, VL-CDR2, and VL-CDR3 shown, respectively, in SEQ ID NO: 150, 151, and 152;
VL-CDR1, VL-CDR2, and VL-CDR3 shown, respectively, in SEQ ID NO: 158, 159, and 160;
VL-CDR1, VL-CDR2, and VL-CDR3 shown, respectively, in SEQ ID NO: 166, 167, and 168;
VL-CDR1, VL-CDR2, and VL-CDR3 shown, respectively, in SEQ ID NO: 174, 175, and 176;
VL-CDR1, VL-CDR2, and VL-CDR3 shown, respectively, in SEQ ID NO: 182, 183, and 184;
VL-CDR1, VL-CDR2, and VL-CDR3 shown, respectively, in SEQ ID NO: 190, 191, and 192;
VL-CDR1, VL-CDR2, and VL-CDR3 shown, respectively, in SEQ ID NO: 198, 199, and 200;
VL-CDR1, VL-CDR2, and VL-CDR3 shown, respectively, in SEQ ID NO: 206, 207, and 208;
VL-CDR1, VL-CDR2, and VL-CDR3 shown, respectively, in SEQ ID NO: 214, 215, and 216;
VL-CDR1, VL-CDR2, and VL-CDR3 shown, respectively, in SEQ ID NO: 222, 223, and 224;
VL-CDR1, VL-CDR2, and VL-CDR3 shown, respectively, in SEQ ID NO: 230, 231, and 232;
VL-CDR1, VL-CDR2, and VL-CDR3 shown, respectively, in SEQ ID NO: 238, 239, and 240;
VL-CDR1, VL-CDR2, and VL-CDR3 shown, respectively, in SEQ ID NO: 246, 247, and 248;
VL-CDR1, VL-CDR2, and VL-CDR3 shown, respectively, in SEQ ID NO: 254, 255, and 256;
VL-CDR1, VL-CDR2, and VL-CDR3 shown, respectively, in SEQ ID NO: 262, 263, and 264;
VL-CDR1, VL-CDR2, and VL-CDR3 shown, respectively, in SEQ ID NO: 270, 271, and 272;
VL-CDR1, VL-CDR2, and VL-CDR3 shown, respectively, in SEQ ID NO: 278, 279, and 280;
VL-CDR1, VL-CDR2, and VL-CDR3 shown, respectively, in SEQ ID NO: 286, 287, and 288;
VL-CDR1, VL-CDR2, and VL-CDR3 shown, respectively, in SEQ ID NO: 294, 295, and 296;
VL-CDR1, VL-CDR2, and VL-CDR3 shown, respectively, in SEQ ID NO: 302, 303, and 304;
VL-CDR1, VL-CDR2, and VL-CDR3 shown, respectively, in SEQ ID NO: 310, 311, and 312;
VL-CDR1, VL-CDR2, and VL-CDR3 shown, respectively, in SEQ ID NO: 318, 319, and 320;
VL-CDR1, VL-CDR2, and VL-CDR3 shown, respectively, in SEQ ID NO: 326, 327, and 328;
or
VL-CDR1, VL-CDR2, and VL-CDR3 shown, respectively, in SEQ ID NO: 334, 335, and 336.
wherein, any one of the above amino acid sequences also includes a derivative sequence that is optionally with at least one amino acid added, deleted, modified, and/or substituted, and is capable of retaining the binding affinity to SEMA4D.

In another preferred embodiment, the VL-CDR3 has the amino acid sequence shown in SEQ ID NO: 438.

In another preferred embodiment, the VL-CDR3 has the amino acid sequence shown in SEQ ID NO: 442.

In another preferred embodiment, the light chain variable region has the amino acid sequence shown in SEQ ID NO: 5, 13, 21, 29, 37, 45, 53, 61, 69, 77, 85, 93, 101, 109, 117, 125, 133, 141, 149, 157, 165, 173, 181, 189, 197, 205, 213, 221, 229, 237, 245, 253, 261, 269, 277, 285, 293, 301, 309, 317, 325, or 333.

In another preferred embodiment, the substitution is the mutation of aspartic acid N at position 97 to serine S, and/or the mutation of glycine G at positon 98 to alanine A.

In another preferred embodiment, the light chain variable region has the amino acid sequence shown in SEQ ID NO: 437.

In another preferred embodiment, the light chain variable region has the amino acid sequence shown in SEQ ID NO: 441.

In another preferred embodiment, the light chain variable region has the amino acid sequence shown in SEQ ID NO: 444.

In another preferred embodiment, the light chain variable region has the amino acid sequence shown in SEQ ID NO: 445.

In a fourth aspect of the present invention, it provides a light chain of an antibody, wherein the light chain comprises the light chain variable region according to the third aspect of the present invention.

In a fifth aspect of the present invention, it provides an antibody, wherein the antibody comprises:
(1) the heavy chain variable region according to the first aspect of the present invention; and/or
(2) the light chain variable region according to the third aspect of the present invention;
or the antibody comprises: the heavy chain according to the second aspect of the present invention; and/or the light chain according to the fourth aspect of the present invention,
wherein, any one of the above amino acid sequences also includes a derivative sequence that is optionally with at least one amino acid added, deleted, modified, and/or substituted, and is capable of retaining the binding affinity to SEMA4D.

In another preferred embodiment, the amino acid sequence of any of the above-mentioned CDRs includes a derivative CDR sequence with 1, 2 or 3 amino acids added, deleted, modified and/or substituted, and the derivative antibody comprising the VH and VL containing the derivative CDR sequence can retain the binding affinity to SEMA4D.

In another preferred embodiment, the ratio (F1/F0) of the binding affinity F1 between the derivatized antibody and SEMA4D to the binding affinity F0 between the corresponding non-derivatized antibody and SEMA4D is 0.5-2, preferably 0.7-1.5, and more preferably 0.8-1.2.

In another preferred embodiment, the number of added, deleted, modified and/or substituted amino acids is 1-5 (such as 1-3, preferably 1-2, more preferably 1).

In another preferred embodiment, the derivative sequence with at least one amino acid added, deleted, modified, and/or substituted, which can retain the binding affinity to SEMA4D, is an amino acid sequence having a homology or sequence identity of at least 96%.

In another preferred embodiment, the antibody further comprises a heavy chain constant region and/or a light chain constant region.

In another preferred embodiment, the heavy chain constant region is of human, and/or the light chain constant region is of human.

In another preferred embodiment, the heavy chain variable region of the antibody further comprises a human-derived framework region, and/or the light chain variable region of the antibody further comprises a human-derived framework region.

In another preferred embodiment, the antibody is selected from the group consisting of: animal-derived antibodies, chimeric antibodies, humanized antibodies, fully human antibodies, and a combination thereof.

In another preferred embodiment, the antibody is a partially or fully humanized or fully human monoclonal antibody.

In another preferred embodiment, the antibody is a double-chain antibody or a single-chain antibody.

In another preferred embodiment, the antibody is a full-length antibody protein or an antigen-binding fragment.

In another preferred embodiment, the antibody is a bispecific antibody or a multispecific antibody.

In another preferred embodiment, the antibody is in the form of a drug conjugate.

In another preferred embodiment, the antibody has one or more properties selected from the group consisting of:
(a) inhibiting tumor cell migration or metastasis;
(b) inhibiting tumor growth.

In another preferred embodiment, the antibody comprises the heavy chain variable region according to the first aspect of the present invention and the light chain variable region according to the third aspect of the present invention;
wherein, the heavy chain variable region and the light chain variable region comprise CDRs selected from the group consisting of:

| VH-CDR 1 sequence number | VH-CDR 2 sequence number | VH-CDR 3 sequence number | VL-CDR 1 sequence number | VL-CDR 2 sequence number | VL-CDR 3 sequence number |
|---|---|---|---|---|---|
| 2 | 3 | 4 | 6 | 7 | 8 |
| 10 | 11 | 12 | 14 | 15 | 16 |
| 18 | 19 | 20 | 22 | 23 | 24 |
| 26 | 27 | 28 | 30 | 31 | 32 |
| 34 | 35 | 36 | 38 | 39 | 40 |
| 42 | 43 | 44 | 46 | 47 | 48 |
| 50 | 51 | 52 | 54 | 55 | 56 |
| 58 | 59 | 60 | 62 | 63 | 64 |
| 66 | 67 | 68 | 70 | 71 | 72 |
| 74 | 75 | 76 | 78 | 79 | 80 |
| 82 | 83 | 84 | 86 | 87 | 88 |
| 90 | 91 | 92 | 94 | 95 | 96 |
| 98 | 99 | 100 | 102 | 103 | 104 |
| 106 | 107 | 108 | 110 | 111 | 112 |
| 114 | 115 | 116 | 118 | 119 | 120 |
| 122 | 123 | 124 | 126 | 127 | 128 |
| 130 | 131 | 132 | 134 | 135 | 136 |
| 138 | 139 | 140 | 142 | 143 | 144 |
| 146 | 147 | 148 | 150 | 151 | 152 |
| 154 | 155 | 156 | 158 | 159 | 160 |
| 162 | 163 | 164 | 166 | 167 | 168 |
| 170 | 171 | 172 | 174 | 175 | 176 |
| 178 | 179 | 180 | 182 | 183 | 184 |
| 186 | 187 | 188 | 190 | 191 | 192 |
| 194 | 195 | 196 | 198 | 199 | 200 |
| 202 | 203 | 204 | 206 | 207 | 208 |
| 210 | 211 | 212 | 214 | 215 | 216 |
| 218 | 219 | 220 | 222 | 223 | 224 |
| 226 | 227 | 228 | 230 | 231 | 232 |
| 234 | 235 | 236 | 238 | 239 | 240 |
| 242 | 243 | 244 | 246 | 247 | 248 |
| 250 | 251 | 252 | 254 | 255 | 256 |
| 258 | 259 | 260 | 262 | 263 | 264 |
| 266 | 267 | 268 | 270 | 271 | 272 |
| 274 | 275 | 276 | 278 | 279 | 280 |
| 282 | 283 | 284 | 286 | 287 | 288 |
| 290 | 291 | 292 | 294 | 295 | 296 |
| 298 | 299 | 300 | 302 | 303 | 304 |
| 306 | 307 | 308 | 310 | 311 | 312 |
| 314 | 315 | 316 | 318 | 319 | 320 |
| 322 | 323 | 324 | 326 | 327 | 328 |
| 330 | 331 | 332 | 334 | 335 | 336 |
| 330 | 436 | 332 | 334 | 335 | 438 |
| 330 | 440 | 332 | 334 | 335 | 438 |
| 330 | 436 | 332 | 334 | 335 | 442 |
| 330 | 440 | 332 | 334 | 335 | 442 | wherein, any one of the above amino acid sequences also includes a derivative sequence that is optionally with at least one amino acid added, deleted, modified, and/or substituted, and is capable of retaining the binding affinity to SEMA4D.

In another preferred embodiment, the heavy chain variable region of the antibody comprises the amino acid sequence shown in SEQ ID NO: 1, 9, 17, 25, 33, 41, 49, 57, 65, 73, 81, 89, 97, 105, 113, 121, 129, 137, 145, 153, 161, 169, 177, 185, 193, 201, 209, 217, 225, 233, 241, 249, 257, 265, 273, 281, 289, 297, 305, 313, 321, or 329; and/or the light chain variable region comprises the amino acid sequence shown in SEQ ID NO: 5, 13, 21, 29, 37, 45, 53, 61, 69, 77, 85, 93, 101, 109, 117, 125, 133, 141, 149, 157, 165, 173, 181, 189, 197, 205, 213, 221, 229, 237, 245, 253, 261, 269, 277, 285, 293, 301, 309, 317, 325, or 333.

In another preferred embodiment, either n is independently 40, 41, 38, 19, 12, 4, 13, or 7.

In another preferred embodiment, the heavy chain variable region of the antibody comprises the amino acid sequence shown in SEQ ID NO: 321, 329, 305, 153, 97, 33, 105, or 57.

In another preferred embodiment, the light chain variable region of the antibody comprises the amino acid sequence shown in SEQ ID NO: 325, 333, 309, 157, 101, 37, 109, or 41.

In another preferred embodiment, the heavy chain variable region of the antibody comprises the amino acid sequence shown in SEQ ID NO: 321, and the light chain variable region of the antibody comprises the amino acid sequence shown in SEQ ID NO: 325.

In another preferred embodiment, the heavy chain variable region of the antibody comprises the amino acid sequence shown in SEQ ID NO: 329, and the light chain variable region of the antibody comprises the amino acid sequence shown in SEQ ID NO: 333.

In another preferred embodiment, the heavy chain variable region of the antibody comprises the amino acid sequence shown in SEQ ID NO: 305, and the light chain variable region of the antibody comprises the amino acid sequence shown in SEQ ID NO: 309.

In another preferred embodiment, the heavy chain variable region of the antibody comprises the amino acid sequence shown in SEQ ID NO: 153, and the light chain variable region of the antibody comprises the amino acid sequence shown in SEQ ID NO: 157.

In another preferred embodiment, the heavy chain variable region of the antibody comprises the amino acid sequence shown in SEQ ID NO: 97, and the light chain variable region of the antibody comprises the amino acid sequence shown in SEQ ID NO: 101.

In another preferred embodiment, the heavy chain variable region of the antibody comprises the amino acid sequence shown in SEQ ID NO: 33, and the light chain variable region of the antibody comprises the amino acid sequence shown in SEQ ID NO: 37.

In another preferred embodiment, the heavy chain variable region of the antibody comprises the amino acid sequence shown in SEQ ID NO: 105, and the light chain variable region of the antibody comprises the amino acid sequence shown in SEQ ID NO: 109.

In another preferred embodiment, the heavy chain variable region of the antibody comprises the amino acid sequence shown in SEQ ID NO: 57, and the light chain variable region of the antibody comprises the amino acid sequence shown in SEQ ID NO: 61.

In another preferred embodiment, the antibody is selected from the group consisting of:

| Antibody number | Clone | VH sequence number | VL sequence number |
|---|---|---|---|
| 1 | 2D5-b1 | 443 | 444 |
| 2 | 5D8-h2b4 | 439 | 445 |
| 3 | 2D5 | 321 | 325 |
| 4 | 5D8 | 329 | 333 |
| 5 | 167H6H5 | 305 | 309 |
| 6 | 31C11G2 | 153 | 157 |
| 7 | 31G10C5 | 97 | 101 |
| 8 | 17H4B2 | 33 | 37 |
| 9 | 32C8F10 | 105 | 109 |
| 10 | 30B1C7 | 57 | 61 |

In another preferred embodiment, the amino acid sequence of the heavy chain variable region has a sequence homology or identity of at least 80%, 85%, 90%, 91%, 92%, 93%, 94%, 95%, 96%, 97%, 98% or 99% with the amino acid sequence shown in SEQ ID NO: 321, SEQ ID NO: 329, SEQ ID NO: 305, SEQ ID NO: 153, SEQ ID NO: 97, SEQ ID NO: 33, SEQ ID NO: 105, SEQ ID NO: 57, SEQ ID NO: 443 or SEQ ID NO: 439 in the sequence listing.

In another preferred embodiment, the amino acid sequence of the light chain variable region has a sequence homology or identity of at least 80%, 85%, 90%, 91%, 92%, 93%, 94%, 95%, 96%, 97%, 98% or 99% with the amino acid sequence shown in SEQ ID NO: 325, SEQ ID NO: 333, SEQ ID NO: 109, SEQ ID NO: 157, SEQ ID NO: 101, SEQ ID NO: 37, SEQ ID NO: 109, SEQ ID NO: 61, SEQ ID NO: 444 or SEQ ID NO: 445 in the sequence listing.

In a sixth aspect of the present invention, it provides a recombinant protein, wherein the recombinant protein comprises:

(i) the heavy chain variable region according to the first aspect of the present invention, the heavy chain according to the second aspect of the present invention, the light chain variable region according to the third aspect of the present invention, the light chain according to the fourth aspect of the present invention, or the antibody according to the fifth aspect of the present invention; and (ii) an optional tag sequence to assist expression and/or purification.

In another preferred embodiment, the tag sequence includes a 6His tag.

In another preferred embodiment, the recombinant protein (or polypeptide) includes a fusion protein.

In another preferred embodiment, the recombinant protein is a monomer, dimer, or multimer.

In another preferred embodiment, the recombinant protein comprises:

(i) an antibody selected from the group consisting of:

| Antibody number | Clone | VH sequence number | VL sequence number |
|---|---|---|---|
| 1 | 2D5-b1 | 443 | 444 |
| 2 | 5D8-h2b4 | 439 | 445 |
| 3 | 2D5 | 321 | 325 |
| 4 | 5D8 | 329 | 333 |
| 5 | 167H6H5 | 305 | 309 |
| 6 | 31C11G2 | 153 | 157 |
| 7 | 31G10C5 | 97 | 101 |
| 8 | 17H4B2 | 33 | 37 |
| 9 | 32C8F10 | 105 | 109 |
| 10 | 30B1C7 | 57 | 61 | and (ii) an optional tag sequence to assist expression and/or purification.

In a seventh aspect of the present invention, it provides a polynucleotide, which encodes a polypeptide selected from the group consisting of:

(1) the heavy chain variable region according to the first aspect of the present invention, the heavy chain according to the second aspect of the present invention, the light chain variable region according to the third aspect of the present invention, the light chain according to the fourth aspect of the present invention, or the antibody according to any one of the fifth aspect of the present invention; and (2) the recombinant protein according to the sixth aspect of the present invention.

In another preferred embodiment, the polynucleotide encoding the heavy chain variable region is shown in SEQ ID NO: 2n+337; and/or the polynucleotide encoding the light chain variable region is shown in SEQ ID NO: 2n+338, wherein either n is independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or 41.

In another preferred embodiment, the polynucleotide encoding the heavy chain variable region sequence and the polynucleotide encoding the light chain variable region sequence are selected from the group consisting of:

| Clone | Sequence number of the polynucleotide encoding VH | Sequence number of the polynucleotide encoding VL |
|---|---|---|
| 2D5 | 417 | 418 |
| 5D8 | 419 | 420 |
| 167H6H5 | 413 | 414 |
| 31C11G2 | 375 | 376 |
| 31G10C5 | 361 | 362 |
| 17H4B2 | 345 | 346 |
| 32C8F10 | 363 | 364 |
| 30B1C7 | 351 | 352. |

In an eighth aspect of the present invention, it provides a vector, which contains the polynucleotide according to the seventh aspect of the present invention.

In another preferred embodiment, the vector includes: bacterial plasmid, phage, yeast plasmid, plant cell virus, mammalian cell virus such as adenovirus, retrovirus, or other vectors.

In a ninth aspect of the present invention, it provides a genetically engineered host cell, wherein the host cell contains the vector according to the eighth aspect of the present invention or the genome thereof is integrated with the polynucleotide according to the seventh aspect of the present invention.

In a tenth aspect of the present invention, it provides an antibody conjugate, which comprises:
(i) an antibody moiety, which is selected from the group consisting of: the heavy chain variable region according to the first aspect of the present invention, the heavy chain according to the second aspect of the present invention, the light chain variable region according to the third aspect of the present invention, the light chain according to the fourth aspect of the present invention, and the antibody according to the fifth aspect of the present invention, and a combination thereof; and
(b) a coupling moiety coupled to the antibody moiety, which is selected from the group consisting of a detectable label, a drug, a toxin, a cytokine, a radionuclide, an enzyme, and a combination thereof.

In another preferred embodiment, the antibody moiety and the coupling moiety are coupled through a chemical bond or a linker.

In an eleventh aspect of the present invention, it provides an immune cell, which expresses or is exposed outside the cell membrane with the antibody according to the fifth aspect of the present invention.

In another preferred embodiment, the immune cell includes NK cells and T cells.

In another preferred embodiment, the immune cell is derived from human or non-human mammals (such as mice).

In a twelfth aspect of the present invention, it provides a pharmaceutical composition, wherein the pharmaceutical composition comprises:
(i) an active ingredient, wherein the active ingredient is selected from the group consisting of: the heavy chain variable region according to the first aspect of the present invention, the heavy chain according to the second aspect of the present invention, the light chain variable region according to the third aspect of the present invention, the light chain according to the fourth aspect of the present invention, and the antibody according to the fifth aspect of the present invention, the recombinant protein according to the sixth aspect of the present invention, the antibody conjugate according to the tenth aspect of the present invention, the immune cell according to the eleventh aspect of the present invention, and combinations thereof; and
(ii) a pharmaceutically acceptable carrier.

In another preferred embodiment, the pharmaceutical composition is a liquid preparation.

In another preferred embodiment, the pharmaceutical composition is an injection.

In another preferred embodiment, the pharmaceutical composition comprises 0.01-99.99% of the antibody according to the fifth aspect of the present invention, the recombinant protein according to the sixth aspect of the present invention, the antibody conjugate according to the tenth aspect of the present invention, the immune cell according to the eleventh aspect of the present invention, or a combination thereof, and 0.01-99.99% of the pharmaceutically acceptable carrier, wherein the percentage is the mass percentage of the pharmaceutical composition.

In a thirteenth aspect of the present invention, it provides use of an active ingredient, wherein the active ingredient is selected from the group consisting of: the heavy chain variable region according to the first aspect of the present invention, the heavy chain according to the second aspect of the present invention, the light chain variable region according to the third aspect of the present invention, the light chain according to the fourth aspect of the present invention, and the antibody according to the fifth aspect of the present invention, the recombinant protein according to the sixth aspect of the present invention, the antibody conjugate according to the tenth aspect of the present invention, the immune cell according to the eleventh aspect of the present invention, and combinations thereof, wherein the active ingredient is used for (a) preparation of a diagnostic reagent or kit; and/or (b) preparation of a medicine for preventing and/or treating diseases associated with abnormal SEMA4D expression or function.

In another preferred embodiment, the diagnostic reagent is a detection piece or a detection plate.

In another preferred embodiment, the disease associated with abnormal SEMA4D expression or function is selected from the group consisting of: cancer, autoimmune diseases and inflammatory diseases.

In another preferred embodiment, the diagnostic reagent or kit is used for:
(1) detection of the SEMA4D protein in a sample; and/or
(2) detection of endogenous SEMA4D protein in tumor cells; and/or
(3) detection of tumor cells expressing SEMA4D protein;
wherein the drug is used to prevent and/or treat diseases associated with abnormal SEMA4D expression or function, and the disease associated with abnormal SEMA4D expression or function is cancer, an autoimmune disease or an inflammatory disease.

In another preferred embodiment, the cancer is colon cancer, lung cancer, head and neck cancer, breast cancer, prostate cancer, ovarian cancer or pancreatic cancer.

In another preferred embodiment, the autoimmune disease or inflammatory disease is multiple sclerosis or arthritis.

In another preferred embodiment, the antibody is in the form of a drug conjugate (ADC).

In another preferred embodiment, the diagnostic reagent or kit is used for diagnosis of SEMA4D related diseases.

In another preferred embodiment, the diagnostic reagent or kit is used for detection of SEMA4D protein in a sample.

In a fourteenth aspect of the present invention, it provides a method for in vitro detection (including diagnostic or non-diagnostic) of SEMA4D protein in a sample, wherein the method comprises the steps:
(1) contacting the sample with the antibody according to the fifth aspect of the present invention in vitro;
(2) detecting whether an antigen-antibody complex is formed, wherein the formation of the complex indicates the presence of SEMA4D protein in the sample.

In a fifteenth aspect of the present invention, it provides a composition for detecting SEMA4D protein in a sample in vitro, which comprises the antibody according to the fifth aspect of the present invention, the recombinant protein according to the sixth aspect of the present invention, the antibody conjugate according to the tenth aspect of the present invention, the immune cell according to the eleventh aspect of the present invention, or a combination thereof, as an active ingredient.

In a sixteenth aspect of the present invention, it provides a detection plate, wherein the detection plate comprises: a substrate (support plate) and a detection strip, wherein the detection strip comprises the antibody according to the fifth aspect of the present invention, the recombinant protein according to the sixth aspect of the present invention, the antibody conjugate according to the tenth aspect of the present invention, the immune cell according to the eleventh aspect of the present invention, or a combination thereof.

In a seventeenth aspect of the present invention, it provides a kit, which comprises:
(1) a first container, which contains the antibody of the present invention; and/or
(2) a second container, which contains a secondary antibody against the antibody of the present invention;
or,
the kit comprises the detection plate according to the sixteenth aspect of the present invention.

In an eighteenth aspect of the present invention, it provides a method for preparing a recombinant polypeptide, wherein the method comprises:
(a) culturing the host cell according to the ninth aspect of the present invention under conditions suitable for expression;
(b) isolating a recombinant polypeptide from the culture, wherein the recombinant polypeptide is the antibody according to the fifth aspect of the present invention or the recombinant protein according to the sixth aspect of the present invention.

In a nineteenth aspect of the present invention, it provides a drug combination, comprising:
(i) a first active ingredient, which comprises the antibody according to the fifth aspect of the present invention, or the recombinant protein according to the sixth aspect of the present invention, or the antibody conjugate according to the tenth aspect of the present invention, or the immune cell according to the eleventh aspect of the present invention, or the pharmaceutical composition according to the twelfth aspect of the present invention, or a combination thereof;
(ii) a second active ingredient, which comprises a second antibody, or a chemotherapeutic agent.

In another preferred embodiment, the second antibody is selected from the group consisting of a CTLA4 antibody and a PD-1 antibody.

In another preferred embodiment, the second antibody is a PD-1 antibody.

In another preferred example, the chemotherapeutic agent is selected from the group consisting of docetaxel, carboplatin, and a combination thereof.

In a twentieth aspect of the present invention, it provides use of a combination for preparation of a medicine for the treatment of diseases associated with abnormal SEMA4D expression or function, wherein the combination comprises the antibody according to the fifth aspect of the present invention, or the recombinant protein according to the sixth aspect of the present invention, or the antibody conjugate according to the tenth aspect of the present invention, or the immune cell according to the eleventh aspect of the present invention, and/or the pharmaceutical composition according to the twelfth aspect of the present invention, and a second antibody or a chemotherapeutic agent.

In another preferred embodiment, the second antibody is selected from the group consisting of a CTLA4 antibody and a PD-1 antibody.

In another preferred embodiment, the second antibody is a PD-1 antibody.

In a twenty-first aspect of the present invention, it provides a method for the treatment of diseases associated with abnormal SEMA4D expression or function, which comprises administering an effective amount of the antibody according to the fifth aspect of the present invention, the recombinant protein according to the sixth aspect of the present invention, the antibody conjugate according to the tenth aspect of the present invention, the immune cell according to the eleventh aspect of the present invention, the pharmaceutical composition of the twelfth aspect of the present invention, or a combination thereof, to a subject in need.

In another preferred embodiment, the disease associated with abnormal SEMA4D expression or function is cancer, an autoimmune disease or an inflammatory disease.

In another preferred embodiment, the cancer is selected from the group consisting of colon cancer, lung cancer, head and neck cancer, breast cancer, prostate cancer, ovarian cancer and pancreatic cancer.

In another preferred embodiment, the autoimmune disease is multiple sclerosis.

In another preferred embodiment, the inflammatory disease is arthritis.

In another preferred embodiment, the method further comprises: administering a safe and effective amount of a second antibody to the subject before, during, and/or after administering the first active ingredient.

In another preferred embodiment, the second antibody is selected from the group consisting of a PD-1 antibody and a CTLA4 antibody.

In another preferred embodiment, the second antibody is a PD-1 antibody.

It should be understood that within the scope of the present invention, the various technical features of the present invention above and the various technical features specifically described hereinafter (as in the embodiments) may be combined with each other to constitute a new or preferred technical solution. Due to space limitations, it is not repeated here.

DETAILED DESCRIPTION

Figure 1:
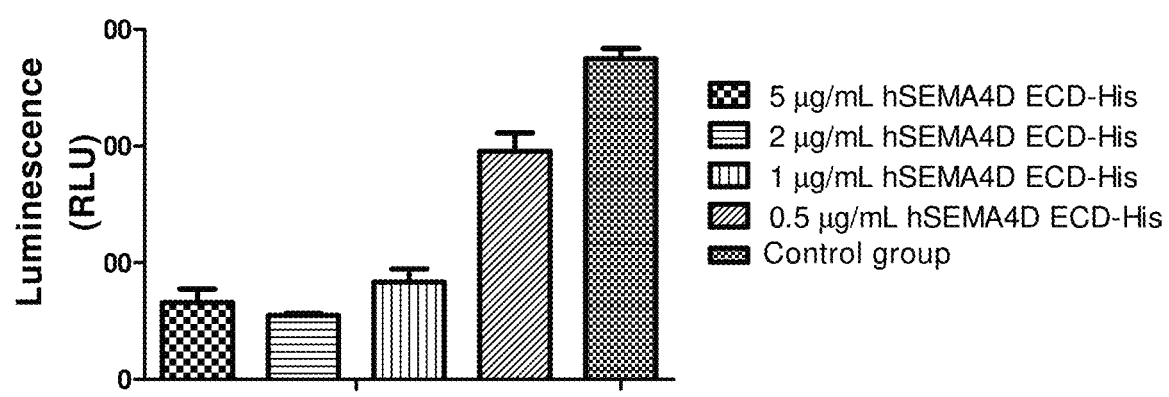
FIG. 1 shows the detection results of the biological activity of purified hSEMA4D ECD-His.

Through extensive and intensive studies, the inventors unexpectedly obtained a group of fully human or humanized SEMA4D antibodies with new amino acid sequences which can recognize different epitopes, through phage display technology and hybridoma technology. The SEMA4D antibodies can bind to human SEMA4D with a high affinity (nM level). The SEMA4D antibodies can block the binding of SEMA4D and the receptor Plexin B1; and at the cellular level, the SEMA4D antibodies can inhibit the shedding of tumor cells. The SEMA4D antibodies or the mutants thereof (such as 2D5-b1, 5D8-h2) of the present invention can effectively neutralize the induction effect of SEMA4D on MDSCs. The results of animal experiments showed that the SEMA4D antibodies or the mutants thereof (such as 2D5-b1, 5D8-h2b4), combined with different immune checkpoint antibodies (such as CTLA4 antibodies, PD-1 antibodies), can effectively inhibit or delay tumor growth, and improve the response rates to CTLA4, PD-1 antibodies, and extend the survival time (For example, in the CT26 model, the combination of SEMA4D antibody of the present invention and a CTLA4 antibody or a PD-1 antibody can significantly inhibit tumor growth). The present invention significantly improves the in vitro activity of the SEMA4D antibody, and broadens the development and application of the SEMA4D antibody in tumor immune combined therapy. On this basis, the present invention has been completed.

The Terms

Antibody

As used herein, the term "antibody" or "immunoglobulin" is a heterotetrameric glycoprotein of about 150,000 daltons with the same structural characteristics, which consists of two identical light chains (L) and two identical heavy chains (H). Each light chain is connected to the heavy chain through a covalent disulfide bond, and the numbers of disulfide bonds between heavy chains of different immunoglobulin isotypes are different. Each heavy and light chain also has regularly spaced intrachain disulfide bonds. Each heavy chain has a variable region (VH) at one end, followed by multiple constant regions. Each light chain has a variable region (VL) at one end and a constant region at the other end; the constant region of the light chain is opposite to the first constant region of the heavy chain, and the variable region of the light chain is opposite to the variable region of the heavy chain. Special amino acid residues form an interface between the variable regions of the light and heavy chains.

As used herein, the term "variable" means that certain parts of the variable region of an antibody differ in sequence, which forms the binding and specificity of various specific antibodies for their specific antigens. However, the variability is not evenly distributed throughout the variable region of the antibody. It is concentrated in three segments called complementary determining regions (CDRs) or hypervariable regions in the light chain and heavy chain variable regions. The more conserved part of the variable region is called the framework region (FR). The variable regions of the natural heavy and light chains each contain four FR regions, which are roughly in the β-folded configuration, connected by the three CDRs that form the connecting loop, and in some cases may form a partly β folded structure. The CDRs in each chain get close through the FR regions and together with the CDRs of the other chain form the antigen-binding site of the antibody (see Kabat et al., NIH Publ. No. 91-3242, Volume I, pages 647-669 (1991)). The constant regions are not directly involved in the binding of antibodies to antigens, but they exhibit different effector functions, such as involved in the antibody-dependent cytotoxicity of antibodies.

The light chains of vertebrate antibodies (immunoglobulins) can be classified into one of two distinct classes (referred to as κ and λ) based on the amino acid sequence of their constant regions. Immunoglobulins can be divided into different types, according to the amino acid sequence of the constant region of the heavy chain. There are five main classes of immunoglobulins: IgA, IgD, IgE, IgG, and IgM, some of which can be further divided into subclasses (isotypes), such as IgG1, IgG2, IgG3, IgG4, IgA, and IgA2. The heavy chain constant regions corresponding to different classes of immunoglobulins are called δ, ε, γ, α, and μ, respectively. The subunit structures and three-dimensional configurations of different classes of immunoglobulins are well known to those skilled in the art.

In general, the antigen-binding properties of an antibody can be described by the three specific regions located in the variable regions of the heavy and light chains, called complementary determining regions (CDR), which divide this segment into 4 framework regions (FR). The amino acid sequences of the four FRs are relatively conservative and do not directly participate in the binding reaction. These CDRs form a circular structure, and get close in space structure through the β sheets formed by the FRs in between. The CDRs on the heavy chain and the CDRs on the corresponding light chain constitute the antigen binding site of the antibody. The amino acid sequences of antibodies of the same type can be compared to determine which amino acids constitute the FR or CDR regions.

The present invention includes not only intact antibodies, but also immunologically active fragments of antibody fragments or fusion proteins formed by antibodies and other sequences. Therefore, the present invention also includes fragments, derivatives and analogs of the antibodies.

In the present invention, antibodies include murine, chimeric, humanized, or fully human antibodies prepared by techniques well known to those skilled in the art. Recombinant antibodies, such as chimeric and humanized monoclonal antibodies, including human and non-human parts, can be obtained by standard DNA recombination techniques, and they are all useful antibodies. A chimeric antibody is a molecule in which different parts come from different animal species, such as a chimeric antibody with a variable region of a monoclonal antibody from a mouse and a constant region from a human immunoglobulin (see, for example, U.S. Pat. Nos. 4,816,567 and 4,816,397, hereby incorporated by reference in its entirety). Humanized antibodies refer to antibody molecules derived from non-human species, having one or more complementary determining regions (CDRs) derived from non-human species and framework regions derived from human immunoglobulin molecules (see U.S. Pat. No. 5,585,089, hereby incorporated by reference in its entirety). These chimeric and humanized monoclonal antibodies can be prepared using recombinant DNA techniques well known in the art.

In the present invention, the antibody may be monospecific, bispecific, trispecific, or more multispecific.

In the present invention, the antibody of the present invention also includes conservative variants thereof, which means that compared with the amino acid sequence of the antibody of the present invention, there are at most 10, preferably at most 8, more preferably at most 5, most preferably at most 3 amino acids replaced by amino acids with the same or similar properties to form a polypeptide. These conservatively variant polypeptides are preferably produced by amino acid substitution according to Table A.

TABLE A

| Initial residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

Isolated Protein

The present invention also provides an isolated protein, comprising one or more of the heavy chain CDR1, heavy chain CDR2 and heavy chain CDR3 of the SEMA4D antibody, and/or one or more of the light chain CDR1, light chain CDR2 and light chain CDR3 of the SEMA4D antibody.

The sequences of the heavy chain CDR1-3 are as follows:
CDR1 shown in SEQ ID NO: 8n+2,
CDR2 shown in SEQ ID NO: 8n+3,
CDR3 shown in SEQ ID NO: 8n+4;

The sequences of the light chain CDR1-3 are as follows:
CDR1' shown in SEQ ID NO: 8n+6,
CDR2' shown in SEQ ID NO: 8n+7, and
CDR3' shown in SEQ ID NO: 8n+8;
each n is independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or 41;
preferably, n is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or 41;
more preferably, n is 40, 41, 38, 19, 12, 4, 13 or 7;
wherein, any one of the above amino acid sequences also includes a derivative sequence that is optionally with at least one amino acid added, deleted, modified, and/or substituted, and is capable of retaining the binding affinity to SEMA4D.

In another preferred embodiment, the sequence with at least one amino acid added, deleted, modified and/or substituted in any of the above amino acid sequences is preferably an amino acid sequence having a homology or sequence identity of at least 80%, preferably at least 85%, more preferably at least 90%, most preferably at least 95% to the above amino acid sequence.

In another preferred embodiment, the isolated protein of the present invention comprises the heavy chain variable region of the SEMA4D antibody and/or the light chain variable region of the SEMA4D antibody, wherein the heavy chain variable region of the antibody comprises the amino acid sequence shown in SEQ ID NO: 8n+1, and the light chain variable region comprises the amino acid sequence shown in SEQ ID NO: 8n+5, wherein either n is independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or 41.

In another preferred embodiment, the isolated protein of the present invention comprises the heavy chain variable region of the SEMA4D antibody and the light chain variable region of the SEMA4D antibody, wherein the heavy chain variable region of the antibody comprises the amino acid sequence shown in SEQ ID NO: 8n+1, and the light chain variable region comprises the amino acid sequence shown in SEQ ID NO: 8n+5, wherein n is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or 41.

In another preferred embodiment, the isolated protein and the amino acid sequence numbers of the heavy chain CDR1-3 and light chain CDR1-3 comprised therein are as shown in Table 1:

TABLE 1

Amino acid sequence numbers of heavy chain CDR1-3 and light chain CDR1-3

| Isolated protein Number | VH-CDR 1 sequence number | VH-CDR 2 sequence number | VH-CDR 3 sequence number | VL-CDR 1 sequence number | VL-CDR 2 sequence number | VL-CDR 3 sequence number |
|---|---|---|---|---|---|---|
| 1 | 2 | 3 | 4 | 6 | 7 | 8 |
| 2 | 10 | 11 | 12 | 14 | 15 | 16 |
| 3 | 18 | 19 | 20 | 22 | 23 | 24 |
| 4 | 26 | 27 | 28 | 30 | 31 | 32 |
| 5 | 34 | 35 | 36 | 38 | 39 | 40 |
| 6 | 42 | 43 | 44 | 46 | 47 | 48 |
| 7 | 50 | 51 | 52 | 54 | 55 | 56 |
| 8 | 58 | 59 | 60 | 62 | 63 | 64 |

TABLE 1-continued

Amino acid sequence numbers of heavy chain CDR1-3 and light chain CDR1-3

| Isolated protein Number | VH-CDR 1 sequence number | VH-CDR 2 sequence number | VH-CDR 3 sequence number | VL-CDR 1 sequence number | VL-CDR 2 sequence number | VL-CDR 3 sequence number |
|---|---|---|---|---|---|---|
| 9  | 66  | 67  | 68  | 70  | 71  | 72  |
| 10 | 74  | 75  | 76  | 78  | 79  | 80  |
| 11 | 82  | 83  | 84  | 86  | 87  | 88  |
| 12 | 90  | 91  | 92  | 94  | 95  | 96  |
| 13 | 98  | 99  | 100 | 102 | 103 | 104 |
| 14 | 106 | 107 | 108 | 110 | 111 | 112 |
| 15 | 114 | 115 | 116 | 118 | 119 | 120 |
| 16 | 122 | 123 | 124 | 126 | 127 | 128 |
| 17 | 130 | 131 | 132 | 134 | 135 | 136 |
| 18 | 138 | 139 | 140 | 142 | 143 | 144 |
| 19 | 146 | 147 | 148 | 150 | 151 | 152 |
| 20 | 154 | 155 | 156 | 158 | 159 | 160 |
| 21 | 162 | 163 | 164 | 166 | 167 | 168 |
| 22 | 170 | 171 | 172 | 174 | 175 | 176 |
| 23 | 178 | 179 | 180 | 182 | 183 | 184 |
| 24 | 186 | 187 | 188 | 190 | 191 | 192 |
| 25 | 194 | 195 | 196 | 198 | 199 | 200 |
| 26 | 202 | 203 | 204 | 206 | 207 | 208 |
| 27 | 210 | 211 | 212 | 214 | 215 | 216 |
| 28 | 218 | 219 | 220 | 222 | 223 | 224 |
| 29 | 226 | 227 | 228 | 230 | 231 | 232 |
| 30 | 234 | 235 | 236 | 238 | 239 | 240 |
| 31 | 242 | 243 | 244 | 246 | 247 | 248 |
| 32 | 250 | 251 | 252 | 254 | 255 | 256 |
| 33 | 258 | 259 | 260 | 262 | 263 | 264 |
| 34 | 266 | 267 | 268 | 270 | 271 | 272 |
| 35 | 274 | 275 | 276 | 278 | 279 | 280 |
| 36 | 282 | 283 | 284 | 286 | 287 | 288 |
| 37 | 290 | 291 | 292 | 294 | 295 | 296 |
| 38 | 298 | 299 | 300 | 302 | 303 | 304 |
| 39 | 306 | 307 | 308 | 310 | 311 | 312 |
| 40 | 314 | 315 | 316 | 318 | 319 | 320 |
| 41 | 322 | 323 | 324 | 326 | 327 | 328 |
| 42 | 330 | 331 | 332 | 334 | 335 | 336 |
| 43 | 330 | 436 | 332 | 334 | 335 | 438 |
| 44 | 330 | 440 | 332 | 334 | 335 | 438 |
| 45 | 330 | 436 | 332 | 334 | 335 | 442 |
| 46 | 330 | 440 | 332 | 334 | 335 | 442 | wherein, any one of the above amino acid sequences also includes a derivative sequence that is optionally with at least one amino acid added, deleted, modified, and/or substituted, and is capable of retaining the binding affinity to SEMA4D.

Preferably, the protein also comprises an antibody heavy chain constant region and/or an antibody light chain constant region, wherein the antibody heavy chain constant region is conventional in the art, preferably a rat antibody heavy chain constant region or a human antibody heavy chain constant region, more preferably a human antibody heavy chain constant region. The antibody light chain constant region is conventional in the art, preferably a rat antibody light chain constant region or a human antibody light chain constant region, more preferably a human antibody light chain constant region.

The protein is a conventional protein in the art. Preferably, it is one or more of an antibody full-length protein, an antigen-antibody binding domain protein fragment, a bispecific antibody, a multispecific antibody, a single chain antibody fragment (scFv), a single domain antibody (sdAb) and a single-domain antibody, as well as a monoclonal antibody or a polyclonal antibody made from the above antibodies. The monoclonal antibody can be developed by a variety of approaches and technologies, including hybridoma technology, phage display technology, single lymphocyte gene cloning technology, etc. The mainstream is to prepare monoclonal antibodies from wild-type or transgenic mice through hybridoma technology.

The antibody full-length protein is a conventional antibody full-length protein in the art, which comprises a heavy chain variable region, a light chain variable region, a heavy chain constant region, and a light chain constant region. The heavy chain variable region and light chain variable region of the protein and human heavy chain constant region and human light chain constant region constitute a fully human antibody full-length protein. Preferably, the antibody full-length protein is IgG1, IgG2, IgG3 or IgG4.

The single-chain antibody is a conventional single-chain antibody in the art, which comprises a heavy chain variable region, a light chain variable region and a short peptide of 15-20 amino acids.

The antigen-antibody binding domain protein fragments are conventional antigen-antibody binding domain protein fragments in the art, which comprise a light chain variable region, a light chain constant region, and an Fd segment of heavy chain constant region. Preferably, the antigen-antibody binding domain protein fragments are Fab and F (ab').

The single domain antibody is a conventional single domain antibody in the art, which comprises a heavy chain variable region and a heavy chain constant region.

The single-domain antibody is a conventional single-domain antibody in the art, which only comprises a heavy chain variable region.

Wherein, the preparation method of the protein is a conventional preparation method in the art. Preferably, the preparation method is: isolating and obtaining the protein from an expression transformant that recombinantly expresses the protein or obtaining the protein by artificially synthesizing a protein sequence. The method of isolating and obtaining the protein from an expression transformant that recombinantly expresses the protein is preferably as follows: cloning a nucleic acid molecule encoding the protein carrying a point mutation into a recombinant vector, and transforming the obtained recombinant vector into a transformant to obtain a recombinant expression transformant, and by culturing the obtained recombinant expression transformant, the protein can be obtained by separation and purification.

Anti-SEMA4D Antibody

The present invention provides an antibody with high specificity and high affinity against SEMA4D, which comprises a heavy chain and a light chain, wherein the heavy chain contains a heavy chain variable region (VH) amino acid sequence, and the light chain contains a light chain variable region (VL) amino acid sequence.

Preferably, the heavy chain variable region (VH) comprises the following three complementary determining regions or CDRs:
CDR1 shown in SEQ ID NO: 8n+2,
CDR2 shown in SEQ ID NO: 8n+3, and
CDR3 shown in SEQ ID NO: 8n+4;
the light chain variable region (VL) comprises the following three complementary determining regions or CDRs:
CDR1' shown in SEQ ID NO: 8n+6,
CDR2' shown in SEQ ID NO: 8n+7, and
CDR3' shown in SEQ ID NO: 8n+8;
each n is independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or 41; preferably n is 40, 41, 38, 19, 12, 4, 13 or 7.

wherein, any one of the above amino acid sequences also includes a derivative sequence that is optionally with at least one amino acid added, deleted, modified, and/or substituted, and is capable of retaining the binding affinity to SEMA4D.

In another preferred embodiment, the sequence with at least one amino acid added, deleted, modified and/or substituted in any of the above amino acid sequences is preferably an amino acid sequence having a homology or sequence identity of at least 80%, preferably at least 85%, more preferably at least 90%, most preferably at least 95% to the above amino acid sequence.

Methods known to those of ordinary skill in the art for determining sequence homology or identity include, but are not limited to: Computational Molecular Biology, Lesk, A. M., Oxford University Press, New York, 1988; Biocomputing: Informatics and Genome Projects, edited by Smith, D. W., Academic Press, New York, 1993; Computer Analysis of Sequence Data, Part I, edited by Griffin, A. M. and Griffin, H. G., Humana Press, New Jersey, 1994; Sequence Analysis in Molecular Biology, von Heinje, G., Academic Press, 1987, and Sequence Analysis Primer, edited by Gribskov, M. and Devereux, J., Stockton Press, New York, 1991, and Carillo, H. and Lipman, D., SIAM J. Applied Math., 48:1073 (1988). The preferred method of determining identity is to obtain the greatest match between the sequences tested. The method of determining identity is compiled in a publicly available computer program. Preferred computer program methods for determining the identity between two sequences include, but are not limited to: GCG package (Devereux, J. et al., 1984), BLASTP, BLASTN, and FASTA (Altschul, S, F. et al., 1990). The BLASTX program is available to the public from NCBI and other sources (BLAST Manual, Altschul, S. et al., NCBI NLM NIH Bethesda, Md. 20894; Altschul, S. et al., 1990). The well-known Smith Waterman algorithm can also be used to determine identity.

The antibody of the present invention may be a double-chain or single-chain antibody, and may be selected from animal-derived antibodies, chimeric antibodies and humanized antibodies, more preferably be selected from humanized antibodies and human-animal chimeric antibodies, more preferably a fully humanized antibody.

The antibody derivatives of the present invention may be single chain antibodies, and/or antibody fragments, such as: Fab, Fab', (Fab')2 or other known antibody derivatives in the art, etc., as well as any one or several of IgA, IgD, IgE, IgG and IgM antibodies or other subtypes.

Wherein, the animal is preferably a mammal, such as a mouse.

The antibody of the present invention may be a chimeric antibody, a humanized antibody, a CDR grafted and/or modified antibody targeting SEMA4D (such as human SEMA4D).

In the above content of the present invention, the number of added, deleted, modified and/or substituted amino acids is preferably not more than 40% of the total number of amino acids in the original amino acid sequence, more preferably not more than 35%, more preferably 1-33%, more preferably 5-30%, more preferably 10-25%, more preferably 15-20%.

In the above content of the present invention, more preferably, the number of added, deleted, modified and/or substituted amino acids may be 1-7, more preferably 1-5, more preferably 1-3, more preferably 1-2.

In another preferred embodiment, the heavy chain variable region of the antibody comprises the amino acid sequence shown in SEQ ID NO: 8n+1, wherein n is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or 41.

In another preferred embodiment, the light chain variable region of the antibody comprises the amino acid sequence shown in SEQ ID NO: 8n+5, wherein n is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or 41.

In another preferred embodiment, the amino acid sequences of the heavy chain variable region and/or the light chain variable region of the antibody targeting SEMA4D are shown in the following Table 2:

TABLE 2

| Antibody number | VH sequence number | VL sequence number |
|---|---|---|
| 1 | 443 | 444 |
| 2 | 439 | 445 |
| 3 | 321 | 325 |
| 4 | 329 | 333 |
| 5 | 305 | 309 |
| 6 | 153 | 157 |
| 7 | 97 | 101 |
| 8 | 33 | 37 |
| 9 | 105 | 109 |
| 10 | 57 | 61 |

In another preferred embodiment, the antibodies targeting SEMA4D are 2D5-b1, 5D8-h2b4, 2D5, 5D8, 167H6H5, 31C11G2, 31G10C5, 17H4B2, 32C8F10 or 30B1C7.

Nucleic Acid

The present invention also provides a nucleic acid, which encodes the above-mentioned isolated protein or the heavy chain variable region or the light chain variable region of the anti-SEMA4D antibody.

Preferably, the nucleotide sequence of the nucleic acid encoding the heavy chain variable region is shown in SEQ ID NO: 2n+337; and/or, the nucleotide sequence of the nucleic acid encoding the light chain variable region is shown in SEQ ID NO: 2n+338, wherein either n is independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or 41.

More preferably, the nucleotide sequence of the nucleic acid encoding the heavy chain variable region is shown in SEQ ID NO: 2n+337, and the nucleotide sequence of the nucleic acid encoding the light chain variable region is shown in SEQ ID NO: 2n+338; wherein, n is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or 41.

The preparation method of the nucleic acid is a conventional preparation method in the art. Preferably, it comprises the following steps: obtaining the nucleic acid molecule encoding the above-mentioned protein by gene cloning technology, or obtaining the nucleic acid molecule encoding the above-mentioned protein by the method of artificial full-length sequence synthesis.

Those skilled in the art know that the base sequence encoding the amino acid sequence of the protein can be replaced, deleted, changed, inserted or added appropriately to provide a polynucleotide homolog. The homolog of the polynucleotide of the present invention can be prepared by replacing, deleting or adding one or more bases of the gene encoding the protein sequence within the scope of maintaining the activity of the antibody.

Vector

The present invention also provides a recombinant expression vector comprising the nucleic acid.

The recombinant expression vector can be obtained by conventional methods in the art, that is, by connecting the nucleic acid molecule of the present invention to various expression vectors, thus being constructed. The expression vector is one of a variety of conventional vectors in the art, as long as it can carry the above-mentioned nucleic acid molecule. The vector preferably includes: various plasmids, cosmids, phage or virus vectors and the like.

The present invention also provides a recombinant expression transformant comprising the above-mentioned recombinant expression vector.

Wherein, the preparation method of the recombinant expression transformant is a conventional preparation method in the art, preferably comprising: being obtained by transforming the recombinant expression vector into a host cell. The host cell is one of a variety of conventional host cells in the art, as long as the recombinant expression vector can replicate itself stably and the nucleic acid carried can be effectively expressed. Preferably, the host cell is *E. coli* TG1 or *E. coli* BL21 cell (for expressing single-chain antibodies or Fab antibodies), or HEK293 or CHO cell (for expressing full-length IgG antibodies). The above-mentioned recombinant expression plasmid is transformed into a host cell to obtain the preferred recombinant expression transformant of the present invention. The transformation method is a conventional transformation method in the art, preferably a chemical transformation method, a heat shock method or an electrotransformation method.

Preparation of Antibodies

The sequence of the DNA molecule for the antibody or a fragment thereof according to the present invention can be obtained by conventional techniques, for example, methods such as PCR amplification or genomic library screening. In addition, the sequences encoding light chain and heavy chain can be fused together, to form a single-chain antibody.

Once a relevant sequence is obtained, recombination methods can be used to obtain the relevant sequence in large quantities. This is usually carried out by cloning the sequence into a vector, transforming a cell with the vector, and then separating the relevant sequence from the proliferated host cell by conventional methods.

In addition, a relevant sequence can be synthesized artificially, especially when the fragment is short in length. Usually, several small fragments are synthesized first, and then are linked together to obtain a fragment with a long sequence.

It has been possible now to obtain a DNA sequence encoding the antibody (or a fragment thereof, or a derivative thereof) according to the present invention completely by chemical synthesis. Then, the DNA sequence can be introduced into various existing DNA molecules (or, for example, vectors) and cells known in the art. In addition, mutations can also be introduced into the protein sequence according to the present invention by chemical synthesis.

The present invention further relates to a vector comprising said suitable DNA sequence and a suitable promoter or a control sequence. These vectors can be used to transform suitable host cells to enable them to express protein.

The host cell can be a prokaryotic cell, such as a bacterial cell; or a lower eukaryotic cell, such as a yeast cell; or a higher eukaryotic cell, such as a mammalian cell. Preferred animal cells include, but are not limited to, CHO-S, HEK-293 cells.

In general, under conditions suitable for expression of the antibody according to the present invention, the host cell obtained is cultured. Then, the antibody according to the present invention is purified by using conventional immunoglobulin purification steps, for example, the conventional separation and purification means well known to those skilled in the art, such as protein A-Sepharose, hydroxyapatite chromatography, gel electrophoresis, dialysis, ion exchange chromatography, hydrophobic chromatography, molecular sieve chromatography or affinity chromatography.

The monoclonal antibody obtained can be identified by conventional means. For example, the binding specificity of a monoclonal antibody can be determined by immunoprecipitation or an in vitro binding assay (such as radioimmunoassay (RIA) or enzyme-linked immunosorbent assay (ELISA)). The binding affinity of a monoclonal antibody can be determined by, for example, the Scatchard analysis (Munson et al., Anal. Biochem., 107: 220 (1980)).

The antibody according to the present invention can be expressed in a cell or on the cell membrane, or is secreted extracellularly. If necessary, the recombinant protein can be separated and purified by various separation methods according to its physical, chemical, and other properties. These methods are well known to those skilled in the art. Examples of these methods include, but are not limited to, conventional renaturation treatment, treatment with a protein precipitant (salting out method), centrifugation, osmotic bacteria disruption, ultrasonic treatment, ultracentrifugation, molecular sieve chromatography (gel filtration), adsorption chromatography, ion exchange chromatography, high performance liquid chromatography (HPLC), various other liquid chromatographic techniques, and combinations of these methods.

Antibody-Drug Conjugate (ADC)

The present invention also provides an antibody-drug conjugate (ADC) based on the antibody according to the present invention.

Typically, the antibody-drug conjugate comprises the antibody and an effector molecule, wherein the antibody is conjugated to the effector molecule, and chemical conjugation is preferred. Preferably, the effector molecule is a therapeutically active drug. In addition, the effector molecule may be one or more of a toxic protein, a chemotherapeutic drug, a small-molecule drug or a radionuclide.

The antibody according to present invention and the effector molecule may be coupled by a coupling agent. Examples of the coupling agent may be any one or more of a non-selective coupling agent, a coupling agent utilizing a carboxyl group, a peptide chain, and a coupling agent utilizing a disulfide bond. The non-selective coupling agent refers to a compound that results in a linkage between an effector molecule and an antibody via a covalent bond, such as glutaraldehyde, etc. The coupling agent utilizing a carboxyl group may be any one or more of cis-aconitic anhydride coupling agents (such as cis-aconitic anhydride) and acyl hydrazone coupling agents (the coupling site is acyl hydrazone).

Certain residues on an antibody (such as Cys or Lys, etc.) are used to link a variety of functional groups, including imaging agents (such as chromophores and fluorophores), diagnostic agents (such as MRI contrast agents and radioisotopes), stabilizers (such as poly(ethylene glycol)) and therapeutic agents. An antibody can be conjugated to a functional agent to form a conjugate of the antibody-functional agent. A functional agent (e.g. a drug, a detection reagent, a stabilizer) is conjugated (covalently linked) to an antibody. A functional agent can be linked to an antibody either directly or indirectly via a linker.

Antibodies can be conjugated to drugs to form antibody-drug conjugates (ADCs). Typically, an ADC comprises a linker between a drug and an antibody. The linker can be a degradable or non-degradable linker. Typically, degradable linkers are easily degraded in an intracellular environment, for example, the linker is degraded at the target site, thereby releasing the drug from the antibody. Suitable degradable linkers include, for example, enzyme-degradable linkers, including peptidyl-containing linkers that can be degraded by protease (e.g. lysosomal protease or endosomal protease) in a cell, or sugar linkers, for example, glucuronide-containing linkers that can be degraded by glucuronidase. Peptidyl linkers may include, for example, dipeptides, such as valine-citrulline, phenylalanine-lysine or valine-alanine. Other suitable degradable linkers include, for example, pH sensitive linkers (e.g. linkers that are hydrolyzed at a pH of below 5.5, such as hydrazone linkers) and linkers that are degraded under reducing conditions (e.g. disulfide-bond linkers). A non-degradable linker typically releases a drug under conditions that the antibody is hydrolyzed by protease.

Prior to linkage to an antibody, a linker has a reactive group capable of reacting with certain amino acid residues, and the linkage is achieved by the reactive group. A thiol-specific reactive group is preferred, and includes, for example, a maleimide compound, a halogenated (e.g. iodo-, bromo- or chloro-substituted) amide; a halogenated (e.g. iodo-, bromo- or chloro-substituted) ester; a halogenated (e.g. iodo-, bromo- or chloro-substituted) methyl ketone, a benzyl halide (e.g. iodide, bromide or chloride); vinyl sulfone, pyridyl disulfide; a mercury derivative such as 3,6-di-(mercurymethyl)dioxane, wherein the counter ion is $CH_3COO^-$, $Cl^-$ or $NO_3^-$; and polymethylene dimethyl sulfide thiosulfonate. The linker may include, for example, a maleimide linked to an antibody via thiosuccimide.

A drug may be any cytotoxic, cytostatic or immunosuppressive drug. In an embodiment, an antibody is linked to a drug via a linker, and the drug has a functional group that can form a bond with the linker. For example, a drug may have an amino group, a carboxyl group, a thiol group, a hydroxyl group, or a ketone group that can form a bond with a linker. When a drug is directly linked to a linker, the drug has a reactive group before being linked to an antibody.

Useful drugs include, for example, anti-tubulin drugs, DNA minor groove binding agents, DNA replication inhibitors, alkylating agents, antibiotics, folic acid antagonists, antimetabolites, chemotherapy sensitizers, topoisomerase inhibitors, vinca alkaloids, etc. Examples of particularly useful cytotoxic drugs include, for example, DNA minor groove binding agents, DNA alkylating agents, and tubulin inhibitors; typical cytotoxic drugs include, for example, auristatins, camptothecins, docamycin/duocarmycins, etoposides, maytansines and maytansinoids (e.g. DM1 and DM4), taxanes, benzodiazepines or benzodiazepine containing drugs (e.g. pyrrolo[1,4]benzodiazepines (PBDs), indolinobenzodiazepines and oxazolidinobenzodiazepines), and vinca alkaloids.

In the present invention, a drug-linker can be used to form an ADC in a simple step. In other embodiments, a bifunctional linker compound can be used to form an ADC in a two-step or multi-step process. For example, a cysteine residue is reacted with the reactive moiety of a linker in a first step, and then the functional group on the linker is reacted with a drug in the subsequent step, so as to form an ADC.

In general, the functional group on a linker is selected so that it can specifically react with the suitable reactive group on a drug moiety. As a non-limiting example, an azide-based moiety can be used to specifically react with the reactive alkynyl group on a drug moiety. The drug is covalently bound to the linker by 1,3-dipolar cycloaddition between the azide and alkynyl group. Other useful functional groups include, for example, ketones and aldehydes (suitable for reacting with hydrazides and alkoxyamines), phosphines (suitable for reacting with azides); isocyanates and isothiocyanates (suitable for reacting with amines and alcohols); and activated esters, for example, N-hydroxysuccinimide esters (suitable for reacting with amines and alcohols). These and other linkage strategies, for example, those described in "Bioconjugation Technology" (2nd Edition (Elsevier)), are well known to those skilled in the art. Those skilled in the art could understand that when a complementary pair of reactive functional groups are selected for a selective reaction between a drug moiety and a linker, each member of the complementary pair can be used for the linker, and can also be used for the drug.

The present invention further provides a method for preparing an ADC, which may further comprise: under conditions sufficient to form an antibody-drug conjugate (ADC), binding an antibody to a drug-linker compound.

In certain embodiments, the method according to the present invention comprises: under conditions sufficient to form an antibody-linker conjugate, binding an antibody to a bifunctional linker compound. In these embodiments, the method according to the present invention further comprises: under conditions sufficient to covalently link the drug moiety to the antibody via a linker, binding the antibody-linker conjugate to the drug moiety.

In some embodiments, an antibody-drug conjugate (ADC) has a formula as follows:

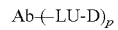

wherein,
Ab is an antibody,
LU is a linker;
D is a drug;
and the subscript p is a value selected from 1 to 8.

Use for Detection and the Kits

The antibody or ADC of the present invention can be used for detection, for example, for detection of samples to provide diagnostic information.

In the present invention, the samples (specimens) used include cells, tissue samples and biopsy specimens. The term "biopsy" used in the present invention shall include all kinds of biopsy known to those skilled in the art. Therefore, the biopsy used in the present invention may include, for example, excision samples of tumors, tissue samples prepared by endoscopic methods or organ puncture or needle biopsy.

The samples used in the present invention include fixed or preserved cells or tissue samples.

The present invention also provides a kit containing the antibody (or a fragment thereof) of the present invention. In a preferred embodiment of the present invention, the kit further includes a container, instructions for use, buffer, and the like. In a preferred example, the antibody of the present invention can be immobilized on a detection plate.

Uses

The present invention also provides use of the antibody, the antibody conjugate ADC, the isolated protein, the recombinant protein, and/or immune cell of the present invention, for example for the preparation of diagnostic preparations or the preparation of drugs.

Preferably, the drug is for prevention and/or treatment of diseases associated with abnormal SEMA4D expression or function.

In the present invention, the diseases associated with abnormal SEMA4D expression or function are conventional diseases associated with abnormal SEMA4D expression or function in the art. Preferably, the disease associated with abnormal SEMA4D expression or function is cancer, an autoimmune disease or an inflammatory disease.

In the present invention, the cancer is a conventional cancer in the art, preferably colon cancer, lung cancer, breast cancer, prostate cancer, ovarian cancer or pancreatic cancer. In the present invention, the autoimmune disease or inflammatory disease is a conventional autoimmune disease or inflammatory disease in the art, preferably multiple sclerosis or arthritis.

Uses of the antibody, the ADC, the isolated protein, the recombinant protein, and/or the immune cell of the present invention include (but are not limited to):

(i) for diagnosis, prevention and/or treatment of tumorigenesis, tumor growth and/or metastasis, especially a tumor with high expression of SEMA4D. The tumor includes (but is not limited to): colon cancer, lung cancer, breast cancer, prostate cancer, ovarian cancer or pancreatic cancer.

(ii) for diagnosis, prevention and/or treatment of autoimmune diseases, including (but not limited to): multiple sclerosis.

(iii) for diagnosis, prevention and/or treatment of inflammatory diseases, including (but not limited to) arthritis.

Pharmaceutical Composition

The present invention further provides a composition. In the preferred examples, the composition is a pharmaceutical composition comprising the antibody, or an active fragment, a fusion protein or an ADC thereof, or a corresponding immune cell, and a pharmaceutically acceptable carrier. In general, these substances may be formulated in a non-toxic, inert and pharmaceutically acceptable aqueous carrier medium, wherein the pH is generally about 5-8, preferably, pH is about 6-8, though the pH value may be varied depending on the nature of the substances to be formulated and the condition to be treated.

The formulated pharmaceutical composition may be administered by conventional routes, including (but not limited to): intratumoral, intraperitoneal, intravenous, or topical administration. Typically, the administration route of the pharmaceutical composition of the present invention is preferably injection or oral administration. The injection administration preferably includes intravenous injection, intramuscular injection, intraperitoneal injection, intradermal injection, or subcutaneous injection. The pharmaceutical composition is in one of a variety of conventional dosage forms in the art, preferably in solid, semi-solid or liquid form, and can be an aqueous solution, a non-aqueous solution or a suspension, and more preferably tablets, capsules, granules, injection or infusion, etc.

The antibody of the present invention can also be used for cell therapy by expressing the nucleotide sequence in the cell. For example, the antibody is used for chimeric antigen receptor T cell immunotherapy (CAR-T) and the like.

The pharmaceutical composition of the present invention is a pharmaceutical composition for prevention and/or treatment of diseases associated with abnormal SEMA4D expression or function.

The pharmaceutical composition according to the present invention can be directly used for binding to a SEMA4D protein molecule, and thus can be used for preventing and treating diseases such as tumors.

The pharmaceutical composition according to the present invention comprises a safe and effective amount (e.g. 0.001-99 wt %, preferably 0.01-90 wt %, preferably 0.1-80 wt %) of the monoclonal antibody according to the present invention (or a conjugate thereof) and a pharmaceutically acceptable carrier or excipient. Such carriers include (but are not limited to): saline, buffers, glucose, water, glycerol, ethanol, and a combination thereof. Pharmaceutical preparations should correspond to the administration modes. The pharmaceutical composition according to the present invention can be prepared in the form of an injection, for example, by a conventional method using physiological saline or an aqueous solution containing glucose and other adjuvants. A pharmaceutical composition, for example, an injection and a solution, should be prepared under aseptic conditions. The administration amount of an active ingredient is a therapeutically effective amount, for example, about 1 μg per kilogram of body weight to about 5 mg per kilogram of body weight daily.

In the present invention, preferably, the pharmaceutical composition of the present invention further comprises one or more pharmaceutical carriers. The pharmaceutical carrier is a conventional pharmaceutical carrier in the art, and the pharmaceutical carrier can be any suitable physiologically or pharmaceutically acceptable pharmaceutical excipient. The pharmaceutical excipient is a conventional pharmaceutical excipient in the art, and preferably includes pharmaceutically acceptable excipients, fillers or diluents. More preferably, the pharmaceutical composition comprises 0.01-99.99% of the above-mentioned protein and 0.01-99.99% of the pharmaceutically acceptable carrier, wherein the percentage is the mass percentage of the pharmaceutical composition.

In the present invention, preferably, the administration amount of the pharmaceutical composition is an effective amount, and the effective amount is an amount that can alleviate or delay the progression of the disease, and the degenerative or traumatic condition. The effective amount can be determined on an individual basis and will be partly based on consideration of the symptoms to be treated and the results sought. Those skilled in the art can determine the effective amount by using the above-mentioned factors such as individual basis and using no more than conventional experiments.

When a pharmaceutical composition is used, a safe and effective amount of an immunoconjugate is administered to a mammal, wherein the safe and effective amount is generally at least about 10 μg per kilogram of body weight, and in most cases, no more than about 50 mg per kilogram of body weight, preferably, the amount is from about 10 μg per kilogram of body weight to about 20 mg per kilogram of body weight. Of course, a specific amount should also depend on the factors such as administration route and physical conditions of a patient, which fall into the skills of skilled physicians.

The present invention provides use of the above-mentioned pharmaceutical composition in the preparation of a medicine for preventing and/or treating diseases associated with abnormal SEMA4D expression or function. Preferably, the disease associated with abnormal SEMA4D expression or function is cancer, an autoimmune disease or an inflammatory disease.

Method and Composition for Detecting SEMA4D Protein in a Sample

The present invention also provides a method for detecting SEMA4D protein in a sample (for example, detecting over-expressing SEMA4D cells), which comprises the following steps: contacting the above-mentioned antibody with a sample to be tested in vitro, and detecting whether the above-mentioned antibody binds to the sample to be tested, to form an antigen-antibody complex.

The meaning of overexpression is conventional in the art, which refers to the overexpression of RNA or protein of SEMA4D protein in the sample to be tested (due to increased transcription, post-transcriptional processing, translation, post-translational processing and protein degradation changes), and local overexpression and increased functional activity (such as in the case of increased enzymatic hydrolysis of the substrate) due to changes in protein transport mode (increased nuclear localization).

In the present invention, the detection method for detecting whether an antigen-antibody complex is formed is a conventional detection method in the art, preferably a flow cytometry (FACS) detection.

The present invention provides a composition for detecting SEMA4D protein in a sample, which comprises the above-mentioned antibody, recombinant protein, antibody conjugate, immune cell, or a combination thereof as an active ingredient. Preferably, it also comprises a compound composed of the functional fragments of the above-mentioned antibody as an active ingredient.

On the basis of conforming to common knowledge in the art, the above-mentioned preferred conditions can be combined arbitrarily to obtain preferred embodiments of the present invention.

The main advantages of the present invention are:
(1) The SEMA4D antibodies can bind to human SEMA4D, with high affinity (nM level).
(2) The SEMA4D antibodies have cross-reactivity with monkey or mouse SEMA4D.
(3) The SEMA4D antibodies can block the binding of SEMA4D and the receptor Plexin B1.
(4) At the cellular level, the SEMA4D antibodies can inhibit the shedding of tumor cells.
(5) At the cellular level, the SEMA4D antibodies can inhibit the production of myeloid suppressor cells (MDSCs).
(6) In mice, the SEMA4D antibodies themselves can effectively delay tumor growth, and the combination with immune checkpoint CTLA4 and PD-1 antibodies can effectively inhibit or delay tumor growth, and increase the response rates to CTLA4 and PD-1 antibodies, and prolong survival time.

The invention is further illustrated below in conjunction with specific embodiments. It should be understood that the examples are not intended to limit the scope of the invention. The experimental methods without detailed conditions in the following examples are generally in accordance with the conditions described in the conventional conditions such as Sambrook. J et al. "Guide to Molecular Cloning Laboratory" (translated by Huang Peitang et al., Beijing: Science Press, 2002), or in accordance with the conditions recommended by the manufacturer (for example, product manuals). Unless otherwise stated, percentages and parts are calculated by weight. Unless otherwise specified, the experimental materials and reagents used in the following examples are commercially available.

The room temperature described in the examples refers to the temperature in the operating room where the test is performed, generally 15-30° C.

Example 1 Preparation of SEMA4D Antibodies by Hybridoma Technology (I) Preparation of Immunogen
A. Protein Immunogen:

The nucleotide sequence (as shown in SEQ ID NO: 421 in the sequence listing) containing the sequence encoding human SEMA4D protein extracellular domain (hSEMA4D ECD) Met22-Arg734 was cloned into the pCP vector carrying a His tag (wherein the cloning step was completed by Shanghai Ruizhi Chemical Research Co., Ltd) and plasmids were prepared according to the established standard molecular biology methods. For specific methods, see Sambrook, J., Fritsch, E. F., and Maniatis T. (1989). Molecular Cloning: A Laboratory Manual, Second Edition (Plainview, New York: Cold Spring Harbor Laboratory Press). CHO-S cells (purchased from Gibco) were transiently transfected with polyetherimide (PEI, purchased from Polyscience), and CDFortiCHO medium (purchased from Gibco) was used for expansion culture at 37° C. After 8-10 days, the cell culture was collected, and the cell components were removed by centrifugation to obtain the culture supernatant containing the extracellular region of human SEMA4D protein. The culture supernatant was loaded onto a Ni affinity chromatography column (purchased from GE Healthcare), and an ultraviolet (UV) detector was used to monitor the change in ultraviolet absorbance (A280 nm). After the sample was loaded, the Ni affinity chromatography column was washed with phosphate buffer (pH7.8) until the UV absorption value returned to the baseline, and then gradient elution was performed with 0-500 mM imidazole. The His-tagged human SEMA4D protein extracellular region eluted from the Ni affinity chromatography column was collected, and the protein was dialyzed into PBS phosphate buffer (pH7.8) with a dialysis card (purchased from Thermo Scientific) at 4° C., and the dialyzed protein was concentrated in an ultrafiltration tube (purchased from Millipore), aseptically filtered at 0.22 µm, and stored in aliquots at −80° C. The purified extracellular domain of human SEMA4D protein was obtained as an immunogen, namely hSEMA4D ECD-His. The immunogen needed a series of quality control tests before use, such as tests of protein concentration, purity, molecular weight, biological activity and so on.

Wherein, the biological activity of the immunogen was detected by the cell shedding experiment (see Example 5 for the specific method). The results are shown in FIG. 1 and Table 3. The immunogen can stimulate tumor cell shedding.

TABLE 3

Detection of biological activity of immunogens

| | Protein immunogen concentration (µg/mL) | | | | |
|---|---|---|---|---|---|
| | 5 | 2 | 1 | 0.5 | 0 |
| Luminescence intensity (RLU) | 131765.75 | 110210.35 | 167051.20 | 391382.50 | 549948.45 |

B. Cellular Immunogen:
The nucleotide sequence containing the sequence encoding the full-length human SEMA4D (as shown in SEQ ID No: 422 in the sequence listing) was cloned into the pLVX-IRES-Hyg vector (purchased from Clontech), and the plasmid was prepared according to the above method. The lentivirus was packaged using X-treme GENE HP DNA Transfection Reagent (purchased from Roche) and 293F/Renca cells (293F was purchased from Invitrogen, and Renca was purchased from ATCC) were infected therewith. The infected cells were cultured for two weeks in a medium containing 100/150 μg/mL antibiotics and 10% fetal calf serum. Subcloning was performed in 96-well culture plates by limiting dilution, and cultured at 37° C. with 5% (v/v) $CO_2$. About 2 weeks later, some monoclonal wells were selected and expanded into 6-well plates. The amplified clones were screened by FACS with a commercial SEMA4D antibody (purchased from R&D Systems). Monoclonal cell lines with better growth and higher fluorescence intensity (MFI) were selected to continue to be expanding cultured and cryopreserved in liquid nitrogen to obtain a stable transgenic cell line expressing human SEMA4D.

TABLE 4

FACS screening and detection results of 293F/Renca cells expressing human

| Sequence number | Transfected cell clone number | SEMA4D antibody | | IgG subtype control | |
|---|---|---|---|---|---|
| | | Positive cells (%) | Mean fluorescence intensity | Positive cells (%) | Mean fluorescence intensity |
| 1 | 293F hSEMA4D 31 | 99.06 | 11769 | 0.30 | 26 |
| 2 | 293F hSEMA4D 54 | 98.82 | 21009 | 0.44 | 26 |
| 3 | 293F hSEMA4D 63 | 99.42 | 13437 | 0.40 | 29 |
| 4 | 293F hSEMA4D 64 | 99.31 | 15379 | 0.47 | 27 |
| 5 | Renca hSEMA4D 5 | 85.08 | 3668 | 0.28 | 39 |
| 6 | Renca hSEMA4D 11 | 86.97 | 5912 | 0.53 | 40 |
| 7 | Renca hSEMA4D 13 | 89.58 | 6885 | 0.16 | 35 |
| 8 | Renca hSEMA4D 49 | 88.53 | 6084 | 0.61 | 39 |

Figure 2A:
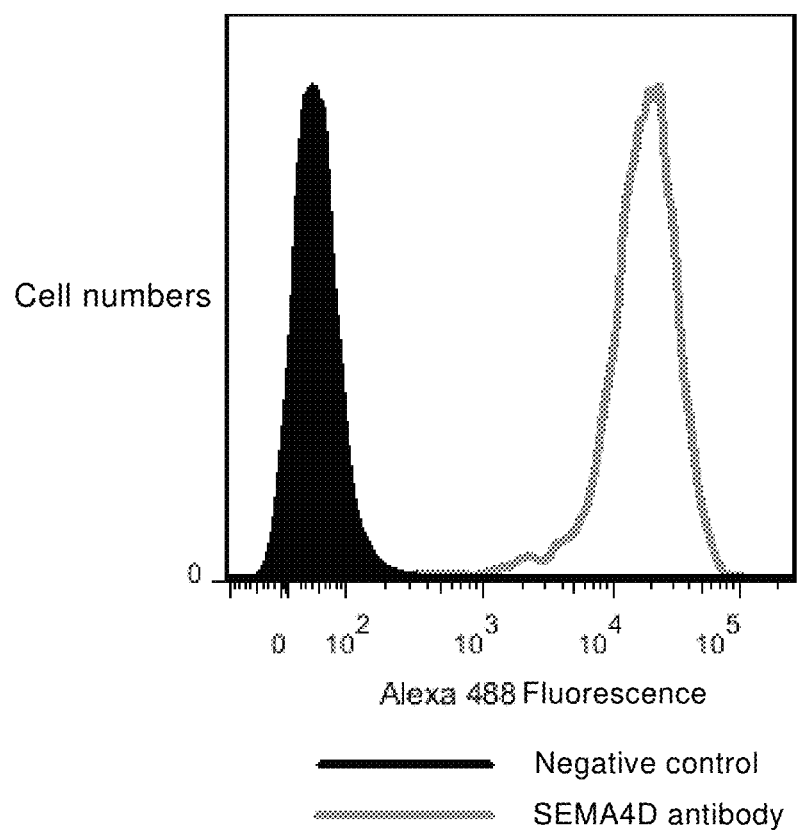
FIGS. 2A and 2B are graphs showing the detection results of human SEMA4D protein expression levels in 293F and Renca recombinant cell lines by flow cytometry (FACS). SEMA4D antibody was purchased from R&D systems; and the negative control refers to an isotype antibody control.
Figure 2B:
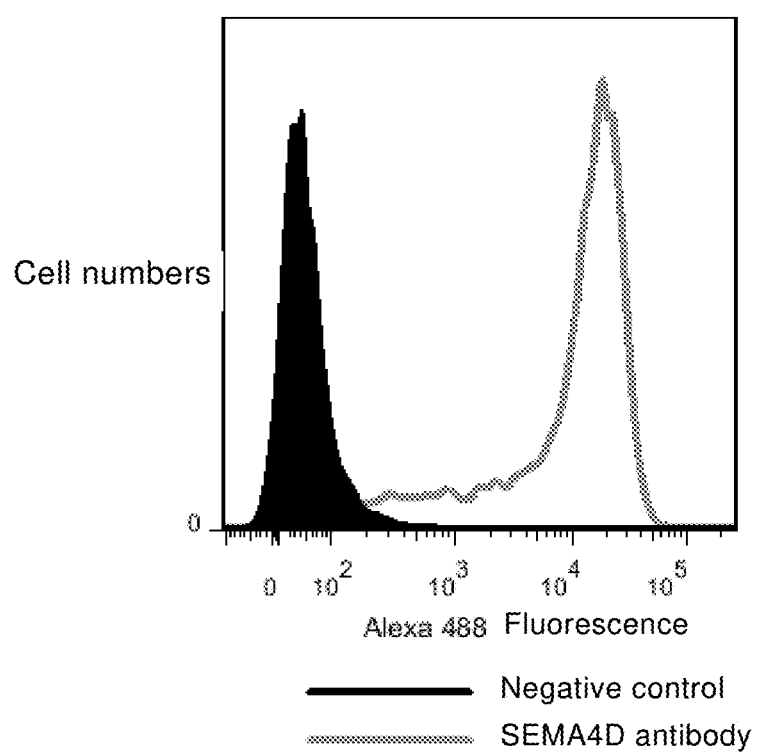

The specific selection results are shown in FIGS. 2A-B and Table 4. In Table 4, positive cells (%) refer to the percentage of number of positive cells in the total number of cells. The results indicate that a series of human SEMA4D expression positive 293F/Renca stable transgenic cell lines have been produced.

C. DNA Immunogen:

The nucleotide sequence containing the sequence encoding the full length of human SEMA4D (as shown in SEQ ID No: 422 in sequence listing, as shown in the cellular immunogen) was cloned into the pCP vector, and the plasmid pCP-hSEMA4D was prepared according to the above method.

(II) Preparation of Hybridoma Cells and Screening of Antibody

Figure 3:
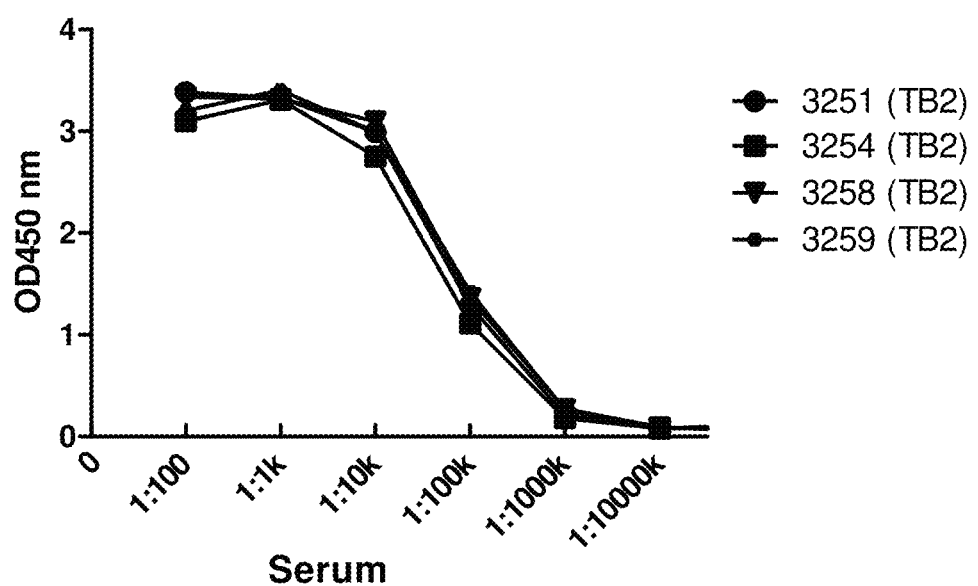
FIG. 3 is a graph showing the detection results of the mice serum antibody titer after immunization with protein immunogen by enzyme-linked immunosorbent assay (ELISA).

A. 6-8 weeks old female SJL mice (purchased from Shanghai Slack Laboratory Animal Co., Ltd.) were used, and the mice were raised under SPF conditions. During the first immunization, the protein immunogen obtained in step (I) (i.e., hSEMA4D ECD-His) was emulsified with Freund's complete adjuvant and injected intraperitoneally with 0.2 mL. That is, each mouse was injected with 50 g protein immunogen. During the boosting immunization, the immunogen was emulsified with Freund's incomplete adjuvant and injected intraperitoneally with 0.2 ml. That is, each mouse was injected with 25 g of protein immunogen. The interval between the initial immunization and the first boosting immunization was 2 weeks. After that, the intervals between each boosting immunization were 3 weeks. Blood was collected 1 week after each boosting immunization, and the antibody titer and specificity of protein immunogen in the serum were detected by ELISA and FACS. The results are shown in FIG. 3 and Table 5.

TABLE 5

ELISA detection of serum antibody titer in a SJL mice after protein immunogen immunization

| OD450 nm batch | Serum dilution | | | | | | Blank control |
|---|---|---|---|---|---|---|---|
| | 1:100 | $1:10^3$ | $1:10^4$ | $1:10^5$ | $1:10^6$ | $1:10^7$ | |
| 3251 (SJL, TB2) | 3.38 | 3.33 | 2.99 | 1.29 | 0.21 | 0.08 | 0.11 |
| 3254 (SJL, TB2) | 3.10 | 3.31 | 2.75 | 1.11 | 0.18 | 0.08 | 0.08 |
| 3258 (SJL, TB2) | 3.34 | 3.32 | 3.10 | 1.36 | 0.27 | 0.09 | 0.06 |
| 3259 (SJL, TB2) | 3.20 | 3.40 | 2.99 | 1.42 | 0.26 | 0.08 | 0.08 |

The results show that the serum of mice immunized with protein immunogen had different degrees of binding to the immunogen, showing antigen-antibody response, and the highest dilution was about one million. Wherein, the blank control was 1% (w/w) BSA, and the batch referred to the mice serum on the seventh day after the second boosting immunization. The data in the table is the value of OD450 nm.

B. 6-8 weeks old female Balb/c and SJL mice (purchased from Shanghai Slack Laboratory Animal Co., Ltd.) were used, and the mice were raised under SPF conditions. Cellular immunogen obtained in step (I) (i.e., 293F hSEMA4D and Renca hSEMA4D) was cultured for expanding in a T-75 cell culture flask to a confluence of 90%, and the medium was aspirated. Cells were washed with DMEM basal medium (purchased from Invitrogen) twice, and then treated with enzyme-free cell dissociation solution (purchased from Invitrogen) at 37° C. until the cells were detached from the wall of the culture dish, and then the cells were collected. Cells were washed twice with DMEM basal medium and counted, and then diluted with phosphate buffer to $2\times10^7$ cells per ml. Wherein, Renca hSEMA4D cells were treated with 10 μg/mL mitomycin C for 4 hours, and then washed twice with phosphate buffer, and diluted to $2\times10^7$ cells per mL. Each mouse was intraperitoneally injected with 0.5 mL of cell suspension during each immunization. The interval between the initial immunization and the first boosting immunization was 2 weeks. After that, the intervals between each boosting immunization were 3 weeks. Blood was collected 1 week after each boosting immunization, and the antibody titer and specificity of the cellular immunogen in the serum were detected by FACS. After the second boosting immunization, the serum antibody titer detected by FACS reached more than 1:1000 (for the specific method, see the relevant content in Example 3).

C. 6-8 weeks old female Balb/c and SJL mice (purchased from Shanghai Slack Laboratory Animal Co., Ltd.) were used, and the mice were raised under SPF conditions. During immunization, the DNA immunogen obtained in step (I) (i.e., pCP-hSEMA4D) was wrapped on 1.0 μm gold particles (purchased from Bio-RAD) and injected with Helios gene gun (Bio-RAD No. 165-2431). Each mouse was injected with 4 μg per immunization, and was immunized 4 times. The interval between the initial immunization and the first boosting immunization was 2 weeks, and so was the intervals between each boosting immunization thereafter. Blood was collected 1 week after each boosting immunization, and the antibody titer and specificity of the protein immunogen in the serum were detected by ELISA and FACS. After the third boosting immunization, the serum antibody titer detected by FACS reached more than 1:1000 (for the specific method, see the relevant content in Example 3).

After steps A, B, and C were completed, each selected mouse was immunized for the last time. 25 μg of protein immunogen A (for mice having immune response against immunogen A), HEK293 or Renca stably transfected cell line expressing human SEMA4D (for mice having immune response against immunogen B) and 25 μg of protein immunogen A (for mice having immune response against immunogen C) were injected intraperitoneally. After 3-4 days, the mice were sacrificed and splenocytes were collected. The spleens were grinded and 70 μm filters were used to remove tissue debris, to obtain spleen cell suspensions. The cells were washed with DMEM basal medium (purchased from invitrogen) by centrifugation at 1000 rpm for 3 times, then mixed with mouse myeloma cells SP2/0 (purchased from ATCC) at a ratio of 4:1 according to the number of viable cells. PEG, 50% (w/v) (purchased from Sigma, catalog number wt1450) mediated cell fusion method was used for cell fusion (see J Immunol Methods. 1980; 35:1-21.). The fused cells were diluted into DMEM medium containing 20% (w/w) fetal bovine serum and 1×HAT. Then the cell solution was added as $1×10^5$ cells/200 μL per well to a 96-well cell culture plate, and placed in a 37° C., 5% (v/v) $CO_2$ incubator for culture. After 9-14 days, ELISA or Acumen (microwell plate cell detection method) was used to screen the supernatants in cell fusion plate. The positive clones with OD450 nm>1.0 in ELISA and MFI value>100 in Acumen were expanded to a 24-well plate, and cultured in the DMEM medium with 10% (w/w) HT fetal bovine serum, at 37° C. and 5% (v/v) $CO_2$. After 3 days of culture, the cell supernatants in the 24-well plate was collected. The supernatants were analyzed for antibody subtypes. Meanwhile, FACS was used to determine the binding activity to CHO-K1 hSEMA4D (for the detection method of binding activity, see Example 3). The ligand receptor binding experiment was performed to determine the blocking activity on SEMA4D receptor (for the detection method of blocking activity, see Example 4). Cell shedding experiment was performed to confirm the inhibitory effect on SEMA4D-induced cell shedding (for detection method of inhibiting cell shedding, see Example 5).

According to the results of the 24-well plate screening, hybridoma cells with average fluorescence intensity MFI value>150 in the FACS experiment and with an inhibitory effect of >20% on SEMA4D-induced cell shedding in the cell shedding experiment were selected as eligible positive clones. Eligible hybridoma cells were subcloned in a 96-well plate by limiting dilution, and cultured in DMEM medium containing 10% (w/w) FBS (purchased from invitrogen) under conditions of 37° C., 5% (v/v) $CO_2$. 10 days after subcloning, ELISA or Acumen was used for preliminary screening, and single positive monoclones were selected and amplified to a 24-well plate to continue culture. Three days later, FACS was used to evaluate the binding activity to CHO-K1 hSEMA4D, and the ligand receptor binding experiment was used to evaluate the blocking activity on SEMA4D receptor, and the cell shedding experiment was used to evaluate the inhibitory effect on SEMA4D-induced cell shedding. Wherein, the evaluation criteria were MFI value>150 and inhibitory effect on SEMA4D-induced cell shedding >50% in cell shedding experiment.

According to the detection results of the 24-well plate samples, the optimal clones were selected and placed and cultured in DMEM medium containing 10% (w/w) FBS (purchased from invitrogen) under conditions of 37° C., 5% (v/v) $CO_2$ for expanding. And the optimal hybridoma cells were obtained and cryopreserved in liquid nitrogen, which can be used for subsequent antibody production and purification.

(III) Production and Purification of Leading Antibodies from Hybridomas

Since the concentration of antibody produced by hybridoma cells was low, which was only about 1-10 g/mL and the resulting antibody concentration varied greatly, and the various proteins produced by cell culture in the medium and the fetal bovine serum components contained in the medium had varying degrees of interference to many biological activity analysis methods, small-scale (1-5 mg) antibody production and purification was required.

The hybridoma cells obtained in step (II) were inoculated into a T-75 cell culture flask and production medium (Hybridoma serum free medium, purchased from Invitrogen) was used for domestication and passage for 3 generations. When the cells grew well, they were inoculated into the cell culture spinner flask. 500 mL of production medium was added to each 2 liter culture spinner flask, and the inoculated cell density was $1.0×10^5$ cells/mL. The bottle was tightly capped and placed in the spinner in the 37° C. incubator at a speed of 3 rpm. After 14 days of continuous spinning culture, the cell culture fluid was collected, filtered to remove the cells, and filtered with a 0.45 m filter membrane until the culture supernatant was clarified. The clarified culture supernatant can be purified immediately or cryopreserved at −30° C.

A 2 mL protein A column (purchased from GE Healthcare) was used to purify the monoclonal antibody from 200 mL of hybridoma cell culture supernatant. The protein A column was first equilibrated with 3 to 5 column volumes of equilibration buffer (PBS phosphate buffer, pH7.4), and then the clarified culture supernatant was loaded onto the protein A column, with a flow rate controlled at 1 mL/min. After the sample was loaded, protein A column was washed with the equilibration buffer. The volume of the equilibration buffer was 3 to 5 times the volume of the protein A column bed. The monoclonal antibody bound to the protein A column was eluted with the eluent (0.1M citrate buffer, pH4.5), and the elution was monitored with a nucleic acid protein detector (A280 ultraviolet absorption peak). The eluted monoclonal antibody was collected, added with 10% (v/v) 1.0 M Tris-HCl, pH8.0 buffer to neutralize the pH. Then immediately dialysis was performed overnight with PBS phosphate buffer, the buffer was changed once on the next day and the dialysis was continued for 3 hours. The dialyzed monoclonal antibody was collected, aseptically filtered with a 0.22 m filter, and stored aseptically, thus obtaining purified SEMA4D antibody as the lead antibody.

The purified SEMA4D antibody was tested and analyzed for protein concentration (A280/1.4), purity, and endotoxicity (Lonza kit). The results are shown in Table 6, which indicated that the endotoxin concentration of the purified lead antibody was within 4.5 EU/mg.

TABLE 6

Detection and analysis of purified SEMA4D antibodies

| Clone number | Antibody purity | Protein concentration (mg/mL) | Endotoxin (EU/mg) |
|---|---|---|---|
| 8G4E12 | >90% | 0.87 | 1.35 |
| 17H4B2 | >90% | 0.94 | 1.38 |
| 12G10H1 | >90% | 0.41 | 2.12 |
| 31G10C5 | >90% | 0.23 | 3.42 |

TABLE 6-continued

Detection and analysis of purified SEMA4D antibodies

| Clone number | Antibody purity | Protein concentration (mg/mL) | Endotoxin (EU/mg) |
|---|---|---|---|
| 32C8F10 | >90% | 0.67 | 0.88 |
| 37C4F7 | >90% | 0.29 | 1.81 |
| 37F11F9 | >90% | 0.16 | 4.17 |
| 38H2E3 | >90% | 0.83 | 1.53 |
| 42B7G2 | >90% | 0.48 | 1.45 |
| 31C11G2 | >90% | 0.49 | 0.55 |
| 84A2C4 | >90% | 0.70 | 0.74 |
| 131H4A2 | >90% | 0.78 | 2.45 |
| 142D6D11 | >90% | 0.53 | 3.99 |

TABLE 6-continued

Detection and analysis of purified SEMA4D antibodies

| Clone number | Antibody purity | Protein concentration (mg/mL) | Endotoxin (EU/mg) |
|---|---|---|---|
| 167H6H5 | >90% | 0.50 | 0.82 |
| 166E12G6 | >90% | 0.70 | 0.38 |

Example 2 Preparation of SEMA4D Antibodies by Phage Display Technology (I) Biotinylation of SEMA4D Protein The protein immunogen prepared in Example 1 (i.e., hSEMA4D ECD-His) was dialyzed with 0.15M $Na_2HCO_3$, and the final concentration was 1 mg/mL. Biotin-NHS (purchased from Sigma Aldrich) was dissolved in DMF to a final concentration of 10 mg/mL. Biotin-X-X-NHS and protein immunogen were mixed at a molar ratio of 8:1. After standing at room temperature for 30 minutes, it was added with 1M $NH_4Cl$ to stop the reaction. Then, it was dialyzed overnight with PBS phosphate buffer (pH 7.4) at 4° C. to remove free biotin and obtain a biotinylated immunogen (i.e., biotinylated hSEMA4D ECD-His). The concentration of biotinylated hSEMA4D ECD-His was determined with a BCA protein concentration determination kit (purchased from Pierce).

The activity of biotinylated hSEMA4D ECD-His was determined by FACS method. The stable transgenic cell line 293F hPlexin B1 expressing the human SEMA4D receptor Plexin B1 (see the relevant content in Example 4 for the specific method of constructing stable transgenic cell line) and 293F cells were expanded in a T-175 cell culture flask to a confluence of 90%. The medium was aspirated, the cells were washed once with PBS phosphate buffer (purchased from Invitrogen), and then treated with cell dissociation fluid (TrypLE™ Express Enzyme, purchased from Life technology), and the cells were collected. After the cells counted, the cells were washed once with PBS phosphate buffer, and diluted to $1\times10^6$ cells per milliliter, and added to the 96-well FACS reaction plate as 100 μL per well. 2% (w/w) fetal calf serum was added to PBS phosphate buffer as FACS buffer, with which the cells were washed once by centrifugation at 2000 rpm 4° C. 100 μL of diluted biotinylated hSEMA4D ECD-His was added to each well and the plate was incubated on ice for 1 hour. The plate was washed twice with the FACS buffer by centrifugation, added with 100 μL of fluorescence (Alexa 488) labeled secondary antibodies (purchased from Invitrogen) per well, and incubated on ice for 1 hour. Cells were washed 3 times by centrifugation with FACS buffer. The cells were suspended with 200 μL of FACS buffer, and FACS (FACS Verse, purchased from BD) was used to detect and analyze the results.

TABLE 7

Detection of the binding reaction between biotinylated hSEMA4D ECD-His and the stable human PlexinB1 cell line (293F hPlexin B1) by FACS

| Mean fluorescence intensity MFI | Biotinylated hSEMA4D ECD-His concentration (nM) | | | | | | | |
|---|---|---|---|---|---|---|---|---|
| Cell line | 666.67 | 222.22 | 66.67 | 22.22 | 6.67 | 2.22 | 0.67 | 0.22 |
| 293F hPlexin B1 | 2237.49 | 1088.87 | 617.83 | 229.40 | 125.06 | 61.90 | 53.11 | 41.84 |
| 293F | 122.45 | 94.70 | 91.31 | 78.16 | 78.47 | 74.91 | 71.67 | 63.12 |

Figure 4:
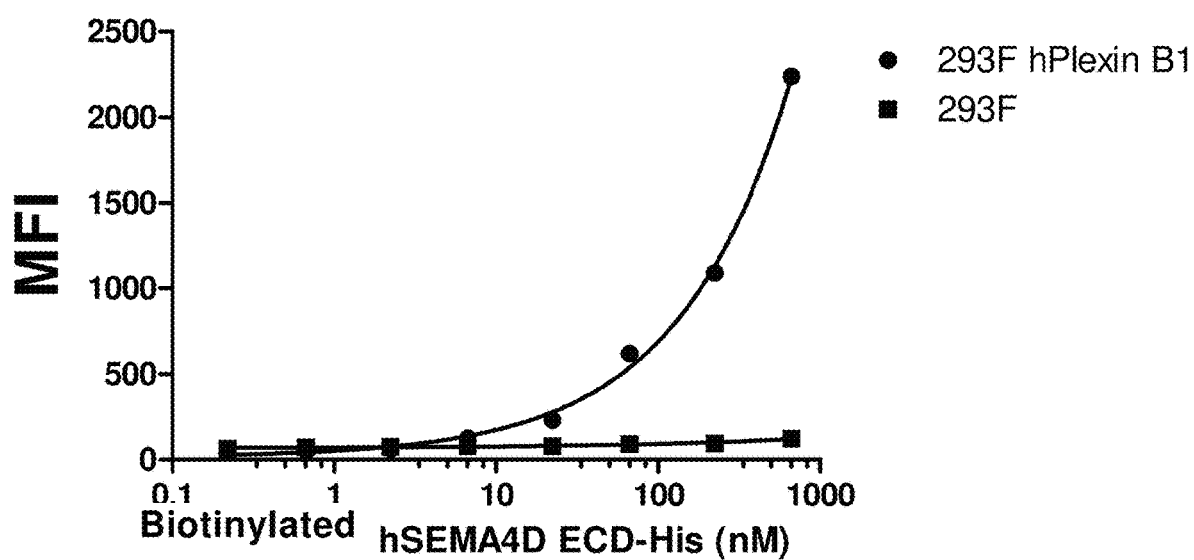
FIG. 4 shows the FACS detection of the binding reaction between biotinylated hSEMA4D ECD-His and the stable human PlexinB1 cell line.

The results are shown in FIG. 4 and Table 7. The biotinylated hSEMA4D ECD-His can bind to the stable transgenic cell line 293F hPlexin B1 expressing the SEMA4D receptor Plexin B1.

(II) Screening of SEMA4D Antibodies by Phage Display Technology

The natural human single-chain antibody (ScFv) phage display library (built by Shanghai Ruizhi Chemical Research Co., Ltd.) was used to screen the leading antibody. Antibodies that bind to SEMA4D were obtained through three rounds of biopanning. The specific process was as follows:

In the first round of biopanning, three tubes A, B, and C were prepared. Tube A was firstly added with 100 μL of streptavidin-conjugated Dynabeads (purchased from Invitrogen) and the phage ScFv antibody library, and tube B was firstly added with 100 μL of streptavidin-conjugated Dynabeads. Then the three tubes were added with 10 mL of blocking solution, namely PBS phosphate buffer solution containing 2% (w/v) skimmed milk powder, and blocked for 2 hours at room temperature, respectively. The liquid in tube C was poured out, and tube C was added with the supernatant collected from tube A after centrifugation, and then added with 20 μg of the biotinylated hSEMA4D ECD-His prepared in step (I), and incubated with shaking at room temperature for 2 hours. And a control tube was set up, just without biotinylated hSEMA4D ECD-His addition, and incubated with shaking at room temperature for 2 hours. Tube B was centrifuged to obtain blocked magnetic beads, added with the mixed solution after incubation, and incubated with shaking at room temperature for 15 minutes. Tube B was placed in a magnetic stand for 30 seconds, washed 5 times with 1 mL PBST, namely a blocking solution containing 0.05% (v/v) Tween-20, and then washed 5 times with blocking solution and PBS buffer. After washing, 1 mL of 10 μg/mL pancreatin was added to each tube and tubes were incubated at 37° C. for 30 minutes to elute the phage bound to the biotinylated hSEMA4D ECD-His. 1 mL of pancreatin solution was added to 4 mL of E. coli TG1

(purchased from LUCIGEN) in the logarithmic growth phase, and the mixture was incubated at 37° C. for 30 minutes to obtain a TG1 culture solution. The TG1 culture solution was gradiently diluted, spreaded on a plate, and incubated overnight at 37° C. The number of clones that bind to biotinylated hSEMA4D ECD-His and the control tube were calculated, and 20-40 clones were selected for sequencing.

Meanwhile, the clones on the plate were washed with 2YT medium (the preparation method of 2YT medium was: adding 10 g yeast extract, 16 g tryptone and 5 g NaCl to 1 L of water, and adjusting it to pH 7.0 with NaOH, and autoclaving) and collected, and inoculated in fresh medium, cultivated to logarithmic phase at 37° C. Helper phage M13KO7 (purchased from NEB, catalog number N0315S) was added, wherein the ratio of helper phage to *E. coli* TG1 was 1:1000, mixed well, and let stand at 37° C. for 30 minutes. Then, the cells were cultured with shaking at 37° C. for 30 minutes, and the cells were collected after centrifugation at 4000 rpm for 10 minutes. Fresh 2YT medium was added, for culture with shaking at 30° C. for 4 hours. Centrifuge at 5000 rpm was performed for 15 minutes. The supernatant was collected, added with 2.5M NaCl solution containing 20% PEG as ¼ of the supernatant volume, and placed on ice overnight. Centrifugation at 5000 rpm was performed at 4° C. for 30 minutes, and the phage pellet was collected and dissolved in PBS buffer. Centrifugation at 10,000 rpm was performed for 10 minutes to remove residual cell debris, and the supernatant was collected for the next round of biopanning.

The second and third rounds of biopanning procedures were the same as the first round, enriching the ScFv antibody sequences that specifically binds to biotinylated hSEMA4D ECD-His. Single clones were selected from the plates in the second and third rounds and cultured in 96-well plates. Each well contained 200 µL of 2YT medium with antibiotics and the cells were cultured overnight at 37° C. and 1000 rpm with shaking. 10 µL of the overnight cultured supernatant was taken and added to 4 mL of antibiotic-containing medium, and cultured for 1.5-2.5 hours at 37° C. with shaking at 250 rpm. IPTG was added to a final concentration of 1 mM, and the cells were cultured with shaking at 30° C. for 16 hours, and centrifuged at 4000 rpm for 10 minutes, thus obtaining the single-chain antibodies from the supernatant.

The ELISA method was used to detect the binding activity of the scFv antibody, obtained by screening, to SEMA4D. The clones with OD450 nm>1.0 were selected for sequencing, and clones with different heavy chain CDR3 sequences were obtained. Then FACS and ligand receptor binding experiments (for specific detection methods, see Example 4 respectively) were used to select clones with an MFI value>200 in the FACS experiment and with a blocking inhibition rate of >50% on the SEMA4D receptor PlexinB1 by the cell lysis supernatant in the ligand receptor binding experiment, to be used as eligible positive clones.

(III) Production and Purification of Lead Antibodies Derived from Phage

According to the sequencing results of positive clones, primers (specific primer sequences are shown in Table 8) were designed to amplify the variable regions of the light chain and the heavy chain respectively by PCR. A 50 µL reaction system was configured, including 0.5 µL of plasmids extracted from the transfected positive clone *E. coli* TG1, 10 pmol of each primer, 25 µL of Q5 high-fidelity DNA polymerase, and water to make up to 50 µL. PCR program was set, comprising pre-denaturation 95° C. for 5 min, denaturation 95° C. for 30 s, annealing 55° C. for 30 s, extension 68° C. for 30 s, and further extension at 68° C. for 1 min after 25 cycles. And the PCR product was obtained. The DNA polymerase used in PCR was purchased from NEB, catalog number E0555L. 5 µl of PCR product was taken for agarose gel electrophoresis detection, and the recovery kit was used to purify the positive samples. Wherein, the recovery kit was QIAquick Gel extraction kit, purchased from Qiagen, catalog number 28706. Ligation reaction was carried out: the reaction system was with a volume of 20 µL, containing 3 µL of fragments to be inserted, 2 µL of digested expression vector, 2 µL of recombinase Exnase, and 4 µL of buffer, and reacted at 37° C. for half an hour to obtain the ligation product, which was the constructed recombinant vector. Wherein, the recombinase was purchased from Vazyme, catalog number C112-01/02; and the buffer was the buffer used in the purchase of the recombinase. The heavy chain variable region was directionally cloned into the expression vector containing sequences encoding a signal peptide and human antibody heavy chain IgG4 (S228P) constant region (wherein, the expression vector was purchased from Invitrogen, and the recombination step was completed by Shanghai Ruizhi Chemical Research Co., Ltd.). The light chain variable region was directionally cloned into the expression vector containing a signal peptide and the human antibody light chain lambda constant region (wherein, the expression vector was purchased from Invitrogen, and the recombination step was completed by Shanghai Ruizhi Chemical Research Co., Ltd.). 10 µL of the ligation product was added to 100 µL of competent cells (Ecos 101 competent cells, purchased from Yeastern, catalog number FYE607), and ice bathed for 30 minutes. Then heat shock in a 42° C. water bath was performed for 90 seconds, and cells were put back on ice for 2 minutes, added with 800 µL of antibiotic-free 2YT medium, and incubated on a 37° C. shaker at 200 rpm for 45 minutes. Then 200 µL of the culture was taken and coated onto LB solid medium containing 100 µg/mL ampicillin, and cultured overnight in a 37° C. incubator. The next day, the primers pTT-EF1a-F and pSV40 for the expression vector (the nucleotide sequences of which were shown in SEQ ID No: 430 and SEQ ID No: 431 in the sequence listing, respectively) were used for configuration of a 30 µL PCR system, to perform colony PCR. The colony PCR system was: 1 µL of either primer, 10 µL of PCR pre-mixture (purchased from Novoprotein), maked up to 20 µL. A pipette tip was used to dip the colony into the PCR reaction system and pipette, and 0.5 µl was aspirated onto another piece of 100 µg/mL ampicillin LB solid petri dish to store the strain. After the PCR reaction, 5 µL of the reaction solution was taken out for agarose gel electrophoresis detection, and the positive samples were sequenced and analyzed [see Kabat, "Sequences of Proteins of Immunological Interest," National Institutes of Health, Bethesda, Md. (1991)].

TABLE 8

Sequence numbers of primers for positive clones

| Clone number | | Forward primer | Reverse primer |
| --- | --- | --- | --- |
| 2D5 | $V_H$ | 423 | 424 |
| | $V_L$ | 425 | 426 |
| 5D8 | $V_H$ | 427 | 424 |
| | $V_L$ | 428 | 429 |

After colony PCR verification, expression vectors with the correct sequences of the recombinant antibody heavy and light chain were transiently transfected into FreeStyle™ 293-F cells (purchased from Invitrogen) to produce antibodies. During transfection, the density of 293-F cells should be 1-1.5×10⁶ cells/mL, and 100 mL of cells required 100 μg of the above-mentioned constructed recombinant vector (wherein the quality ratio of the recombinant heavy chain vector and light chain vector was 2:3) and 200 μg of the transfection reagent polyethyleneimine (PEI). The recombinant vector and PEI were added to 5 mL culture medium respectively, and the mixture was allowed to stand at room temperature for 5 minutes. After filtration with a 0.22 μm filter, the mixture of recombinant vector and PEI was allowed to stand at room temperature for 15 minutes. Then the above mixture was slowly added to the cells, and cultured in a 37° C., 8% (v/v) $CO_2$ incubator at 120 rpm. After 7 days, the cell culture solution was centrifuged at 3500 g for 30 minutes, and the supernatant was collected and filtered with a 0.22 μm filter.

A 1 mL protein A column (purchased from GE Healthcare) was used to purify the monoclonal antibody from 200 mL of clear supernatant. The protein A column was first equilibrated with a equilibration buffer (PBS phosphate buffer, pH7.2), and then the supernatant was loaded onto the protein A column, with a flow rate controlled at 3 mL/min. After the sample was loaded, protein A column was washed with the equilibration buffer. The volume of the equilibration buffer was 20 times the volume of the protein A column bed. The monoclonal antibody bound to the protein A column was eluted with the eluent (0.1M glycine hydrochloride buffer, pH3.0), and the elution was monitored with an ultraviolet detector (A280 ultraviolet absorption peak). The eluted antibody was collected, added with 10% (v/v) 1.0M Tris-HCl buffer to neutralize the pH. Then immediately dialysis was performed overnight with PBS phosphate buffer. The dialyzed monoclonal antibody was collected, aseptically filtered with a 0.22 m filter, and stored aseptically, thus obtaining purified SEMA4D antibody as the lead antibody.

The leading antibody was tested and analyzed for protein concentration (A280/1.4), purity, and endotoxicity (Lonza kit). The results are shown in Table 9. The results showed that the lead antibody endotoxin concentration was within 1.0 EU/mg.

TABLE 9

Detection and analysis of purified SEMA4D antibodies

| Clone number | Antibody purity | Protein concentration (mg/mL) | Endotoxin (EU/mg) |
|---|---|---|---|
| 2D5 | >90% | 0.57 | 0.90 |
| 5D8 | >90% | 2.25 | 0.60 |

Example 3 Identification of Lead Antibodies

A. Detection of the Binding Activity of Antibodies to SEMA4D Protein by Enzyme-Linked Immunosorbent Assay (ELISA)

The leading antibodies obtained in Examples 1 and 2 were subjected to a binding reaction with human SEMA4D.

Figure 5A:
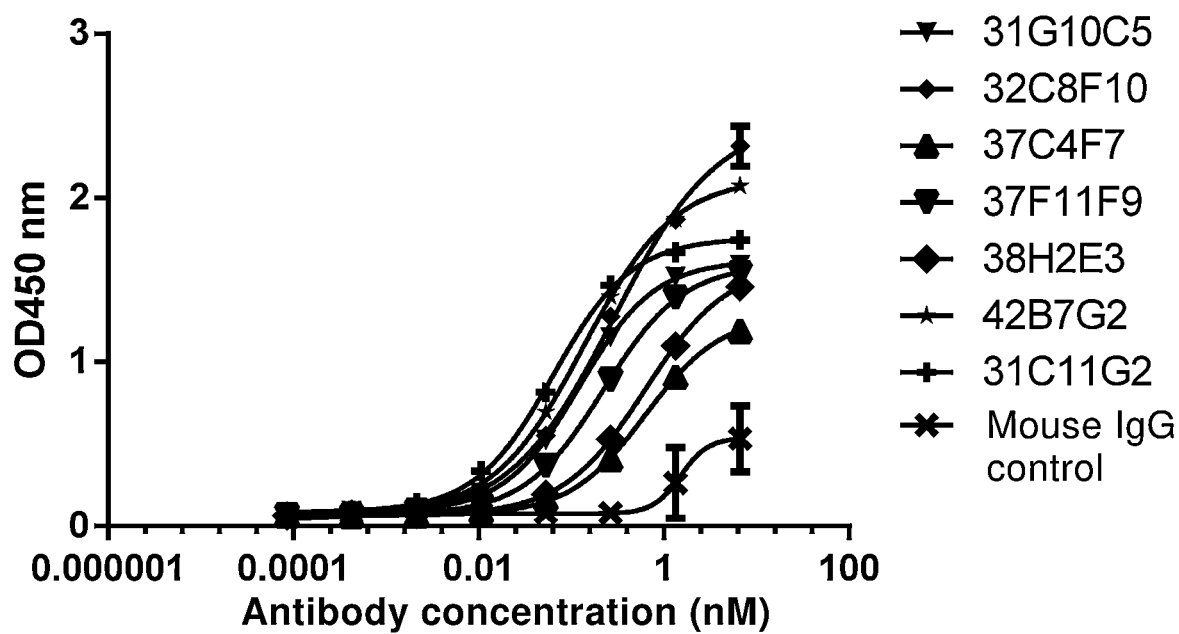
FIG. 5A and FIG. 5B show the detection results of the binding activity of purified SEMA4D antibody to hSEMA4D ECD-His by enzyme-linked immunosorbent assay.
Figure 5B:
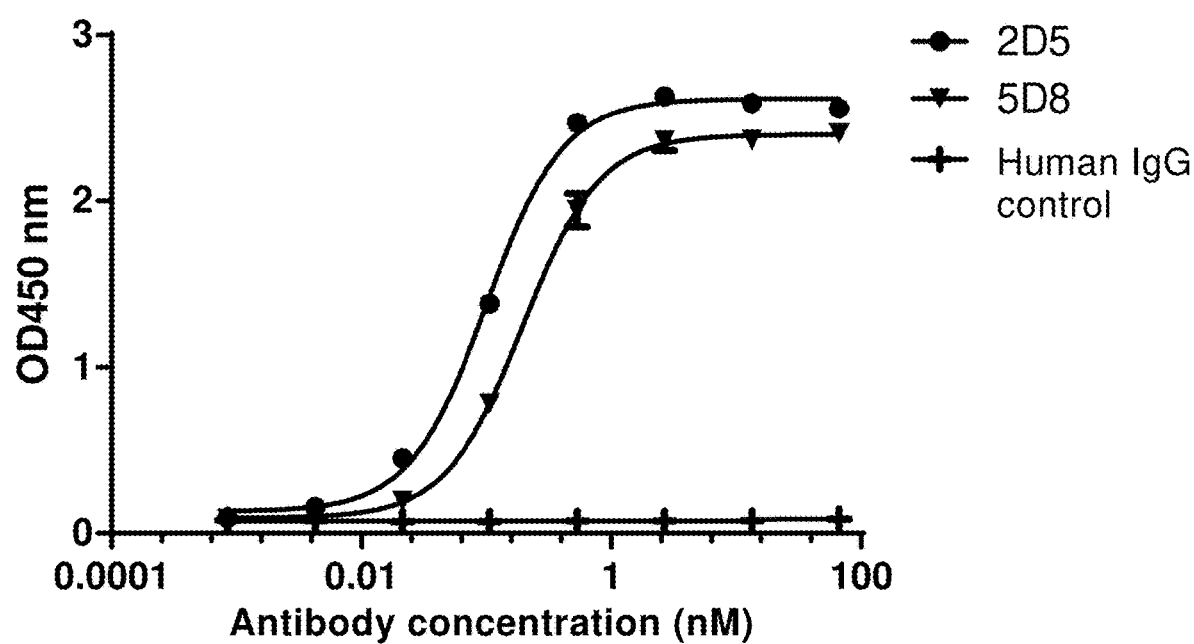

First, hSEMA4D ECD-His was diluted with PBS to a final concentration of 1.0 μg/mL, and then was added to a 96-well ELISA plate, 100 μL per well, sealed with plastic film and incubated overnight at 4° C. On the next day, the plate was washed with a plate washing solution, that is, PBS buffer containing 0.05% (v/v) Tween20, for 4 times, and added with blocking solution, that is, PBS buffer containing 0.05% (v/v) Tween20 and 2% (w/w) BSA, blocked at 37° C. for 1 hour. The blocking solution was poured out and the plate was washed 4 times with the plate washing solution. 100 μL of the purified leading antibodies obtained in Examples 1 and 2 was added to each well. After incubation at 37° C. for 1 hour, the plate was washed 4 times with a plate washing solution. 100 μL of horseradish peroxidase (HRP) labeled secondary antibody (purchased from Sigma) was added at a dilution of 1:10000 to each well, and the plate was incubated at 37° C. for 1 hour, and washed 4 times with a plate washing solution. 100 μL TMB substrate was added to each well, and the plate was incubated at room temperature for 5 minutes, and added with 100 μL stop solution (1.0N HCl) to each well. A microplate reader (SpectraMax M5e, purchased from Molecular Device) was used to read the A450 nm value. The results are shown in FIGS. 5A-5B and Tables 10-11. The results show that the purified antibodies had binding activity with human SEMA4D protein at the ELISA level. Wherein, the data in the table was the OD450 nm value.

TABLE 10

Detection of the binding activity of purified SEMA4D antibodies to hSEMA4D ECD-His by ELISA

| OD450 nm | Antibody concentration (nM) | | | | | | |
|---|---|---|---|---|---|---|---|
| Clone number | 6.67 | 1.33 | 0.267 | 0.0533 | 0.0107 | 0.00213 | 0.00427 | 0.000085 |
| 31G10C5 | 1.5906 | 1.5181 | 1.1505 | 0.5259 | 0.1974 | 0.1086 | 0.0915 | 0.0694 |
| 32C8F10 | 2.3158 | 1.8696 | 1.2768 | 0.5510 | 0.2067 | 0.0858 | 0.0685 | 0.0699 |
| 37C4F7 | 1.1916 | 0.9104 | 0.4099 | 0.1620 | 0.0864 | 0.0673 | 0.0623 | 0.0661 |
| 37F11F9 | 1.5421 | 1.3912 | 0.8904 | 0.3650 | 0.1308 | 0.0929 | 0.0638 | 0.0658 |
| 38H2E3 | 1.4596 | 1.0986 | 0.5313 | 0.1935 | 0.0878 | 0.0738 | 0.0744 | 0.0635 |
| 42B7G2 | 2.0733 | 1.8718 | 1.3989 | 0.6956 | 0.2496 | 0.1100 | 0.0851 | 0.0753 |
| 31C11G2 | 1.7445 | 1.6682 | 1.4693 | 0.8174 | 0.3366 | 0.1412 | 0.0939 | 0.0753 |
| Mouse IgG control | 0.5327 | 0.2639 | 0.0791 | 0.0805 | 0.08135 | 0.0718 | 0.07885 | 0.0686 |

TABLE 11

Detection of the binding activity of purified SEMA4D antibodies to hSEMA4D ECD-His by ELISA

| | OD450 nm Antibody concentration (nM) | | | | | | | |
|---|---|---|---|---|---|---|---|---|
| Clone number | 66.7 | 13.3 | 2.67 | 0.533 | 0.107 | 0.0213 | 0.0427 | 0.00085 |
| 2D5 | 2.5600 | 2.5915 | 2.6312 | 2.4705 | 1.3837 | 0.4508 | 0.1579 | 0.0924 |
| 5D8 | 2.4082 | 2.3677 | 2.3631 | 1.9461 | 0.7801 | 0.1972 | 0.1021 | 0.0863 |
| Human IgG control | 0.0859 | 0.0766 | 0.0740 | 0.0748 | 0.0717 | 0.0714 | 0.0754 | 0.0781 |

B. Detection of the Binding of Antibodies to SEMA4D Stable Cell Line by Flow Cytometry (FACS)

The nucleotide sequence containing the sequence encoding the full-length human SEMA4D (as shown in SEQ ID No: 422 in the sequence listing, as shown in the same cellular immunogen) was cloned into the pLVX-IRES-Hyg vector (purchased from Clontech), and the plasmid was prepared according to the above method. The lentivirus was packaged using X-treme GENE HP DNA Transfection Reagent (purchased from Roche) and CHO-K1 cells (purchased from ATCC) were infected therewith. The infected cells were cultured for two weeks in a medium containing 600 μg/mL antibiotics and 10% fetal calf serum. The limiting dilution method was used for subcloning and screening in 96-well culture plates (for specific methods, see the preparation of cellular immunogens above). Similarly, the nucleotide sequences containing the sequences encoding monkey and murine full length SEMA4D (such as SEQ ID No: 432, SEQ ID No: 433 in the sequence listing) were cloned into the pLVX-IRES-Puro vector (purchased from Clontech), and lentivirus was packaged and infected CHO-K1 cells (purchased from ATCC). The infected cells were cultured for two weeks in a medium containing 3 μg/mL antibiotics and 10% fetal calf serum, and were subcloned and screened. The amplified clones were screened by FACS with commercial anti-human and monkey SEMA4D antibodies (purchased from Abcam) and anti-mouse SEMA4D antibodies (purchased from eBioscience). Monoclonal cell lines with better growth and higher fluorescence intensity (MFI) were selected to continue to be expanding cultured and cryopreserved in liquid nitrogen to obtain stable transgenic cell lines expressing human, monkey and mouse SEMA4D (i.e., CHO-K1 hSEMA4D, CHO-K1 cSEMA4D and CHO-K1 mSEMA4D).

TABLE 12

FACS screening and detection results of CHO-K1 cells expressing human, monkey and mouse SEMA4D

| | | SEMA4D antibody | | IgG subtype control | |
|---|---|---|---|---|---|
| Sequence number | Transfected cell clone number | Positive cells (%) | Mean fluorescence intensity | Positive cells (%) | Mean fluorescence intensity |
| 1 | CHO-K1 hSEMA4D 35 | 96.55 | 6871 | 1.39 | 33 |
| 2 | CHO-K1 cSEMA4D 1A1 | 99.73 | 5992 | 2.42 | 40 |
| 3 | CHO-K1 mSEMA4D 3A4 | 99.79 | 22070 | 29.83 | 86 |

Figure 6A:
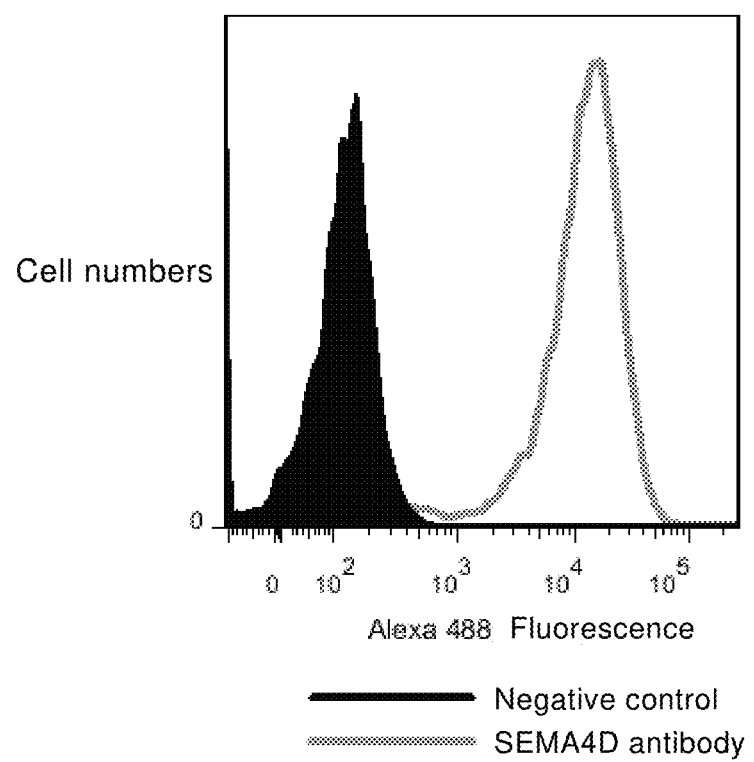
FIG. 6A, FIG. 6B and FIG. 6C are graphs showing the detection results of the expression levels of human, monkey, and murine SEMA4D proteins in the CHO-K1 recombinant cell line by flow cytometry. SEMA4D antibody was purchased from R&D systems or eBioscience; and the negative control refers to an isotype antibody control.
Figure 6B:
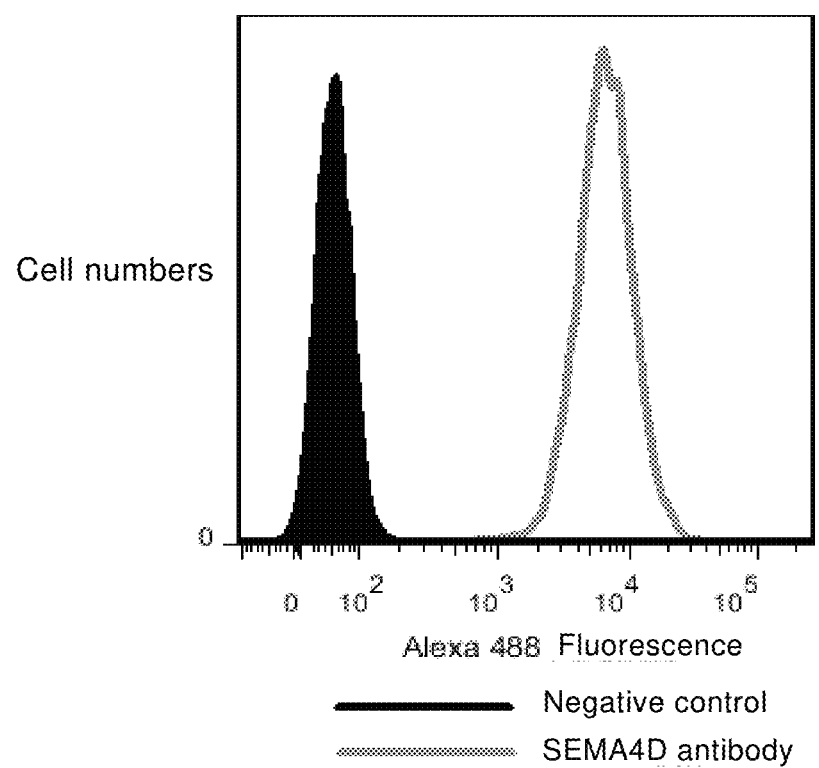
Figure 6C:
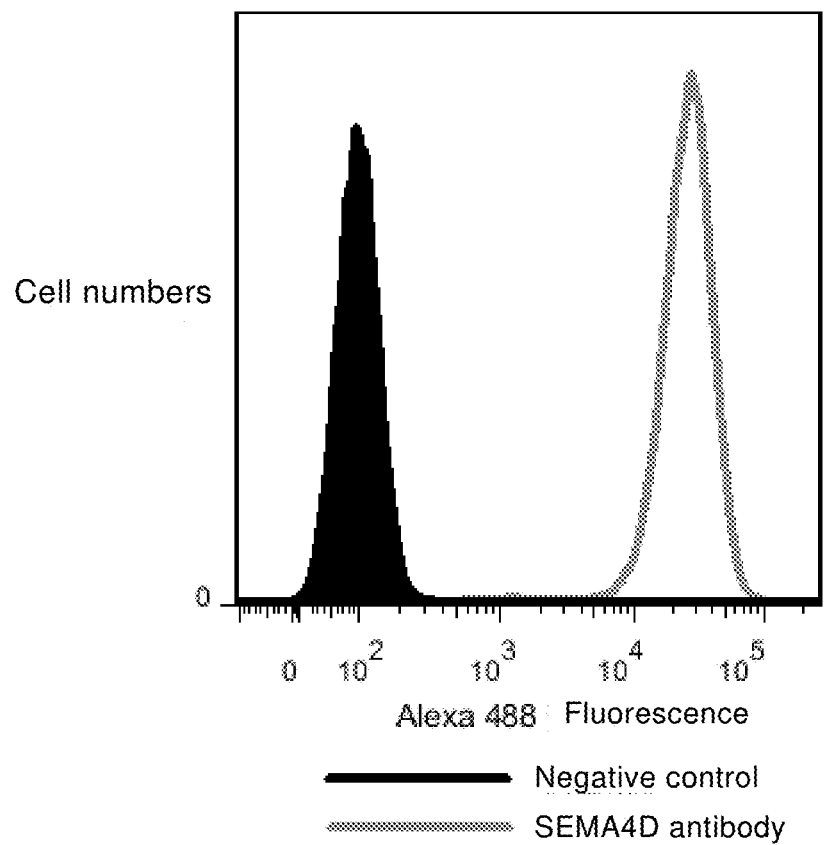

The selection results are shown in FIGS. 6A-6C and Table 12. In Table 12, positive cells (%) refer to the percentage of number of positive cells in the total number of cells. The results indicate that a series of human, monkey and mouse SEMA4D expression positive CHO-K1 cell lines have been produced.

Figure 7A:
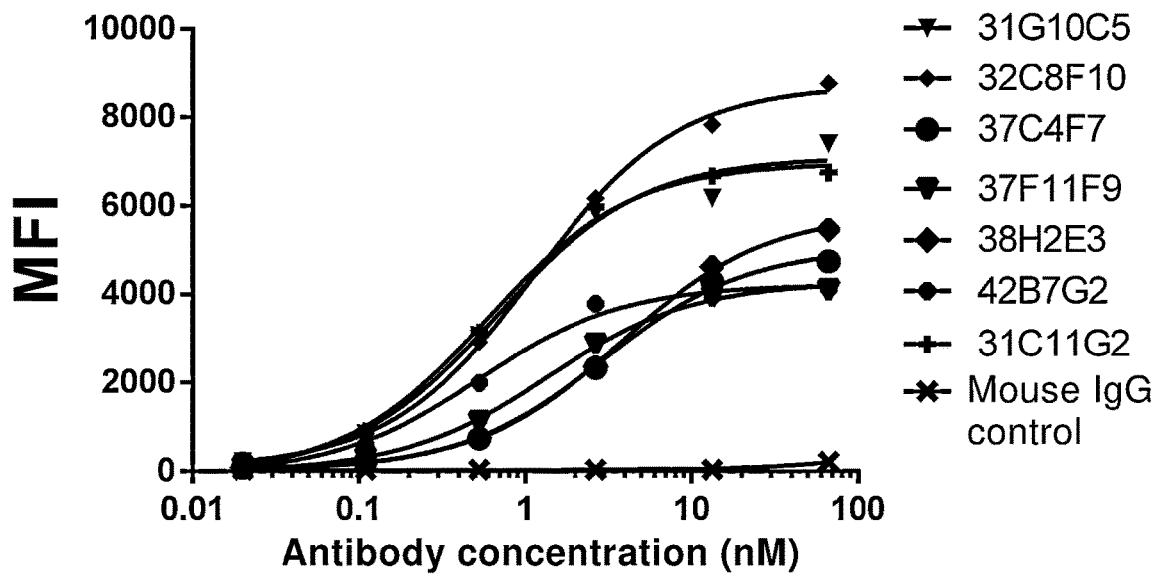
FIGS. 7A and 7B are detection results of the binding activity of purified SEMA4D antibodies to human SEMA4D recombinant cells CHO-K1 hSEMA4D by flow cytometry experiments.
Figure 7B:
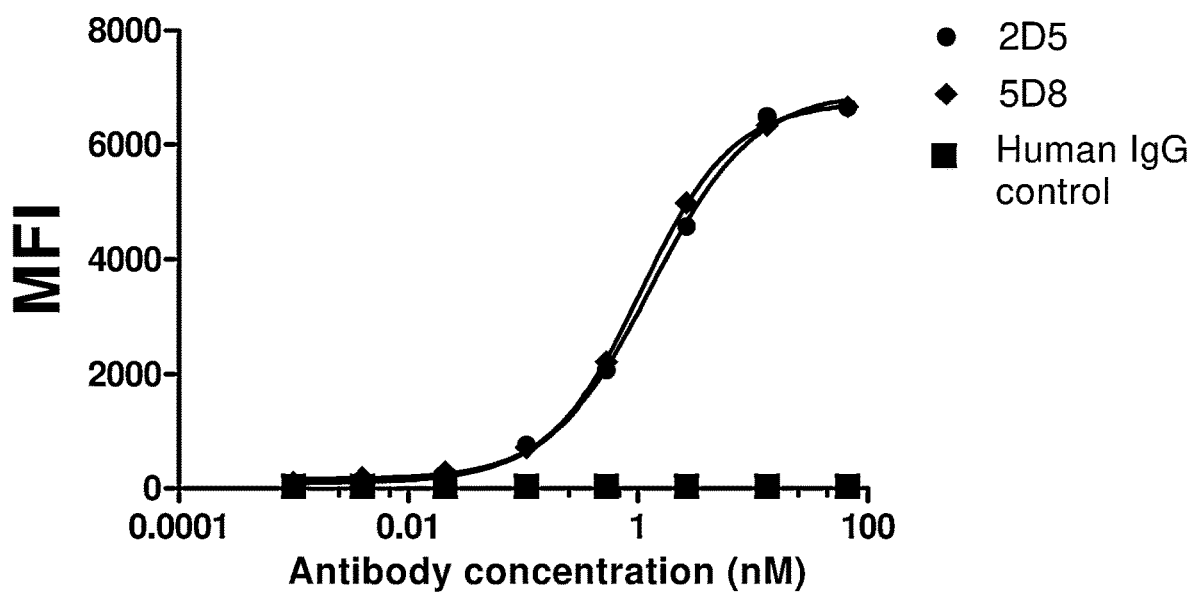

The obtained stable CHO-K1 hSEMA4D cell line and CHO-K1 were expanded to a confluence of 90% in T-175 cell culture flasks. The medium was aspirated, the cells were washed once with PBS buffer (purchased from Invitrogen), and then treated with cell dissociation fluid (TrypLE™ Express Enzyme, purchased from Life technology), and the cells were collected. After the cells counted, the cells were washed once with PBS phosphate buffer, and diluted to $3 \times 10^6$ cells per milliliter, and added to the 96-well FACS reaction plate as 100 μL per well. 2% (w/w) fetal calf serum was added to PBS phosphate buffer as FACS buffer, with which the cells were washed once by centrifugation at 2000 rpm 4° C. 100 μL of diluted and purified leading antibodies was added to each well and the plate was incubated for 1 hour on ice. The plate was washed twice with the FACS buffer by centrifugation, added with 100 μL of fluorescence (Alexa 488) labeled secondary antibodies (purchased from Invitrogen) per well, and incubated on ice for 1 hour. Cells were washed 2 times by centrifugation with FACS buffer. The cells were suspended with 200 μL of FACS buffer, and FACS (FACS Verse, purchased from BD) was used to detect and analyze the results. The results are shown in FIGS. 7A-7B and Tables 13-14.

TABLE 13

FACS detection of the binding activity of purified SEMA4D antibodies and human SEMA4D recombinant cells (CHO-K1 hSEMA4D)

| Clone number | MFI Antibody concentration (nM) | | | | | | | |
|---|---|---|---|---|---|---|---|---|
| | 66.7 | 13.3 | 2.67 | 0.534 | 0.107 | 0.0213 | 0.00427 | 0.000853 |
| 31G10C5 | 7410.89 | 6182.44 | 5855.91 | 3074.86 | 854.91 | 1224.62 | 85.52 | 47.02 |
| 32C8F10 | 8761.39 | 7832.27 | 6172.32 | 2921.47 | 831.56 | 217.52 | 86.19 | 47.32 |
| 37C4F7 | 4742.60 | 4287.70 | 2341.61 | 738.49 | 209.77 | 76.61 | 45.42 | 36.85 |
| 37F11F9 | 4106.23 | 3956.55 | 2875.10 | 1115.32 | 307.69 | 100.57 | 51.02 | 38.21 |
| 38H2E3 | 5472.84 | 4625.70 | 2371.69 | 763.33 | 215.22 | 78.68 | 45.39 | 36.69 |
| 42B7G2 | 4124.42 | 3951.36 | 3786.30 | 1995.57 | 597.89 | 173.14 | 68.87 | 41.25 |
| 31C11G2 | 6754.96 | 6667.02 | 5971.43 | 3140.19 | 905.98 | 247.81 | 87.34 | 46.73 |
| Mouse IgG control | 214.00 | 40.20 | 35.63 | 36.52 | 36.10 | 35.82 | 35.45 | 35.50 |

TABLE 14

FACS detection of the binding activity of purified SEMA4D antibodies and human SEMA4D recombinant cells (CHO-K1 hSEMA4D)

| Clone number | MFI Antibody concentration (nM) | | | | | | | |
|---|---|---|---|---|---|---|---|---|
| | 66.7 | 13.3 | 2.67 | 0.534 | 0.107 | 0.0213 | 0.00427 | 0.000853 |
| 2D5 | 6648.79 | 6492.92 | 4574.97 | 2075.64 | 754.48 | 213.61 | 82.31 | 45.81 |
| 5D8 | 6661.27 | 6339.14 | 4982.36 | 2213.93 | 708.49 | 288.70 | 184.60 | 102.83 |
| Human IgG control | 39.99 | 35.79 | 35.90 | 37.40 | 37.99 | 38.22 | 37.41 | 37.19 |

The results show that the leading antibodies can bind to the human SEMA4D protein on the cell surface. Wherein, the data MFI in the table is the average fluorescence intensity values of the cell populations measured.

Figure 8A:
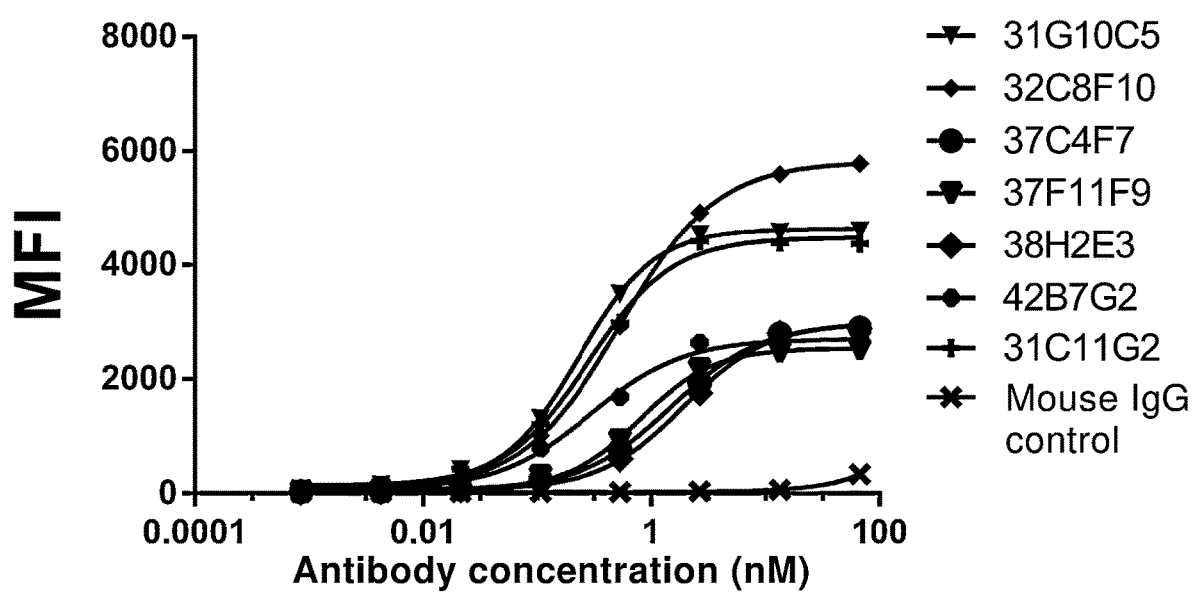
FIGS. 8A and 8B are detection results of the binding activity of purified SEMA4D antibodies to monkey SEMA4D recombinant cells CHO-K1 cSEMA4D by flow cytometry experiments.
Figure 8B:
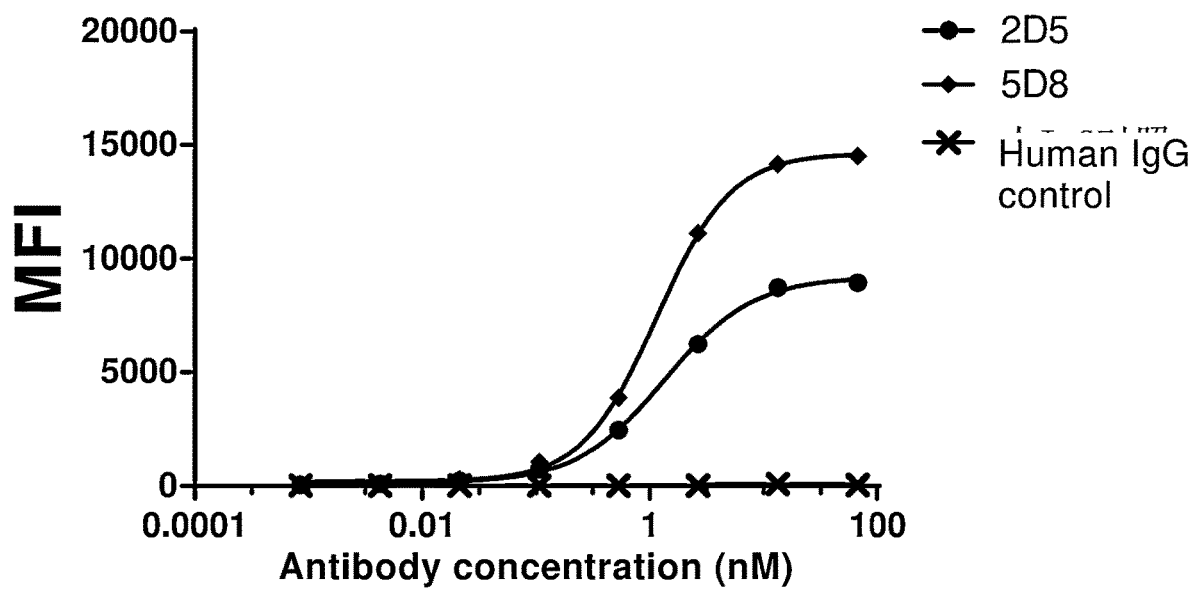
Figure 9A:
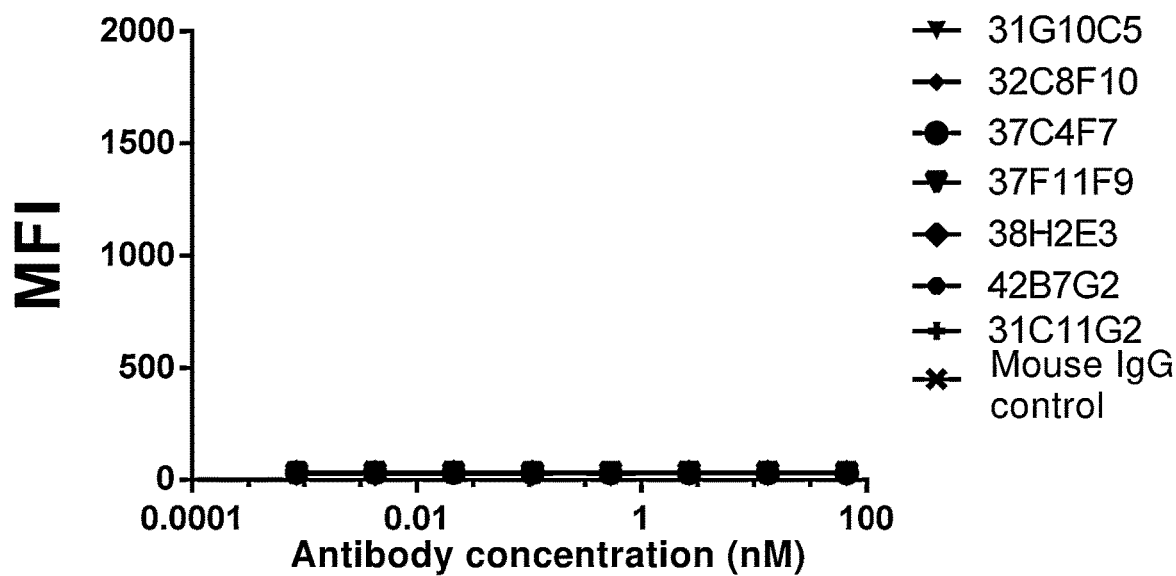
FIGS. 9A and 9B are detection results of the binding activity of purified SEMA4D antibodies to murine SEMA4D recombinant cells CHO-K1 mSEMA4D by flow cytometry experiments.
Figure 9B:
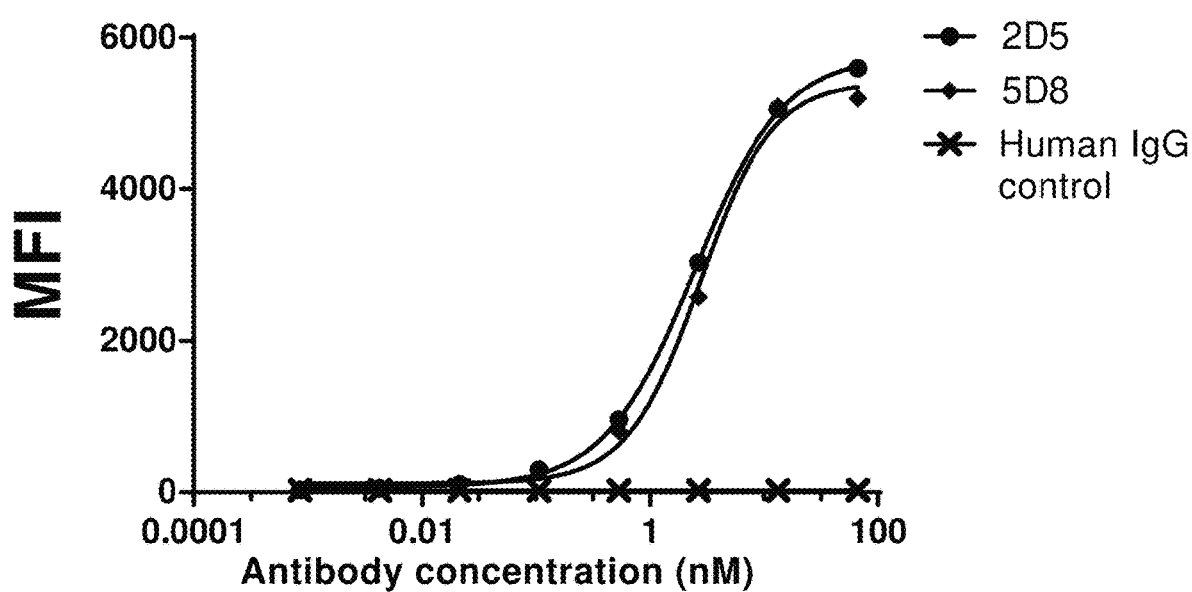

Similarly, the obtained CHO-K1 cSEMA4D, CHO-K1 mSEMA4D stable transgenic cell lines and CHO-K1 were expanded and cultured in T-175 cell culture flasks, and processed and collected. After the cells were counted, they were diluted with PBS to $2\times10^6$ cells per milliliter. After washing, 100 μL of diluted and purified leading antibodies was added to each well and the plate was incubated for 1 hour on ice. The plate was washed twice with the FACS buffer by centrifugation, added with 100 μL of fluorescence (Alexa 488) labeled secondary antibodies (purchased from Invitrogen) per well, and incubated on ice for 1 hour. Cells were washed 2 times by centrifugation with FACS buffer. The cells were suspended with 200 μL of FACS buffer, FACS (FACS Verse, purchased from BD) was used to detect and analyze the results. The results are shown in FIGS. 8-9 and Tables 15-18.

TABLE 15

FACS detection of the binding activity of purified SEMA4D antibodies to monkey SEMA4D recombinant cells (CHO-K1 cSEMA4D)

| Clone number | MFI Antibody concentration (nM) | | | | | | | |
|---|---|---|---|---|---|---|---|---|
| | 66.7 | 13.3 | 2.67 | 0.534 | 0.107 | 0.0213 | 0.00427 | 0.000853 |
| 31G10C5 | 4604.46 | 4577.05 | 4539.26 | 3492.46 | 1313.06 | 414.45 | 151.62 | 61.55 |
| 32C8F10 | 5782.65 | 5594.22 | 4915.67 | 2925.85 | 1013.02 | 291.20 | 97.56 | 49.69 |
| 37C4F7 | 2899.53 | 2791.26 | 1944.91 | 759.87 | 236.58 | 79.37 | 38.25 | 29.02 |
| 37F11F9 | 2523.27 | 2477.19 | 2170.39 | 925.03 | 299.57 | 103.12 | 45.35 | 29.48 |
| 38H2E3 | 2885.18 | 2800.94 | 1753.64 | 601.00 | 209.62 | 69.10 | 35.03 | 26.06 |
| 42B7G2 | 2666.85 | 2591.70 | 2638.81 | 1692.85 | 793.08 | 215.85 | 92.73 | 54.45 |
| 31C11G2 | 4373.45 | 4389.07 | 4419.95 | 2984.70 | 1209.06 | 421.68 | 139.33 | 81.40 |
| Mouse IgG control | 338.66 | 65.57 | 37.75 | 24.89 | 25.38 | 23.11 | 22.47 | 22.92 |

TABLE 16

FACS detection of the binding activity of purified SEMA4D antibodies to monkey SEMA4D recombinant cells (CHO-K1 cSEMA4D)

| Clone number | MFI Antibody concentration (nM) | | | | | | | |
|---|---|---|---|---|---|---|---|---|
| | 66.7 | 13.3 | 2.67 | 0.534 | 0.107 | 0.0213 | 0.00427 | 0.000853 |
| 2D5 | 8964.94 | 8749.24 | 6246.59 | 2460.77 | 737.65 | 233.43 | 91.10 | 53.25 |
| 5D8 | 14516.07 | 14155.24 | 11117.54 | 3881.55 | 1064.27 | 289.51 | 106.08 | 60.93 |
| Human IgG control | 48.92 | 86.71 | 33.31 | 32.07 | 31.55 | 31.64 | 31.61 | 31.63 |

TABLE 17

FACS detection of the binding activity of purified SEMA4D antibodies to mouse SEMA4D recombinant cells (CHO-K1 mSEMA4D)

| Clone number | MFI Antibody concentration (nM) | | | | | | | |
|---|---|---|---|---|---|---|---|---|
| | 66.7 | 13.3 | 2.67 | 0.534 | 0.107 | 0.0213 | 0.00427 | 0.000853 |
| 31G10C5 | 32.42 | 30.89 | 30.09 | 30.28 | 29.57 | 29.64 | 29.75 | 30.06 |
| 32C8F10 | 31.71 | 30.65 | 30.74 | 29.77 | 30.22 | 29.51 | 30.21 | 30.37 |
| 37C4F7 | 29.98 | 29.78 | 29.99 | 29.19 | 30.10 | 30.79 | 30.49 | 30.23 |
| 37F11F9 | 31.00 | 30.05 | 30.57 | 30.86 | 29.67 | 30.54 | 30.07 | 29.67 |
| 38H2E3 | 29.99 | 31.01 | 30.68 | 29.49 | 30.52 | 30.15 | 29.93 | 30.11 |
| 42B7G2 | 35.29 | 30.70 | 30.99 | 31.72 | 30.38 | 31.56 | 30.29 | 31.05 |
| 31C11G2 | 31.44 | 31.33 | 30.47 | 30.66 | 30.64 | 30.77 | 31.37 | 30.93 |
| Mouse IgG control | 34.68 | 30.28 | 30.38 | 29.50 | 29.83 | 30.50 | 30.15 | 29.77 |

TABLE 18

FACS detection of the binding activity of purified SEMA4D antibodies to mouse SEMA4D recombinant cells (CHO-K1 mSEMA4D)

| Clone number | MFI Antibody concentration (nM) | | | | | | | |
|---|---|---|---|---|---|---|---|---|
| | 66.7 | 13.3 | 2.67 | 0.534 | 0.107 | 0.0213 | 0.00427 | 0.000853 |
| 2D5 | 5595.94 | 5051.43 | 3032.37 | 958.11 | 299.57 | 107.65 | 50.64 | 34.88 |
| 5D8 | 5195.19 | 5088.39 | 2579.81 | 801.40 | 264.31 | 88.24 | 46.01 | 33.82 |
| Human IgG control | 26.69 | 23.82 | 23.90 | 23.66 | 24.15 | 24.08 | 23.72 | 25.03 |

The results show that the leading antibodies can bind to the monkey SEMA4D protein on the cell surface and have a cross-reactivity with monkey SEMA4D. Only two antibodies, 2D5 and 5D8, can bind to the mouse SEMA4D expressed on the cell surface, and have cross-reactivity with mouse SEMA4D. Wherein, the data MFI in the table is the average fluorescence intensity values of the cell populations measured.

Example 4 Detection of the Blocking by Purified SEMA4D Antibodies on the Binding of SEMA4D to its Receptor PlexinB1

The receptor ligand binding experiment was used to detect whether the SEMA4D antibodies block the binding of SEMA4D to its receptor PlexinB1.

The nucleotide sequence containing the sequence encoding the full-length human Plexin B1 (as shown in SEQ ID No: 434 in the sequence listing) was cloned into the pLVX-IRES-Puro vector (purchased from Clontech), and the plasmid was prepared according to the above method. The lentivirus was packaged using X-treme GENE HP DNA Transfection Reagent (purchased from Roche) and 293F cells (purchased from Invitrogen) were infected therewith. The infected cells were cultured for two weeks in a medium containing 0.25 µg/mL antibiotics and 10% fetal calf serum. The limiting dilution method was used for subcloning and screening in 96-well culture plates (for specific methods, see the preparation of cellular immunogens above). The amplified clones were screened by FACS with a commercial anti-human Plexin B1 antibody (purchased from R&D Systems). Monoclonal cell lines with better growth and higher fluorescence intensity (MFI) were selected to continue to be expanding cultured and cryopreserved in liquid nitrogen to obtain a stable transgenic cell line expressing human Plexin B1, namely 293F hPlexin B1.

Figure 10:
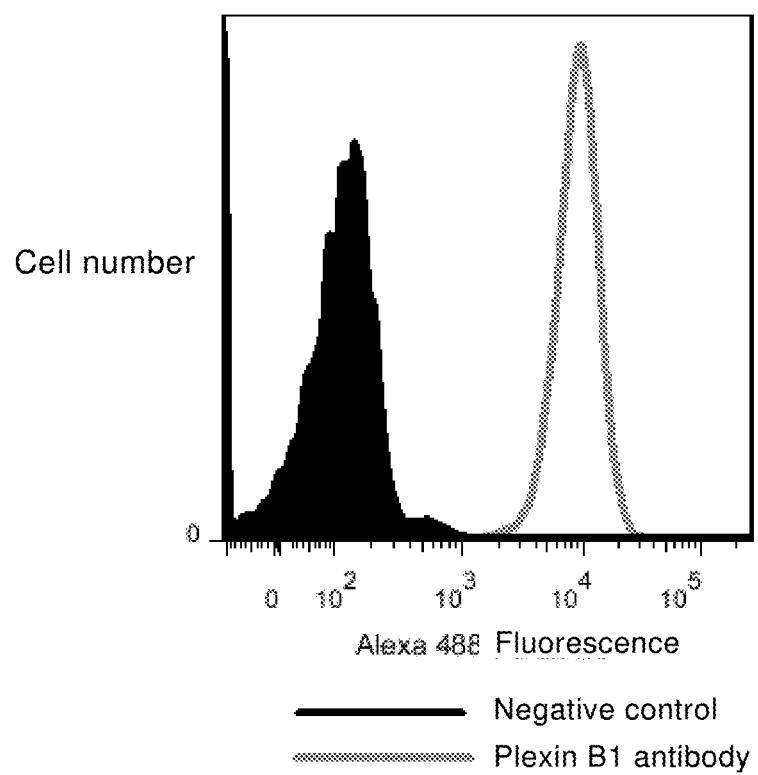
FIG. 10 is a graph showing the detection result of human Plexin B1 protein expression level in 293F recombinant cell line by flow cytometry. Plexin B1 antibody was purchased from R&D systems; and the negative control refers to an isotype antibody control.

The selection results are shown in FIG. 10 and Table 19. In Table 19, positive cells (%) refer to the percentage of number of positive cells in the total number of cells.

TABLE 19

FACS screening and detection results of 293F cells expressing human Plexin B1

| Number | Transfected cell clone number | Plexin B1 antibody | | IgG subtype control | |
|---|---|---|---|---|---|
| | | Positive cells (%) | Mean fluorescence intensity | Positive cells (%) | Mean fluorescence intensity |
| 1 | 293F hPlexin B1 41 | 99.87 | 6381 | 2.74 | 27 |

The results indicate that a 293F cell line with positive human Plexin B1 expression had been prepared.

Figure 11A:
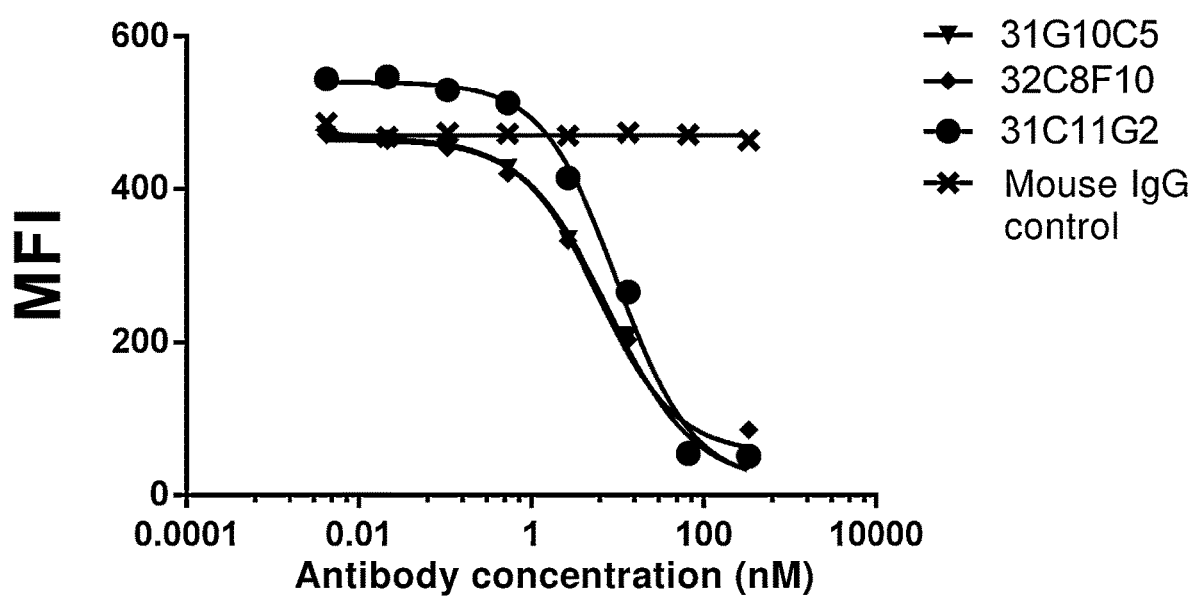
FIGS. 11A and 11B are graphs showing the results of the blocking of the binding activity of biotinylated hSEMA4D ECD-His to SEMA4D receptor Plexin B1 by purified SEMA4D antibodies.
Figure 11B:
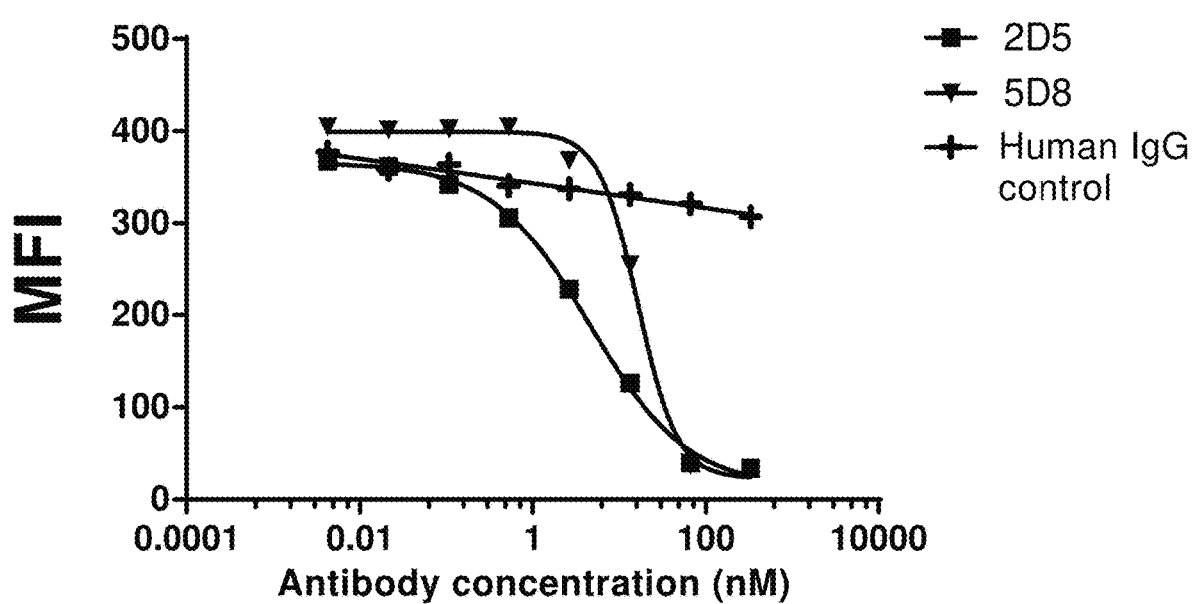

The obtained stable 293F hPlexin B1 cell line was expanded to a confluence of 90% in a T-175 cell culture flask. The medium was aspirated, the cells were washed once with PBS buffer (purchased from Invitrogen), and then treated with cell dissociation fluid (TrypLE™ Express Enzyme, purchased from Life technology), and the cells were collected. After the cells counted, the cells were washed once with PBS phosphate buffer, and diluted to $1\times10^6$ cells per milliliter, and added to the 96-well FACS reaction plate as 100 μL per well. 2% (w/w) fetal calf serum was added to PBS phosphate buffer as FACS buffer, with which the cells were washed once by centrifugation at 2000 rpm 4° C. Meanwhile, the purified leading antibody and biotinylated hSEMA4D ECD-His were mixed and incubated on ice for 30 minutes. Then 100 μL of the mixture was added to each well and the plate was incubated on ice for 1 hour. The plate was washed twice with the FACS buffer by centrifugation, added with 100 μL of fluorescence (Alexa 488) labeled secondary antibodies (purchased from Invitrogen) per well, and incubated on ice for 1 hour. Cells were washed 2 times by centrifugation with FACS buffer. The cells were suspended with 200 μL of FACS buffer, and FACS (FACS Verse, purchased from BD) was used to detect and analyze the results. The results are shown in FIGS. 11A-11B and Tables 20-21.

TABLE 20

FACS detection of the blocking of the purified SEMA4D antibodies on the binding activity of SEMA4D and its receptor Plexin B1

| Clone number | MFI Antibody concentration (nM) | | | | | | | |
|---|---|---|---|---|---|---|---|---|
| | 333 | 66.7 | 13.3 | 2.67 | 0.534 | 0.107 | 0.0213 | 0.00427 |
| 31G10C 5 | 45.42 | 54.25 | 208.75 | 334.28 | 427.01 | 459.80 | 465.81 | 470.22 |
| 32C8F10 | 85.08 | 55.54 | 203.75 | 332.55 | 420.38 | 454.20 | 463.37 | 471.25 |
| 31C11G2 | 50.84 | 54.21 | 265.98 | 414.69 | 512.62 | 529.83 | 547.28 | 544.13 |
| Mouse IgG control | 463.78 | 471.20 | 473.80 | 469.98 | 472.07 | 473.48 | 468.24 | 486.11 |

TABLE 21

FACS detection of the blocking of the purified SEMA4D antibodies on the binding activity of SEMA4D and its receptor Plexin B1

| Clone number | MFI Antibody concentration (nM) | | | | | | | |
|---|---|---|---|---|---|---|---|---|
| | 333 | 66.7 | 13.3 | 2.67 | 0.534 | 0.107 | 0.0213 | 0.00427 |
| 2D5 | 33.87 | 39.61 | 126.29 | 228.09 | 306.02 | 342.41 | 362.03 | 367.84 |
| 5D8 | 32.24 | 37.69 | 254.64 | 368.53 | 404.92 | 402.69 | 401.61 | 404.76 |
| Human IgG control | 307.11 | 321.33 | 331.46 | 337.64 | 341.15 | 364.13 | 358.98 | 377.82 |

The results showed that 31G10C5, 32C8F10, 31C11G2 and 2D5, 5D8 antibodies can block the binding of SEMA4D to its receptor Plexin B1. Wherein, the data MFI in the table is the average fluorescence intensity values of the cell populations measured.

Figure 12A:
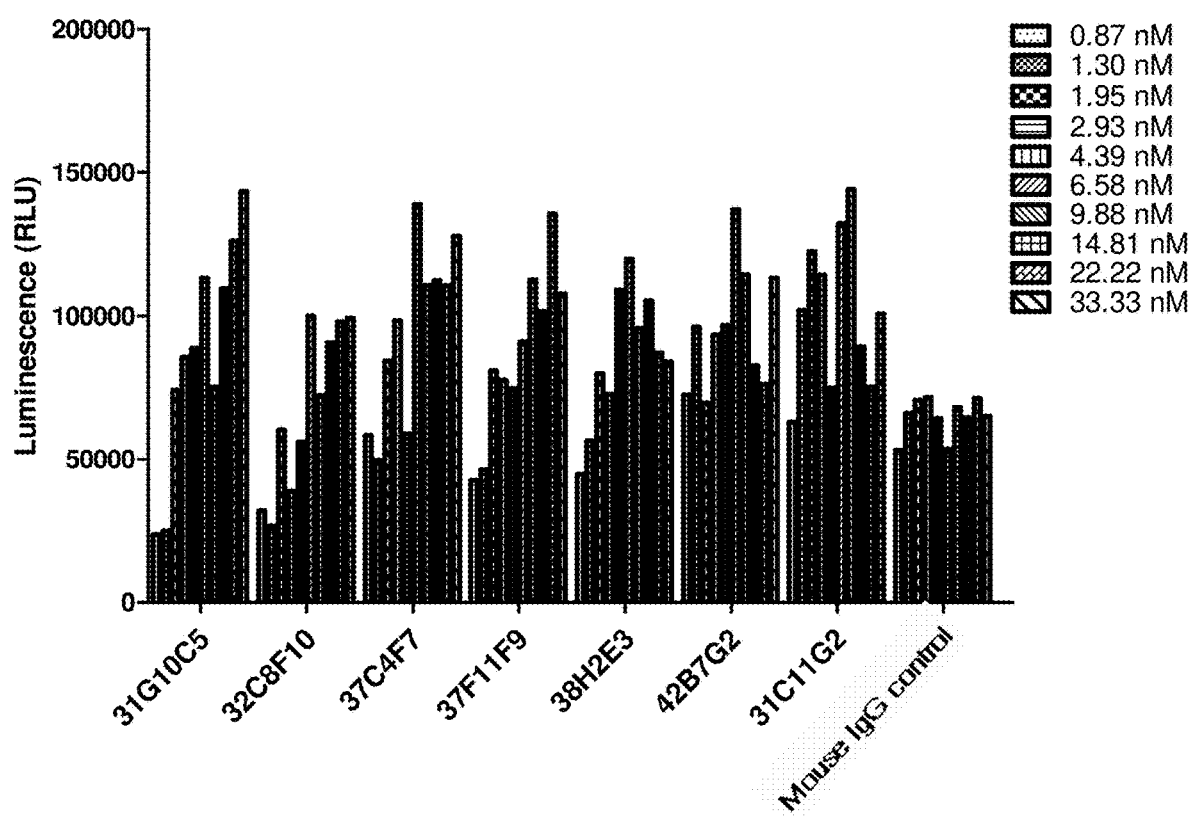
FIGS. 12A and 12B are graphs showing the results of the blocking of the SEMA4D protein-induced cell shedding by purified SEMA4D antibodies.
Figure 12B:
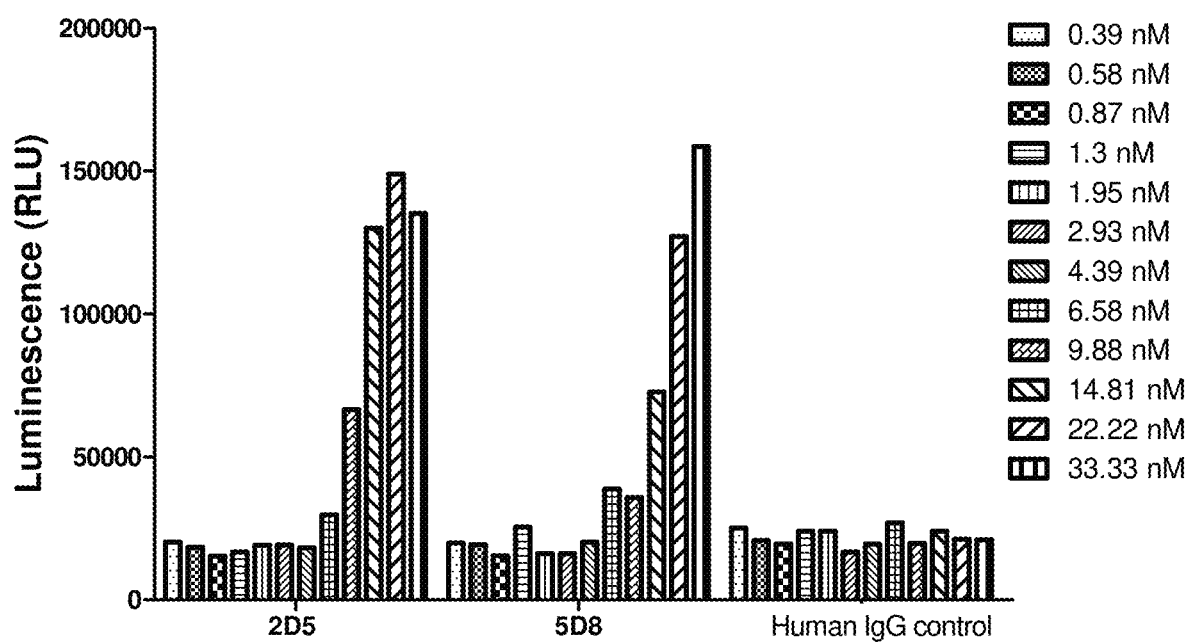

Example 5 Detection of the Blocking of the Inducing Effect of SEMA4D on Cell Shedding by Purified SEMA4D Purified Antibodies The obtained stable transgenic cell line expressing human Plexin B1, namely 293F hPlexin B1, was domesticated. A method of gradually reducing fetal bovine serum, that is, gradually reducing from 10% (w/w) to serum-free, was used, and then the cells were cultured with FreeStyle 293F medium (purchased from Invitrogen). The 96-well plate was added with 50 μL of fibronectin at a concentration of 5 μg/mL, and incubated overnight at 4° C. All remaining liquid was aspirated and the plate was placed in a clean bench to air dry. After the cells were counted, they were diluted to $2\times10^6$ cells per milliliter, added as 50 μL per well to a 96-well plate, and incubated overnight at 37° C. and 5% (v/v) $CO_2$. 50 μL of the purified leading antibodies and 50 μL of hSEMA4D ECD-His were mixed and incubated on ice for 2 minutes. Then 100 μL of the mixture was added to a 96-well plate and the plated was incubated at 37° C. for 2 hours. The cells were washed once with PBS phosphate buffer, added with an equal volume ratio of medium and CellTiter-Glo® Reagent (purchased from Promega). The experimental operation strictly followed the requirements of the kit instructions. A brief description of the specific experiment is as follows: before the measurement, the 96-well plate was placed at room temperature for 30 minutes, added with the same volume of CellTiter-Glo© reagent as the cell culture medium, placed on a shaker for 2 minutes to induce cell lysis, and then placed at room temperature for 10 minutes to stabilize the luminescence signal, and finally a microplate reader (SpectraMax M5e, purchased from Molecular Device) was used to read the luminescence intensity. The results are shown in FIGS. 12A-12B and Tables 22-23.

Example 6 Identification of Epitope Bound by SEMA4D Antibodies by Competitive FACS The purified hybridoma SEMA4D antibodies and fully human SEMA4D antibody were subjected to competitive flow cytometry (FACS) to analyze whether the epitopes bound by different antibodies competed with that bound by the reference antibody VX15.

The obtained stable CHO-K1 hSEMA4D cell line was expanded to a confluence of 90% in a T-175 cell culture flask. The medium was aspirated, the cells were washed once with PBS buffer (purchased from Invitrogen), and then treated with cell dissociation fluid (TrypLE™ Express Enzyme, purchased from Life technology), and the cells were collected. After the cells counted, the cells were washed once with PBS phosphate buffer, and diluted to $3\times10^6$ cells per milliliter, and added to the 96-well FACS reaction plate as 100 μL per well. 2% (w/w) fetal calf serum was added to PBS phosphate buffer as FACS buffer, with which the cells were washed once by centrifugation at 2000 rpm 4° C. 100 μL of the leading antibodies and IgG control diluted to a concentration of 6 μg/mL was added to each well and the plate was incubated for 1 hour on ice. Then 100 μL of fluorescent (Alexa 488) labeled competitive antibody and IgG control diluted to a concentration of 0.67 μg/mL was added to each well, and the plate was incubated for 1 hour on ice in the dark. Cells were washed 2 times by centrifu-

TABLE 22

Purified SEMA4D antibody blocks the inducing effect of SEMA4D protein on cell shedding

| | Luminescence (RLU) Antibody concentration (nM) | | | | | | | | | |
|---|---|---|---|---|---|---|---|---|---|---|
| Clone number | 33.33 | 22.22 | 14.81 | 9.88 | 6.58 | 4.39 | 2.93 | 1.95 | 1.30 | 0.87 |
| 31G10C5 | 143299 | 126099 | 109496 | 75270 | 113045 | 88708 | 85655 | 74122 | 24846 | 23686 |
| 32C8F10 | 99185 | 97891 | 90679 | 72226 | 99962 | 56086 | 38706 | 60308 | 26604 | 32037 |
| 37C4F7 | 127790 | 110456 | 112260 | 110539 | 138606 | 58967 | 98258 | 84340 | 49793 | 58362 |
| 37F11F9 | 107667 | 135449 | 101415 | 112565 | 90959 | 74665 | 77629 | 80991 | 46294 | 42469 |
| 38H2E3 | 83901 | 87025 | 105125 | 95655 | 119750 | 108942 | 72613 | 79955 | 56415 | 44696 |
| 42B7G2 | 113019 | 76112 | 82631 | 114202 | 136947 | 96666 | 93388 | 69694 | 96123 | 72429 |
| 31C11G2 | 100509 | 75213 | 89295 | 144059 | 132151 | 74820 | 114189 | 122338 | 101960 | 63009 |
| Mouse IgG control | 65078 | 71250 | 64531 | 68114 | 53568 | 64271 | 71547 | 70694 | 66019 | 53229 |

TABLE 23

Purified SEMA4D antibody blocks the inducing effect of SEMA4D protein on cell shedding

| | Luminescence (RLU) Antibody concentration (nM) | | | | | | | | | | | |
|---|---|---|---|---|---|---|---|---|---|---|---|---|
| Clone number | 100.00 | 66.67 | 44.44 | 29.63 | 19.75 | 13.17 | 8.78 | 5.85 | 3.90 | 2.60 | 1.73 | 1.16 |
| 2D5 | 135157 | 148891 | 129943 | 66580 | 29739 | 18259 | 19262 | 19070 | 16755 | 15299 | 18460 | 20247 |
| 5D8 | 1585301 | 27052 | 72714 | 35764 | 38746 | 20221 | 16241 | 16105 | 25449 | 15499 | 19323 | 19824 |
| Human IgG control | 21023 | 21215 | 24067 | 19742 | 26975 | 19580 | 16712 | 24067 | 24075 | 19589 | 20718 | 25152 |

The results indicate that the purified antibodies can significantly block the inducing effect of SEMA4D on cell shedding. The data in the table is the average luminescence intensity value of the measured cell population, to reflect the number of living cells.

gation with FACS buffer. The cells were suspended with 200 μL of FACS buffer, and FACS (FACS Verse, purchased from BD) was used to detect and analyze the results. The results are shown in Tables 24-25.

TABLE 24

Purified SEMA4D antibodies compete with VX15 for the binding
to the CHO-K1 hSEMA4D stable transgenic cell line

| Clone number | 31G10C5 | 32C8F10 | 37C4F7 | 37F11F9 | 38H2E3 | 42B7G2 | 31C11G2 |
|---|---|---|---|---|---|---|---|
| Alexa 488-VX15 | 42% | 42% | 20% | 25% | 21% | 15% | 44% |

TABLE 25

Purified SEMA4D antibodies compete with VX15 for the binding
to the CHO-K1 hSEMA4D stable transgenic cell line

| Clone number | Alexa 488-2D5 | Alexa 488-5D8 | Alexa 488-VX15 |
|---|---|---|---|
| 2D5 | 97% | 70% | 98% |
| 5D8 | 55% | 96% | 95% |
| VX15 | 96% | 98% | 97% |

The results show that the epitopes bound by different SEMA4D antibodies had varying degrees of competition. Wherein, (1) 31G10C5, 32C8F10, 37C4F7, 37F11F9, 38H2E3, 42B7G2, or 31C11G2 did not compete at the epitope bound by the reference antibody VX15, so the epitopes thereof might be different;

(2) 2D5 and 5D8 competed at the epitope bound by the reference antibody VX15, and the epitopes might be similar.

Wherein, the data in Tables 24 and 25 are the inhibition rates (%) of the binding of the original antibodies to the stable CHO-K1 hSEMA4D cell line after the addition of the competitive antibody.

Example 7 Determination of Amino Acid Sequences of Light and Heavy Chain Variable Regions A. Determination of Amino Acid Sequences of Light and Heavy Chain Variable Regions of SEMA4D Antibodies Prepared by Hybridoma Isolation of total RNA: after the subclonal culture supernatant corresponding to the leading antibodies selected in Example 1 was tested for antigen binding (that is, after the verification and activity determination in Examples 3-5), 5×10[7] hybridoma cells were collected by centrifugation, added with 1 mL Trizol and mixed well and transferred to a 1.5 mL centrifuge tube, and allowed to stand at room temperature for 5 minutes. The tube was added with 0.2 mL chloroform, shaked for 15 seconds, let stand for 2 minutes, and centrifuged at 12000 g at 4° C. for 5 minutes. The supernatant was taken and transferred to a new 1.5 mL centrifuge tube. 0.5 mL of isopropanol was added, and the liquid in the tube was gently mixed, and let stand at room temperature for 10 minutes. After centrifuged at 12000 g for 15 minutes at 4° C., the supernatant was discarded. 1 mL of 75% (v/v) ethanol was added, and the precipitate was gently washed, centrifuged at 12000 g at 4° C. for 5 minutes. The supernatant was discarded, and the precipitate was dried, and added with DEPC-treated $H_2O$ for dissolution (55° C. water bath to promote dissolution for 10 minutes). The total RNA was obtained.

Reverse transcription and PCR: 1 g of total RNA was taken, and a 20 ul system was configured, added with reverse transcriptase and reacted at 37° C. for 20 minutes, and the reaction was terminated at 85° C. for 10 seconds. 50 μl PCR system was configured, comprising 1 μL cDNA, 25 μmol of each primer, 1 μl DNA polymerase and a matching buffer system, and 250 mol dNTPs. PCR program was set, comprising pre-denaturation 95° C. for 3 min, denaturation 95° C. for 30 s, annealing 55° C. for 30 s, extension 72° C. for 30 s, and further extension at 72° C. for 5 min after 30 cycles. And the PCR product was obtained. The kit used for reverse transcription was PrimeScript RT Master Mix, purchased from Takara, catalog number RR036; and the enzyme used for PCR was GoTaq G2 Hot Start Green Master Mix, purchased from Promega, catalog number M7423. The PCR primers were Mouse Ig Primer Set, catalog number 69831-3 (purchased from Novagen).

Cloning and sequencing: 5 μl of PCR product was taken for agarose gel electrophoresis detection, and the column recovery kit was used to purify the positive samples. Wherein, the recovery kit was NucleoSpin® Gel & PCR Clean-up, purchased from MACHEREY-NAGEL, catalog number 740609. Ligation reaction was carried out: the reaction system was with a volume of 10 μL, containing 50 ng of sample, 50 ng of T carrier, 0.5 μL of ligase, and 1 μL of buffer, and reacted at 16° C. for half an hour to obtain the ligation product. Wherein the ligation kit was pMD™ 18-T Vector Cloning Kit, catalog number 6011 (purchased from Takara). 5 μL of the ligation product was taken and add into 100 μL of competent cells (Ecos 101 competent cells, purchased from Yeastern, catalog number FYE607), ice bathed for 5 minutes. Then heat shock was carried out in a 42° C. water bath for 1 minute, and put back on ice for 1 minute, added with 500 μl of antibiotic-free LB medium, resuscitated on a 37° C. shaker at 200 RPM for 30 minutes. 200 μl of the culture was taken and spreaded on LB solid medium containing antibiotics and incubated overnight at 37° C. in an incubator. The next day, the primers M13F and M13R on the T vector were used to configure a 30 μL PCR system to perform colony PCR. A pipette tip was used to dip the colony into the PCR reaction system and pipette, and 0.5 μL was aspirated onto another piece of 100 μg/mL ampicillin LB solid petri dish to save the strain. After the PCR reaction, 5 μL of the reaction solution was taken out for agarose gel electrophoresis detection, and the positive samples were sequenced and analyzed [see Kabat, "Sequences of Proteins of Immunological Interest," National Institutes of Health, Bethesda, Md. (1991)]. The sequencing results are shown in Tables 26-27.

B. Determination of Amino Acid Sequences of Light and Heavy Chain Variable Regions of Fully Human SEMA4D Antibodies Prepared by Phage Display Technology For the cloning and sequencing of the fully human SEMA4D antibody prepared by the phage display technology of the present invention, see to part (III) of Example 2. Tables 26-27 also contain the sequencing results of this part.

TABLE 26

SEMA4D antibody amino acid sequence numbers

| Clone number | Heavy chain protein | | | | Light chain protein | | | |
| --- | --- | --- | --- | --- | --- | --- | --- | --- |
| | Variable region | CDR1 | CDR2 | CDR3 | Variable region | CDR1 | CDR2 | CDR3 |
| 8G4E12 | 1 | 2 | 3 | 4 | 5 | 6 | 7 | 8 |
| 10F5E11 | 9 | 10 | 11 | 12 | 13 | 14 | 15 | 16 |
| 16C6D11 | 17 | 18 | 19 | 20 | 21 | 22 | 23 | 24 |
| 17D4A3 | 25 | 26 | 27 | 28 | 29 | 30 | 31 | 32 |
| 17H4B2 | 33 | 34 | 35 | 36 | 37 | 38 | 39 | 40 |
| 24D4E5 | 41 | 42 | 43 | 44 | 45 | 46 | 47 | 48 |
| 28G7B10 | 49 | 50 | 51 | 52 | 53 | 54 | 55 | 56 |
| 30B1C7 | 57 | 58 | 59 | 60 | 61 | 62 | 63 | 64 |
| 12G10H1 | 65 | 66 | 67 | 68 | 69 | 70 | 71 | 72 |
| 17A10A2 | 73 | 74 | 75 | 76 | 77 | 78 | 79 | 80 |
| 25C1B3 | 81 | 82 | 83 | 84 | 85 | 86 | 87 | 88 |
| 28D2E1 | 89 | 90 | 91 | 92 | 93 | 94 | 95 | 96 |
| 31G10C5 | 97 | 98 | 99 | 100 | 101 | 102 | 103 | 104 |
| 32C8F10 | 105 | 106 | 107 | 108 | 109 | 110 | 111 | 112 |
| 35D2B9 | 113 | 114 | 115 | 116 | 117 | 118 | 119 | 120 |
| 37C4F7 | 121 | 122 | 123 | 124 | 125 | 126 | 127 | 128 |
| 37F11F9 | 129 | 130 | 131 | 132 | 133 | 134 | 135 | 136 |
| 38H2E3 | 137 | 138 | 139 | 140 | 141 | 142 | 143 | 144 |
| 42B7G2 | 145 | 146 | 147 | 148 | 149 | 150 | 151 | 152 |
| 31C11G2 | 153 | 154 | 155 | 156 | 157 | 158 | 159 | 160 |
| 80G1G1 | 161 | 162 | 163 | 164 | 165 | 166 | 167 | 168 |
| 80E7E2 | 169 | 170 | 171 | 172 | 173 | 174 | 175 | 176 |
| 84A2C4 | 177 | 178 | 179 | 180 | 181 | 182 | 183 | 184 |
| 88B4D4 | 185 | 186 | 187 | 188 | 189 | 190 | 191 | 192 |
| 89G3E8 | 193 | 194 | 195 | 196 | 197 | 198 | 199 | 200 |
| 90H5D3 | 201 | 202 | 203 | 204 | 205 | 206 | 207 | 208 |
| 90F3B2 | 209 | 210 | 211 | 212 | 213 | 214 | 215 | 216 |
| 118C7E6 | 217 | 218 | 219 | 220 | 221 | 222 | 223 | 224 |
| 131H4A2 | 225 | 226 | 227 | 228 | 229 | 230 | 231 | 232 |
| 132G4B6 | 233 | 234 | 235 | 236 | 237 | 238 | 239 | 240 |
| 144D3B11 | 241 | 242 | 243 | 244 | 245 | 246 | 247 | 248 |
| 133G11E12 | 249 | 250 | 251 | 252 | 253 | 254 | 255 | 256 |
| 134C11G10 | 257 | 258 | 259 | 260 | 261 | 262 | 263 | 264 |
| 134D3B6 | 265 | 266 | 267 | 268 | 269 | 270 | 271 | 272 |
| 138E9A2 | 273 | 274 | 275 | 276 | 277 | 278 | 279 | 280 |
| 138F9B5 | 281 | 282 | 283 | 284 | 285 | 286 | 287 | 288 |
| 142D6D11 | 289 | 290 | 291 | 292 | 293 | 294 | 295 | 296 |
| 145E10H5 | 297 | 298 | 299 | 300 | 301 | 302 | 303 | 304 |
| 167H6H5 | 305 | 306 | 307 | 308 | 309 | 310 | 311 | 312 |
| 166E12G6 | 313 | 314 | 315 | 316 | 317 | 318 | 319 | 320 |
| 2D5 | 321 | 322 | 323 | 324 | 325 | 326 | 327 | 328 |
| 5D8 | 329 | 330 | 331 | 332 | 333 | 334 | 335 | 336 |

Wherein, the numbers in Table 26 are the sequence numbers in the sequence listing. For example, the amino acid sequence of the heavy chain protein variable region of 8G4E12 is SEQ ID No: 1, and the amino acid sequence of CDR1 in the heavy chain protein variable region of 8G4E12 is SEQ ID No: 2.

TABLE 27

SEMA4D antibody gene nucleotide sequence numbers

| Clone number | Heavy chain protein variable region | Light chain protein variable region |
| --- | --- | --- |
| 8G4E12 | 337 | 338 |
| 10F5E11 | 339 | 340 |
| 16C6D11 | 341 | 342 |
| 17D4A3 | 343 | 344 |
| 17H4B2 | 345 | 346 |
| 24D4E5 | 347 | 348 |
| 28G7B10 | 349 | 350 |
| 30B1C7 | 351 | 352 |
| 12G10H1 | 353 | 354 |
| 17A10A2 | 355 | 356 |
| 25C1B3 | 357 | 358 |
| 28D2E1 | 359 | 360 |
| 31G10C5 | 361 | 362 |
| 32C8F10 | 363 | 364 |
| 35D2B9 | 365 | 366 |
| 37C4F7 | 367 | 368 |
| 37F11F9 | 369 | 370 |
| 38H2E3 | 371 | 372 |
| 42B7G2 | 373 | 374 |
| 31C11G2 | 375 | 376 |
| 80G1G1 | 377 | 378 |
| 80E7E2 | 379 | 380 |
| 84A2C4 | 381 | 382 |
| 88B4D4 | 383 | 384 |
| 89G3E8 | 385 | 386 |
| 90H5D3 | 387 | 388 |
| 90F3B2 | 389 | 390 |
| 118C7E6 | 391 | 392 |
| 131H4A2 | 393 | 394 |
| 132G4B6 | 395 | 396 |
| 144D3B11 | 397 | 398 |
| 133G11E12 | 399 | 400 |

TABLE 27-continued

SEMA4D antibody gene nucleotide sequence numbers

| Clone number | Heavy chain protein variable region | Light chain protein variable region |
|---|---|---|
| 134C11G10 | 401 | 402 |
| 134D3B6 | 403 | 404 |
| 138E9A2 | 405 | 406 |
| 138F9B5 | 407 | 408 |
| 142D6D11 | 409 | 410 |
| 145E10H5 | 411 | 412 |
| 167H6H5 | 413 | 414 |
| 166E12G6 | 415 | 416 |
| 2D5 | 417 | 418 |
| 5D8 | 419 | 420 |

Wherein, the numbers in Table 27 are the sequence numbers ("SEQ ID NO:" numbers) in the sequence listing. For example, the nucleotide sequence encoding the amino acid sequence of the heavy chain protein variable region of 8G4E12 is SEQ ID No: 337, and the nucleotide sequence encoding the amino acid sequence of the light chain protein variable region of 8G4E12 is SEQ ID No: 338.

The nucleotide sequence encoding the CDR1 in the heavy chain protein variable region of 8G4E12 is from position 91 to position 105 in SEQ ID NO: 337 in the sequence listing;
the nucleotide sequence encoding the CDR2 in the heavy chain protein variable region of 8G4E12 is from position 148 to position 198 in SEQ ID NO: 337 in the sequence listing;
the nucleotide sequence encoding the CDR3 in the heavy chain protein variable region of 8G4E12 is from position 295 to position 321 in SEQ ID NO: 337 in the sequence listing;
the nucleotide sequence encoding the CDR1 in the light chain protein variable region of 8G4E12 is from position 70 to position 102 in SEQ ID NO: 338 in the sequence listing;
the nucleotide sequence encoding the CDR2 in the light chain protein variable region of 8G4E12 is from position 148 to position 168 in SEQ ID NO: 338 in the sequence listing;
the nucleotide sequence encoding the CDR3 in the light chain protein variable region of 8G4E12 is from position 265 to position 291 in SEQ ID NO: 338 in the sequence listing;
the nucleotide sequence encoding the CDR1 in the heavy chain protein variable region of 10F5E11 is from position 91 to position 105 in SEQ ID NO: 339 in the sequence listing;
the nucleotide sequence encoding the CDR2 in the heavy chain protein variable region of 10F5E11 is from position 148 to position 198 in SEQ ID NO: 339 in the sequence listing;
the nucleotide sequence encoding the CDR3 in the heavy chain protein variable region of 10F5E11 is from position 295 to position 321 in SEQ ID NO: 339 in the sequence listing;
the nucleotide sequence encoding the CDR1 in the light chain protein variable region of 10F5E11 is from position 70 to position 117 in SEQ ID NO: 340 in the sequence listing;
the nucleotide sequence encoding the CDR2 in the light chain protein variable region of 10F5E11 is from position 163 to position 183 in SEQ ID NO: 340 in the sequence listing;
the nucleotide sequence encoding the CDR3 in the light chain protein variable region of 10F5E11 is from position 280 to position 306 in SEQ ID NO: 340 in the sequence listing;
the nucleotide sequence encoding the CDR1 in the heavy chain protein variable region of 16C6D11 is from position 91 to position 105 in SEQ ID NO: 341 in the sequence listing;
the nucleotide sequence encoding the CDR2 in the heavy chain protein variable region of 16C6D11 is from position 148 to position 198 in SEQ ID NO: 341 in the sequence listing;
the nucleotide sequence encoding the CDR3 in the heavy chain protein variable region of 16C6D11 is from position 295 to position 318 in SEQ ID NO: 341 in the sequence listing;
the nucleotide sequence encoding the CDR1 in the light chain protein variable region of 16C6D11 is from position 70 to position 102 in SEQ ID NO: 342 in the sequence listing; the nucleotide sequence encoding the CDR2 in the light chain protein variable region of 16C6D11 is from position 148 to position 168 in SEQ ID NO: 342 in the sequence listing;
the nucleotide sequence encoding the CDR3 in the light chain protein variable region of 16C6D11 is from position 265 to position 291 in SEQ ID NO: 342 in the sequence listing;
the nucleotide sequence encoding the CDR1 in the heavy chain protein variable region of 17D4A3 is from position 91 to position 105 in SEQ ID NO: 343 in the sequence listing;
the nucleotide sequence encoding the CDR2 in the heavy chain protein variable region of 17D4A3 is from position 148 to position 204 in SEQ ID NO: 343 in the sequence listing;
the nucleotide sequence encoding the CDR3 in the heavy chain protein variable region of 17D4A3 is from position 301 to position 330 in SEQ ID NO: 343 in the sequence listing;
the nucleotide sequence encoding the CDR1 in the light chain protein variable region of 17D4A3 is from position 70 to position 117 in SEQ ID NO: 344 in the sequence listing;
the nucleotide sequence encoding the CDR2 in the light chain protein variable region of 17D4A3 is from position 163 to position 183 in SEQ ID NO: 344 in the sequence listing;
the nucleotide sequence encoding the CDR3 in the light chain protein variable region of 17D4A3 is from position 280 to position 306 in SEQ ID NO: 344 in the sequence listing;
the nucleotide sequence encoding the CDR1 in the heavy chain protein variable region of 17H4B2 is from position 91 to position 105 in SEQ ID NO: 345 in the sequence listing;
the nucleotide sequence encoding the CDR2 in the heavy chain protein variable region of 17H4B2 is from position 148 to position 198 in SEQ ID NO: 345 in the sequence listing;
the nucleotide sequence encoding the CDR3 in the heavy chain protein variable region of 17H4B2 is from position 295 to position 321 in SEQ ID NO: 345 in the sequence listing;
the nucleotide sequence encoding the CDR1 in the light chain protein variable region of 17H4B2 is from position 70 to position 105 in SEQ ID NO: 346 in the sequence listing;

the nucleotide sequence encoding the CDR2 in the light chain protein variable region of 17H4B2 is from position 151 to position 171 in SEQ ID NO: 346 in the sequence listing;

the nucleotide sequence encoding the CDR3 in the light chain protein variable region of 17H4B2 is from position 268 to position 300 in SEQ ID NO: 346 in the sequence listing;

the nucleotide sequence encoding the CDR1 in the heavy chain protein variable region of 24D4E5 is from position 91 to position 108 in SEQ ID NO: 347 in the sequence listing;

the nucleotide sequence encoding the CDR2 in the heavy chain protein variable region of 24D4E5 is from position 151 to position 198 in SEQ ID NO: 347 in the sequence listing;

the nucleotide sequence encoding the CDR3 in the heavy chain protein variable region of 24D4E5 is from position 295 to position 327 in SEQ ID NO: 347 in the sequence listing;

the nucleotide sequence encoding the CDR1 in the light chain protein variable region of 24D4E5 is from position 70 to position 99 in SEQ ID NO: 348 in the sequence listing;

the nucleotide sequence encoding the CDR2 in the light chain protein variable region of 24D4E5 is from position 145 to position 165 in SEQ ID NO: 348 in the sequence listing;

the nucleotide sequence encoding the CDR3 in the light chain protein variable region of 24D4E5 is from position 262 to position 285 in SEQ ID NO: 348 in the sequence listing;

the nucleotide sequence encoding the CDR1 in the heavy chain protein variable region of 28G7B10 is from position 91 to position 105 in SEQ ID NO: 349 in the sequence listing;

the nucleotide sequence encoding the CDR2 in the heavy chain protein variable region of 28G7B10 is from position 148 to position 198 in SEQ ID NO: 349 in the sequence listing;

the nucleotide sequence encoding the CDR3 in the heavy chain protein variable region of 28G7B10 is from position 295 to position 333 in SEQ ID NO: 349 in the sequence listing;

the nucleotide sequence encoding the CDR1 in the light chain protein variable region of 28G7B10 is from position 70 to position 102 in SEQ ID NO: 350 in the sequence listing;

the nucleotide sequence encoding the CDR2 in the light chain protein variable region of 28G7B10 is from position 148 to position 168 in SEQ ID NO: 350 in the sequence listing;

the nucleotide sequence encoding the CDR3 in the light chain protein variable region of 28G7B10 is from position 265 to position 288 in SEQ ID NO: 350 in the sequence listing;

the nucleotide sequence encoding the CDR1 in the heavy chain protein variable region of 30B1C7 is from position 91 to position 105 in SEQ ID NO: 351 in the sequence listing;

the nucleotide sequence encoding the CDR2 in the heavy chain protein variable region of 30B1C7 is from position 148 to position 198 in SEQ ID NO: 351 in the sequence listing;

the nucleotide sequence encoding the CDR3 in the heavy chain protein variable region of 30B1C7 is from position 295 to position 315 in SEQ ID NO: 351 in the sequence listing;

the nucleotide sequence encoding the CDR1 in the light chain protein variable region of 30B1C7 is from position 70 to position 102 in SEQ ID NO: 352 in the sequence listing;

the nucleotide sequence encoding the CDR2 in the light chain protein variable region of 30B1C7 is from position 148 to position 168 in SEQ ID NO: 352 in the sequence listing;

the nucleotide sequence encoding the CDR3 in the light chain protein variable region of 30B1C7 is from position 265 to position 291 in SEQ ID NO: 352 in the sequence listing;

the nucleotide sequence encoding the CDR1 in the heavy chain protein variable region of 12G10H1 is from position 91 to position 105 in SEQ ID NO: 353 in the sequence listing;

the nucleotide sequence encoding the CDR2 in the heavy chain protein variable region of 12G10H1 is from position 148 to position 198 in SEQ ID NO: 353 in the sequence listing;

the nucleotide sequence encoding the CDR3 in the heavy chain protein variable region of 12G10H1 is from position 295 to position 324 in SEQ ID NO: 353 in the sequence listing;

the nucleotide sequence encoding the CDR1 in the light chain protein variable region of 12G10H1 is from position 70 to position 114 in SEQ ID NO: 354 in the sequence listing;

the nucleotide sequence encoding the CDR2 in the light chain protein variable region of 12G10H1 is from position 160 to position 180 in SEQ ID NO: 354 in the sequence listing;

the nucleotide sequence encoding the CDR3 in the light chain protein variable region of 12G10H1 is from position 277 to position 303 in SEQ ID NO: 354 in the sequence listing;

the nucleotide sequence encoding the CDR1 in the heavy chain protein variable region of 17A10A2 is from position 91 to position 105 in SEQ ID NO: 355 in the sequence listing;

the nucleotide sequence encoding the CDR2 in the heavy chain protein variable region of 17A10A2 is from position 148 to position 198 in SEQ ID NO: 355 in the sequence listing;

the nucleotide sequence encoding the CDR3 in the heavy chain protein variable region of 17A10A2 is from position 295 to position 321 in SEQ ID NO: 355 in the sequence listing;

the nucleotide sequence encoding the CDR1 in the light chain protein variable region of 17A10A2 is from position 70 to position 99 in SEQ ID NO: 356 in the sequence listing;

the nucleotide sequence encoding the CDR2 in the light chain protein variable region of 17A10A2 is from position 145 to position 165 in SEQ ID NO: 356 in the sequence listing;

the nucleotide sequence encoding the CDR3 in the light chain protein variable region of 17A10A2 is from position 262 to position 288 in SEQ ID NO: 356 in the sequence listing;

the nucleotide sequence encoding the CDR1 in the heavy chain protein variable region of 25C1B3 is from position 91 to position 105 in SEQ ID NO: 357 in the sequence listing;

the nucleotide sequence encoding the CDR2 in the heavy chain protein variable region of 25C1B3 is from position 148 to position 198 in SEQ ID NO: 357 in the sequence listing;

the nucleotide sequence encoding the CDR3 in the heavy chain protein variable region of 25C1B3 is from position 295 to position 321 in SEQ ID NO: 357 in the sequence listing;

the nucleotide sequence encoding the CDR1 in the light chain protein variable region of 25C1B3 is from position 70 to position 117 in SEQ ID NO: 358 in the sequence listing;

the nucleotide sequence encoding the CDR2 in the light chain protein variable region of 25C1B3 is from position 163 to position 183 in SEQ ID NO: 358 in the sequence listing;

the nucleotide sequence encoding the CDR3 in the light chain protein variable region of 25C1B3 is from position 280 to position 306 in SEQ ID NO: 358 in the sequence listing;

the nucleotide sequence encoding the CDR1 in the heavy chain protein variable region of 28D2E1 is from position 91 to position 105 in SEQ ID NO: 359 in the sequence listing;

the nucleotide sequence encoding the CDR2 in the heavy chain protein variable region of 28D2E1 is from position 148 to position 204 in SEQ ID NO: 359 in the sequence listing;

the nucleotide sequence encoding the CDR3 in the heavy chain protein variable region of 28D2E1 is from position 301 to position 330 in SEQ ID NO: 359 in the sequence listing;

the nucleotide sequence encoding the CDR1 in the light chain protein variable region of 28D2E1 is from position 70 to position 117 in SEQ ID NO: 360 in the sequence listing;

the nucleotide sequence encoding the CDR2 in the light chain protein variable region of 28D2E1 is from position 163 to position 183 in SEQ ID NO: 360 in the sequence listing;

the nucleotide sequence encoding the CDR3 in the light chain protein variable region of 28D2E1 is from position 280 to position 306 in SEQ ID NO: 360 in the sequence listing;

the nucleotide sequence encoding the CDR1 in the heavy chain protein variable region of 31G10C5 is from position 91 to position 105 in SEQ ID NO: 361 in the sequence listing;

the nucleotide sequence encoding the CDR2 in the heavy chain protein variable region of 31G10C5 is from position 148 to position 198 in SEQ ID NO: 361 in the sequence listing;

the nucleotide sequence encoding the CDR3 in the heavy chain protein variable region of 31G10C5 is from position 295 to position 318 in SEQ ID NO: 361 in the sequence listing;

the nucleotide sequence encoding the CDR1 in the light chain protein variable region of 31G10C5 is from position 70 to position 99 in SEQ ID NO: 362 in the sequence listing;

the nucleotide sequence encoding the CDR2 in the light chain protein variable region of 31G10C5 is from position 145 to position 165 in SEQ ID NO: 362 in the sequence listing;

the nucleotide sequence encoding the CDR3 in the light chain protein variable region of 31G10C5 is from position 262 to position 288 in SEQ ID NO: 362 in the sequence listing;

the nucleotide sequence encoding the CDR1 in the heavy chain protein variable region of 32C8F10 is from position 91 to position 105 in SEQ ID NO: 363 in the sequence listing;

the nucleotide sequence encoding the CDR2 in the heavy chain protein variable region of 32C8F10 is from position 148 to position 198 in SEQ ID NO: 363 in the sequence listing;

the nucleotide sequence encoding the CDR3 in the heavy chain protein variable region of 32C8F10 is from position 295 to position 318 in SEQ ID NO: 363 in the sequence listing;

the nucleotide sequence encoding the CDR1 in the light chain protein variable region of 32C8F10 is from position 70 to position 99 in SEQ ID NO: 364 in the sequence listing;

the nucleotide sequence encoding the CDR2 in the light chain protein variable region of 32C8F10 is from position 145 to position 165 in SEQ ID NO: 364 in the sequence listing;

the nucleotide sequence encoding the CDR3 in the light chain protein variable region of 32C8F10 is from position 262 to position 288 in SEQ ID NO: 364 in the sequence listing;

the nucleotide sequence encoding the CDR1 in the heavy chain protein variable region of 35D2B9 is from position 91 to position 105 in SEQ ID NO: 365 in the sequence listing;

the nucleotide sequence encoding the CDR2 in the heavy chain protein variable region of 35D2B9 is from position 148 to position 198 in SEQ ID NO: 365 in the sequence listing;

the nucleotide sequence encoding the CDR3 in the heavy chain protein variable region of 35D2B9 is from position 295 to position 324 in SEQ ID NO: 365 in the sequence listing;

the nucleotide sequence encoding the CDR1 in the light chain protein variable region of 35D2B9 is from position 70 to position 99 in SEQ ID NO: 366 in the sequence listing;

the nucleotide sequence encoding the CDR2 in the light chain protein variable region of 35D2B9 is from position 145 to position 165 in SEQ ID NO: 366 in the sequence listing;

the nucleotide sequence encoding the CDR3 in the light chain protein variable region of 35D2B9 is from position 262 to position 288 in SEQ ID NO: 366 in the sequence listing;

the nucleotide sequence encoding the CDR1 in the heavy chain protein variable region of 37C4F7 is from position 91 to position 105 in SEQ ID NO: 367 in the sequence listing;

the nucleotide sequence encoding the CDR2 in the heavy chain protein variable region of 37C4F7 is from position 148 to position 198 in SEQ ID NO: 367 in the sequence listing;

the nucleotide sequence encoding the CDR3 in the heavy chain protein variable region of 37C4F7 is from position 295 to position 333 in SEQ ID NO: 367 in the sequence listing;

the nucleotide sequence encoding the CDR1 in the light chain protein variable region of 37C4F7 is from position 70 to position 117 in SEQ ID NO: 368 in the sequence listing;

the nucleotide sequence encoding the CDR2 in the light chain protein variable region of 37C4F7 is from position 163 to position 183 in SEQ ID NO: 368 in the sequence listing;

the nucleotide sequence encoding the CDR3 in the light chain protein variable region of 37C4F7 is from position 265 to position 291 in SEQ ID NO: 368 in the sequence listing;

the nucleotide sequence encoding the CDR1 in the heavy chain protein variable region of 37F11F9 is from position 91 to position 105 in SEQ ID NO: 369 in the sequence listing;

the nucleotide sequence encoding the CDR2 in the heavy chain protein variable region of 37F11F9 is from position 148 to position 198 in SEQ ID NO: 369 in the sequence listing;

the nucleotide sequence encoding the CDR3 in the heavy chain protein variable region of 37F11F9 is from position 295 to position 336 in SEQ ID NO: 369 in the sequence listing;

the nucleotide sequence encoding the CDR1 in the light chain protein variable region of 37F11F9 is from position 70 to position 102 in SEQ ID NO: 370 in the sequence listing;

the nucleotide sequence encoding the CDR2 in the light chain protein variable region of 37F11F9 is from position 148 to position 168 in SEQ ID NO: 370 in the sequence listing;

the nucleotide sequence encoding the CDR3 in the light chain protein variable region of 37F11F9 is from position 265 to position 291 in SEQ ID NO: 370 in the sequence listing;

the nucleotide sequence encoding the CDR1 in the heavy chain protein variable region of 38H2E3 is from position 91 to position 105 in SEQ ID NO: 371 in the sequence listing;

the nucleotide sequence encoding the CDR2 in the heavy chain protein variable region of 38H2E3 is from position 148 to position 198 in SEQ ID NO: 371 in the sequence listing;

the nucleotide sequence encoding the CDR3 in the heavy chain protein variable region of 38H2E3 is from position 295 to position 333 in SEQ ID NO: 371 in the sequence listing;

the nucleotide sequence encoding the CDR1 in the light chain protein variable region of 38H2E3 is from position 70 to position 117 in SEQ ID NO: 372 in the sequence listing;

the nucleotide sequence encoding the CDR2 in the light chain protein variable region of 38H2E3 is from position 163 to position 183 in SEQ ID NO: 372 in the sequence listing;

the nucleotide sequence encoding the CDR3 in the light chain protein variable region of 38H2E3 is from position 280 to position 306 in SEQ ID NO: 372 in the sequence listing;

the nucleotide sequence encoding the CDR1 in the heavy chain protein variable region of 42B7G2 is from position 91 to position 105 in SEQ ID NO: 373 in the sequence listing;

the nucleotide sequence encoding the CDR2 in the heavy chain protein variable region of 42B7G2 is from position 148 to position 198 in SEQ ID NO: 373 in the sequence listing;

the nucleotide sequence encoding the CDR3 in the heavy chain protein variable region of 42B7G2 is from position 295 to position 336 in SEQ ID NO: 373 in the sequence listing;

the nucleotide sequence encoding the CDR1 in the light chain protein variable region of 42B7G2 is from position 70 to position 114 in SEQ ID NO: 374 in the sequence listing;

the nucleotide sequence encoding the CDR2 in the light chain protein variable region of 42B7G2 is from position 160 to position 180 in SEQ ID NO: 374 in the sequence listing;

the nucleotide sequence encoding the CDR3 in the light chain protein variable region of 42B7G2 is from position 280 to position 306 in SEQ ID NO: 374 in the sequence listing;

the nucleotide sequence encoding the CDR1 in the heavy chain protein variable region of 31C11G2 is from position 91 to position 105 in SEQ ID NO: 375 in the sequence listing;

the nucleotide sequence encoding the CDR2 in the heavy chain protein variable region of 31C11G2 is from position 148 to position 198 in SEQ ID NO: 375 in the sequence listing;

the nucleotide sequence encoding the CDR3 in the heavy chain protein variable region of 31C11G2 is from position 295 to position 318 in SEQ ID NO: 375 in the sequence listing;

the nucleotide sequence encoding the CDR1 in the light chain protein variable region of 31C11G2 is from position 70 to position 99 in SEQ ID NO: 376 in the sequence listing;

the nucleotide sequence encoding the CDR2 in the light chain protein variable region of 31C11G2 is from position 145 to position 165 in SEQ ID NO: 376 in the sequence listing;

the nucleotide sequence encoding the CDR3 in the light chain protein variable region of 31C11G2 is from position 262 to position 288 in SEQ ID NO: 376 in the sequence listing;

the nucleotide sequence encoding the CDR1 in the heavy chain protein variable region of 80G1G1 is from position 91 to position 105 in SEQ ID NO: 377 in the sequence listing;

the nucleotide sequence encoding the CDR2 in the heavy chain protein variable region of 80G1G1 is from position 148 to position 195 in SEQ ID NO: 377 in the sequence listing;

the nucleotide sequence encoding the CDR3 in the heavy chain protein variable region of 80G1G1 is from position 292 to position 318 in SEQ ID NO: 377 in the sequence listing;

the nucleotide sequence encoding the CDR1 in the light chain protein variable region of 80G1G1 is from position 70 to position 99 in SEQ ID NO: 378 in the sequence listing;

the nucleotide sequence encoding the CDR2 in the light chain protein variable region of 80G1G1 is from position 145 to position 165 in SEQ ID NO: 378 in the sequence listing;

the nucleotide sequence encoding the CDR3 in the light chain protein variable region of 80G1G1 is from position 262 to position 288 in SEQ ID NO: 378 in the sequence listing;

the nucleotide sequence encoding the CDR1 in the heavy chain protein variable region of 80E7E2 is from position 91 to position 105 in SEQ ID NO: 379 in the sequence listing;

the nucleotide sequence encoding the CDR2 in the heavy chain protein variable region of 80E7E2 is from position 148 to position 198 in SEQ ID NO: 379 in the sequence listing;

the nucleotide sequence encoding the CDR3 in the heavy chain protein variable region of 80E7E2 is from position 295 to position 321 in SEQ ID NO: 379 in the sequence listing;

the nucleotide sequence encoding the CDR1 in the light chain protein variable region of 80E7E2 is from position 70 to position 114 in SEQ ID NO: 380 in the sequence listing;

the nucleotide sequence encoding the CDR2 in the light chain protein variable region of 80E7E2 is from position 160 to position 180 in SEQ ID NO: 380 in the sequence listing;

the nucleotide sequence encoding the CDR3 in the light chain protein variable region of 80E7E2 is from position 277 to position 303 in SEQ ID NO: 380 in the sequence listing;

the nucleotide sequence encoding the CDR1 in the heavy chain protein variable region of 84A2C4 is from position 91 to position 105 in SEQ ID NO: 381 in the sequence listing;

the nucleotide sequence encoding the CDR2 in the heavy chain protein variable region of 84A2C4 is from position 148 to position 198 in SEQ ID NO: 381 in the sequence listing;

the nucleotide sequence encoding the CDR3 in the heavy chain protein variable region of 84A2C4 is from position 295 to position 321 in SEQ ID NO: 381 in the sequence listing;

the nucleotide sequence encoding the CDR1 in the light chain protein variable region of 84A2C4 is from position 70 to position 114 in SEQ ID NO: 382 in the sequence listing;

the nucleotide sequence encoding the CDR2 in the light chain protein variable region of 84A2C4 is from position 160 to position 180 in SEQ ID NO: 382 in the sequence listing;

the nucleotide sequence encoding the CDR3 in the light chain protein variable region of 84A2C4 is from position 277 to position 303 in SEQ ID NO: 382 in the sequence listing;

the nucleotide sequence encoding the CDR1 in the heavy chain protein variable region of 88B4D4 is from position 91 to position 105 in SEQ ID NO: 383 in the sequence listing;

the nucleotide sequence encoding the CDR2 in the heavy chain protein variable region of 88B4D4 is from position 148 to position 195 in SEQ ID NO: 383 in the sequence listing;

the nucleotide sequence encoding the CDR3 in the heavy chain protein variable region of 88B4D4 is from position 292 to position 318 in SEQ ID NO: 383 in the sequence listing;

the nucleotide sequence encoding the CDR1 in the light chain protein variable region of 88B4D4 is from position 70 to position 99 in SEQ ID NO: 384 in the sequence listing;

the nucleotide sequence encoding the CDR2 in the light chain protein variable region of 88B4D4 is from position 145 to position 165 in SEQ ID NO: 384 in the sequence listing;

the nucleotide sequence encoding the CDR3 in the light chain protein variable region of 88B4D4 is from position 262 to position 288 in SEQ ID NO: 384 in the sequence listing;

the nucleotide sequence encoding the CDR1 in the heavy chain protein variable region of 89G3E8 is from position 91 to position 105 in SEQ ID NO: 385 in the sequence listing;

the nucleotide sequence encoding the CDR2 in the heavy chain protein variable region of 89G3E8 is from position 148 to position 195 in SEQ ID NO: 385 in the sequence listing;

the nucleotide sequence encoding the CDR3 in the heavy chain protein variable region of 89G3E8 is from position 292 to position 333 in SEQ ID NO: 385 in the sequence listing;

the nucleotide sequence encoding the CDR1 in the light chain protein variable region of 89G3E8 is from position 70 to position 117 in SEQ ID NO: 386 in the sequence listing;

the nucleotide sequence encoding the CDR2 in the light chain protein variable region of 89G3E8 is from position 163 to position 183 in SEQ ID NO: 386 in the sequence listing;

the nucleotide sequence encoding the CDR3 in the light chain protein variable region of 89G3E8 is from position 280 to position 306 in SEQ ID NO: 386 in the sequence listing;

the nucleotide sequence encoding the CDR1 in the heavy chain protein variable region of 90H5D3 is from position 91 to position 105 in SEQ ID NO: 387 in the sequence listing;

the nucleotide sequence encoding the CDR2 in the heavy chain protein variable region of 90H5D3 is from position 148 to position 195 in SEQ ID NO: 387 in the sequence listing;

the nucleotide sequence encoding the CDR3 in the heavy chain protein variable region of 90H5D3 is from position 292 to position 318 in SEQ ID NO: 387 in the sequence listing;

the nucleotide sequence encoding the CDR1 in the light chain protein variable region of 90H5D3 is from position 70 to position 99 in SEQ ID NO: 388 in the sequence listing;

the nucleotide sequence encoding the CDR2 in the light chain protein variable region of 90H5D3 is from position 145 to position 165 in SEQ ID NO: 388 in the sequence listing;

the nucleotide sequence encoding the CDR3 in the light chain protein variable region of 90H5D3 is from position 262 to position 288 in SEQ ID NO: 388 in the sequence listing;

the nucleotide sequence encoding the CDR1 in the heavy chain protein variable region of 90F3B2 is from position 91 to position 105 in SEQ ID NO: 389 in the sequence listing;

the nucleotide sequence encoding the CDR2 in the heavy chain protein variable region of 90F3B2 is from position 148 to position 195 in SEQ ID NO: 389 in the sequence listing;

the nucleotide sequence encoding the CDR3 in the heavy chain protein variable region of 90F3B2 is from position 292 to position 333 in SEQ ID NO: 389 in the sequence listing;

the nucleotide sequence encoding the CDR1 in the light chain protein variable region of 90F3B2 is from position 70 to position 117 in SEQ ID NO: 390 in the sequence listing;

the nucleotide sequence encoding the CDR2 in the light chain protein variable region of 90F3B2 is from position 163 to position 183 in SEQ ID NO: 390 in the sequence listing;

the nucleotide sequence encoding the CDR3 in the light chain protein variable region of 90F3B2 is from position 280 to position 306 in SEQ ID NO: 390 in the sequence listing;

the nucleotide sequence encoding the CDR1 in the heavy chain protein variable region of 118C7E6 is from position 91 to position 105 in SEQ ID NO: 391 in the sequence listing;

the nucleotide sequence encoding the CDR2 in the heavy chain protein variable region of 118C7E6 is from position 148 to position 198 in SEQ ID NO: 391 in the sequence listing;

the nucleotide sequence encoding the CDR3 in the heavy chain protein variable region of 118C7E6 is from position 295 to position 333 in SEQ ID NO: 391 in the sequence listing;

the nucleotide sequence encoding the CDR1 in the light chain protein variable region of 118C7E6 is from position 70 to position 102 in SEQ ID NO: 392 in the sequence listing;

the nucleotide sequence encoding the CDR2 in the light chain protein variable region of 118C7E6 is from position 148 to position 168 in SEQ ID NO: 392 in the sequence listing;

the nucleotide sequence encoding the CDR3 in the light chain protein variable region of 118C7E6 is from position 265 to position 291 in SEQ ID NO: 392 in the sequence listing;

the nucleotide sequence encoding the CDR1 in the heavy chain protein variable region of 131H4A2 is from position 91 to position 105 in SEQ ID NO: 393 in the sequence listing;

the nucleotide sequence encoding the CDR2 in the heavy chain protein variable region of 131H4A2 is from position 148 to position 198 in SEQ ID NO: 393 in the sequence listing;

the nucleotide sequence encoding the CDR3 in the heavy chain protein variable region of 131H4A2 is from position 295 to position 312 in SEQ ID NO: 393 in the sequence listing;

the nucleotide sequence encoding the CDR1 in the light chain protein variable region of 131H4A2 is from position 70 to position 102 in SEQ ID NO: 394 in the sequence listing;

the nucleotide sequence encoding the CDR2 in the light chain protein variable region of 131H4A2 is from position 148 to position 168 in SEQ ID NO: 394 in the sequence listing;

the nucleotide sequence encoding the CDR3 in the light chain protein variable region of 131H4A2 is from position 265 to position 291 in SEQ ID NO: 394 in the sequence listing;

the nucleotide sequence encoding the CDR1 in the heavy chain protein variable region of 132G4B6 is from position 91 to position 105 in SEQ ID NO: 395 in the sequence listing;

the nucleotide sequence encoding the CDR2 in the heavy chain protein variable region of 132G4B6 is from position 148 to position 198 in SEQ ID NO: 395 in the sequence listing;

the nucleotide sequence encoding the CDR3 in the heavy chain protein variable region of 132G4B6 is from position 295 to position 327 in SEQ ID NO: 395 in the sequence listing;

the nucleotide sequence encoding the CDR1 in the light chain protein variable region of 132G4B6 is from position 70 to position 102 in SEQ ID NO: 396 in the sequence listing;

the nucleotide sequence encoding the CDR2 in the light chain protein variable region of 132G4B6 is from position 148 to position 168 in SEQ ID NO: 396 in the sequence listing;

the nucleotide sequence encoding the CDR3 in the light chain protein variable region of 132G4B6 is from position 265 to position 291 in SEQ ID NO: 396 in the sequence listing;

the nucleotide sequence encoding the CDR1 in the heavy chain protein variable region of 144D3B11 is from position 91 to position 105 in SEQ ID NO: 397 in the sequence listing;

the nucleotide sequence encoding the CDR2 in the heavy chain protein variable region of 144D3B11 is from position 148 to position 198 in SEQ ID NO: 397 in the sequence listing;

the nucleotide sequence encoding the CDR3 in the heavy chain protein variable region of 144D3B11 is from position 295 to position 321 in SEQ ID NO: 397 in the sequence listing;

the nucleotide sequence encoding the CDR1 in the light chain protein variable region of 144D3B11 is from position 70 to position 117 in SEQ ID NO: 398 in the sequence listing;

the nucleotide sequence encoding the CDR2 in the light chain protein variable region of 144D3B11 is from position 163 to position 183 in SEQ ID NO: 398 in the sequence listing;

the nucleotide sequence encoding the CDR3 in the light chain protein variable region of 144D3B11 is from position 280 to position 306 in SEQ ID NO: 398 in the sequence listing;

the nucleotide sequence encoding the CDR1 in the heavy chain protein variable region of 133G11E12 is from position 91 to position 105 in SEQ ID NO: 399 in the sequence listing;

the nucleotide sequence encoding the CDR2 in the heavy chain protein variable region of 133G11E12 is from position 148 to position 198 in SEQ ID NO: 399 in the sequence listing;

the nucleotide sequence encoding the CDR3 in the heavy chain protein variable region of 133G11E12 is from position 295 to position 327 in SEQ ID NO: 399 in the sequence listing;

the nucleotide sequence encoding the CDR1 in the light chain protein variable region of 133G11E12 is from position 70 to position 102 in SEQ ID NO: 400 in the sequence listing;

the nucleotide sequence encoding the CDR2 in the light chain protein variable region of 133G11E12 is from position 148 to position 168 in SEQ ID NO: 400 in the sequence listing;

the nucleotide sequence encoding the CDR3 in the light chain protein variable region of 133G11E12 is from position 265 to position 291 in SEQ ID NO: 400 in the sequence listing;

the nucleotide sequence encoding the CDR1 in the heavy chain protein variable region of 134C11G10 is from position 91 to position 105 in SEQ ID NO: 401 in the sequence listing;

the nucleotide sequence encoding the CDR2 in the heavy chain protein variable region of 134C11G10 is from position 148 to position 198 in SEQ ID NO: 401 in the sequence listing;

the nucleotide sequence encoding the CDR3 in the heavy chain protein variable region of 134C11G10 is from position 295 to position 327 in SEQ ID NO: 401 in the sequence listing;

the nucleotide sequence encoding the CDR1 in the light chain protein variable region of 134C11G10 is from position 70 to position 102 in SEQ ID NO: 402 in the sequence listing;

the nucleotide sequence encoding the CDR2 in the light chain protein variable region of 134C11G10 is from position 148 to position 168 in SEQ ID NO: 402 in the sequence listing;

the nucleotide sequence encoding the CDR3 in the light chain protein variable region of 134C11G10 is from position 265 to position 291 in SEQ ID NO: 402 in the sequence listing;

the nucleotide sequence encoding the CDR1 in the heavy chain protein variable region of 134D3B6 is from position 91 to position 105 in SEQ ID NO: 403 in the sequence listing;

the nucleotide sequence encoding the CDR2 in the heavy chain protein variable region of 134D3B6 is from position 148 to position 198 in SEQ ID NO: 403 in the sequence listing;

the nucleotide sequence encoding the CDR3 in the heavy chain protein variable region of 134D3B6 is from position 295 to position 312 in SEQ ID NO: 403 in the sequence listing;

the nucleotide sequence encoding the CDR1 in the light chain protein variable region of 134D3B6 is from position 70 to position 102 in SEQ ID NO: 404 in the sequence listing;

the nucleotide sequence encoding the CDR2 in the light chain protein variable region of 134D3B6 is from position 148 to position 168 in SEQ ID NO: 404 in the sequence listing;

the nucleotide sequence encoding the CDR3 in the light chain protein variable region of 134D3B6 is from position 265 to position 291 in SEQ ID NO: 404 in the sequence listing;

the nucleotide sequence encoding the CDR1 in the heavy chain protein variable region of 138E9A2 is from position 91 to position 105 in SEQ ID NO: 405 in the sequence listing;

the nucleotide sequence encoding the CDR2 in the heavy chain protein variable region of 138E9A2 is from position 148 to position 198 in SEQ ID NO: 405 in the sequence listing;

the nucleotide sequence encoding the CDR3 in the heavy chain protein variable region of 138E9A2 is from position 295 to position 327 in SEQ ID NO: 405 in the sequence listing;

the nucleotide sequence encoding the CDR1 in the light chain protein variable region of 138E9A2 is from position 70 to position 117 in SEQ ID NO: 406 in the sequence listing;

the nucleotide sequence encoding the CDR2 in the light chain protein variable region of 138E9A2 is from position 163 to position 183 in SEQ ID NO: 406 in the sequence listing;

the nucleotide sequence encoding the CDR3 in the light chain protein variable region of 138E9A2 is from position 280 to position 306 in SEQ ID NO: 406 in the sequence listing;

the nucleotide sequence encoding the CDR1 in the heavy chain protein variable region of 138F9B5 is from position 91 to position 105 in SEQ ID NO: 407 in the sequence listing;

the nucleotide sequence encoding the CDR2 in the heavy chain protein variable region of 138F9B5 is from position 148 to position 198 in SEQ ID NO: 407 in the sequence listing;

the nucleotide sequence encoding the CDR3 in the heavy chain protein variable region of 138F9B5 is from position 295 to position 336 in SEQ ID NO: 407 in the sequence listing;

the nucleotide sequence encoding the CDR1 in the light chain protein variable region of 138F9B5 is from position 70 to position 102 in SEQ ID NO: 408 in the sequence listing;

the nucleotide sequence encoding the CDR2 in the light chain protein variable region of 138F9B5 is from position 148 to position 168 in SEQ ID NO: 408 in the sequence listing;

the nucleotide sequence encoding the CDR3 in the light chain protein variable region of 138F9B5 is from position 265 to position 291 in SEQ ID NO: 408 in the sequence listing;

the nucleotide sequence encoding the CDR1 in the heavy chain protein variable region of 142D6D11 is from position 91 to position 105 in SEQ ID NO: 409 in the sequence listing;

the nucleotide sequence encoding the CDR2 in the heavy chain protein variable region of 142D6D11 is from position 148 to position 198 in SEQ ID NO: 409 in the sequence listing;

the nucleotide sequence encoding the CDR3 in the heavy chain protein variable region of 142D6D11 is from position 295 to position 321 in SEQ ID NO: 409 in the sequence listing;

the nucleotide sequence encoding the CDR1 in the light chain protein variable region of 142D6D11 is from position 70 to position 102 in SEQ ID NO: 410 in the sequence listing;

the nucleotide sequence encoding the CDR2 in the light chain protein variable region of 142D6D11 is from position 148 to position 168 in SEQ ID NO: 410 in the sequence listing;

the nucleotide sequence encoding the CDR3 in the light chain protein variable region of 142D6D11 is from position 265 to position 291 in SEQ ID NO: 410 in the sequence listing;

the nucleotide sequence encoding the CDR1 in the heavy chain protein variable region of 145E10H5 is from position 91 to position 105 in SEQ ID NO: 411 in the sequence listing;

the nucleotide sequence encoding the CDR2 in the heavy chain protein variable region of 145E10H5 is from position 148 to position 198 in SEQ ID NO: 411 in the sequence listing;

the nucleotide sequence encoding the CDR3 in the heavy chain protein variable region of 145E10H5 is from position 295 to position 321 in SEQ ID NO: 411 in the sequence listing;

the nucleotide sequence encoding the CDR1 in the light chain protein variable region of 145E10H5 is from position 70 to position 102 in SEQ ID NO: 412 in the sequence listing;

the nucleotide sequence encoding the CDR2 in the light chain protein variable region of 145E10H5 is from position 148 to position 168 in SEQ ID NO: 412 in the sequence listing;

the nucleotide sequence encoding the CDR3 in the light chain protein variable region of 145E10H5 is from position 265 to position 291 in SEQ ID NO: 412 in the sequence listing;

the nucleotide sequence encoding the CDR1 in the heavy chain protein variable region of 167H6H5 is from position 91 to position 105 in SEQ ID NO: 413 in the sequence listing;

the nucleotide sequence encoding the CDR2 in the heavy chain protein variable region of 167H6H5 is from position 148 to position 198 in SEQ ID NO: 413 in the sequence listing;

the nucleotide sequence encoding the CDR3 in the heavy chain protein variable region of 167H6H5 is from position 295 to position 318 in SEQ ID NO: 413 in the sequence listing;

the nucleotide sequence encoding the CDR1 in the light chain protein variable region of 167H6H5 is from position 70 to position 105 in SEQ ID NO: 414 in the sequence listing;

the nucleotide sequence encoding the CDR2 in the light chain protein variable region of 167H6H5 is from position 151 to position 171 in SEQ ID NO: 414 in the sequence listing;

the nucleotide sequence encoding the CDR3 in the light chain protein variable region of 167H6H5 is from position 268 to position 294 in SEQ ID NO: 414 in the sequence listing;

the nucleotide sequence encoding the CDR1 in the heavy chain protein variable region of 166E12G6 is from position 91 to position 105 in SEQ ID NO: 415 in the sequence listing;

the nucleotide sequence encoding the CDR2 in the heavy chain protein variable region of 166E12G6 is from position 148 to position 204 in SEQ ID NO: 415 in the sequence listing;

the nucleotide sequence encoding the CDR3 in the heavy chain protein variable region of 166E12G6 is from position 301 to position 330 in SEQ ID NO: 415 in the sequence listing;

the nucleotide sequence encoding the CDR1 in the light chain protein variable region of 166E12G6 is from position 70 to position 117 in SEQ ID NO: 416 in the sequence listing;

the nucleotide sequence encoding the CDR2 in the light chain protein variable region of 166E12G6 is from position 163 to position 183 in SEQ ID NO: 416 in the sequence listing;

the nucleotide sequence encoding the CDR3 in the light chain protein variable region of 166E12G6 is from position 280 to position 306 in SEQ ID NO: 416 in the sequence listing;

the nucleotide sequence encoding the CDR1 in the heavy chain protein variable region of 2D5 is from position 91 to position 111 in SEQ ID NO: 417 in the sequence listing;

the nucleotide sequence encoding the CDR2 in the heavy chain protein variable region of 2D5 is from position 154 to position 201 in SEQ ID NO: 417 in the sequence listing;

the nucleotide sequence encoding the CDR3 in the heavy chain protein variable region of 2D5 is from position 298 to position 333 in SEQ ID NO: 417 in the sequence listing;

the nucleotide sequence encoding the CDR1 in the light chain protein variable region of 2D5 is from position 67 to position 99 in SEQ ID NO: 418 in the sequence listing;

the nucleotide sequence encoding the CDR2 in the light chain protein variable region of 2D5 is from position 145 to position 165 in SEQ ID NO: 418 in the sequence listing;

the nucleotide sequence encoding the CDR3 in the light chain protein variable region of 2D5 is from position 262 to position 294 in SEQ ID NO: 418 in the sequence listing;

the nucleotide sequence encoding the CDR1 in the heavy chain protein variable region of 5D8 is from position 91 to position 105 in SEQ ID NO: 419 in the sequence listing;

the nucleotide sequence encoding the CDR2 in the heavy chain protein variable region of 5D8 is from position 148 to position 195 in SEQ ID NO: 419 in the sequence listing;

the nucleotide sequence encoding the CDR3 in the heavy chain protein variable region of 5D8 is from position 292 to position 333 in SEQ ID NO: 419 in the sequence listing;

the nucleotide sequence encoding the CDR1 in the light chain protein variable region of 5D8 is from position 67 to position 105 in SEQ ID NO: 420 in the sequence listing;

the nucleotide sequence encoding the CDR2 in the light chain protein variable region of 5D8 is from position 151 to position 171 in SEQ ID NO: 420 in the sequence listing;

the nucleotide sequence encoding the CDR3 in the light chain protein variable region of 5D8 is from position 268 to position 300 in SEQ ID NO: 420 in the sequence listing.

Example 8 Transformation of Antibody Sequence

A. Point Mutations in Antibody Sequence Hot Spots

PCR-mediated site-directed mutagenesis was used to transform the hot spots of antibody sequences. The principle is: a circular plasmid was used as a template, and a pair of perfectly matched primers was used to introduce mutations for PCR amplification. Because the template was a plasmid extracted from E. coli that was methylated and modified and was sensitive to DpnI, while the PCR product was an unmethylated open-circle plasmid with a gap, the template can be eliminated by DpnI digestion method, and only the newly amplified mutant plasmids remained in the final product.

The specific operation method was that firstly the codon corresponding to each amino acid was determined according to the codon table. Then the nucleotide mutation sites were determined. For example, when aspartic acid N needed to be mutated to asparagine D, wherein the codon corresponding to aspartic acid is AAT, and the codon corresponding to asparagine is GAT or GAC, the AAT was chosen to be mutated into GAT and only one site was needed to be mutated. Then the mutation site and its adjacent base sequence was determined, and the primers of the mutation sequence with the mutation site as the center were designed for PCR amplification. The product was digested with DpnI for 1-3 hours and then transformed into DH5a. Single colonies were picked and cultured and sequenced the next day after the plate coated.

The hot spots in CDR sequences of antibody 5D8 were subjected to point mutations. There were 4 mutable sites in total. That is, there were 2 in heavy chain, wherein aspartic acid N at position 52 was mutated to asparagine D, or serine S at position 54 was mutated to alanine A; and there were 2 in light chain, wherein aspartic acid N at position 97 was mutated to serine S, or glycine G at position 98 was mutated to alanine A. The sequencing results are shown in Table 28.

TABLE 28

Amino acid sequence numbers of point mutated SEMA4D antibodies

| Clone number | Heavy chain protein | | | | Light chain protein | | | |
|---|---|---|---|---|---|---|---|---|
| | Variable region | CDR1 | CDR2 | CDR3 | Variable region | CDR1 | CDR2 | CDR3 |
| 5D8-h1 | 435 | 330 | 436 | 332 | 437 | 334 | 335 | 438 |
| 5D8-h2 | 439 | 330 | 440 | 332 | 437 | 334 | 335 | 438 |
| 5D8-h3 | 435 | 330 | 436 | 332 | 441 | 334 | 335 | 442 |
| 5D8-h4 | 439 | 330 | 440 | 332 | 441 | 334 | 335 | 442 |

B. Back Mutations in the Framework Region of Antibody Sequence

The sequences of the 2D5 heavy chain and light chain variable regions were input into Ig BLAST for analysis.

For the heavy chain variable region, considering the number of amino acids that needed to be back-mutated and the frequency of the mutant amino acids in the germline, IGHV2-70*01 was selected as the mutation reference template. According to the results of the germline blast comparison on the Abysis website, and considering the number of amino acids that needed to be back-mutated and the frequency of the mutant amino acids in the germline, JH1 was selected to complete the J region splicing. By comparison, the inventors mutated lysine K at position 5 to arginine R, threonine T at position 10 to alanine A, alanine A at position 21 to threonine T, and serine S at position 23 to threonine T.

For the light chain variable region, considering the number of amino acids that needed to be back-mutated and the frequency of the mutant amino acids in the germline, IGLV3-1*01 was selected as the mutation reference template. According to the results of the germline blast comparison on the Abysis website, and considering the number of amino acids that needed to be back-mutated and the frequency of the mutant amino acids in the germline, JH1 was selected to complete the J region splicing. By comparison, the inventor mutated Serine S at position 2 to Tyrosine Y, Alanine A at position 7 to Proline P, Proline P at position 42 to Serine S, Alanine A at position 76 to glycine G, and Leucine L at position 80 to methionine M.

A similar method was used to design mutations in the framework regions of the 5D8-h2 heavy chain and light chain variable regions. The sequencing results are shown in Table 29.

TABLE 29

Amino acid sequence numbers of SEMA4D framework region back mutated antibodies

| Clone number | Heavy chain protein | | | | Light chain protein | | | |
|---|---|---|---|---|---|---|---|---|
| | Variable region | CDR1 | CDR2 | CDR3 | Variable region | CDR1 | CDR2 | CDR3 |
| 2D5-b1 | 443 | 322 | 323 | 324 | 444 | 326 | 327 | 328 |
| 5D8-h2b4 | 439 | 330 | 440 | 332 | 445 | 334 | 335 | 438 |

Example 9 Detection of the Activity of SEMA4D Antibodies to Inhibit MDSCs

CD33 magnetic beads (purchased from Miltenyi Biotech, catalog number 130-045-501) were used to sort human peripheral blood mononuclear cells (PBMCs). 1e5 cells from each well were taken and added to a 96-well plate. Then the plated was added with 100 μg/mL hSEMA4D ECD-hFc and 10 μg/mL, 100 μg/mL, or 500 μg/mL SEMA4D antibody. After mixed thoroughly, the plate was incubated for 72 hours at 37° C., washed once with FACS buffer (PBS+2% FBS) after incubation, and centrifuged at 2000 rpm for 5 minutes. Then fluorescently labeled CD33 antibody, CD11b antibody, and HLA-DR antibody were added, and the plate was incubated at 4° C. for 1 hour in the dark. Then it was washed twice with FACS buffer and centrifuged at 2000 rpm for 5 minutes. Then the precipitate was resuspended with 200 μL FACS buffer, and detected on FACS CantoII machine.

Figure 13:
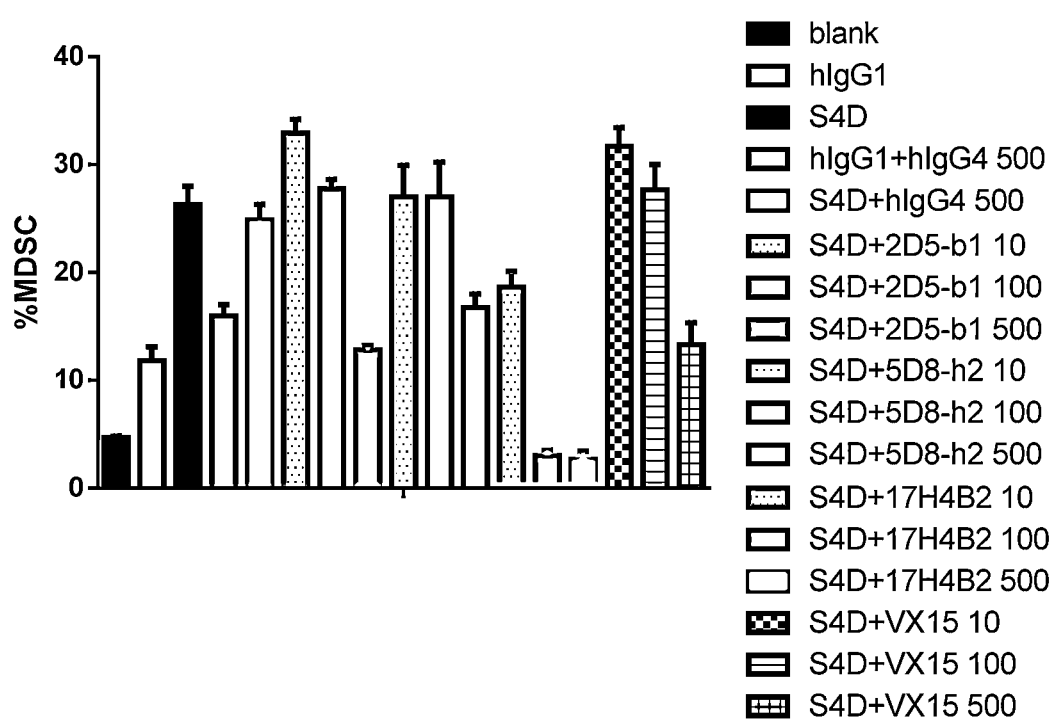
FIG. 13 shows the neutralizing effect by SEMA4D antibodies on the induction of myeloid suppressor cells (MDSCs) by SEMA4D protein.

The cell population of $CD33^+CD11b^+HLA-DR^{-/low}$ was considered as MDSC, and the proportions of MDSC population in the control group and the experimental group were counted. The experimental results are shown in FIG. 13 and Table 30.

TABLE 30

SEMA4D antibodies inhibit MDSC activity

| Group | Proportion of MDSCs under different concentration of antibody treatment % | | |
|---|---|---|---|
| | 10 μg/mL | 100 μg/mL | 500 μg/mL |
| SEMA4D + 2D5-b1 | 32.9 | 27.8 | 12.8 |
| SEMA4D + 5D8-h2 | 27.0 | 27.0 | 16.8 |
| SEMA4D + 17H4B2 | 18.7 | 3.0 | 2.7 |
| SEMA4D + VX15 | 31.7 | 27.7 | 13.3 |

TABLE 30-continued

SEMA4D antibodies inhibit MDSC activity

| Group | Proportion of MDSCs under different concentration of antibody treatment % | | |
|---|---|---|---|
| | 10 μg/mL | 100 μg/mL | 500 μg/mL |
| SEMA4D + IgG control group | — | — | 24.9 |
| IgG control group | — | — | 16.0 |

The results show that SEMA4D antibodies 2D5-b1, 5D8-h2, 17H4B2 and reference antibody VX15 can effectively neutralize the induction effect of SEMA4D on MDSC cell population. Wherein, 100 μg/mL 17H4B2 antibody was able to completely inhibit the effect of SEMA4D, which was significantly stronger than that of reference antibody VX15. In the table, the IgG control group refers to the group that only added with human IgG, without SEMA4D treatment.

Example 10 Phage Display Technology Realizes SEMA4D Antibody Affinity Maturation Antibodies with high binding affinity to SEMA4D were obtained through four rounds of biopanning. The specific process was as follows.

After the 2D5 heavy chain variable region and light chain variable region were obtained, primers were designed and constructed on the phage vector pCAN to form a phage-scFv recombinant vector. The TG1 bacteria containing the scFv recombinant vector was induced overnight to express by IPTG, and then the bacterial periplasmic protein (PPE) was extracted. The binding ability of biotinylated hSEMA4D ECD-His antigen and scFv was detected by Octet Red, and the off-rate determined was 3.94E-03.

The constructed scFv fragment was used as a template, and random mutations were made to each site in the CDR region, and the wild-type codons maintained a ratio of 50%. After the scFv fragments amplified by PCR were connected to the pCAN phage vector, they were transferred into the host bacteria TG1 (purchased from LUCIGEN) by electrotransformation. Fifty clones were randomly selected for sequencing, and the successfully constructed random mutation library was inoculated into fresh medium and cultivated to logarithmic phase at 37° C. Helper phage M13KO7 (purchased from NEB, catalog number N0315S) was added, wherein the ratio of helper phage to E. coli TG1 was 1:1000, mixed well, and let stand at 37° C. for 30 minutes. Then, the cells were cultured with shaking at 37° C. for 30 minutes, and the cells were collected after centrifugation for 10 minutes. Fresh 2YT medium was added, for culture with shaking at 30° C. for 4 hours. The supernatant was collected, added with NaCl solution containing 20% PEG as ¼ of the supernatant volume, and placed on ice overnight. Centrifugation was performed and the phage pellet was collected and dissolved in PBS buffer. Centrifugation at 10,000 rpm was performed for 10 minutes to remove residual cell debris, and the supernatant was collected for the biopanning.

In the first round of biopanning, three tubes A, B, and C were prepared. Tube A was firstly added with 100 μL of streptavidin-conjugated Dynabeads (purchased from Invitrogen) and the ScFv antibody library, and tube B was firstly added with 100 μL of streptavidin-conjugated Dynabeads. Then they were blocked at room temperature for 2 hours. The liquid in tube C was poured out, and tube C was added with the supernatant collected from tube A after centrifugation, and then added with 30 nM of biotinylated hSEMA4D ECD-His, and incubated with shaking at room temperature for 2 hours. And a control tube was set up, just without biotinylated hSEMA4D ECD-His addition, and incubated with shaking at room temperature for 2 hours. Tube B was centrifuged to obtain blocked magnetic beads, added with the mixed solution after incubation, and incubated with shaking at room temperature for 15 minutes. Tube B was placed in a magnetic stand for 30 seconds, washed 5 times with a blocking solution containing 0.05% (v/v) Tween-20, and then washed 5 times with blocking solution and PBS buffer. After washing, 1 mL of 10 μg/mL pancreatin was added to each tube and tubes were incubated at 37° C. for 30 minutes to elute the phage bound to the biotinylated hSEMA4D ECD-His. 1 mL of pancreatin solution was added to 4 mL of E. coli TG1 in the logarithmic growth phase, and the solution was incubated at 37° C. for 30 minutes to obtain a TG1 culture solution. The TG1 culture solution was gradiently diluted, spreaded on a plate, and incubated overnight at 37° C. The number of clones that bind to biotinylated hSEMA4D ECD-His and the control tube were calculated, and 20-40 clones were selected for sequencing. Meanwhile, the clones on the plate were washed with 2YT medium and collected, and inoculated in fresh medium, cultivated to logarithmic phase at 37° C. The helper phage M13KO7 was added and packaged according to the method described above, for the next round of panning.

The steps of the second to fourth rounds of biopanning were basically the same as those of the first round. The panning method adopted an affinity-driven panning scheme. That is, from the second round of panning, the concentration of the biotinylated hSEMA4D ECD-His antigen added was gradiently decreased. After four rounds of panning, ScFv antibody sequences that specifically bind to biotinylated hSEMA4D ECD-His were effectively enriched.

Single clones were selected from the plates in the third and fourth rounds and cultured in 96-well plates. Each well contained 200 μL of 2YT medium with antibiotics and the cells were cultured overnight at 37° C. with shaking. 10 μL of the overnight cultured supernatant was taken and added to 400 μL of antibiotic-containing medium, and cultured for 1.5-2.5 hours with shaking. IPTG was added to a final concentration of 1 mM, and the cells were cultured with shaking at 30° C. for 16 hours, and centrifuged, thus obtaining the single-chain antibodies.

The ELISA method was used to detect the binding activity of the scFv antibody, obtained by screening, to SEMA4D. The clones with OD450 nm>1.0 were selected for sequencing, and clones with different scFv sequences were obtained.

Candidate clones were put into freshly prepared culture medium and cultured overnight at 37° C. with shaking. 40 μL of overnight culture was added to 4 mL of culture solution and cultured with shaking at 37° C. for 2 hours. IPTG was added to a final concentration of 1 mM and the culture was incubated with shaking at 30° C. for 16 hours, and then centrifuged at 4000 rpm for 10 minutes, and the supernatant was discarded. The bacterial pellet was resuspended in 500 μL ice-cold 1×TES solution, and then added with 750 μL ice-cold ⅕×TES solution, and the pellet was resuspended by vortex. After incubated on ice for 30 min, the solution was transferred to a 1.5 mL centrifuge tube and centrifuged at 12,000 r/min for 10 min. The supernatant (i.e., soluble antibodies in the cytoplasm) was carefully transfered to a clean tube. The supernatant contained the scFv antibodies in the bacteria, and then these scFv antibodies were further detected off-rate with Octet-Red. According to the Off-rate ranking, the off-rate of clone 2D5-b1-3D9 was reduced by 45 times compared with the wild type, and the light chain variable region sequence was No. 446.

According to the results of off-rate detection, primers were designed to amplify the variable regions of the light chain and heavy chain respectively by PCR. A 50 μL reaction system was configured, including 0.5 μL of plasmids extracted from the transfected positive clone E. coli TG1, 10 pmol of each primer, 25 μL of Q5 high-fidelity DNA polymerase, and water to make up to 50 μL. PCR program was set, comprising pre-denaturation 95° C. for 5 min, denaturation 95° C. for 30 s, annealing 55° C. for 30 s, extension 68° C. for 30 s. And the PCR product was obtained. The DNA polymerase used in PCR was purchased from NEB, catalog number E0555L. 5 μl of PCR product was taken for agarose gel electrophoresis detection, and the recovery kit was used to purify the positive samples. Wherein, the recovery kit was QIAquick Gel extraction kit, purchased from Qiagen, catalog number 28706. Ligation reaction was carried out: the reaction system was with a volume of 20 μL, containing 3 μL of fragments to be inserted, 2 μL of digested expression vector, 2 μL of recombinase Exnase, and 4 μL of buffer, and reacted at 37° C. for half an hour to obtain the ligation product, which was the constructed recombinant vector. Wherein, the recombinase was purchased from Vazyme, catalog number C112-01/02; and the buffer was the buffer used in the purchase of the recombinase. The heavy chain variable region was directionally cloned into the expression vector containing sequences encoding a signal peptide and human antibody heavy chain IgG4 (S228P) constant region (wherein, the expression vector was purchased from Invitrogen, and the recombination step was completed by Shanghai Ruizhi Chemical Research Co., Ltd.). The light chain variable region was directionally cloned into the expression vector containing a signal peptide and the human antibody light chain lambda constant region (wherein, the expression vector was purchased from Invitrogen, and the recombination step was completed by Shanghai Ruizhi Chemical Research Co., Ltd.). 10 μL of the ligation product was added to 100 μL of competent cells (Ecos 101 competent cells, purchased from Yeastern, catalog number FYE607), and ice bathed for 30 minutes. Then heat shock in a 42° C. water bath was performed for 90 seconds, and cells were put back on ice for 2 minutes, added with 800 μL of antibiotic-free 2YT medium, and incubated on a 37° C. shaker at 200 rpm for 45 minutes. Then 200 μL of the culture was taken and coated onto LB solid medium containing 100 μg/mL ampicillin, and cultured overnight in a 37° C. incubator. The next day, the primers pTT-EF1a-F and pSV40 for the expression vector (the nucleotide sequences of which were shown in SEQ ID No: 430 and SEQ ID No: 431 in the sequence listing, respectively) were used for configuration of a 30 μL PCR system, to perform colony PCR. The colony PCR system was: 1 μL of either primer, 10 μL of PCR pre-mixture (purchased from Novoprotein), maked up to 20 μL. A pipette tip was used to dip the colony into the PCR reaction system and pipette, and 0.5 μl was aspirated onto another piece of 100 μg/mL ampicillin LB solid petri dish to store the strain. After the PCR reaction, 5 μL of the reaction solution was taken out for agarose gel electrophoresis detection, and the positive samples were sequenced and analyzed [see Kabat, "Sequences of Proteins of Immunological Interest," National Institutes of Health, Bethesda, Md. (1991)].

After colony PCR verification, expression vectors with the correct sequences of the recombinant antibody heavy and light chain were transiently transfected into FreeStyle™ 293-F cells (purchased from Invitrogen) to produce antibodies. A 1 mL protein A column (purchased from GE Healthcare) was used to purify the monoclonal antibody from 200 mL of clear supernatant. The dialyzed monoclonal antibody was collected, aseptically filtered with a 0.22 μm filter, and stored aseptically, thus obtaining purified SEMA4D antibody.

The purified antibody was tested and analyzed for protein concentration (A280/1.4), purity, and endotoxicity (Lonza kit). The antibody endotoxin concentration was within 1.0 EU/mg.

The anti-human Fc IgG (purchased from Geneway) was coupled and immobilized on the surface of the CM5 chip (purchased from GE) by the amino coupling method, and FC1 was used as the reference channel. The coupling and immobilization process was as follows: the freshly prepared mixture of 50 mM N-hydroxysuccinimide (NHS) and 200 mM 1-(3-dimethylaminopropyl)-3-ethylcarbodiimide hydrochloride (EDC) with a molar ratio of 1:1 was used to activate the chip. Then 10-50 μg/mL anti-human Fc IgG diluted in 10 mM sodium acetate buffer (pH 5.0) was injected. The remaining activated sites were blocked with 1M ethanolamine. Then, buffer containing HBS-EP was used to dilute the 2D5-b1-3D9 antibody prepared to 5 ug/ml and the antibodies were captured on the chip at a flow rate of 10 ul/min to obtain a response value of about 100-300RU. Then, the purified hSEMA4D ECD-His was diluted to 100 nM and let flow across the chip surface at a flow rate of 30 L/min. At the end of each cycle, the chip surface was regenerated with 10 mM Glycine at pH 1.5. The kinetic rate constant needed to be subtracted from the blank control, and the data was fitted with the global fit analysis method 1:1 combined with the model (see the Biacore operation manual for operation). The dissociation equilibrium rate constant (KD) was calculated according to the following formula: KD=kd/ka, wherein Kd is the dissociation constant and Ka is the binding constant. Part of the experimental results are shown in Table 31. Table 31 shows that the affinity KD of the 2D5-b1-3D9 antibody is $1.84 \times 10^{-10}$ M.

TABLE 31

Detection results of affinity between antibodies and human hSEMA4D

| Clone number | ka (1/Ms) | kd (1/s) | KD (M) |
|---|---|---|---|
| 2D5-b1 | $5.11 \times 10^5$ | $1.03 \times 10^{-3}$ | $2.01 \times 10^{-9}$ |
| 2D5-b1-3D9 | $5.83 \times 10^5$ | $1.07 \times 10^{-4}$ | $1.84 \times 10^{-10}$ |

Example 111 In Vivo Experiments in Mice to Detect the Tumor Growth Inhibitory Activity of SEMA4D Antibodies A. Detection of the Tumor Growth Inhibitory Activity of SEMA4D Antibodies Combined with CTLA4 Antibody in Mice Female BALB/c mice (16-19 g, approximately 6-8 weeks old, purchased from Shanghai Lingchang Biological Technology Co., Ltd.) were received and raised at SPF level. After being adapted for at least one week, the experiment was started. CT26 cells were diluted with phosphate buffer PBS to $1 \times 10^7$ cells per milliliter, and it was ensured that the viability of CT26 cells was greater than 90%. CT26 cells were inoculated subcutaneously on the right side of the trunk of 50 BALB/c mice in a volume of 0.05 ml per mouse. After inoculation, the mice were randomly divided into 5 groups according to their body weight and the order of inoculation, with 10 mice in each group. SEMA4D antibody single-administration group: mice were intraperitoneally injected with 60 mg/kg SEMA4D antibody on the 2nd, 5th, 8th, 11th, 14th, 17th, 21st, 24th and 28th day after vaccination. CTLA4 antibody single-administration group: mice were intraperitoneally injected with 100 µg of CTLA4 antibody on the 8th day after vaccination, and intraperitoneally injected with 50 µg of CTLA4 antibody on the 11th and 14th day after vaccination. SEMA4D antibody and CTLA4 antibody combination group: mice were intraperitoneally injected with 60 mg/kg of SEMA4D antibody on the 2nd, 5th, 8th, 11th, 14th, 17th, 21st, 24th and 28th day after vaccination, meanwhile intraperitoneally injected with 100 µg of CTLA4 antibody on the 8th day after vaccination, and intraperitoneally injected with 50 µg of CTLA4 antibody on the 11th and 14th day after vaccination. Control group: mice were intraperitoneally injected with 60 mg/kg of human IgG4 on the 2nd, 5th, 8th, 11th, 14th, 17th, 21st, 24th and 28th day after vaccination, meanwhile intraperitoneally injected with 100 µg of mouse IgG2b on the 8th day after vaccination, and intraperitoneally injected with 50 µg of mouse IgG2b on the 11th and 14th day after vaccination. The mice were observed every day and their body weights were recorded, and the volumes of the inoculated tumor were measured 3 times a week. When the tumor volume of the mouse exceeded the end point, that is, the tumor volume>2000 mm$^3$, the mouse was anesthetized and killed. On the 20th day after vaccination, the tumor volumes of some mice had exceeded the endpoint.

The rate of body weight change (RCBW) of mice was calculated according to the following formula: RCBW (%)= $(BW_t-BW_0)/BW_0 \times 100\%$, wherein $BW_t$ is the average body weight after a specific number of days, and $BW_0$ is the average weight of the mice on the day of vaccination. The tumor volume was calculated according to the following formula: tumor volume=(length×width$^2$)/2, wherein length is the long diameter of the tumor, and width is the short diameter of the tumor. Tumor growth inhibition rate (TGI %) was calculated according to the following formula: TGI %=$(1-TV_t/TV_{vi}) \times 100\%$, wherein $TV_t$ is the average tumor volume of mice in the administration group after a specific number of days, and $TV_{vi}$ is the average tumor volume of mice in the control group after a specific number of days.

B. Detection of the Tumor Growth Inhibitory Activity of SEMA4D Antibodies Combined with PD-1 Antibody in Mice Female BALB/c mice (16-19 g, approximately 6-8 weeks old, purchased from Shanghai Lingchang Biological Technology Co., Ltd.) were received and raised at SPF level. After being adapted for at least one week, the experiment was started. CT26 cells were diluted with phosphate buffer PBS to 1×10$^7$ cells per milliliter, and it was ensured that the viability of CT26 cells was greater than 90%. CT26 cells were inoculated subcutaneously on the right side of the trunk of 60 BALB/c mice in a volume of 0.05 ml per mouse. After inoculation, the mice were randomly divided into 6 groups according to their body weight and the order of inoculation, with 10 mice in each group. SEMA4D antibody single-administration group: mice were intraperitoneally injected with 60 mg/kg SEMA4D antibody on the 2nd, 5th, 8th, 11th, 14th, 17th, 21st, 24th and 28th day after vaccination. PD-1 antibody single-administration group: mice were intraperitoneally injected with 5 mg/kg of PD-1 antibody from the 3rd day after vaccination, twice a week, for 2 weeks. SEMA4D antibody and PD-1 antibody combination group: mice were intraperitoneally injected with 60 mg/kg of SEMA4D antibody on the 2nd, 5th, 8th, 11th, 14th, 17th, 21st, 24th and 28th day after vaccination, meanwhile intraperitoneally injected with 5 mg/kg of PD-1 antibody from the 3rd day after vaccination, twice a week, for 2 weeks. Control group: mice were intraperitoneally injected with 60 mg/kg of human IgG4 on the 2nd, 5th, 8th, 11th, 14th, 17th, 21st, 24th and 28th day after vaccination, meanwhile intraperitoneally injected with 5 mg/kg of rat Ig from the 3rd day after vaccination, twice a week, for 2 weeks. The mice were observed every day and their body weights were recorded, and the volumes of the inoculated tumor were measured 3 times a week. When the tumor volume of the mouse exceeded the end point, that is, the tumor volume>2000 mm$^3$, the mouse was anesthetized and killed. On the 19th day after vaccination, the tumor volumes of some mice had exceeded the endpoint.

Figure 14A:
FIG. 14A, FIG. 14B and FIG. 14C are detection results of the activity of the combination of SEMA4D antibodies and PD-1 antibodies to inhibit tumor growth and prolong survival in mice by in vivo experiments.
Figure 14B:
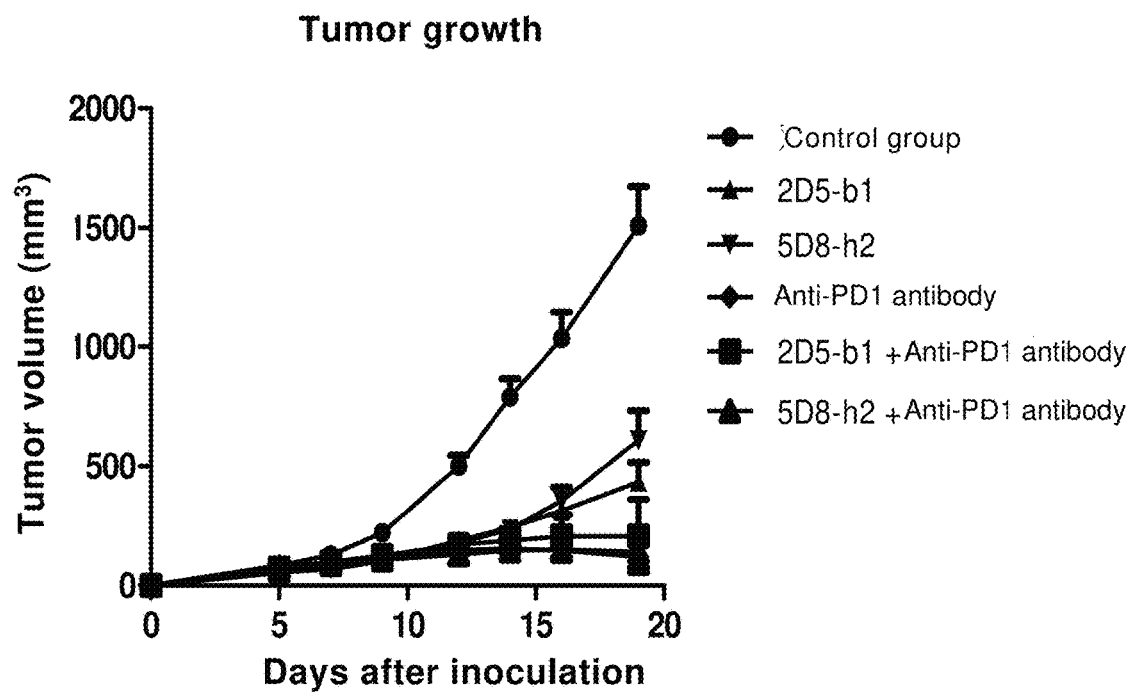
Figure 14C:
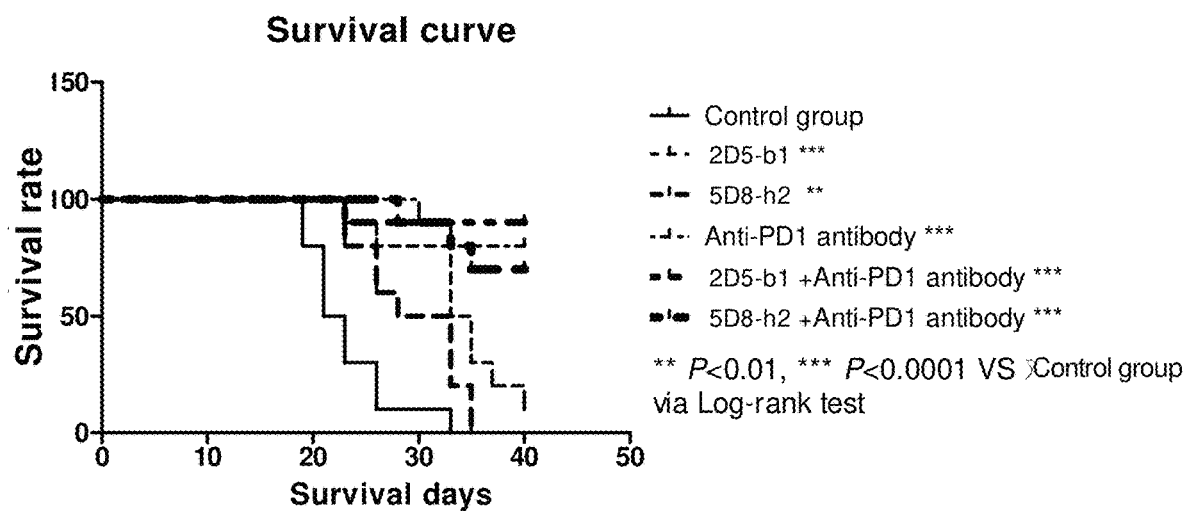

The same method was used to analyze the data before the mouse tumor volume reached the endpoint (within 19 days after inoculation), and to analyze the in tumor occurrence and changes of survival period of the mouse. The experimental results are shown in FIGS. 14A-14C and Table 31. Wherein, the tumor growth of mice in different groups was analyzed by Two-way RM ANOVA statistical method, and the P value<0.05 was considered as statistically different. The values are given in the form of mean±standard error.

TABLE 32

In vivo experiments in mice to detect the effect of combination of SEMA4D antibodies and PD-1 antibody on tumor growth and survival

| Group | Tumor volume average value | Tumor volume standard error | Number of animals without tumor | Median survival |
|---|---|---|---|---|
| 2D5-b1 antibody single-administration group | 434.23 | 82.08 | 0 | 34.0 |
| 5D8-h2 antibody single-administration group | 608.76 | 124.25 | 0 | 30.5 |
| PD-1 antibody single-administration group | 121.58 | 34.89 | 4 | 48 |
| 2D5-b1 antibody and PD-1 antibody combination group | 207.70 | 152.68 | 8 | Did not reach |
| 5D8-h2 antibody and PD-1 antibody combination group | 140.10 | 66.05 | 6 | Did not reach |
| Control group | 1509.35 | 162.89 | 0 | 22.0 |

Explanation of Results:

Compared with control group, no experimental group showed significant difference in mouse body weight.

In the SEMA4D antibody single-administration experimental group, SEMA4D antibody can significantly inhibit tumor growth.

In the of SEMA4D antibody and PD-1 antibody combination group, the combination of SEMA4D antibody and PD-1 antibody can further synergistically inhibit or delay tumor growth. This shows that the combination of SEMA4D antibody can significantly increase the response rate of mice vaccinated with CT26 to PD-1 antibody monotherapy and prolong the survival period, suggesting that SEMA4D may induce immune cell infiltration, thus enhancing the therapeutic effect of PD-1 tumor immunotherapy.

All publications mentioned herein are incorporated by reference as if each individual document was cited as a reference in the present application. It should be understood that, after reading the above teachings of the present invention, those skilled in the art can make various modifications and changes. These equivalent forms are also within the scope defined by the claims appended hereto.

Sequence information of the present invention
8G4E12 Heavy Chain Variable Region SEQ ID No. 1

EVQLVESGGGLVKPGGSLKLSCAASGFTFSDYGMYWVRQAPEKGLEGVAYISSGSS

TIYSVDKVKGRFTISRDNAKNTLFLQMTSLRSEDTAMYYCATWLPGNAMDYWGQG

TSVTVSS

8G4E12 Heavy Chain CDR1

SEQ ID No. 2

DYGMY

8G4E12 Heavy Chain CDR2

SEQ ID No. 3

YISSGSSTIYSVDKVKG

8G4E12 Heavy Chain CDR3

SEQ ID No. 4

WLPGNAMDY

8G4E12 Light Chain Variable Region

SEQ ID No. 5

DILLTQSPAILSVSPGQRVSFSCRASQSIGTSIHWYQQRTNGSPRLLIKYASESISGIPSR

FSGSGSGTDFTLSINSVESEDIADYYCQQSIRWPYTFGGGTKLEIK

8G4E12 Light Chain CDR1

SEQ ID No. 6

RASQSIGTSIH

8G4E12 Light Chain CDR2

SEQ ID No. 7

YASESIS

8G4E12 Light Chain CDR3

SEQ ID No. 8

QQSIRWPYT

10F5E11 Heavy Chain Variable Region

SEQ ID No. 9

QVQLQQSGAELVKPGASVKLSCKATGYTFTGYWIEWVKQRPGHGLEWIGEILPGSG

STKYNEKFKDRATFTEDTSSNTAYMQLSSLTTEDSAIYYCARGGLDSFFDYWGQGTT

LTVSS

10F5E11 Heavy Chain CDR1

SEQ ID No. 10

GYWIE

10F5E11 Heavy Chain CDR2

SEQ ID No. 11

EILPGSGSTKYNEKFKD

10F5E11 Heavy Chain CDR3

SEQ ID No. 12

GGLDSFFDY

10F5E11 Light Chain Variable Region

SEQ ID No. 13

DVLMTQTPLSLPVSLGDQASISCRSSQIIVHSNGNTYLEWYLQKPGQSPKLLIYKVSN

RFSGVPDRFSGSGSGTDFTLKISRVEAEDLGVYYCFQGSYVPWTFGGGTKLEIK

10F5E11 Light Chain CDR1

SEQ ID No. 14

RSSQIIVHSNGNTYLE

10F5E11 Light Chain CDR2

SEQ ID No. 15

KVSNRFS

10F5E11 Light Chain CDR3

SEQ ID No. 16

FQGSYVPWT

16C6D11 Heavy Chain Variable Region

SEQ ID No. 17

EVQLQQSVAELVRPGATVKLSCTTSGFNIQNTYMHWVKQRPEQGLEWIGRIDPASG

-continued

NTIYAPKFQGRATITADTSSNTAYLQLSSLTSEDTAIYYCARMDGYYDPYWGQGTLV

TVSA

16C6D11 Heavy Chain CDR1                                        SEQ ID No. 18

NTYMH

16C6D11 Heavy Chain CDR2                                        SEQ ID No. 19

RIDPASGNTIYAPKFQG

16C6D11 Heavy Chain CDR3                                        SEQ ID No. 20

MDGYYDPY

16C6D11 Light Chain Variable Region                             SEQ ID No. 21

DILLTQSPAILSVSPGERVSFSCRASQSTGTSIHWYQQRTNGSPRLLIKYTSESISGIPSR

FSGSGSGTDFTLTINSVESEDIGDYYCRQSISRPFTFGSGTKLEMK

16C6D11 Light Chain CDR1                                        SEQ ID No. 22

RASQSTGTSIH

16C6D11 Light Chain CDR2                                        SEQ ID No. 23

YTSESIS

16C6D11 Light Chain CDR3                                        SEQ ID No. 24

RQSISRPFT

17D4A3 Heavy Chain Variable Region                              SEQ ID No. 25

EVKLVESGGGLVQPGGSLSLSCAASGFTFTDYYMSWVRQPPGKALEWLGFIRNKAN

GYTTECSASVKGRFTISRDNSQNILYLQMNALRAEDSATYYCATYGRLGYTMDYWG

QGTSVTVSS

17D4A3 Heavy Chain CDR1                                         SEQ ID No. 26

DYYMS

17D4A3 Heavy Chain CDR2                                         SEQ ID No. 27

FIRNKANGYTTECSASVKG

17D4A3 Heavy Chain CDR3                                         SEQ ID No. 28

YGRLGYTMDY

17D4A3 Light Chain Variable Region                              SEQ ID No. 29

DVLMTQTPLSLPVSLGDQASISCRSSQSIVHSNGNTYLEWYLQKPGQSPKLLIYKVSN

RFSGVPDRFSGSGSGTDFTLKINRVEAEDLGVYYCFQGSHVPWTFGGGTKLEIK

17D4A3 Light Chain CDR1                                         SEQ ID No. 30

RSSQSIVHSNGNTYLE

17D4A3 Light Chain CDR2                                         SEQ ID No. 31

KVSNRFS

17D4A3 Light Chain CDR3                                         SEQ ID No. 32

FQGSHVPWT

17H4B2 Heavy Chain Variable Region                              SEQ ID No. 33

QVQLQQPGAELVRPGSSVKLSCKASGHTLTGFWMHWVRQRPIPGLEWIGNIDPSDSE

THYNQKFEDKATLTVDKSSNTAYMLLSSLTSEDSAVYYCAREGGTGYFDVWGTGT

TVTVSS

17H4B2 Heavy Chain CDR1

-continued

GFWMH

17H4B2 Heavy Chain CDR2　　　　　　　　　　　　　　　　SEQ ID No. 34

NIDPSDSETHYNQKFED　　　　　　　　　　　　　　　　　　SEQ ID No. 35

17H4B2 Heavy Chain CDR3

EGGTGYFDV　　　　　　　　　　　　　　　　　　　　　　SEQ ID No. 36

17H4B2 Light Chain Variable Region

EFVLTQSPTTLAASPGEKITITCSASSSISSNYLHWYQQKPGFSPKLLIYRTSNLASGVP　　SEQ ID No. 37

ARFSGSGSGTSYSLTIGTMEAEDVATYYCQKGSSIPRMYTFGGGTKLEIK

17H4B2 Light Chain CDR1

SASSSISSNYLH　　　　　　　　　　　　　　　　　　　　　SEQ ID No. 38

17H4B2 Light Chain CDR2

RTSNLAS　　　　　　　　　　　　　　　　　　　　　　　SEQ ID No. 39

17H4B2 Light Chain CDR3

QKGSSIPRMYT　　　　　　　　　　　　　　　　　　　　　SEQ ID No. 40

24D4E5 Heavy Chain Variable Region

DVQLQESGPGLVKPSQSLSLTCSVTGYSITSNYYWNWIRQFPGNKLEWMGYISYDGS　　　SEQ ID No. 41

NDYNPSLKNRISITRDTSKNQFFLRLNSVTTEDTATYFCARVTSGYLYYFDNWGQGT

TLTVSS

24D4E5 Heavy Chain CDR1

SNYYWN　　　　　　　　　　　　　　　　　　　　　　　SEQ ID No. 42

24D4E5 Heavy Chain CDR2

YISYDGSNDYNPSLKN　　　　　　　　　　　　　　　　　　SEQ ID No. 43

24D4E5 Heavy Chain CDR3

VTSGYLYYFDN　　　　　　　　　　　　　　　　　　　　　SEQ ID No. 44

24D4E5 Light chain variable region

EIVLTQSPAITAASLGQKVTITCSASSSVSYMHWYQQRSGTSPKPWIYEISKLASGVP　　SEQ ID No. 45

ARFSGSGSGTSYSLTISSMEAEDAAIYYCQQWNFPLTFGAGTKLELK

24D4E5 Light Chain CDR1

SASSSVSYMH　　　　　　　　　　　　　　　　　　　　　SEQ ID No. 46

24D4E5 Light Chain CDR2

EISKLAS　　　　　　　　　　　　　　　　　　　　　　　SEQ ID No. 47

24D4E5 Light Chain CDR3

QQWNFPLT　　　　　　　　　　　　　　　　　　　　　　SEQ ID No. 48

28G7B10 Heavy Chain Variable Region

DVKLVESGEDLVKPGGSLKVSCAASGFTFRDYAMSWVRQTPEKRLEWVAYISSGGD　　　SEQ ID No. 49

YIYYADSVKGRFTISRDNARNTLYLQMTSLRSEDTAMYFCTRDPSFYGRGYYFDYW

GQGTSLTVSS

28G7B 10 Heavy Chain CDR1

DYAMS　　　　　　　　　　　　　　　　　　　　　　　SEQ ID No. 50

28G7B10 Heavy Chain CDR2　　　　　　　　　　　　　　　SEQ ID No. 51

-continued

YISSGGDYIYYADSVKG

28G7B 10 Heavy Chain CDR3 — SEQ ID No. 52

DPSFYGRGYYFDY

28G7B 10 Light Chain Variable Region — SEQ ID No. 53

DIVMTQSHKFMSASVGDRVSITCKASQDVGATVAWYQQKPGQSPKLLIYWASTRHT
GVPDRFTGSGSGTDFTLTINNVQSEDLADYFCQQYSNYPTFGGGTKLEIK

28G7B 10 Light Chain CDR1 — SEQ ID No. 54

KASQDVGATVA

28G7B10 Light Chain CDR2 — SEQ ID No. 55

WASTRHT

28G7B 10 Light Chain CDR3 — SEQ ID No. 56

QQYSNYPT

30B1C7 Heavy Chain Variable Region — SEQ ID No. 57

EVQLQQSVAELVRPGASVKLSCTVSGFNIKNTYMHWVKQRPEQGLEWIGRIDPANG
DTKYDPKFQAKATVTADTSSNTAYLHLSSLTSEDTAIYYCVEDDYGLGSWGQGTTL
TVSS

30B1C7 Heavy Chain CDR1 — SEQ ID No. 58

NTYMH

30B1C7 Heavy Chain CDR2 — SEQ ID No. 59

RIDPANGDTKYDPKFQA

30B1C7 Heavy Chain CDR3 — SEQ ID No. 60

DDYGLGS

30B1C7 Light Chain Variable Region — SEQ ID No. 61

DIVMTQSQKFMSTSVGDRVSVTCKASQNVGSNVAWYQQKPGQSPKSLIYATSHRYS
GVPDRFTGSGSGTDFTLTISNVQSEDLAEYFCQHYNNYPYTFGGGTKLEIK

30B1C7 Light Chain CDR1 — SEQ ID No. 62

KASQNVGSNVA

30B1C7 Light Chain CDR2 — SEQ ID No. 63

ATSHRYS

30B1C7 Light Chain CDR3 — SEQ ID No. 64

QHYNNYPYT

12G10H1 Heavy Chain Variable Region — SEQ ID No. 65

EVQLQQSGPVLVKPGASVKISCKASGYTFTDYYMNWVKQSHGKSLEWIGDINPDNG
FTSYNQKFKGKATLTVDRSSSTAYMEFRSLTSEDSAVYYCARDGSSAYGMDYWGQ
GTSVTVSS

12G10H1 Heavy Chain CDR1 — SEQ ID No. 66

DYYMN

12G10H1 Heavy Chain CDR2 — SEQ ID No. 67

DINPDNGFTSYNQKFKG

12G10H1 Heavy Chain CDR3 — SEQ ID No. 68

DGSSAYGMDY

-continued

12G10H1 Light chain variable region
SEQ ID No. 69
DIVLTQSPASLAVSLGQRATISCRASESVSIHGTHLMHWYQQKPGQPPKLLIYAASNL
ESGVPARFSGSGSETDFTLNIHTVEEEDAATYFCQQSIEEPRTFGGGTKVEIK 12G10H1 Light Chain CDR1
SEQ ID No. 70
RASESVSIHGTHLMH 12G10H1 Light Chain CDR2
SEQ ID No. 71
AASNLES 12G10H1 Light Chain CDR3
SEQ ID No. 72
QQSIEEPRT 17A10A2 Heavy Chain Variable Region
SEQ ID No. 73
EVQLQQSGPELVKPGASVKISCKASGYSFTGYYMHWVKQSHGNILDWIGYIYPYNG
VSTYNQRFKGKATLTVDKSSSTAYMELRSLTSEDSAVYYCAKGASGYDGDYWGQG
TTLTVSS 17A10A2 Heavy Chain CDR1
SEQ ID No. 74
GYYMH 17A10A2 Heavy Chain CDR2
SEQ ID No. 75
YIYPYNGVSTYNQRFKG 17A10A2 Heavy Chain CDR3
SEQ ID No. 76
GASGYDGDY 17A10A2 Light Chain Variable Region
SEQ ID No. 77
QIVLTQSPAIMSASPGEKVTITCSATSVVSYMHWFQQKPGTSPKLWIYLTSNLASGVP
ARFSGSGSGTSYSLTISRMEAEDAATYYCQQRSSYPPTFGGGTKLEIK 17A10A2 Light Chain CDR1
SEQ ID No. 78
SATSVVSYMH 17A10A2 Light Chain CDR2
SEQ ID No. 79
LTSNLAS 17A10A2 Light Chain CDR3
SEQ ID No. 80
QQRSSYPPT 25C1B3 Heavy Chain Variable Region
SEQ ID No. 81
QVQLQQSGAELMKPGASVKLSCKATGYTFTGYWIEWVKQRPGHGFEWIGEILPGSG
TTKYNKKFQGKATITADTSSNTAYIQLSSLTTEDSAMYYCARGGQDHFFADWGQGT
TLTVSS 25C1B3 Heavy Chain CDR1
SEQ ID No. 82
GYWIE 25C1B3 Heavy Chain CDR2
SEQ ID No. 83
EILPGSGTTKYNKKFQG 25C1B3 Heavy Chain CDR3
SEQ ID No. 84
GGQDHFFAD 25C1B3 Light Chain Variable Region
SEQ ID No. 85
DILMTQSPLSLPVSLGDQASISCRSSQTIVHSNGDTYLEWYLQKPGQSPKLLIYKVSN

RFSGVPDRFSGSGSGTDFTLKISRVEAEDLGIYYCFQGSYVPWTFGGGTRLEIK

25C1B3 Light Chain CDR1

RSSQTIVHSNGDTYLE

SEQ ID No. 86

25C1B3 Light Chain CDR2

KVSNRFS

SEQ ID No. 87

25C1B3 Light Chain CDR3

FQGSYVPWT

SEQ ID No. 88

28D2E1 Heavy Chain Variable Region

EVKLEESGGGLVQPGGSLSLSCAASGFTFTDYYMSWVRQPPGKAPEWLGFIRNRAY

GYTTEYSASVKGRFTFSRDNSQSILFLHMNALRPEDSATYYCARYPLLGYALDYWG

QGTSVTVSS

SEQ ID No. 89

28D2E1 Heavy Chain CDR1

DYYMS

SEQ ID No. 90

28D2E1 Heavy Chain CDR2

FIRNRAYGYTTEYSASVKG

SEQ ID No. 91

28D2E1 Heavy Chain CDR3

YPLLGYALDY

SEQ ID No. 92

28D2E1 Light Chain Variable Region

DVLMTQTPLSLPVSLGDQASISCRSSQSIVHSNGNTYLEWYLQKPGQSPKLLIYKVSN

RFSGVPDRFSGSGSGTDFTLKISRVEAEDLGIYYCFQVSHVPWTFGGGTKLEIK

SEQ ID No. 93

28D2E1 Light Chain CDR1

RSSQSIVHSNGNTYLE

SEQ ID No. 94

28D2E1 Light Chain CDR2

KVSNRFS

SEQ ID No. 95

28D2E1 Light Chain CDR3

FQVSHVPWT

SEQ ID No. 96

31G10C5 Heavy Chain Variable Region

EVQLQQSGAELVRPGASVKLSCTASGFNIKDDYIHWVKQRPEQGLEWIGWIDPANG

HIEYASNFQAKATITADTSSNTAYLQLSSLTSEDTAVYYCTTGDYDGFTYWGQGTLV

TVST

SEQ ID No. 97

31G10C5 Heavy Chain CDR1

DDYIH

SEQ ID No. 98

31G10C5 Heavy Chain CDR2

WIDPANGHIEYASNFQA

SEQ ID No. 99

31G10C5 Heavy Chain CDR3

GDYDGFTY

SEQ ID No. 100

31G10C5 Light Chain Variable Region

QIVLTQSPAIMSASPGEKVTISCSARSSVSYMYWYQQKPGSSPKPWIYRTSNLASGVP

ARFSGSGSGTSYSLTISSMEAEDAATYYCQHYHTYPYTFGGGTKLEIK

SEQ ID No. 101

31G10C5 Light Chain CDR1

SARSSVSYMY

SEQ ID No. 102

| | |
|---|---|
| 31G10C5 Light Chain CDR2<br>RTSNLAS | SEQ ID No. 103 |
| 31G10C5 Light Chain CDR3<br>QHYHTYPYT | SEQ ID No. 104 |
| 32C8F10 Heavy Chain Variable Region<br>EVQLQQSGAELVRPGASVKLSCTASGFNIKDEYIHWVKQRPEQGLEWIGWIDPANG<br>HTEYASRFQAKATITADTSSNTAYLQLSSLTSEDTAVYYCTTGDYDGFAYWGQGTL<br>VTVST | SEQ ID No. 105 |
| 32C8F10 Heavy Chain CDR1<br>DEYIH | SEQ ID No. 106 |
| 32C8F10 Heavy Chain CDR2<br>WIDPANGHTEYASRFQA | SEQ ID No. 107 |
| 32C8F10 Heavy Chain CDR3<br>GDYDGFAY | SEQ ID No. 108 |
| 32C8F10 Light Chain Variable Region<br>QIVLTQSPAIMSASPGEKVTISCSARSSVSYMYWYQQKPGSSPKPWIYRTSNLASGVP<br>ARFSGSGSGTSYSLTISSMEAEDAATYYCQHYHTYPYTFGGGTKLEIK | SEQ ID No. 109 |
| 32C8F10 Light Chain CDR1<br>SARSSVSYMY | SEQ ID No. 110 |
| 32C8F10 Light Chain CDR2<br>RTSNLAS | SEQ ID No. 111 |
| 32C8F10 Light Chain CDR3<br>QHYHTYPYT | SEQ ID No. 112 |
| 35D2B9 Heavy Chain Variable Region<br>QVQLQQPGAEVVKPGASVKLSCKASGYTVTSYWMHWVKQRPGQGLEWIGMIHPN<br>GISTNYNEKFKSKATLTGDKSSSTAYMQLSSLTSEDSAVYFCARGGDSDYYFDYWG<br>QGTTLTVSS | SEQ ID No. 113 |
| 35D2B9 Heavy Chain CDR1<br>SYWMH | SEQ ID No. 114 |
| 35D2B9 Heavy Chain CDR2<br>MIHPNGISTNYNEKFKS | SEQ ID No. 115 |
| 35D2B9 Heavy Chain CDR3<br>GGDSDYYFDY | SEQ ID No. 116 |
| 35D2B9 Light Chain Variable Region<br>QIVLTQSPAIMSASPGEKVTMTCSASSSVSYMYWYQQKPGSSPRLWIYDTSNLVSGV<br>PARFSGSRSGTSYSLTLSSMEAEDAATYYCQQYSGYPYTFGGGTKLEIK | SEQ ID No. 117 |
| 35D2B9 Light Chain CDR1<br>SASSSVSYMY | SEQ ID No. 118 |
| 35D2B9 Light Chain CDR2<br>DTSNLVS | SEQ ID No. 119 |

| | |
|---|---|
| 35D2B9 Light Chain CDR3<br><br>QQYSGYPYT | SEQ ID No. 120 |
| 37C4F7 Heavy Chain Variable Region<br><br>EFQLQQSGPEVVKPGASVKISCKASGYSFTDYNMNWMKQSKGKSLEWIGVINPNYG<br><br>TTTYNQNFKGKATLTVDQSSSTAYMQLNSLTSEDSAVYYCARDMYYVYAYYTMDY<br><br>WGQGTSVTVSS | SEQ ID No. 121 |
| 37C4F7 Heavy Chain CDR1<br><br>DYNMN | SEQ ID No. 122 |
| 37C4F7 Heavy Chain CDR2<br><br>VINPNYGTTTYNQNFKG | SEQ ID No. 123 |
| 37C4F7 Heavy Chain CDR3<br><br>DMYYVYAYYTMDY | SEQ ID No. 124 |
| 37C4F7 Light Chain Variable Region<br><br>DVVMTQTPLSLPVSLGDQASISCRSSQSLVHSNGHTYLHWYLQRPGQSPTLLIYKVS<br><br>NRFSGVPDRFSGSGSGTDFTLKISRVEAEDLGVYFCSQGTHVPWTFGGGTKLEIK | SEQ ID No. 125 |
| 37C4F7 Light Chain CDR1<br><br>RSSQSLVHSNGHTYLH | SEQ ID No. 126 |
| 37C4F7 Light Chain CDR2<br><br>KVSNRFS | SEQ ID No. 127 |
| 37C4F7 Light Chain CDR3<br><br>SQGTHVPWT | SEQ ID No. 128 |
| 37F11F9 Heavy Chain Variable Region<br><br>EVQLQQSGPVLVKPGASVKMSCKASGYTFTDYYMNWVKQSHGKSLEWIGLINPYS<br><br>GGSTFNQKFKAKATLTVDKSSSSAYMDLNSLTSEDSAVYYCARVGDYYGVTHGM<br><br>DYWGQGTSVTVSS | SEQ ID No. 129 |
| 37F11F9 Heavy Chain CDR1<br><br>DYYMN | SEQ ID No. 130 |
| 37F11F9 Heavy Chain CDR2<br><br>LINPYSGGSTFNQKFKA | SEQ ID No. 131 |
| 37F11F9 Heavy Chain CDR3<br><br>VGDYYGVTHGMDY | SEQ ID No. 132 |
| 37F11F9 Light Chain Variable Region<br><br>DIVMTPSQKFMSTTVGDRVSITCKASQNVGTAVAWYQQKPGQSPTILIYSASNRYTG<br><br>VPDRFTGSGSGTDFTLTISNMKSEDLADYFCQQYYIYPFTFAAGTKLELK | SEQ ID No. 133 |
| 37F11F9 Light Chain CDR1<br><br>KASQNVGTAVA | SEQ ID No. 134 |
| 37F11F9 Light Chain CDR2<br><br>SASNRYT | SEQ ID No. 135 |
| 37F11F9 Light Chain CDR3<br><br>QQYYIYPFT | SEQ ID No. 136 |
| 38H2E3 Heavy Chain Variable Region | |

-continued

```
EFQLQQSGPEVVKPGASVKISCKASGYSFTDYNMNWMKQSKGKSLEWIGVISPDYG
```
SEQ ID No. 137
```
TTTYNQNFKDKATLTVDQSSSTAYMQLNSLTSEDSAVYYCAKDMYVVYAYYTMD

YWGHGTSVTVSS
```

38H2E3 Heavy Chain CDR1

SEQ ID No. 138
```
DYNMN
```

38H2E3 Heavy Chain CDR2

SEQ ID No. 139
```
VISPDYGTTTYNQNFKD
```

38H2E3 Heavy Chain CDR3

SEQ ID No. 140
```
DMYVVYAYYTMDY
```

38H2E3 Light Chain Variable Region

SEQ ID No. 141
```
DVVMTQTPLSLPVSLGDQASISCRSSQSLVHSNGHTYLHWYLQRPGQSPTLLIYKVS

NRFSGVPDRVSGSGSGTDFTLKISRVEAEDLGVYFCSQGTHVPRTFGGGTKLEIK
```

38H2E3 Light Chain CDR1

SEQ ID No. 142
```
RSSQSLVHSNGHTYLH
```

38H2E3 Light Chain CDR2

SEQ ID No. 143
```
KVSNRFS
```

38H2E3 Light Chain CDR3

SEQ ID No. 144
```
SQGTHVPRT
```

42B7G2 Heavy Chain Variable Region

SEQ ID No. 145
```
QVQLQQSGAELARPGASVKLSCKASGYTFTDYGISWVKQRTGQGLEWIGEIYLRND

NSYYNEKFKGKATLTADKSSNTAYMELRSLTSEDSAVYFCARWGDHGNNYEDAMD

YWGQGTSVTVSS
```

42B7G2 Heavy Chain CDR1

SEQ ID No. 146
```
DYGIS
```

42B7G2 Heavy Chain CDR2

SEQ ID No. 147
```
EIYLRNDNSYYNEKFKG
```

42B7G2 Heavy Chain CDR3

SEQ ID No. 148
```
WGDHGNNYEDAMDY
```

42B7G2 Light Chain Variable Region

SEQ ID No. 149
```
DIVLTQSPASLAMSLGKRATISCRASESVSIIGSNLIHWYQQKPGQPPKLLIYHASNLE

TGVPARFSGSGSRTDFTLTIDPVEEDDVAIYYCLQSRKVPYTFGGGTKLEIK
```

42B7G2 Light Chain CDR1

SEQ ID No. 150
```
RASESVSIIGSNLIH
```

42B7G2 Light Chain CDR2

SEQ ID No. 151
```
HASNLET
```

42B7G2 Light Chain CDR3

SEQ ID No. 152
```
LQSRKVPYT
```

31C11G2 Heavy Chain Variable Region

SEQ ID No. 153
```
EVQLQQSGAELVRPGASVKLSCTASGFNIKDEYIHWVKQRPEQGLEWIGWIDPANG

HTEYASRFQAKATITADTSSNTAYLQLSSLTSEDTAVYYCTTGDYDGFVYWGQGTL
```

-continued

VTVST

31C11G2 Heavy Chain CDR1　　　　　　　　　　　　　　　　SEQ ID No. 154
DEYIH

31C11G2 Heavy Chain CDR2　　　　　　　　　　　　　　　　SEQ ID No. 155
WIDPANGHTEYASRFQA

31C11G2 Heavy Chain CDR3　　　　　　　　　　　　　　　　SEQ ID No. 156
GDYDGFVY

31C11G2 Light Chain Variable Region　　　　　　　　　　SEQ ID No. 157
QIVLTQSPAIMSASPGEKVTIFCSARSSVSYMYWYQQKPGSSPKPWIYRTSNLASGVP
ARFSGSGSGTSYSLTISSMEAEDAATYYCQHYHTYPYTFGGGTKLEIK 31C11G2 Light Chain CDR1　　　　　　　　　　　　　　　　SEQ ID No. 158
SARSSVSYMY 31C11G2 Light Chain CDR2　　　　　　　　　　　　　　　　SEQ ID No. 159
RTSNLAS 31C11G2 Light Chain CDR3　　　　　　　　　　　　　　　　SEQ ID No. 160
QHYHTYPYT 80G1G1 Heavy Chain Variable Region　　　　　　　　　　　SEQ ID No. 161
QVQLKESGPGLVAPSQSLSITCTVSGFSLSSYGVDWVRQPPGKDLEWLGVIWGGGTT
IYNSALMSRLNITKDNSKNQVFLKMNSLQSDDTAMYYCAKRGYYGYFDYWGQGTT
LTVSS 80G1G1 Heavy Chain CDR1　　　　　　　　　　　　　　　　SEQ ID No. 162
SYGVD 80G1G1 Heavy Chain CDR2　　　　　　　　　　　　　　　　SEQ ID No. 163
VIWGGGTTIYNSALMS 80G1G1 Heavy Chain CDR3　　　　　　　　　　　　　　　　SEQ ID No. 164
RGYYGYFDY 80G1G1 Light Chain Variable Region　　　　　　　　　　　SEQ ID No. 165
QIVLTQSPAIMSASPGEKVTMTCSASSSVSYMYWYHQKPGSSPRLLIYDTSNLAFGVP
VRFSGRGSGTSYSLTISRMEAEDAATYYCQQWSSYPLTFGAGTKLELK 80G1G1 Light Chain CDR1　　　　　　　　　　　　　　　　SEQ ID No. 166
SASSSVSYMY 80G1G1 Light Chain CDR2　　　　　　　　　　　　　　　　SEQ ID No. 167
DTSNLAF 80G1G1 Light Chain CDR3　　　　　　　　　　　　　　　　SEQ ID No. 168
QQWSSYPLT 80E7E2 Heavy Chain Variable Region　　　　　　　　　　　SEQ ID No. 169
EVKLVESGGGLVQPGSSMKLSCTASGFTFSDYYMAWVRQVPDKGLEWVANINYDG
NNPYYVDSLKSRFIISRDNAKNILYLQMSSLKSEDTATYYCARDISPGYFDHWGQGT
TLTVSS 80E7E2 Heavy Chain CDR1　　　　　　　　　　　　　　　　SEQ ID No. 170
DYYMA

| | |
|---|---|
| 80E7E2 Heavy Chain CDR2<br>NINYDGNNPYYVDSLKS | SEQ ID No. 171 |
| 80E7E2 Heavy Chain CDR3<br>DISPGYFDH | SEQ ID No. 172 |
| 80E7E2 Light Chain Variable Region<br>DIVLTQSPASLAVSLGQRATISCRASESVSIHGTHLMHWYQQKPGQPPKLLIYAASNLESGVPARFSGSGSETDFTLNIHPVEEEDAAIYFCQQSIEDPHTFGGGTKLEIK | SEQ ID No. 173 |
| 80E7E2 Light Chain CDR1<br>RASESVSIHGTHLMH | SEQ ID No. 174 |
| 80E7E2 Light Chain CDR2<br>AASNLES | SEQ ID No. 175 |
| 80E7E2 Light Chain CDR3<br>QQSIEDPHT | SEQ ID No. 176 |
| 84A2C4 Heavy Chain Variable Region<br>EVKLVESGGGLVQPGSSMKLSCTASGFTFSDYYMAWVRQVPDKGLEWVANINYDGNNPYYVDSLKTRFIISRDNAKNILYLQMSSLKSEDTATYYCARDISPGYFDHWGQGTTLTVSS | SEQ ID No. 177 |
| 84A2C4 Heavy Chain CDR1<br>DYYMA | SEQ ID No. 178 |
| 84A2C4 Heavy Chain CDR2<br>NINYDGNNPYYVDSLKT | SEQ ID No. 179 |
| 84A2C4 Heavy Chain CDR3<br>DISPGYFDH | SEQ ID No. 180 |
| 84A2C4 Light Chain Variable Region<br>DIVLTQSPASLAVSLGQRATISCRASESVSIHGTHLMHWYQQKPGQPPKLLIYAASNLESGVPARFSGSGSETDFTLNIHPVEEEDAAIYFCQQSIEDPHTFGGGTKLEIK | SEQ ID No. 181 |
| 84A2C4 Light Chain CDR1<br>RASESVSIHGTHLMH | SEQ ID No. 182 |
| 84A2C4 Light Chain CDR2<br>AASNLES | SEQ ID No. 183 |
| 84A2C4 Light Chain CDR3<br>QQSIEDPHT | SEQ ID No. 184 |
| 88B4D4 Heavy Chain Variable Region<br>QVQLKESGPGLVAPSQSLSITCTVSGFSLISYGVDWVRQPPGKGLEWLGVIWGVGITKYNSALMSRLSISKDNSKSQVFLKMNSLQTDDTAMYYCAKRGYYGYFDYWGQGTTLTVSS | SEQ ID No. 185 |
| 88B4D4 Heavy Chain CDR1<br>SYGVD | SEQ ID No. 186 |
| 88B4D4 Heavy Chain CDR2<br>VIWGVGITKYNSALMS | SEQ ID No. 187 |

88B4D4 Heavy Chain CDR3

RGYYGYFDY

SEQ ID No. 188

88B4D4 Light Chain Variable Region

QIVLTQSPAIMSASPGEKVTMTCSASSSVSYMYWYQQKPGASPRLLIYDTSNLASGVPVRFSGSGSGTSYSLTISQMETEDAATYYCQQWSSYPLTFGAGTKLELK

SEQ ID No. 189

88B4D4 Light Chain CDR1

SASSSVSYMY

SEQ ID No. 190

88B4D4 Light Chain CDR2

DTSNLAS

SEQ ID No. 191

88B4D4 Light Chain CDR3

QQWSSYPLT

SEQ ID No. 192

89G3E8 Heavy Chain Variable Region

QVQLKESGPGLVAPSQSLSITCTVSGFSLTSYGVDWVRQPPGKGLEWLGVIWGGGNTNYNSALMSRLSISKDNSKSQVFLKMNSLQTDDTAMYYCAKSPDFVSSYSYAMDYWGQGTSVTVSS

SEQ ID No. 193

89G3E8 Heavy Chain CDR1

SYGVD

SEQ ID No. 194

89G3E8 Heavy Chain CDR2

VIWGGGNTNYNSALMS

SEQ ID No. 195

89G3E8 Heavy Chain CDR3

SPDFVSSYSYAMDY

SEQ ID No. 196

89G3E8 Light Chain Variable Region

DVLMTQTPLSLPVSLGDQASISCRSSQRIVHSNGNTYLQWYLQKPGQSPKLLIYKVSNRFSGVPDRFSGSGSGTDFTLKISRVEAEDLGVYYCFQSSYVPPTFGGGTKLEIK

SEQ ID No. 197

89G3E8 Light Chain CDR1

RSSQRIVHSNGNTYLQ

SEQ ID No. 198

89G3E8 Light Chain CDR2

KVSNRFS

SEQ ID No. 199

89G3E8 Light Chain CDR3

FQSSYVPPT

SEQ ID No. 200

90H5D3 Heavy Chain Variable Region

QVHLKESGPGLVAPSQNLSITCTVSGFSLTSYGVDWVRQPPGKGLEWLGVTWGGGNTKYNSALMSRLHISKDNSKSQVFLKMNSLQTDDTAVYYCAKRGYYGYFDYWGQGATLTVSS

SEQ ID No. 201

90H5D3 Heavy Chain CDR1

SYGVD

SEQ ID No. 202

90H5D3 Heavy Chain CDR2

VTWGGGNTKYNSALMS

SEQ ID No. 203

90H5D3 Heavy Chain CDR3

RGYYGYFDY

SEQ ID No. 204

90H5D3 Light Chain Variable Region

-continued

QIVLTQSPAIMSASPGEKVTMTCSASSSVSYMYWYQQKPGSSPRLLIYDTSNLASGVP
VRFGGSGSGTSYSLTIFRMEAEDAATYYCQQWSSYPLTFGAGTKLELK
   SEQ ID No. 205

90H5D3 Light Chain CDR1
SASSSVSYMY
   SEQ ID No. 206

90H5D3 Light Chain CDR2
DTSNLAS
   SEQ ID No. 207

90H5D3 Light Chain CDR3
QQWSSYPLT
   SEQ ID No. 208

90F3B2 Heavy Chain Variable Region
QVQLKESGPGLVAPSQSLSITCTVSGFSLTSYGVDWVRQPPGKGLEWLGVIWGGGST
NYNSALMSRLSISKDNSKSQIFLKMNSLQTDDTAMYYCAKSPDFVSSYSYAMDYWG
QGTSVTVSS
   SEQ ID No. 209

90F3B2 Heavy Chain CDR1
SYGVD
   SEQ ID No. 210

90F3B2 Heavy Chain CDR2
VIWGGGSTNYNSALMS
   SEQ ID No. 211

90F3B2 Heavy Chain CDR3
SPDFVSSYSYAMDY
   SEQ ID No. 212

90F3B2 Light Chain Variable Region
DVLMTQTPLSLPVSLGDQASISCRSSQRIVHSNGNTYLQWYLQKPGQSPKLLIYKVS
NRFSGVPDRFSGSGSGTDFTLKISRVEAEDLGVYYCFQSSYVPPTFGGGTKLEIK
   SEQ ID No. 213

90F3B2 Light Chain CDR1
RSSQRIVHSNGNTYLQ
   SEQ ID No. 214

90F3B2 Light Chain CDR2
KVSNRFS
   SEQ ID No. 215

90F3B2 Light Chain CDR3
FQSSYVPPT
   SEQ ID No. 216

118C7E6 Heavy Chain Variable Region
EVQLQQSGPELVKPGASVKIPCKASGYTFTDYNMDWVKQSHGKSLEWIGDINPNNG
GTIYNQKFKGKATLTVDKSASTAYMELRSLTSEDTAVYYCARSSIYYDYDGGFAYW
GQGTLVTVSA
   SEQ ID No. 217

118C7E6 Heavy Chain CDR1
DYNMD
   SEQ ID No. 218

118C7E6 Heavy Chain CDR2
DINPNNGGTIYNQKFKG
   SEQ ID No. 219

118C7E6 Heavy Chain CDR3
SSIYYDYDGGFAY
   SEQ ID No. 220

118C7E6 Light Chain Variable Region
DIQMTQSPASLSASVGETVTITCRASGNIHNYLAWYQQKQGKSPQLLVYNAKTLAD
GVPSRFSGSGSGTQYSLKINSLQPEDFGTYYCQHFWSIPFTFGSGTKLEIK
   SEQ ID No. 221

-continued

| | |
|---|---|
| 118C7E6 Light Chain CDR1<br><br>RASGNIHNYLA | SEQ ID No. 222 |
| 118C7E6 Light Chain CDR2<br><br>NAKTLAD | SEQ ID No. 223 |
| 118C7E6 Light Chain CDR3<br><br>QHFWSIPFT | SEQ ID No. 224 |
| 131H4A2 Heavy Chain Variable Region<br><br>QIQLQQSGAELVKPGTSVQISCKASEYDFSRYWMNWVKHRPGEGLEWIGQIYPGDG<br><br>DINYNGKFEAKATLTADKSSSTAFMQLSGLTSEDSAVYFCARGIAMDYWGQGTSVT<br><br>VSS | SEQ ID No. 225 |
| 131H4A2 Heavy Chain CDR1<br><br>RYWMN | SEQ ID No. 226 |
| 131H4A2 Heavy Chain CDR2<br><br>QIYPGDGDINYNGKFEA | SEQ ID No. 227 |
| 131H4A2 Heavy Chain CDR3<br><br>GIAMDY | SEQ ID No. 228 |
| 131H4A2 Light Chain Variable Region<br><br>DIQMTQSTSSLTASLGDRVTISCRASQDVSNYLNWHQQKPDGTVKLLIYYTSRLQSG<br><br>VPSRFSGSGSGTDYSLTISNLEQEDIATYFCQQGNTLPWTFGGGTKLEIK | SEQ ID No. 229 |
| 131H4A2 Light Chain CDR1<br><br>RASQDVSNYLN | SEQ ID No. 230 |
| 131H4A2 Light Chain CDR2<br><br>YTSRLQS | SEQ ID No. 231 |
| 131H4A2 Light Chain CDR3<br><br>QQGNTLPWT | SEQ ID No. 232 |
| 132G4B6 Heavy Chain Variable Region<br><br>EVMLVESGGGLVKPGGSLKLSCAASGFTFSSYTMSWVRQTPEKRLEWVATISGGGD<br><br>YTHYADSVKGRFTISRDNAKNTLYLQMNSLRSEDTALYYCARQGFSTVVTTGDWG<br><br>QGTTLTVSS | SEQ ID No. 233 |
| 132G4B6 Heavy Chain CDR1<br><br>SYTMS | SEQ ID No. 234 |
| 132G4B6 Heavy Chain CDR2<br><br>TISGGGDYTHYADSVKG | SEQ ID No. 235 |
| 132G4B6 Heavy Chain CDR3<br><br>QGFSTVVTTGD | SEQ ID No. 236 |
| 132G4B6 Light Chain Variable Region<br><br>DIVMTQSQKFMSTTVGDRVSITCKASQSVGAAVAWYQQKPGQSPKLLIYSASTRYT<br><br>GVPDRFTGSGSGTDFTLNIRRMQSEDLAEYFCQQYRSYPLTFGSGTKLEIK | SEQ ID No. 237 |
| 132G4B6 Light Chain CDR1<br><br>KASQSVGAAVA | SEQ ID No. 238 |
| 132G4B6 Light Chain CDR2 | |

-continued

| | |
|---|---|
| SASTRYT | SEQ ID No. 239 |
| 132G4B6 Light Chain CDR3 | |
| QQYRSYPLT | SEQ ID No. 240 |
| 144D3B11 Heavy Chain Variable Region | SEQ ID No. 241 |
| QVQMQQSGAELMKPGASVKLSCKANGYTFSGYWIEWVKQRPGHGLEWIGEILPGS | |
| DSPKYSAKFKGKATITADTSSNTAYMQLSSLTTEDSAIYYCAKGGNTSFFDFWGQGT | |
| TLTVSS | |
| 144D3B11 Heavy Chain CDR1 | SEQ ID No. 242 |
| GYWIE | |
| 144D3B11 Heavy Chain CDR2 | SEQ ID No. 243 |
| EILPGSDSPKYSAKFKG | |
| 144D3B11 Heavy Chain CDR3 | SEQ ID No. 244 |
| GGNTSFFDF | |
| 144D3B11 Light Chain Variable Region | SEQ ID No. 245 |
| DVLMTQTPLSLPVSLGDQASISCRSSQRIVHSNGNTYLEWYLQKPGQSPKLLIYKVST | |
| RFSGVPDRFSGSGSGTDFTLKISRVEAEDLGVYYCFQGSFVPWTFGGGTKLEIK | |
| 144D3B11 Light Chain CDR1 | SEQ ID No. 246 |
| RSSQRIVHSNGNTYLE | |
| 144D3B11 Light Chain CDR2 | SEQ ID No. 247 |
| KVSTRFS | |
| 144D3B11 Light Chain CDR3 | SEQ ID No. 248 |
| FQGSFVPWT | |
| 133G11E12 Heavy Chain Variable Region | SEQ ID No. 249 |
| EVMLVESGGGLVKPGGSLKLSCAASGFTFSSYTMSWVRQTPEKRLEWVATISGGGD | |
| YTHYPDSVKGRFTISRDNAKDTLYLQMNSLRSEDTALYYCARQGFSTVVMTGDWG | |
| QGTTLTVSS | |
| 133G11E12 Heavy Chain CDR1 | SEQ ID No. 250 |
| SYTMS | |
| 133G11E12 Heavy Chain CDR2 | SEQ ID No. 251 |
| TISGGGDYTHYPDSVKG | |
| 133G11E12 Heavy Chain CDR3 | SEQ ID No. 252 |
| QGFSTVVMTGD | |
| 133G11E12 Light Chain Variable Region | SEQ ID No. 253 |
| DIVMTQSQKFMSTTVGDRVSITCKASQSVGTAVAWYQQKPGQSPNLLIYSASTRYTG | |
| VPDRFTGSGSGTDFTLNIRNMQSEDLAEYFCQQYRSYPLTFGSGTKLEIK | |
| 133G11E12 Light Chain CDR1 | SEQ ID No. 254 |
| KASQSVGTAVA | |
| 133G11E12 Light Chain CDR2 | SEQ ID No. 255 |
| SASTRYT | |
| 133G11E12 Light Chain CDR3 | SEQ ID No. 256 |

QQYRSYPLT

134C11G10 Heavy Chain Variable Region

SEQ ID No. 257

EVMLVESGGGLVKPGGSLKLSCEASGFTFNTYTMSWIRQTPEKRLEWVATINGGGT

NAYYLDSVKGRFTISRDNAKNTLYLQMSSLRSEDTALYYCARQGFTTVVPTGDWGQ

GTTLTVSS

134C11G10 Heavy Chain CDR1

SEQ ID No. 258

TYTMS

134C11G10 Heavy Chain CDR2

SEQ ID No. 259

TINGGGTNAYYLDSVKG

134C11G10 Heavy Chain CDR3

SEQ ID No. 260

QGFTTVVPTGD

134C11G10 Light Chain Variable Region

SEQ ID No. 261

DIVMTQSQKFMSSTIGDRVSITCKASQSVGAAIAWYQQKPGQSPKLLIYSASSRYTGV

PNRFTGSGSGTDFTLTIDNVQSEDLSDYVCQQYRSYPLTFGSGTKLEVR

134C11G10 Light Chain CDR1

SEQ ID No. 262

KASQSVGAAIA

134C11G10 Light Chain CDR2

SEQ ID No. 263

SASSRYT

134C11G10 Light Chain CDR3

SEQ ID No. 264

QQYRSYPLT

134D3B6 Heavy Chain Variable Region

SEQ ID No. 265

QIQLQQSGAELVKSGTSVKISCKASEYDFSRYWMNWVKHRPGEGLEWIGQIYPGDG

DINYNGKFEAKATLTADKSSSTAFMQLSGLTSEDSAVYFCARGIAMDFWGQGTSVT

VSS

134D3B6 Heavy Chain CDR1

SEQ ID No. 266

RYWMN

134D3B6 Heavy Chain CDR2

SEQ ID No. 267

QIYPGDGDINYNGKFEA

134D3B6 Heavy Chain CDR3

SEQ ID No. 268

GIAMDF

134D3B6 Light Chain Variable Region

SEQ ID No. 269

DIQMTQSTSSLTASLGDRVTISCRASQDVSNYLNWHQQKPDGTVKLLIYYTSRLQSG

VPSRFSGSGSGTDYSLTITNLEQEDIATYFCQQGNTLPWTFGGGTKLEII

134D3B6 Light Chain CDR1

SEQ ID No. 270

RASQDVSNYLN

134D3B6 Light Chain CDR2

SEQ ID No. 271

YTSRLQS

134D3B6 Light Chain CDR3

SEQ ID No. 272

QQGNTLPWT

138E9A2 Heavy Chain Variable Region

SEQ ID No. 273

QVQLQQSGPELVKPGASVKLSCKASGYTFTNYDINWVKQRPGQGLEWIGWIYPGDG

-continued

STKSKEKFRGKATLTVDTSSSTAYMELHSLTSEDSAVYLCARDYGTPYYAMDYWG

QGTSVTVSS

138E9A2 Heavy Chain CDR1

SEQ ID No. 274

NYDIN

138E9A2 Heavy Chain CDR2

SEQ ID No. 275

WIYPGDGSTKSKEKFRG

138E9A2 Heavy Chain CDR3

SEQ ID No. 276

DYGTPYYAMDY

138E9A2 Light Chain Variable Region

SEQ ID No. 277

DVLMTQTPLSLPVSLGDQASISCRSSQSIIQSNGNTYLEWYLQKPGQSPKLLIYKVSN

RFSGVPDRFSGSGSGTDFTLKISRVEAEDLGVYYCFQGSFVPWTFGGGTNLEIK

138E9A2 Light Chain CDR1

SEQ ID No. 278

RSSQSIIQSNGNTYLE

138E9A2 Light Chain CDR2

SEQ ID No. 279

KVSNRFS

138E9A2 Light Chain CDR3

SEQ ID No. 280

FQGSFVPWT

138F9B5 Heavy Chain Variable Region

SEQ ID No. 281

EVQLVESGGDLVKPGGSLKLSCAASGFTFNNDGMSWVRQTPDKRLEWVASISSDGS

YSFYPDNVKGRFTISRDNAKNTLYLQMSSLKSEDTAMYYCASQRGYYGNSLAWFA

YWGQGTLVTVSA

138F9B5 Heavy Chain CDR1

SEQ ID No. 282

NDGMS

138F9B5 Heavy Chain CDR2

SEQ ID No. 283

SISSDGSYSFYPDNVKG

138F9B5 Heavy Chain CDR3

SEQ ID No. 284

QRGYYGNSLAWFAY

138F9B5 Light Chain Variable Region

SEQ ID No. 285

DILLTQSPVILSVSPGERVSFSCRASQSIGTSIHWYQQRTNGSPRLLIKYASESMSGIPS

RFSGSGSGTDFTLSINSVESEDIADYFCQQSKTWPLTFGAGTTLELK

138F9B5 Light Chain CDR1

SEQ ID No. 286

RASQSIGTSIH

138F9B5 Light Chain CDR2

SEQ ID No. 287

YASESMS

138F9B5 Light Chain CDR3

SEQ ID No. 288

QQSKTWPLT

142D6D11 Heavy Chain Variable Region

SEQ ID No. 289

EVHLVESGGGLVKPGGSLKLSCAASGFTFSDYGMHWVRQAPEKGLDWVAYISSGG

TTIYYADTVKGRFTISRDNAKNTLFLQMTTLGSDDTAMYSCARTRPGDAMDYWGQ

GTSVTVSS

-continued

142D6D11 Heavy Chain CDR1

DYGMH

SEQ ID No. 290

142D6D11 Heavy Chain CDR2

YISSGGTTIYYADTVKG

SEQ ID No. 291

142D6D11 Heavy Chain CDR3

TRPGDAMDY

SEQ ID No. 292

142D6D11 Light Chain Variable Region

DILLTQSPAILSVSPGERVSFSCRASQSAGTSIHWYQQRTNGSPRLLIKYTSESISGIPSR

FSGSGSGTDFTLSINSVESEDIADYYCQQSLRWPFTFGSGTRLEIK

SEQ ID No. 293

142D6D11 Light Chain CDR1

RASQSAGTSIH

SEQ ID No. 294

142D6D11 Light Chain CDR2

YTSESIS

SEQ ID No. 295

142D6D11 Light Chain CDR3

QQSLRWPFT

SEQ ID No. 296

145E10H5 Heavy Chain Variable Region

QVQLQQPEAELVKPGASVKMSCKASGYTFPRYWITWMRQRPGQGLEWIGDIFPSSE

YTHYNEKFRRKATLTVDTSSSIAYIQLSSLTSEDSAVYYCARGEYDAWFAYWGQGT

LVTVSA

SEQ ID No. 297

145E10H5 Heavy Chain CDR1

RYWIT

SEQ ID No. 298

145E10H5 Heavy Chain CDR2

DIFPSSEYTHYNEKFRR

SEQ ID No. 299

145E10H5 Heavy Chain CDR3

GEYDAWFAY

SEQ ID No. 300

145E10H5 Light Chain Variable Region

DIQMTQTTSSLSVSLGDRVTISCRASQDISNYLNWYQQKPDGTVKLLIYYTSRLDSGV

PSRFSGSGSGTDYSLTISNLEQEDLATYFCQQGNTLPPTFGGGTKLEIR

SEQ ID No. 301

145E10H5 Light Chain CDR1

RASQDISNYLN

SEQ ID No. 302

145E10H5 Light Chain CDR2

YTSRLDS

SEQ ID No. 303

145E10H5 Light Chain CDR3

QQGNTLPPT

SEQ ID No. 304

167H6H5 Heavy Chain Variable Region

EVQLQQSGAELVRPGASVKLSCTTSGFNIKDEHMYWVKQRPEQGLEWIA WIDPEND

NTEYASKFQGKATITADTSSNTVYLQLSNLTSEDTAVYFCTTGDYDGFTYWGQGTL

VTVSA

SEQ ID No. 305

167H6H5 Heavy Chain CDR1

DEHMY

SEQ ID No. 306

167H6H5 Heavy Chain CDR2

-continued

WIDPENDNTEYASKFQG  SEQ ID No. 307

167H6H5 Heavy Chain CDR3
GDYDGFTY  SEQ ID No. 308

167H6H5 Light Chain Variable Region
EIVLTQSPTTMAASPGEKITITCSASSSISSNFLHWFQQKPRFSPKLLIYRTSNLASGVP
ARFSGSGSGTSYSLTIGTMEAEDVATYYCQQGSFMPFTFGTGTKLELK  SEQ ID No. 309

167H6H5 Light Chain CDR1
SASSSISSNFLH  SEQ ID No. 310

167H6H5 Light Chain CDR2
RTSNLAS  SEQ ID No. 311

167H6H5 Light Chain CDR3
QQGSFMPFT  SEQ ID No. 312

166E12G6 Heavy Chain Variable Region
EVKLVESGGGLVQPGGSLSLSCVTSGFTFTDYYMSWVRQSPGKALEWLGFIRNKAY
GDTTEYSESVKGRFTISRDNSQSILYLHMNALRAEDSATYYCARYPRTGYALDYWG
QGTSVTVSS  SEQ ID No. 313

166E12G6 Heavy Chain CDR1
DYYMS  SEQ ID No. 314

166E12G6 Heavy Chain CDR2
FIRNKAYGDTTEYSESVKG  SEQ ID No. 315

166E12G6 Heavy Chain CDR3
YPRTGYALDY  SEQ ID No. 316

166E12G6 Light Chain Variable Region
DVFMTQTPLSLPVSLGDQASISCRSSQSIVHSNGNTYLEWYLQKPGQSPKLLIYKVSN
RFPGVPDRFSGSGSGTDFTLKINRVEAEDLGVYYCFQVSHVPYTFGGGTKLEIK  SEQ ID No. 317

166E12G6 Light Chain CDR1
RSSQSIVHSNGNTYLE  SEQ ID No. 318

166E12G6 Light Chain CDR2
KVSNRFP  SEQ ID No. 319

166E12G6 Light Chain CDR3
FQVSHVPYT  SEQ ID No. 320

2D5 Heavy Chain Variable Region
QVTLKESGPTLVKPTQTLTLACSFSGFSLTTTGVAVTWIRQPPGKALEWLALIDWDD
DKYYSTSLKTRLTISKDTSKNQVVLTMTNMDPVDTATYYCARIASGDSGGYFADWG
QGTLVTVSS  SEQ ID No. 321

2D5 Heavy Chain CDR1
TTGVAVT  SEQ ID No. 322

2D5 Heavy Chain CDR2
LIDWDDDKYYSTSLKT  SEQ ID No. 323

2D5 Heavy Chain CDR3
  SEQ ID No. 324

```
IASGDSGGYFAD
2D5 Light Chain Variable Region                                          SEQ ID No. 325
SSELTQAPSVSVSPGQTASITCSGDKLDDKYVYWYQQKPGQPPVLVIYRDNKRPSGIP
ERFSGSNSGNTATLTISATQALDEADYYCQAWESSSDQYVFGTGTKVTVL 2D5 Light Chain CDR1                                                     SEQ ID No. 326
SGDKLDDKYVY 2D5 Light Chain CDR2                                                     SEQ ID No. 327
RDNKRPS 2D5 Light Chain CDR3                                                     SEQ ID No. 328
QAWESSSDQYV 5D8 Heavy Chain Variable Region                                          SEQ ID No. 329
QVQLQESGAGLLKPSETLSLTCAVYGGSFSGYYWSWIRQPPGKGLEWIGEINHSGST
NYNPSLKSRVTISVDTSKNQFSLKLSSVTAADTAVYYCARTRYYGSGSWSLFDYWG
QGTLVTVSS 5D8 Heavy Chain CDR1                                                     SEQ ID No. 330
GYYWS 5D8 Heavy Chain CDR2                                                     SEQ ID No. 331
EINHSGSTNYNPSLKS 5D8 Heavy Chain CDR3                                                     SEQ ID No. 332
TRYYGSGSWSLFDY 5D8 Light Chain Variable Region                                          SEQ ID No. 333
QPVLTQPPSASGAPGQTVTISCSGGNSNVGTNTVNWYQQLPGTAPKLLIYYDDLLAS
GVSDRFSGSKSGTSASLAISGLQAEEEADYYCAAWDDTLNGWVFGGGTKLTVL 5D8 Light Chain CDR1                                                     SEQ ID No. 334
SGGNSNVGTNTVN 5D8 Light Chain CDR2                                                     SEQ ID No. 335
YDDLLAS 5D8 Light Chain CDR3                                                     SEQ ID No. 336
AAWDDTLNGWV Nucleotide sequence numbers
8G4E12 Heavy chain variable region nucleotide sequence                   SEQ ID No. 337
GAGGTGCAGCTGGTGGAGTCTGGGGGAGGCTTAGTGAAGCCTGGAGGGTCCCTG
AAACTCTCCTGTGCAGCCTCTGGATTCACTTTCAGTGACTATGGAATGTACTGGG
TTCGTCAGGCTCCAGAGAAGGGGCTGGAGGGGGTTGCATACATTAGTAGTGGCA
GTAGTACCATCTACTCTGTAGACAAAGTGAAGGGCCGATTCACCATCTCCAGAGA
CAATGCCAAGAACACCCTGTTCCTGCAAATGACCAGTCTGAGGTCTGAGGACAC
GGCCATGTATTACTGTGCAACGTGGCTACCGGGAAATGCTATGGACTACTGGGGT
CAAGGAACCTCAGTCACCGTCTCCTCA 8G4E12 Light chain variable region nucleotide sequence                   SEQ ID No. 338
GACATCTTGCTGACTCAGTCTCCAGCCATCCTGTCTGTGAGTCCAGGACAAAGAG
TCAGTTTCTCCTGCAGGGCCAGTCAGAGCATTGGCACAAGCATACACTGGTATCA
GCAAAGAACAAATGGTTCTCCAAGGCTTCTCATAAAGTATGCTTCTGAGTCTATC
```

-continued

TCTGGGATCCCTTCCAGGTTTAGTGGCAGTGGATCAGGGACAGATTTTACTCTTA

GCATCAACAGTGTGGAGTCTGAAGATATTGCAGATTATTACTGTCAACAAAGTAT

TAGGTGGCCGTACACATTCGGAGGGGGGACCAAGCTGGAAATAAAA

10F5E11 Heavy chain variable region nucleotide sequence  SEQ ID No. 339

CAGGTTCAGCTCCAGCAGTCTGGAGCTGAGCTGGTGAAGCCTGGGGCCTCAGTG

AAGCTTTCCTGCAAGGCTACTGGCTACACATTCACTGGCTACTGGATAGAGTGGG

TAAAGCAGAGGCCTGGACATGGCCTTGAGTGGATTGGAGAGATTTTACCTGGAA

GTGGTAGTACTAAGTACAATGAAGTTCAAGGACAGGGCCACATTCACTGAAG

ATACATCCTCCAACACAGCCTACATGCAACTCAGCAGCCTGACAACTGAGGACTC

TGCCATCTATTACTGTGCAAGAGGGGGGTTGGACAGTTTCTTTGACTACTGGGGC

CAAGGCACCACTCTCACAGTCTCCTCA

10F5E11 Light chain variable region nucleotide sequence  SEQ ID No. 340

GATGTTTTGATGACCCAAACTCCACTCTCCCTGCCTGTCAGTCTTGGAGATCAAG

CCTCCATCTCTTGCAGATCTAGTCAGATCATTGTACATAGTAATGGAAACACCTA

TTTAGAATGGTACCTGCAGAAACCAGGCCAGTCTCCAAAGCTCCTGATCTACAAG

GTTTCCAACCGATTTTCTGGGGTCCCAGACAGGTTCAGTGGCAGTGGATCAGGGA

CAGATTTCACACTCAAGATCAGCAGAGTGGAGGCTGAGGATCTGGGAGTTTATT

ACTGCTTTCAAGGTTCATATGTTCCGTGGACGTTCGGTGGAGGCACCAAACTGGA

AATCAAA

16C6D11 Heavy chain variable region nucleotide sequence  SEQ ID No. 341

GAGGTTCAGCTGCAGCAGTCTGTGGCAGAGCTTGTGAGGCCAGGGGCCACAGTG

AAGTTGTCCTGCACAACTTCTGGCTTCAACATTCAAAACACCTATATGCACTGGG

TGAAGCAGAGGCCTGAACAGGGCCTGGAGTGGATTGGAAGGATTGATCCTGCGA

GTGGTAATACTATATATGCCCCGAAGTTCCAGGGCAGGGCCACTATTACTGCAGA

CACATCCTCCAACACAGCCTACCTGCAGCTCAGCAGCCTGACATCTGAGGACACT

GCCATCTATTACTGTGCTAGAATGGATGGTTACTACGATCCTTACTGGGGCCAAG

GGACTCTGGTCACTGTCTCTGCA

16C6D11 Light chain variable region nucleotide sequence  SEQ ID No. 342

GACATCTTGCTGACTCAGTCTCCAGCCATCCTGTCTGTGAGTCCAGGAGAAAGAG

TCAGTTTCTCCTGCAGGGCCAGTCAGAGCACTGGCACAAGCATACACTGGTATCA

GCAAAGAACAAATGGTTCTCCAAGGCTTCTCATAAAGTATACTTCTGAGTCTATT

TCTGGGATCCCTTCCAGGTTTAGTGGCAGTGGATCAGGGACAGATTTTACTCTTA

CCATCAACAGTGTGGAGTCTGAAGATATTGGAGATTATTACTGTCGACAAAGTAT

TAGCAGGCCATTCACGTTCGGCTCGGGGACAAAGTTGGAAATGAAA

17D4A3 Heavy Chain Variable Region Nucleotide Sequence  SEQ ID No. 343

GAGGTGAAGCTGGTGGAGTCTGGAGGAGGCTTGGTACAGCCTGGGGGTTCTCTG

AGTCTCTCCTGTGCAGCTTCTGGATTCACCTTCACTGATTACTACATGAGCTGGGT

CCGCCAGCCTCCAGGGAAGGCACTTGAGTGGTTGGGTTTTATTAGAAACAAAGCT

AATGGTTACACAACAGAGTGCAGTGCATCTGTGAAGGGTCGATTCACCATCTCCA

GAGATAATTCCCAAAACATCCTCTATCTTCAAATGAATGCCCTGAGAGCTGAGGA

-continued

CAGTGCCACTTATTACTGTGCAACATATGGGAGATTGGGATATACTATGGACTAC

TGGGGTCAAGGAACCTCAGTCACCGTCTCCTCA

17D4A3 Light Chain Variable Region Nucleotide Sequence  SEQ ID No. 344

GATGTTTTGATGACCCAAACTCCACTCTCCCTGCCTGTCAGTCTTGGAGATCAAG

CCTCCATCTCTTGCAGATCTAGTCAGAGCATTGTACATAGTAATGGAAACACCTA

TTTAGAATGGTACCTGCAGAAACCAGGCCAGTCTCCAAAGCTCCTGATCTACAAA

GTTTCCAACCGATTTTCTGGGGTCCCAGACAGGTTCAGTGGCAGTGGATCAGGGA

CAGATTTCACACTCAAGATCAACAGAGTGGAGGCTGAGGATCTGGGAGTTTATT

ACTGCTTTCAAGGTTCACATGTTCCGTGGACGTTCGGTGGAGGCACCAAGCTGGA

AATCAAA

17H4B2 Heavy Chain Variable Region Nucleotide Sequence  SEQ ID No. 345

CAGGTCCAACTGCAGCAGCCTGGGGCTGAGCTGGTGAGGCCTGGGTCTTCAGTG

AAGCTGTCCTGCAAGGCTTCTGGCCACACCCTCACCGGGTTCTGGATGCATTGGG

TGAGGCAGAGGCCTATACCAGGCCTTGAATGGATTGGTAACATTGACCCTTCTGA

TAGTGAAACTCACTACAATCAAAAGTTCGAGGACAAGGCCACATTGACTGTAGA

CAAATCCTCCAACACAGCCTACATGCTACTCAGCAGCCTGACATCTGAGGACTCT

GCGGTCTATTACTGTGCAAGAGAGGGGGGGACCGGGTACTTCGATGTCTGGGC

ACAGGGACCACGGTCACCGTCTCCTCA

17H4B2 Light Chain Variable Region Nucleotide Sequence  SEQ ID No. 346

GAATTTGTGCTCACCCAGTCTCCAACCACCCTGGCTGCATCTCCCGGGGAGAAGA

TCACTATCACCTGCAGTGCCAGCTCAAGTATAAGTTCCAATTACTTGCATTGGTA

TCAGCAGAAGCCAGGATTCTCCCCTAAACTCTTGATTTATAGGACATCCAATCTG

GCTTCTGGAGTCCCAGCTCGCTTCAGTGGCAGTGGGTCTGGGACCTCTTACTCTC

TCACAATTGGCACCATGGAGGCTGAAGATGTTGCCACTTACTACTGCCAGAAGG

GTAGTAGTATACCACGCATGTACACGTTCGGAGGGGGGACCAAGCTGGAAATAA

AA

24D4E5 Heavy Chain Variable Region Nucleotide Sequence  SEQ ID No. 347

GATGTACAGCTTCAGGAGTCAGGACCTGGCCTCGTGAAACCTTCTCAGTCTCTGT

CTCTCACCTGCTCTGTCACTGGCTACTCCATCACCAGTAATTATTACTGGAACTGG

ATCCGGCAGTTTCCAGGAAACAAACTGGAGTGGATGGGCTACATAAGCTACGAT

GGTAGCAATGACTACAACCCATCTCTCAAAAATCGAATCTCCATCACTCGTGACA

CATCTAAGAACCAGTTTTTCCTGAGGTTGAATTCTGTGACTACTGAGGACACAGC

CACATATTTCTGTGCAAGAGTGACCTCAGGCTACCTGTACTACTTTGACAACTGG

GGCCAAGGCACCACTCTCACAGTCTCCTCA

24D4E5 Light Chain Variable Region Nucleotide Sequence  SEQ ID No. 348

GAAATTGTGCTCACTCAGTCTCCAGCCATCACAGCTGCATCTCTGGGGCAAAAGG

TCACCATCACCTGCAGTGCCAGTTCAAGTGTAAGTTACATGCACTGGTACCAGCA

GAGGTCAGGCACCTCCCCCAAACCATGGATTTATGAAATATCCAAACTGGCTTCT

GGAGTCCCAGCTCGCTTCAGTGGCAGTGGGTCTGGGACCTCTTACTCTCTCACAA

TCAGCAGCATGGAGGCTGAAGATGCTGCCATTTATTACTGCCAGCAGTGGAATTT

TCCGCTCACGTTCGGTGCTGGGACCAAGCTGGAGCTGAAA

28G7B10 Heavy Chain Variable Region Nucleotide Sequence

SEQ ID No. 349

GACGTGAAGCTGGTGGAGTCTGGGGAAGACTTAGTGAAGCCTGGAGGGTCCCTG

AAAGTCTCCTGTGCAGCCTCTGGATTCACTTTCCGTGACTATGCCATGTCTTGGGT

TCGCCAGACTCCAGAGAAGAGGCTGGAGTGGGTCGCATACATTAGTAGTGGTGG

TGATTATATCTACTATGCAGACTCTGTGAAGGGCCGATTCACCATATCCAGAGAC

AATGCCAGGAACACCCTATACCTACAAATGACCAGTCTGAGGTCTGAGGACACA

GCCATGTATTTCTGTACAAGAGATCCCTCCTTCTACGGCAGAGGATATTATTTTG

ACTATTGGGGCCAAGGCACCAGTCTCACAGTCTCCTCA

28G7B 10 Light Chain Variable Region Nucleotide Sequence

SEQ ID No. 350

GACATTGTGATGACCCAGTCTCACAAATTCATGTCCGCATCAGTAGGAGACAGG

GTCAGCATCACCTGCAAGGCCAGTCAGGATGTGGGTGCTACTGTAGCCTGGTATC

AACAGAAACCAGGGCAATCTCCTAAACTACTGATTTACTGGGCATCCACCCGGC

ACACTGGAGTCCCTGATCGCTTCACAGGCAGTGGATCTGGGACAGATTTCACTCT

CACCATTAACAATGTGCAGTCTGAAGACTTGGCAGATTATTTCTGTCAGCAATAT

AGCAACTATCCGACGTTCGGTGGAGGCACCAAGCTGGAAATCAAA

30B1C7 Heavy Chain Variable Region Nucleotide Sequence

SEQ ID No. 351

GAGGTTCAGCTGCAGCAGTCTGTGGCAGAGCTTGTGAGGCCAGGGGCCTCAGTC

AAGTTGTCCTGCACAGTTTCTGGCTTCAACATTAAAAACACCTATATGCACTGGG

TGAAGCAGAGGCCTGAACAGGGCCTGGAATGGATTGGAAGGATTGATCCTGCGA

ATGGTGATACTAAATATGACCCGAAGTTCCAGGCCAAGGCCACTGTAACTGCAG

ACACATCCTCCAACACAGCCTACCTGCATCTCAGTAGCCTGACATCTGAGGACAC

TGCCATCTATTACTGTGTAGAGGATGATTACGGCCTTGGGTCCTGGGGCCAAGGC

ACCACTCTCACAGTTTCCTCA

30B1C7 Light Chain Variable Region Nucleotide Sequence

SEQ ID No. 352

GACATTGTGATGACCCAGTCTCAAAAATTCATGTCCACATCAGTTGGAGACAGGG

TCAGCGTCACCTGCAAGGCCAGTCAGAATGTGGGTTCTAATGTAGCCTGGTATCA

ACAGAAACCTGGGCAATCTCCTAAATCACTGATTTACGCGACATCTCACCGCTAC

AGTGGAGTCCCTGATCGCTTCACAGGCAGTGGATCTGGGACAGATTTCACTCTCA

CCATCAGCAATGTGCAGTCTGAAGACTTGGCAGAGTATTTCTGTCAGCATTATAA

CAACTATCCGTACACGTTCGGAGGGGGGACCAAGCTGGAAATAAAA

12G10H1 Heavy Chain Variable Region Nucleotide Sequence

SEQ ID No. 353

GAGGTCCAGCTGCAACAATCTGGACCTGTACTGGTGAAGCCTGGGGCTTCAGTG

AAGATATCCTGTAAGGCTTCTGGATACACGTTCACTGACTACATGAACTGGG

TGAAGCAGAGCCATGGAAAGAGCCTTGAGTGGATTGGAGATATTAATCCTGACA

ATGGTTTTACTAGTTACAACCAGAAGTTCAAGGGCAAGGCCACATTGACTGTTGA

CAGGTCCTCCAGCACAGCCTACATGGAGTTCCGCAGCCTGACATCTGAGGACTCT

GCAGTCTATTACTGTGCCAGAGACGGTAGTAGCGCCTATGGTATGGACTATTGGG

GTCAAGGAACCTCAGTCACCGTCTCCTCC

12G10H1 Light Chain Variable Region Nucleotide Sequence

SEQ ID No. 354

GACATTGTGCTGACCCAGTCTCCAGCTTCTTTGGCTGTGTCTCTAGGGCAGAGGG

-continued

CCACCATCTCCTGCAGAGCCAGTGAAAGTGTCAGTATTCATGGTACTCATTTAAT

GCACTGGTACCAACAGAAACCAGGACAGCCACCCAAACTCCTCATCTATGCTGC

ATCCAACCTAGAATCTGGAGTCCCTGCCAGGTTCAGTGGCAGTGGGTCTGAGACA

GACTTCACCCTCAACATCCATACTGTGGAGGAGGAGGATGCTGCAACCTATTTCT

GTCAGCAAAGTATTGAGGAACCTCGGACGTTCGGTGGAGGCACCAAGGTGGAAA

TCAAA

17A10A2 Heavy Chain Variable Region Nucleotide Sequence  SEQ ID No. 355

GAGGTTCAACTGCAGCAGTCTGGACCTGAGCTGGTGAAGCCTGGGGCTTCAGTG

AAGATATCCTGCAAGGCTTCTGGTTACTCATTCACTGGCTACTACATGCACTGGG

TGAAGCAGAGCCATGGAAATATCCTCGATTGGATTGGATATATTTATCCTTACAA

TGGTGTTTCTACCTACAACCAGAGATTCAAGGGCAAGGCCACATTGACTGTAGAC

AAGTCCTCTAGCACAGCCTACATGGAGCTCCGCAGCCTGACATCTGAGGACTCTG

CAGTCTATTACTGTGCAAAGGGGGCTAGTGGTTACGACGGTGACTACTGGGGCC

AAGGCACCACTCTCACAGTCTCCTCA

17A10A2 Light Chain Variable Region Nucleotide Sequence  SEQ ID No. 356

CAAATTGTTCTCACCCAGTCTCCAGCAATCATGTCTGCATCTCCAGGGGAGAAGG

TCACCATAACCTGCAGTGCCACCTCAGTTGTAAGTTACATGCACTGGTTCCAGCA

GAAGCCAGGCACTTCTCCCAAACTCTGGATTTATCTCACATCCAACCTGGCTTCT

GGAGTCCCTGCTCGCTTCAGTGGCAGTGGATCTGGGACCTCTTACTCTCTCACAA

TCAGCCGAATGGAGGCTGAAGATGCTGCCACTTATTACTGCCAGCAAAGGAGTA

GTTACCCACCCACGTTCGGAGGGGGGACCAAGCTGGAAATAAAA

25C1B3 Heavy Chain Variable Region Nucleotide Sequence  SEQ ID No. 357

CAGGTTCAGCTGCAGCAGTCTGGAGCTGAGCTGATGAAGCCTGGGGCCTCAGTG

AAGCTTTCCTGCAAGGCAACTGGCTACACATTCACTGGCTACTGGATAGAGTGGG

TAAAGCAGAGGCCTGGACATGGCTTTGAGTGGATTGGAGAGATTTTACCTGGAA

GTGGTACCACTAAATACAATAAGAAGTTCCAGGGCAAGGCCACAATCACTGCAG

ATACATCCTCCAACACAGCCTACATACAACTCAGTAGCCTGACAACTGAGGACTC

TGCCATGTATTACTGTGCAAGAGGGGGACAGGACCACTTCTTTGCCGACTGGGGC

CAAGGCACCACTCTCACAGTCTCCTCA

25C1B3 Light Chain Variable Region Nucleotide Sequence  SEQ ID No. 358

GATATTTTGATGACCCAAAGTCCACTCTCCCTGCCTGTCAGTCTTGGAGATCAAG

CCTCCATCTCTTGCAGATCAAGTCAGACCATTGTACATAGTAATGGAGACACCTA

TTTAGAATGGTACCTGCAGAAACCAGGCCAGTCTCCAAAGCTCCTGATCTACAAA

GTTTCCAACCGATTTTCTGGGGTCCCAGACAGGTTCAGTGGCAGTGGTTCAGGGA

CAGATTTCACACTCAAGATCAGCAGAGTGGAGGCTGAGGATCTGGGAATTTATT

ACTGCTTTCAAGGTTCATATGTTCCGTGGACGTTCGGTGGAGGCACCAGGCTGGA

AATCAAA

28D2E1 Heavy Chain Variable Region Nucleotide Sequence  SEQ ID No. 359

GAGGTGAAGCTGGAGGAGTCTGGAGGAGGCTTGGTACAGCCGGGGGGTTCTCTG

AGTCTCTCCTGTGCAGCTTCTGGATTCACCTTCACTGACTACTACATGAGCTGGGT

CCGCCAGCCTCCAGGGAAGGCACCTGAGTGGTTGGGTTTTATTAGAAACAGAGC

-continued

TTATGGTTACACAACAGAGTACAGTGCATCTGTGAAGGGTCGGTTCACCTTCTCC

AGAGATAATTCCCAAAGCATCCTCTTTCTTCATATGAATGCCCTGAGACCTGAGG

ACAGTGCCACTTATTACTGTGCAAGATATCCTTTATTAGGGTATGCTTTGGACTA

CTGGGGTCAAGGAACCTCAGTCACCGTCTCCTCA

28D2E1 Light Chain Variable Region Nucleotide Sequence   SEQ ID No. 360

GATGTCTTGATGACCCAAACTCCACTCTCCCTGCCTGTCAGTCTTGGAGATCAAG

CCTCCATCTCTTGCAGATCTAGTCAGAGTATTGTACATAGTAATGGAAACACCTA

TTTAGAATGGTACCTGCAGAAACCAGGCCAGTCTCCAAAGCTCCTGATCTACAAA

GTTTCCAACCGATTTTCTGGGGTCCCAGACAGGTTCAGTGGCAGTGGATCAGGGA

CAGATTTCACACTCAAGATCAGCAGAGTGGAGGCTGAGGATCTGGGAATTTATT

ACTGCTTTCAAGTTTCACATGTTCCGTGGACGTTCGGTGGAGGCACCAAGCTGGA

AATCAAA

31G10C5 Heavy Chain Variable Region Nucleotide Sequence   SEQ ID No. 361

GAGGTTCAGCTGCAGCAGTCTGGGGCTGAGCTTGTGAGGCCAGGGGCCTCAGTC

AAGTTGTCCTGCACAGCTTCTGGCTTTAACATTAAAGACGACTATATACACTGGG

TGAAGCAGAGGCCTGAACAGGGCCTGGAGTGGATTGGATGGATTGATCCTGCGA

ATGGTCATATTGAATATGCCTCGAACTTCCAGGCCAAGGCCACTATTACAGCAGA

CACATCCTCCAACACAGCCTACCTGCAGCTCAGCAGCCTGACATCTGAGGACACT

GCCGTCTATTACTGTACTACGGGGGATTACGACGGGTTTACTTACTGGGGCCAAG

GGACTCTGGTCACTGTCTCTACA

31G10C5 Light Chain Variable Region Nucleotide Sequence   SEQ ID No. 362

CAAATTGTTCTCACCCAGTCTCCAGCAATCATGTCTGCATCTCCAGGGGAGAAGG

TCACCATATCCTGCAGTGCCAGGTCAAGTGTAAGTTACATGTATTGGTACCAGCA

GAAGCCAGGATCCTCCCCCAAACCCTGGATTTATCGAACATCCAACCTGGCTTCT

GGAGTCCCTGCTCGCTTCAGTGGCAGTGGGTCTGGGACCTCTTACTCTCTCACAA

TCAGCAGCATGGAGGCTGAAGATGCTGCCACTTATTACTGCCAGCACTATCATAC

TTACCCGTACACGTTCGGGGGGGGGACCAAGCTGGAAATAAAA

32C8F10 Heavy Chain Variable Region Nucleotide Sequence   SEQ ID No. 363

GAGGTTCAGCTGCAGCAGTCTGGGGCTGAGCTTGTGAGGCCAGGGGCCTCAGTC

AAGTTGTCCTGCACAGCTTCTGGCTTTAACATTAAAGACGAATATATACACTGGG

TGAAACAGAGGCCTGAACAGGGCCTGGAGTGGATTGGCTGGATTGATCCTGCGA

ATGGTCATACTGAATATGCCTCGAGGTTCCAGGCCAAGGCCACTATAACAGCAG

ACACATCCTCCAACACAGCCTACTTGCAGCTCAGCAGCCTGACATCTGAGGACAC

TGCCGTCTATTACTGTACTACGGGGGATTACGACGGGTTTGCTTACTGGGCCAA

GGGACTCTGGTCACTGTCTCTACA

32C8F10 Light Chain Variable Region Nucleotide Sequence   SEQ ID No. 364

CAAATTGTTCTCACCCAGTCTCCAGCAATCATGTCTGCATCTCCAGGGGAGAAGG

TCACCATATCCTGCAGTGCCAGGTCAAGTGTAAGTTACATGTATTGGTACCAGCA

GAAGCCAGGATCCTCCCCCAAACCCTGGATTTATCGCACATCCAACCTGGCTTCT

GGAGTCCCTGCTCGCTTCAGTGGCAGTGGGTCTGGGACCTCTTACTCTCTCACAA

-continued

TCAGCAGCATGGAGGCTGAAGATGCTGCCACTTATTACTGCCAGCATTATCATAC

TTACCCGTACACGTTCGGAGGGGGGACCAAGCTGGAAATAAAG

35D2B9 Heavy Chain Variable Region Nucleotide Sequence SEQ ID No. 365

CAGGTCCAACTGCAGCAGCCTGGGGCTGAGGTGGTAAAGCCTGGGGCTTCAGTG

AAGTTGTCCTGCAAGGCTTCTGGCTACACTGTCACCAGCTACTGGATGCACTGGG

TGAAGCAGAGGCCTGGACAAGGCCTTGAGTGGATTGGAATGATTCATCCTAATG

GTATTAGTACTAACTACAATGAGAAGTTCAAGAGCAAGGCCACACTGACTGGAG

ACAAATCCTCCAGCACAGCCTACATGCAACTCAGCAGCCTGACATCTGAGGACTC

TGCGGTCTATTTCTGTGCAAGAGGGGGGGATAGTGACTACTACTTTGACTACTGG

GGCCAAGGCACCACTCTCACAGTCTCCTCA

35D2B9 Light Chain Variable Region Nucleotide Sequence SEQ ID No. 366

CAAATTGTTCTCACCCAGTCTCCAGCAATCATGTCTGCATCTCCAGGGGAAAAGG

TCACCATGACCTGCAGTGCCAGCTCAAGTGTAAGTTACATGTACTGGTACCAGCA

GAAGCCAGGCTCCTCCCCCAGACTCTGGATTTATGACACATCCAACCTGGTTTCT

GGAGTCCCTGCTCGCTTCAGTGGCAGTAGGTCTGGGACCTCTTATTCTCTCACAC

TCAGCAGCATGGAGGCTGAAGATGCTGCCACTTATTACTGCCAGCAGTACAGTG

GTTACCCATACACGTTCGGAGGGGGGACCAAGCTGGAAATAAAA

37C4F7 Heavy Chain Variable Region Nucleotide Sequence SEQ ID No. 367

GAGTTCCAGCTGCAGCAGTCTGGACCTGAGGTGGTGAAGCCTGGCGCTTCAGTG

AAGATATCCTGCAAGGCTTCTGGTTACTCATTCACTGACTACAACATGAACTGGA

TGAAGCAGAGCAAAGGAAAGAGTCTTGAGTGGATTGGAGTAATCAATCCTAACT

ATGGCACTACTACTTACAATCAGAACTTCAAGGGCAAGGCCACATTGACTGTAG

ACCAATCTTCCAGCACAGCCTACATGCAGCTCAACAGCCTGACATCTGAAGACTC

TGCAGTCTATTACTGTGCAAGAGACATGTACTATGTTTACGCTTACTATACTATG

GACTACTGGGGTCAAGGAACCTCAGTCACCGTCTCCTCA

37C4F7 Light Chain Variable Region Nucleotide Sequence SEQ ID No. 368

GATGTTGTGATGACCCAAACTCCACTCTCCCTGCCTGTCAGTCTTGGAGATCAAG

CCTCCATCTCTTGCAGATCTAGTCAGAGCCTTGTACACAGTAATGGACACACCTA

TTTACATTGGTACCTGCAGAGGCCAGGCCAGTCTCCAACGCTCCTGATCTACAAA

GTTTCCAACCGATTTTCTGGGGTCCCAGACAGGTTCAGTGGCAGTGGATCCGGGA

CAGATTTCACACTCAAGATCAGCAGAGTGGAGGCTGAGGATCTGGGAGTTTATTT

CTGCTCTCAAGGTACACATGTTCCGTGGACGTTCGGTGGAGGCACCAAGCTGGAA

ATCAAA

37F11F9 Heavy Chain Variable Region Nucleotide Sequence SEQ ID No. 369

GAGGTCCAGCTGCAACAGTCTGGACCTGTGCTGGTGAAGCCTGGGGCTTCAGTG

AAGATGTCCTGTAAGGCTTCTGGATACACATTCACTGACTATTATATGAACTGGG

TGAAGCAGAGCCATGGAAAGAGCCTTGAGTGGATTGGACTTATTAATCCTTACA

GCGGTGGTAGTACCTTCAACCAGAAGTTCAAGGCCAAGGCCACATTGACTGTCG

ACAAGTCCTCCAGTTCAGCCTACATGGACCTCAACAGCCTGACATCTGAAGACTC

TGCAGTCTATTACTGTGCAAGAGTTGGAGATGGTTACTACGGGGTTACCCATGGT

ATGGACTATTGGGGTCAAGGAACCTCAGTCACCGTCTCCTCA

37F11F9 Light Chain Variable Region Nucleotide Sequence

SEQ ID No. 370

GACATTGTGATGACCCCGTCTCAAAAATTCATGTCCACAACAGTAGGAGACAGG

GTCAGCATCACCTGCAAGGCCAGTCAGAATGTGGGTACTGCTGTAGCCTGGTATC

AACAGAAACCAGGACAATCTCCCACAATACTGATTTACTCAGCATCCAATCGGTA

TACTGGAGTCCCTGATCGCTTCACAGGCAGTGGATCGGGGACAGATTTCACTCTC

ACCATTAGCAATATGAAGTCTGAAGACCTGGCAGATTATTTCTGTCAGCAATACT

ACATCTATCCGTTCACGTTCGCTGCTGGGACCAAGCTGGAACTGAAA

38H2E3 Heavy Chain Variable Region Nucleotide Sequence

SEQ ID No. 371

GAGTTCCAGCTGCAGCAGTCTGGACCTGAGGTGGTGAAGCCTGGCGCTTCAGTG

AAGATATCCTGCAAGGCTTCTGGTTACTCATTCACTGACTACAACATGAACTGGA

TGAAACAGAGCAAAGGAAAGAGTCTTGAGTGGATTGGAGTAATCAGTCCTGACT

ATGGCACTACTACTTACAATCAGAACTTCAAAGACAAGGCCACATTGACTGTGG

ACCAATCTTCCAGCACAGCCTACATGCAGCTCAACAGCCTGACATCTGAAGACTC

TGCAGTCTATTACTGTGCAAAAGACATGTACTATGTTTACGCTTACTATACTATG

GACTACTGGGGTCACGGAACCTCAGTCACCGTCTCCTCA

38H2E3 Light Chain Variable Region Nucleotide Sequence

SEQ ID No. 372

GATGTTGTGATGACCCAAACTCCACTCTCCCTGCCTGTCAGTCTTGGAGATCAAG

CCTCCATCTCTTGCAGATCTAGTCAGAGCCTTGTACACAGTAATGGACACACCTA

TTTACATTGGTACCTGCAGAGGCCAGGCCAGTCTCCAACGCTCCTGATCTACAAA

GTATCCAACCGATTTTCTGGGGTCCCAGACAGGGTCAGTGGCAGTGGATCCGGG

ACAGATTTCACACTCAAGATCAGCAGAGTGGAGGCTGAGGATCTGGGAGTTTAT

TTCTGTTCTCAAGGTACACATGTTCCGAGGACGTTCGGTGGAGGCACCAAGCTGG

AAATCAAA

42B7G2 Heavy Chain Variable Region Nucleotide Sequence

SEQ ID No. 373

CAGGTTCAGCTGCAGCAGTCTGGAGCTGAACTGGCGAGGCCTGGGGCTTCAGTG

AAGCTGTCCTGCAAGGCTTCTGGCTACACCTTCACAGACTATGGTATAAGCTGGG

TGAAGCAGAGAACTGGACAGGGCCTTGAGTGGATTGGAGAGATTTATCTTAGAA

ATGATAATAGTTACTACAATGAAAAGTTCAAGGGCAAGGCCACACTGACTGCAG

ATAAATCCTCCAACACAGCGTACATGGAGCTCCGCAGTCTGACATCTGAGGACTC

TGCGGTCTATTTCTGTGCGAGATGGGGGGACCATGGTAACAACTACGAGGATGCT

ATGGACTACTGGGGTCAAGGAACCTCAGTCACCGTCTCCTCA

42B7G2 Light Chain Variable Region Nucleotide Sequence

SEQ ID No. 374

GACATTGTGCTGACCCAATCTCCAGCTTCTTTGGCTATGTCTCTAGGGAAGAGGG

CCACCATCTCCTGCAGAGCCAGCGAAAGTGTCAGTATTATTGGTTCTAATTTAAT

ACACTGGTACCAACAGAAACCAGGACAGCCACCCAAACTCCTCATCTATCATGC

ATCCAATCTAGAAACTGGAGTCCCTGCCAGGTTCAGTGGCAGTGGGTCTAGAAC

AGACTTCACCCTCACCATTGATCCTGTGGAGGAAGATGATGTTGCAATCTATTAC

TGTCTACAAAGTAGGAAGGTTCCGTACACGTTCGGAGGGGGGACCAAGCTGGAA

ATAAAA

31C11G2 Heavy Chain Variable Region Nucleotide Sequence

SEQ ID No. 375

-continued

GAGGTTCAGCTGCAGCAGTCTGGGGCTGAGCTTGTGAGGCCAGGGGCCTCAGTC

AAGTTGTCCTGCACAGCTTCTGGCTTTAACATTAAAGACGAATATATACACTGGG

TGAAACAGAGGCCTGAACAGGGCCTGGAGTGGATTGGCTGGATTGATCCTGCGA

ATGGTCATACTGAATATGCCTCGAGGTTCCAGGCCAAGGCCACTATAACAGCAG

ACACATCCTCCAACACAGCCTACTTGCAGCTCAGCAGCCTGACATCTGAGGACAC

TGCCGTCTATTACTGTACTACGGGGGATTACGACGGGTTTGTTTATTGGGGCCAA

GGGACTCTGGTCACTGTCTCTACA

31C11G2 Light Chain Variable Region Nucleotide Sequence SEQ ID No. 376

CAAATTGTCCTCACCCAGTCGCCAGCAATCATGTCTGCATCTCCAGGGGAGAAGG

TCACCATATTCTGCAGTGCCAGGTCAAGTGTAAGTTACATGTATTGGTACCAACA

GAAGCCAGGATCCTCCCCCAAACCCTGGATTTATCGCACATCCAACCTGGCTTCT

GGAGTCCCTGCTCGCTTCAGTGGCAGTGGGTCTGGGACCTCTTACTCTCTCACAA

TCAGCAGCATGGAGGCTGAAGATGCTGCCACTTATTACTGCCAGCATTATCATAC

TTACCCGTACACGTTCGGAGGGGGGACCAAGCTGGAAATAAAA

80G1G1 Heavy Chain Variable Region Nucleotide Sequence SEQ ID No. 377

CAGGTGCAGCTGAAGGAGTCAGGACCTGGCCTGGTGGCGCCCTCACAGAGCCTG

TCCATCACTTGCACTGTCTCTGGGTTTTCATTATCCAGCTATGGTGTAGACTGGGT

TCGCCAGCCTCCAGGAAAAGATCTGGAATGGCTGGGAGTAATATGGGGTGGTGG

AACCACAATTTATAATTCAGCTCTCATGTCCAGACTGAACATCACCAAAGACAAC

TCCAAGAACCAAGTTTTCCTAAAAATGAACAGTCTGCAAAGTGATGACACAGCC

ATGTACTACTGTGCCAAGCGGGGATACTATGGTTACTTTGACTACTGGGGCCAAG

GCACCACTCTCACAGTCTCCTCA

80G1G1 Light Chain Variable Region Nucleotide Sequence SEQ ID No. 378

CAAATTGTTCTCACCCAGTCTCCAGCAATCATGTCTGCTTCTCCAGGGGAGAAGG

TCACCATGACCTGCAGTGCCAGCTCAAGTGTAAGTTACATGTACTGGTACCACCA

GAAGCCAGGATCCTCCCCCAGACTCCTGATTTATGACACATCCAATCTGGCTTTT

GGAGTCCCTGTTCGCTTCAGTGGCAGGGGGTCTGGGACCTCTTACTCTCTCACAA

TCAGCCGCATGGAGGCTGAAGATGCTGCCACTTATTACTGCCAGCAGTGGAGTA

GTTACCCGCTCACGTTCGGAGCTGGGACCAAGCTGGAGCTGAAA

80E7E2 Heavy Chain Variable Region Nucleotide Sequence SEQ ID No. 379

GAAGTGAAGCTGGTGGAGTCTGGGGGAGGCTTAGTGCAGCCTGGAAGTTCCATG

AAACTCTCCTGCACAGCCTCTGGATTCACTTTCAGTGACTATTACATGGCTTGGG

TCCGCCAGGTTCCAGATAAGGGTCTAGAATGGGTTGCAAACATTAATTATGATGG

GAATAACCCCTACTATGTGGACTCCTTGAAGAGCCGTTTCATCATCTCGAGAGAC

AATGCAAAGAACATTCTATACCTGCAAATGAGCAGTCTGAAGTCTGAGGACACA

GCCACGTATTACTGTGCAAGAGATATTTCTCCGGGGTACTTTGACCACTGGGGCC

AAGGCACCACTCTCACAGTCTCCTCA

80E7E2 Light Chain Variable Region Nucleotide Sequence SEQ ID No. 380

GACATTGTGCTGACCCAATCTCCAGCTTCTTTGGCTGTGTCTCTAGGGCAGAGGG

CCACCATCTCCTGCAGAGCCAGTGAAAGTGTCAGTATTCATGGTACTCATTTAAT

GCACTGGTACCAACAGAAACCAGGACAGCCACCCAAACTCCTCATCTATGCTGC

-continued

ATCCAACCTAGAATCTGGAGTCCCTGCCAGGTTCAGTGGCAGTGGGTCTGAGACA

GACTTCACCCTCAACATCCATCCTGTGGAGGAGGAGGATGCTGCAATCTATTTCT

GTCAGCAAAGTATTGAGGATCCTCACACGTTCGGAGGGGGGACCAAGCTGGAAA

TAAAA

84A2C4 Heavy Chain Variable Region Nucleotide Sequence SEQ ID No. 381

GAAGTGAAGCTGGTGGAGTCTGGGGGAGGCTTAGTGCAGCCTGGAAGTTCCATG

AAACTCTCCTGCACAGCCTCTGGATTCACTTTCAGTGACTATTACATGGCTTGGG

TCCGCCAGGTTCCAGATAAGGGTCTAGAATGGGTTGCAAACATTAATTATGATGG

GAATAATCCCTACTATGTGGACTCCTTGAAGACCCGTTTCATCATCTCGAGAGAC

AATGCAAAGAACATTCTATACCTGCAAATGAGCAGTCTGAAGTCTGAGGACACA

GCCACGTATTACTGTGCAAGAGATATTTCTCCGGGGTATTTTGACCACTGGGGCC

AAGGCACCACTCTCACAGTCTCCTCA

84A2C4 Light Chain Variable Region Nucleotide Sequence SEQ ID No. 382

GACATTGTGCTGACCCAATCTCCAGCTTCTTTGGCTGTGTCTCTAGGGCAGAGGG

CCACCATCTCCTGCAGAGCCAGTGAAAGTGTCAGTATTCATGGTACTCATTTAAT

GCACTGGTACCAACAGAAACCAGGACAGCCACCCAAACTCCTCATCTATGCTGC

ATCCAACCTAGAATCTGGAGTCCCTGCCAGGTTCAGTGGCAGTGGGTCTGAGACA

GACTTCACCCTCAACATCCATCCTGTGGAGGAGGAGGATGCTGCAATCTATTTCT

GTCAGCAAAGTATTGAGGATCCTCACACGTTCGGAGGGGGGACCAAGCTGGAAA

TAAAA

88B4D4 Heavy Chain Variable Region Nucleotide Sequence SEQ ID No. 383

CAAGTGCAGCTGAAGGAGTCAGGACCTGGCCTGGTGGCGCCCTCACAGAGCCTG

TCCATCACTTGCACTGTCTCTGGGTTTTCATTAATCAGCTATGGTGTAGACTGGGT

TCGCCAGCCTCCAGGAAAGGGTCTGGAGTGGCTGGGAGTTATATGGGGTGTTGG

AATCACAAAATATAATTCAGCTCTCATGTCCAGACTGAGTATCAGCAAAGACAA

CTCCAAGAGCCAAGTTTTCTTAAAAATGAACAGTCTGCAAACTGATGACACAGCC

ATGTACTACTGTGCCAAACGGGGATACTATGGTTATTTTGACTACTGGGGCCAGG

GCACTACTCTCACAGTCTCCTCA

88B4D4 Light Chain Variable Region Nucleotide Sequence SEQ ID No. 384

CAAATTGTTCTCACCCAGTCTCCAGCTATCATGTCTGCATCTCCAGGGGAGAAGG

TCACCATGACCTGCAGTGCCAGCTCAAGTGTAAGTTACATGTACTGGTACCAGCA

GAAGCCAGGAGCCTCCCCCAGACTCCTGATTTATGACACATCCAACCTGGCTTCT

GGAGTCCCTGTTCGTTTCAGTGGCAGTGGGTCTGGGACCTCTTACTCTCTCACAA

TCAGCCAAATGGAGACTGAAGATGCTGCCACGTATTACTGCCAGCAGTGGAGTA

GTTACCCGCTCACGTTCGGTGCTGGGACCAAGCTGGAGCTGAAA

89G3E8 Heavy Chain Variable Region Nucleotide Sequence SEQ ID No. 385

CAGGTGCAACTGAAGGAGTCAGGACCTGGCCTGGTGGCGCCCTCACAGAGCCTG

TCCATCACTTGCACTGTCTCTGGGTTTTCATTAACCAGCTATGGTGTAGACTGGGT

TCGCCAGCCTCCAGGAAAGGGTCTGGAGTGGCTGGGAGTAATATGGGGTGGTGG

AAACACAAATTATAATTCAGCTCTCATGTCCAGACTGAGCATCAGCAAAGACAA

-continued

CTCCAAGAGCCAAGTTTTCTTAAAAATGAACAGTCTACAAACTGATGACACAGCC

ATGTACTACTGTGCCAAATCCCCCGACTTCGTTAGTAGCTATTCCTATGCTATGG

ACTACTGGGGTCAAGGAACCTCCGTCACCGTCTCCTCA

89G3E8 Light Chain Variable Region Nucleotide Sequence  SEQ ID No. 386

GATGTTTTGATGACCCAAACTCCACTCTCCCTGCCTGTCAGTCTTGGAGATCAAG

CCTCCATCTCTTGCAGATCTAGTCAGAGAATTGTACATAGTAATGGAAACACCTA

TTTACAATGGTACCTGCAGAAACCAGGCCAGTCTCCAAAGCTCCTGATCTACAAA

GTTTCCAACCGATTTTCTGGGGTCCCAGACAGGTTCAGTGGCAGTGGATCAGGGA

CAGATTTCACACTCAAGATCAGCAGAGTGGAGGCTGAGGATCTGGGAGTTTATT

ACTGCTTTCAAAGTTCATATGTTCCTCCGACGTTCGGTGGAGGCACCAAGCTGGA

AATCAAA

90H5D3 Heavy Chain Variable Region Nucleotide Sequence  SEQ ID No. 387

CAGGTACACCTGAAGGAGTCAGGACCTGGCCTGGTGGCGCCCTCACAGAACCTG

TCCATCACTTGCACTGTCTCTGGGTTTTCATTAACCAGCTATGGTGTGGACTGGGT

CCGCCAGCCTCCAGGAAAGGGTCTGGAGTGGCTGGGAGTAACATGGGGTGGTGG

AAATACAAAATATAATTCAGCTCTCATGTCCAGACTGCACATCAGCAAAGACAA

CTCCAAGAGCCAAGTTTTCTTAAAAATGAACAGTCTGCAAACTGATGACACAGCC

GTATACTACTGTGCCAAACGGGGGTACTATGGTTACTTTGACTACTGGGGCCAAG

GCGCCACTCTCACAGTCTCCTCA

90H5D3 Light Chain Variable Region Nucleotide Sequence  SEQ ID No. 388

CAAATTGTTCTCACCCAGTCTCCAGCAATCATGTCTGCATCTCCAGGGGAGAAGG

TCACCATGACCTGCAGTGCCAGCTCAAGTGTAAGTTACATGTACTGGTACCAGCA

GAAGCCCGGATCCTCCCCCAGACTCCTGATTTATGACACATCCAACCTGGCTTCT

GGAGTCCCTGTTCGCTTCGGTGGCAGTGGATCTGGGACCTCTTACTCTCTCACAA

TCTTCCGAATGGAGGCTGAAGATGCTGCCACTTATTACTGCCAGCAGTGGAGTAG

TTACCCGCTCACGTTCGGTGCTGGGACCAAGCTGGAGCTGAAA

90F3B2 Heavy Chain Variable Region Nucleotide Sequence  SEQ ID No. 389

CAGGTGCAACTGAAGGAGTCAGGACCTGGCCTGGTGGCGCCCTCACAGAGCCTG

TCCATCACTTGCACTGTCTCTGGGTTTTCATTAACCAGCTATGGTGTAGACTGGGT

TCGCCAGCCTCCAGGAAAGGGTCTGGAGTGGCTGGGAGTAATATGGGGTGGTGG

AAGCACAAATTATAATTCAGCTCTCATGTCCAGACTGAGCATCAGCAAAGACAA

CTCCAAGAGCCAAATTTTCTTAAAAATGAACAGTCTGCAAACTGATGACACAGCC

ATGTACTACTGTGCCAAATCCCCCGACTTCGTTAGTAGCTATTCCTATGCTATGG

ACTACTGGGGTCAAGGAACCTCCGTCACCGTCTCCTCA

90F3B2 Light Chain Variable Region Nucleotide Sequence  SEQ ID No. 390

GATGTTTTGATGACCCAAACTCCACTCTCCCTGCCTGTCAGTCTTGGAGATCAAG

CCTCCATCTCTTGCAGATCTAGTCAGAGAATTGTACATAGTAATGGAAACACCTA

TTTACAATGGTACCTGCAGAAACCAGGCCAGTCTCCAAAGCTCCTGATCTACAAA

GTTTCCAACCGATTTTCTGGGGTCCCAGACAGGTTCAGTGGCAGTGGATCAGGGA

CAGATTTCACACTCAAGATCAGCAGAGTGGAGGCTGAGGATCTGGGAGTTTATT

ACTGCTTTCAAAGTTCATATGTTCCTCCGACGTTCGGTGGAGGCACCAAGCTGGA

-continued

AATCAAA

118C7E6 Heavy Chain Variable Region Nucleotide Sequence

SEQ ID No. 391

GAGGTCCAGCTGCAACAGTCTGGACCTGAGCTGGTGAAGCCTGGGGCTTCAGTG

AAGATACCCTGCAAGGCTTCTGGATACACATTCACTGACTACAACATGGACTGGG

TGAAGCAGAGCCATGGAAAGAGCCTTGAGTGGATTGGAGATATTAATCCTAACA

ATGGTGGTACTATCTACAACCAGAAGTTCAAGGGCAAGGCCACATTGACTGTAG

ACAAGTCCGCCAGCACAGCCTACATGGAGCTCCGCAGCCTGACATCTGAGGACA

CTGCAGTCTATTACTGTGCAAGATCCTCAATCTACTATGATTACGACGGAGGGTT

TGCTTACTGGGGCCAAGGGACTCTGGTCACTGTCTCTGCA

118C7E6 Light Chain Variable Region Nucleotide Sequence

SEQ ID No. 392

GACATCCAGATGACTCAGTCTCCAGCCTCCCTATCTGCATCTGTGGGAGAAACTG

TCACCATCACATGTCGAGCAAGTGGGAATATTCACAATTATTTAGCATGGTATCA

GCAGAAACAGGGAAAATCTCCTCAGCTCCTGGTCTATAATGCAAAAACCTTAGC

AGATGGTGTGCCATCAAGGTTCAGTGGCAGTGGATCAGGAACACAATATTCTCTC

AAGATCAACAGCCTGCAGCCTGAAGATTTTGGGACTTATTACTGTCAACATTTTT

GGAGTATTCCATTCACGTTCGGCTCGGGGACAAAGTTGGAAATAAAA

131H4A2 Heavy Chain Variable Region Nucleotide Sequence

SEQ ID No. 393

CAGATTCAGCTGCAGCAGTCTGGGGCTGAGCTGGTGAAGCCTGGGACCTCAGTG

CAGATTTCCTGCAAAGCTTCTGAATACGATTTCAGTCGCTACTGGATGAACTGGG

TGAAACACAGGCCTGGAGAGGGTCTTGAATGGATTGGACAGATTTATCCTGGAG

ATGGTGACATTAATTACAACGGAAAGTTCGAGGCCAAGGCCACACTGACTGCAG

ACAAATCCTCCAGCACAGCCTTCATGCAGCTCAGCGGCCTGACCTCTGAGGACTC

TGCGGTCTATTTCTGTGCAAGAGGGATTGCTATGGACTACTGGGGTCAGGGAACC

TCAGTCACCGTCTCCTCA

131H4A2 Light Chain Variable Region Nucleotide Sequence

SEQ ID No. 394

GATATCCAGATGACACAGAGTACATCCTCCCTGACTGCCTCTCTGGGAGACAGAG

TCACCATCAGTTGCAGGGCAAGTCAGGACGTTAGTAATTATCTAAACTGGCATCA

GCAGAAACCAGATGGAACTGTTAAACTCCTGATCTACTACACATCAAGATTACA

GTCAGGAGTCCCATCAAGGTTCAGTGGCAGTGGGTCTGGAACAGATTATTCTCTC

ACCATTAGCAACCTGGAACAAGAAGATATTGCCACTTACTTTTGCCAACAGGGTA

ATACGCTTCCGTGGACGTTCGGTGGAGGCACCAAGCTGGAAATCAAA

132G4B6 Heavy Chain Variable Region Nucleotide Sequence

SEQ ID No. 395

GAAGTGATGCTGGTGGAGTCTGGGGGAGGCTTAGTGAAGCCTGGAGGGTCCCTG

AAACTCTCCTGTGCAGCCTCTGGATTCACTTTCAGTAGCTATACCATGTCTTGGGT

TCGCCAGACTCCGGAGAAGAGGCTGGAGTGGGTCGCAACCATTAGTGGTGGTGG

TGATTACACCCACTATGCAGACAGTGTGAAGGGTCGATTCACCATCTCCAGAGAC

AATGCCAAGAACACCCTGTACCTGCAAATGAACAGTCTGAGGTCTGAGGACACG

GCCTTATATTACTGTGCAAGACAAGGTTTTTCTACGGTAGTAACTACGGGGGACT

GGGGCCAAGGCACCACTCTCACAGTCTCCTCA

132G4B6 Light Chain Variable Region Nucleotide Sequence

SEQ ID No. 396

-continued

GACATTGTGATGACCCAGTCTCAAAAATTCATGTCCACAACAGTAGGAGACAGG

GTCAGCATCACCTGCAAGGCCAGTCAGAGTGTGGGTGCTGCTGTAGCCTGGTATC

AACAGAAACCAGGACAATCTCCTAAACTACTGATTTATTCAGCTTCCACTCGTTA

CACTGGAGTCCCTGATCGCTTCACAGGCAGTGGATCTGGGACAGATTTCACTCTC

AATATTAGGAGAATGCAGTCTGAAGACCTGGCAGAGTATTTCTGTCAGCAATATA

GGAGCTATCCTCTCACGTTCGGCTCGGGGACAAAGTTGGAAATAAAA

144D3B11 Heavy Chain Variable Region Nucleotide Sequence  SEQ ID No. 397

CAGGTTCAGATGCAGCAGTCTGGAGCTGAACTGATGAAGCCTGGGGCCTCAGTG

AAACTTTCCTGTAAGGCTAATGGCTACACATTCAGTGGCTACTGGATAGAGTGGG

TAAAGCAGAGGCCTGGCCATGGCCTTGAGTGGATTGGAGAGATTTTACCTGGAA

GTGATAGTCCTAAGTACAGTGCGAAGTTCAAGGGCAAGGCCACAATTACTGCAG

ATACATCCTCCAACACAGCCTACATGCAACTCAGCAGCCTGACAACTGAGGACTC

TGCCATCTATTACTGTGCTAAAGGGGGTAATACGTCCTTCTTTGACTTCTGGGGC

CAAGGCACCACTCTCACAGTCTCCTCA

144D3B11 Light Chain Variable Region Nucleotide Sequence  SEQ ID No. 398

GATGTTTTGATGACCCAAACTCCACTCTCCCTGCCTGTCAGTCTTGGAGATCAAG

CCTCCATCTCTTGCAGATCTAGTCAGCGCATTGTACATAGTAATGGAAACACCTA

TTTAGAATGGTACCTGCAGAAACCAGGCCAGTCTCCAAAGCTCCTGATCTACAAA

GTTTCCACCCGATTTTCTGGAGTCCCAGACAGGTTCAGTGGCAGTGGATCAGGGA

CAGATTTCACACTCAAGATCAGCAGAGTGGAGGCTGAGGATCTGGGAGTTTATT

ACTGCTTTCAAGGTTCATTTGTTCCGTGGACGTTCGGTGGAGGCACCAAGCTGGA

AATTAAA

133G11E12 Heavy Chain Variable Region Nucleotide Sequence  SEQ ID No. 399

GAAGTGATGCTGGTGGAGTCTGGGGGAGGCTTAGTGAAGCCTGGAGGGTCCCTG

AAACTCTCCTGTGCAGCCTCTGGATTCACTTTTAGTAGTTATACCATGTCTTGGGT

TCGCCAGACTCCGGAGAAGAGGCTGGAGTGGGTCGCAACCATTAGTGGTGGTGG

TGATTACACCCACTATCCAGACAGTGTGAAGGGTCGATTCACCATCTCCAGAGAC

AATGCCAAGGACACCCTGTACCTGCAAATGAACAGTCTGAGGTCTGAGGACACG

GCCTTATATTACTGTGCAAGACAAGGTTTTTCTACGGTAGTAATGACGGGGGACT

GGGGCCAAGGCACCACTCTCACAGTTTCCTCA

133G11E12 Light Chain Variable Region Nucleotide Sequence  SEQ ID No. 400

GACATTGTGATGACCCAGTCTCAAAAATTCATGTCCACAACAGTAGGAGACAGG

GTCAGCATCACCTGCAAGGCCAGTCAGAGTGTGGGTACTGCTGTAGCCTGGTATC

AACAGAAACCAGGACAATCTCCTAACCTACTGATTTACTCAGCTTCCACTCGTTA

CACTGGAGTCCCTGATCGCTTCACAGGCAGTGGGTCTGGGACAGATTTCACTCTC

AATATTAGGAATATGCAGTCTGAAGACCTGGCAGAATATTTCTGTCAACAATATA

GGAGCTATCCTCTCACGTTCGGCTCGGGGACAAAGTTGGAAATAAAA

134C11G10 Heavy Chain Variable Region Nucleotide Sequence  SEQ ID No. 401

GAAGTGATGCTGGTGGAGTCTGGGGGAGGCTTAGTGAAGCCTGGAGGGTCCCTG

AAACTCTCCTGTGAAGCCTCTGGATTCACTTTCAATACCTATACCATGTCTTGGAT

TCGCCAGACTCCGGAGAAGAGGCTGGAGTGGGTCGCAACCATTAATGGTGGTGG

| | |
|---|---|
| TACTAATGCCTACTATCTAGACAGTGTGAAGGGTCGATTCACCATCTCCAGAGAC | |
| AATGCCAAGAACACCCTGTACCTGCAAATGAGTAGTCTGAGGTCTGAAGACACG | |
| GCCTTGTATTACTGTGCACGACAAGGTTTTACTACCGTTGTACCTACGGGGACT | |
| GGGGCCAAGGCACCACTCTCACAGTCTCCTCA | |
| 134C11G10 Light Chain Variable Region Nucleotide Sequence<br>GACATTGTGATGACCCAGTCTCAAAAATTCATGTCCTCAACAATAGGAGACAGG | SEQ ID No. 402 |
| GTCAGCATCACCTGTAAGGCCAGTCAGAGTGTGGGTGCTGCTATTGCCTGGTATC | |
| AACAGAAGCCAGGACAATCTCCTAAGTTACTGATTTACTCAGCATCCAGTCGGTA | |
| CACTGGAGTCCCTAATCGCTTCACAGGCAGTGGATCTGGGACAGATTTCACTCTC | |
| ACCATTGACAATGTGCAGTCTGAAGACCTGTCAGATTATGTCTGTCAGCAATATC | |
| GCAGCTATCCTCTCACGTTCGGCTCGGGGACAAAATTGGAGGTGAGA | |
| 134D3B6 Heavy Chain Variable Region Nucleotide Sequence<br>CAGATTCAGCTGCAGCAGTCTGGGGCTGAGCTGGTGAAGTCTGGGACCTCAGTG | SEQ ID No. 403 |
| AAGATTTCCTGCAAAGCTTCTGAATACGATTTCAGTCGCTACTGGATGAACTGGG | |
| TGAAACACAGGCCTGGAGAGGGTCTTGAATGGATTGGACAGATTTATCCTGGAG | |
| ATGGTGACATTAATTACAACGGAAAGTTCGAGGCCAAGGCCACACTGACTGCAG | |
| ACAAATCCTCCAGCACAGCCTTCATGCAGCTCAGCGGCCTGACCTCTGAGGACTC | |
| TGCGGTCTATTTCTGTGCAAGAGGGATTGCTATGGACTTCTGGGGTCAGGGAACC | |
| TCAGTCACCGTCTCCTCA | |
| 134D3B6 Light Chain Variable Region Nucleotide Sequence<br>GATATCCAGATGACACAGAGTACATCCTCCCTGACTGCCTCTCTGGGAGACAGAG | SEQ ID No. 404 |
| TCACCATCAGTTGCAGGGCAAGTCAGGACGTTAGTAATTATCTAAACTGGCATCA | |
| ACAGAAACCAGACGGAACTGTTAAACTCCTGATCTACTACACATCAAGATTACA | |
| GTCAGGAGTCCCATCAAGGTTCAGTGGCAGTGGGTCTGGAACAGATTATTCTCTC | |
| ACCATTACCAACCTGGAGCAAGAAGATATTGCCACTTACTTTTGCCAACAGGGGA | |
| ATACGCTTCCGTGGACGTTCGGTGGAGGCACCAAGCTGGAAATCATA | |
| 138E9A2 Heavy Chain Variable Region Nucleotide Sequence<br>CAGGTTCAGCTGCAGCAGTCTGGACCTGAACTGGTGAAGCCCGGGGCTTCAGTG | SEQ ID No. 405 |
| AAGTTGTCCTGCAAGGCTTCTGGCTACACCTTCACAAACTACGATATAAACTGGG | |
| TGAAGCAGAGGCCTGGACAGGGACTTGAGTGGATTGGATGGATTTATCCTGGAG | |
| ATGGTAGTACTAAGTCCAAAGAGAAATTCAGGGGCAAGGCCACATTGACTGTAG | |
| ATACTTCCTCCAGTACAGCGTACATGGAACTGCACAGCCTGACATCTGAGGACTC | |
| TGCGGTCTATCTCTGTGCAAGAGACTACGGCACCCCCTACTATGCTATGGACTAC | |
| TGGGGTCAAGGAACCTCAGTCACCGTCTCCTCA | |
| 138E9A2 Light Chain Variable Region Nucleotide Sequence<br>GATGTTTTGATGACCCAAACTCCACTCTCCCTGCCTGTCAGTCTTGGAGATCAAG | SEQ ID No. 406 |
| CCTCCATCTCTTGCAGATCTAGTCAGAGTATTATACAGAGTAATGGAAACACCTA | |
| TTTAGAGTGGTACCTGCAGAAACCAGGCCAGTCTCCAAAGCTCCTAATCTACAAA | |
| GTTTCCAACCGATTTTCTGGGGTCCCAGACAGGTTCAGTGGCAGTGGATCAGGGA | |
| CAGATTTCACACTCAAGATCAGCAGAGTGGAGGCTGAGGATCTGGGAGTTTATT | |

ACTGCTTTCAAGGTTCATTTGTTCCGTGGACGTTCGGTGGAGGCACCAACCTGGA

AATCAAA

138F9B5 Heavy Chain Variable Region Nucleotide Sequence   SEQ ID No. 407

GAGGTGCAGCTGGTGGAGTCTGGGGGAGACTTAGTGAAGCCTGGAGGGTCCCTG

AAACTCTCCTGTGCAGCCTCTGGATTCACTTTCAATAACGATGGCATGTCTTGGG

TTCGCCAGACTCCAGACAAGAGGCTGGAGTGGGTCGCAAGCATTAGTAGTGATG

GTAGTTACTCCTTCTATCCAGACAATGTGAAGGGGCGATTCACCATCTCCAGAGA

CAATGCCAAGAACACCCTGTACCTGCAAATGAGCAGTCTGAAGTCAGAGGACAC

AGCCATGTATTACTGTGCAAGTCAGAGGGGTTATTATGGTAATAGCCTCGCCTGG

TTTGCTTACTGGGGCCAAGGGACTCTGGTCACTGTCTCTGCA

138F9B5 Light Chain Variable Region Nucleotide Sequence   SEQ ID No. 408

GACATCTTGCTGACTCAGTCTCCAGTCATCCTGTCTGTGAGTCCAGGAGAAAGAG

TCAGTTTCTCCTGCAGGGCCAGTCAGAGCATTGGCACAAGCATACACTGGTATCA

GCAAAGAACAAATGGTTCTCCAAGGCTTCTCATAAAGTATGCTTCTGAGTCTATG

TCTGGGATCCCTTCCAGGTTTAGTGGCAGTGGCTCAGGGACAGATTTTACTCTTA

GCATCAACAGTGTGGAGTCTGAAGATATTGCAGATTATTTCTGTCAACAAAGTAA

AACCTGGCCGCTCACGTTCGGTGCTGGGACCACGCTGGAGCTGAAA

142D6D11 Heavy Chain Variable Region Nucleotide Sequence   SEQ ID No. 409

GAGGTGCACTTGGTGGAGTCTGGGGGAGGCTTAGTGAAGCCTGGAGGGTCCCTG

AAACTCTCCTGTGCAGCCTCTGGATTCACTTTCAGTGACTATGGAATGCACTGGG

TTCGTCAGGCTCCAGAGAAGGGGCTGGACTGGGTTGCATACATTAGTAGTGGCG

GTACTACCATCTACTATGCAGACACAGTGAAGGGCCGATTCACCATCTCCAGAGA

CAATGCCAAGAACACCCTCTTCCTGCAAATGACCACTCTGGGGTCTGACGACACG

GCCATGTATTCCTGTGCAAGGACCCGTCCCGGGGATGCTATGGACTACTGGGGTC

AAGGAACCTCAGTCACCGTCTCCTCA

142D6D11 Light Chain Variable Region Nucleotide Sequence   SEQ ID No. 410

GACATCTTGCTGACTCAGTCTCCAGCCATCCTGTCTGTGAGTCCAGGAGAAAGAG

TCAGTTTCTCCTGCAGGGCCAGTCAGAGCGCTGGCACAAGCATACACTGGTATCA

GCAAAGAACAAATGGTTCTCCAAGGCTTCTCATCAAGTATACGTCTGAGTCTATC

TCTGGGATCCCTTCCAGGTTTAGTGGCAGTGGATCAGGGACAGACTTTACTCTTA

GCATCAACAGTGTGGAGTCTGAAGATATTGCAGATTATTACTGTCAACAAAGTCT

TAGGTGGCCATTCACGTTCGGCTCGGGGACAAGGTTGGAAATAAAA

145E10H5 Heavy Chain Variable Region Nucleotide Sequence   SEQ ID No. 411

CAGGTCCAACTGCAGCAGCCTGAGGCTGAGCTTGTGAAGCCTGGGGCTTCAGTG

AAGATGTCCTGCAAGGCCTCTGGCTACACCTTCCCCAGGTATTGGATAACCTGGA

TGAGACAGAGGCCTGGACAAGGCCTTGAATGGATTGGAGATATTTTTCCTAGTAG

TGAGTATACTCACTACAATGAAGTTCAGGAGGAAGGCCACTCTGACTGTTGA

CACATCCTCCAGTATAGCCTACATACAACTCAGCAGCCTGACATCTGAGGACTCT

GCGGTCTATTATTGTGCAAGAGGGGAATATGACGCCTGGTTTGCTTACTGGGGCC

AAGGGACTCTGGTCACTGTCTCTGCA

145E10H5 Light Chain Variable Region Nucleotide Sequence

-continued

```
GATATCCAGATGACACAGACCCACATCCTCCCTGTCTGTCTCTCTGGGAGACAGAG
TCACCATCAGTTGCAGGGCAAGTCAGGACATTAGTAATTATTTAAATTGGTATCA
GCAGAAACCAGATGGAACTGTTAAACTCCTGATCTACTACACATCAAGATTAGA
CTCAGGAGTCCCATCAAGGTTCAGTGGCAGTGGGTCTGGAACAGATTATTCTCTC
ACCATTAGCAACCTGGAGCAAGAAGATCTTGCCACTTACTTTTGCCAACAGGGTA
ATACGCTTCCTCCGACGTTCGGTGGAGGCACCAAGCTGGAGATCAGA
```
SEQ ID No. 412

167H6H5 Heavy Chain Variable Region Nucleotide Sequence
```
GAGGTTCAGCTGCAGCAGTCTGGGGCTGAGCTTGTGAGGCCAGGGGCCTCAGTC
AAGTTGTCCTGCACAACTTCTGGCTTTAACATTAAAGACGAGCATATGTATTGGG
TGAAGCAGAGGCCTGAACAGGGCCTGGAGTGGATTGCATGGATTGATCCTGAGA
ATGATAATACTGAATATGCCTCGAAGTTCCAGGGCAAGGCCACTATAACAGCAG
ACACATCCTCCAACACAGTCTACCTGCAACTCAGCAACCTGACATCTGAGGACAC
TGCCGTCTATTTCTGTACTACGGGAGATTACGACGGGTTTACTTACTGGGGCCAA
GGGACTCTGGTCACTGTCTCTGCA
```
SEQ ID No. 413

167H6H5 Light Chain Variable Region Nucleotide Sequence
```
GAAATTGTGCTCACCCAGTCTCCAACCACCATGGCTGCATCTCCCGGGGAGAAGA
TCACTATCACCTGCAGTGCCAGCTCAAGTATAAGTTCCAATTTCTTGCATTGGTTT
CAGCAGAAGCCAAGATTCTCCCCTAAAACTCTTGATTTATAGGACATCCAATCTGG
CTTCTGGAGTCCCAGCTCGCTTCAGTGGCAGTGGGTCTGGGACCTCTTACTCTCTC
ACAATTGGCACCATGGAGGCTGAGGATGTTGCCACTTACTACTGCCAGCAGGGT
AGTTTTATGCCGTTCACGTTCGGTACTGGGACCAAACTGGAGCTGAAA
```
SEQ ID No. 414

166E12G6 Heavy Chain Variable Region Nucleotide Sequence
```
GAGGTGAAATTGGTGGAGTCTGGAGGAGGATTGGTACAGCCTGGGGGTTCGCTG
AGTCTCTCCTGTGTAACTTCTGGATTCACCTTCACTGATTACTACATGAGCTGGGT
CCGCCAGTCTCCAGGGAAGGCACTTGAGTGGTTGGGTTTTATTAGAAACAAAGCT
TATGGTGACACAACAGAGTACAGTGAATCTGTGAAGGGTCGGTTCACCATCTCCA
GAGATAATTCCCAAAGCATCCTCTATCTTCACATGAATGCCCTGAGAGCTGAAGA
CAGTGCCACTTACTACTGCGCAAGATATCCTCGGACAGGCTATGCTCTGGACTAC
TGGGGTCAAGGAACCTCAGTCACCGTCTCCTCA
```
SEQ ID No. 415

166E12G6 Light Chain Variable Region Nucleotide Sequence
```
GATGTTTTCATGACCCAAACTCCACTCTCCCTGCCTGTCAGTCTTGGAGATCAAG
CCTCCATCTCTTGCAGATCTAGTCAGAGTATTGTCCATAGTAATGGAAACACCTA
TTTAGAATGGTACCTGCAGAAACCAGGCCAGTCTCCAAAGCTCCTGATCTACAAA
GTTTCCAACCGATTTCCTGGGGTCCCAGACAGGTTCAGTGGCAGTGGATCAGGGA
CAGATTTCACACTCAAGATCAACAGAGTGGAGGCTGAGGATCTGGGAGTTTATT
ACTGCTTTCAGGTTTCACATGTTCCGTACACGTTCGGAGGGGGGACCAAGCTGGA
AATAAAA
```
SEQ ID No. 416

2D5 Heavy Chain Variable Region Nucleotide Sequence
```
CAGGTCACCTTGAAGGAGTCTGGTCCTACGCTGGTTAAACCCACACAGACCCTCA
CGCTGGCCTGCAGCTTCTCTGGGTTCTCACTCACCACTACTGGGGTGGCTGTGAC
```
SEQ ID No. 417

-continued

CTGGATCCGCCAGCCCCCAGGGAAGGCCCTGGAGTGGCTTGCACTCATTGATTGG

GATGATGATAAATACTACAGCACATCTCTGAAGACCAGGCTCACCATCTCCAAG

GACACCTCCAAAAACCAGGTGGTCCTTACAATGACCAACATGGACCCTGTGGAC

ACAGCCACATATTACTGTGCACGCATCGCGAGCGGTGATTCCGGAGGTTACTTTG

CCGACTGGGGCCAGGGAACCCTGGTCACCGTCTCCTCA

2D5 Light Chain Variable Region Nucleotide Sequence  SEQ ID No. 418

TCTTCTGAGCTGACTCAGGCACCCTCAGTGTCCGTGTCTCCAGGACAGACAGCCA

GCATCACCTGTTCTGGAGATAAGTTGGACGATAAATATGTTTACTGGTATCAACA

GAAGCCAGGCCAGCCCCCTGTCCTGGTCATCTATCGTGATAACAAGCGGCCCTCT

GGGATCCCTGAGAGATTCTCTGGCTCCAACTCTGGGAACACAGCCACTCTGACCA

TCAGCGCGACCCAGGCTCTGGATGAGGCCGACTATTACTGTCAGGCGTGGGAAA

GTAGTAGTGATCAGTATGTCTTCGGAACTGGGACCAAGGTCACCGTCCTA

5D8 Heavy Chain Variable Region Nucleotide Sequence  SEQ ID No. 419

CAGGTGCAACTGCAGGAGTCGGGCGCAGGACTGTTGAAGCCTTCGGAGACCCTG

TCCCTCACCTGCGCTGTCTATGGTGGGTCCTTCAGTGGTTACTACTGGAGCTGGA

TCCGCCAGCCCCCAGGGAAGGGGCTGGAGTGGATTGGGAAATCAATCATAGTG

GAAGCACCAACTACAACCCGTCCCTCAAGAGTCGAGTCACCATATCAGTAGACA

CGTCCAAGAACCAGTTCTCCCTGAAGCTGAGCTCTGTGACCGCTGCGGACACGGC

CGTGTATTACTGTGCGAGAACAAGATACTATGGTTCGGGGAGCTGGTCGCTTTTT

GACTACTGGGGCCAGGGAACCCTGGTCACCGTCTCCTCA

5D8 Light Chain Variable Region Nucleotide Sequence  SEQ ID No. 420

CAGCCTGTGCTGACTCAGCCACCCTCAGCGTCTGGGGCCCCCGGACAGACAGTCA

CCATCTCTTGTTCTGGAGGCAACTCCAACGTCGGAACTAATACTGTGAATTGGTA

TCAGCAACTCCCAGGAACGGCTCCCAAACTCCTCATCTATTATGATGATCTACTG

GCCTCAGGGGTCTCTGACCGATTCTCTGGCTCCAAGTCTGGCACCTCAGCCTCCC

TGGCCATCAGTGGACTCCAGGCTGAGGAGGAGGCTGATTATTACTGTGCAGCAT

GGGATGACACCCTGAATGGTTGGGTGTTCGGCGGAGGGACCAAGCTGACTGTCC

TA

Nucleotide sequence encoding Met22-Arg734 of human SEMA4D protein extracellular
domain (hSEMA4D ECD)  SEQ ID No. 421

MAFAPIPRITWEHREVHLVQFHEPDIYNYSALLLSEDKDTLYIGAREAVFAVNALNIS

EKQHEVYWKVSEDKKAKCAEKGKSKQTECLNYIRVLQPLSATSLYVCGTNAFQPAC

DHLNLTSFKFLGKNEDGKGRCPFDPAHSYTSVMVDGELYSGTSYNFLGSEPIISRNSS

HSPLRTEYAIPWLNEPSFVFADVIRKSPDSPDGEDDRVYFFFTEVSVEYEFVFRVLIPR

IARVCKGDQGGLRTLQKKWTSFLKARLICSRPDSGLVFNVLRDVFVLRSPGLKVPVF

YALFTPQLNNVGLSAVCAYNLSTAEEVFSHGKYMQSTTVEQSHTKWVRYNGPVPKP

RPGACIDSEARAANYTSSLNLPDKTLQFVKDHPLMDDSVTPIDNRPRLIKKDVNYTQI

VVDRTQALDGTVYDVMFVSTDRGALHKAISLEHAVHIIEETQLFQDFEPVQTLLLSS

KKGNRFVYAGSNSGVVQAPLAFCGKHGTCEDCVLARDPYCAWSPPTATCVALHQT

ESPSRGLIQEMSGDASVCPDKSKGSYRQHFFKHGGTAELKCSQKSNLARVFWKFQN

GVLKAESPKYGLMGRKNLLIFNLSEGDSGVYQCLSEERVKNKTVFQVVAKHVLEVK

-continued

VVPKPVVAPTLSVVQTEGSRIATKVLVASTQGSSPPTPAVQATSSGAITLPPKPAPTGT

SCEPKIVINTVPQLHSEKTMYLKSSDNR

Nucleotide sequence encoding the full length of human SEMA4D

SEQ ID No. 422 atgaggatgtgcaccccattaggggggctgctcatggcccttgcagtgatgtttgggacagcgatggcatttgcacccatacccgg atcacctgggagcacagagaggtgcacctggtgcagtttcatgagccagacatctacaactactcagccttgctgctgagcgagga caaggacaccttgtacataggtgcccggaggcggtcttcgctgtgaacgcactcaacatctccgagaagcagcatgaggtgtatt ggaaggtctcagaagacaaaaaagcaaaatgtgcagaaaaggggaaatcaaaacagacagagtgcctcaactacatccgggtgc tgcagccactcagcgccacttcccttttacgtgtgtgggaccaacgcattccagccggcctgtgaccacctgaacttaacatcctttaa gtttctggggaaaaatgaagatggcaaaggaagatgtcccctttgacccagcacacagctacacatccgtcatggttgatggagaact ttattcggggacgtcgtataattttttgggaagtgaacccatcatctcccgaaattcttcccacagtcctctgaggacagaatatgcaat cccttggctgaacgagcctagtttcgtgtttgctgacgtgatccgaaaaagcccagacagccccgacggtgaggatgacagggtct acttcttcttcacggaggtgtctgtggagtatgagtttgtgttcagggtgctgatcccacggatagcaagagtgtgcaaggggggacca gggcggcctgaggaccttgcagaagaaatggacctccttcctgaaagcccgactcatctgctcccggccagacagcggcttggtc ttcaatgtgctgcgggatgtcttcgtgctcaggtccccgggcctgaaggtgcctgtgttctatgcactcttcacccacagctgaaca acgtggggctgtcggcagtgtgcgcctacaacctgtccacagccgaggaggtcttctcccacgggaagtacatgcagagcaccac agtggagcagtcccacaccaagtgggtgcgctataatggcccggtacccaagccgcggcctggagcgtgcatcgacagcgagg cacggggccgccaactacaccagctccttgaatttgccagacaagacgctgcagttcgttaaagaccacccttttgatggatgactcgg taaccccaatagacaacaggcccaggttaatcaagaaagatgtgaactacacccagatcgtggtggaccggacccaggccctgg atgggactgtctatgatgtcatgtttgtcagcacagaccggggagctctgcacaaagccatcagcctcgagcacgctgttcacatca tcgaggagacccagctcttccaggactttgagccagtccagaccctgctgctgtcttcaaagaagggcaacaggtttgtctatgctg gctctaactcgggcgtggtccaggcccgctggccttctgtgggaagcacggcacctgcgaggactgtgtgctggcgcgggacc cctactgcgcctggagcccgcccacagcgacctgcgtggctctgcaccagaccgagagcccagcaggggtttgattcaggaga tgagcggcgatgcttctgtgtgcccgataaaagtaaaggaagttaccggcagcattttttcaagcacggtggcacagcggaactg aaatgctcccaaaaatccaacctggcccgggtcttttggaagttccagaatggcgtgttgaaggccgagagccccaagtacggtctt atgggcagaaaaaacttgctcatcttcaacttgtcagaaggagacagtggggtgtaccagtgcctgtcagaggagagggttaagaa caaaacggtcttccaagtggtcgccaagcacgtcctggaagtgaaggtggttccaaagcccgtagtggcccccaccttgtcagttgt tcagacagaaggtagtaggattgccaccaaagtgttggtggcatccacccaagggtcttctcccccaaccccagccgtgcaggcc acctcctcggggccatcacccttcctcccaagcctgcgcccaccggcacatcctgcgaaccaaagatcgtcatcaacacggtcc cccagctccactcggagaaaaccatgtatcttaagtccagcgacaaccgcctcctcatgtccctcttcctcttcttctttgttctcttcctc tgcctctttttctacaactgctataagggatacctgcccagacagtgcttgaaattccgctcggccctactaattgggaagaagaagcc caagtcagatttctgtgaccgtgagcagagcctgaaggagacgttagtagagccaggagcttctcccagcagaatggggagcac cccaagccagccctggacaccggctatgagaccgagcaagacaccatcaccagcaaagtccccacggatagggaggactcaca gaggatcgacgacctttctgccagggacaagcccctttgacgtcaagtgtgagctgaagttcgctgactcagacgcagatggagact ga Designed phage primers (specific primer sequences are as follows)
2D5 VH forward primer SEQ ID No. 423

CTTGTCGCGATTCTTAAGGGTGTCCAGTGC CAGGTCACCTTGAAGGAGTC

2D5 5D8 VH Reverse Primer

SEQ ID No. 424

AGGGAACACGGAAGGGCCCTTGGTGCTAGCTGAGGAGACGGTGACCAGGG

2D5 VL forward primer

SEQ ID No. 425

CTCCTCCTCCACTGCACAGGGTCTCTCTCCTCTTCTGAGCTGACTCAGGC

2D5 VL Reverse Primer

AGTGACCGAGGGGGCAGCCTTGGGTTGACCTAGGACGGTGACCTTGGTCC

SEQ ID No. 426

5D8 VH forward primer

CTTGTCGCGATTCTTAAGGGTGTCCAGTGC CAGGTGCAACTGCAGGAGTC

SEQ ID No. 427

5D8 VL forward primer

CTCCTCCTCCACTGCACAGGGTCTCTCTCCCAGCCTGTGCTGACTCAGCC

SEQ ID No. 428

5D8 VL Reverse Primer

AGTGACCGAGGGGGCAGCCTTGGGTTGACCTAGGACAGTCAGCTTGGTCC

SEQ ID No. 429 pTT-EF1a-F gcccttttg agtttgga

SEQ ID No. 430 pSV40 cactgcattc tagttgtg

SEQ ID No. 431

Nucleotide Sequence of Full Length Monkey SEMA4D

SEQ ID No. 432

SEMA4Datgaggatgtgcatccctattagggggctgctcatggcccttgcagtgatgtttgggacagcgatggcttttgcaccca tacccccggatcacctgggagcacagagaggtgcgcctggtgcagtttcacgagccggacatctacaactactcagccttgctgctg agcgaggacaaggacaccttgtacataggcgcccgggaggcggtcttcgctgtgaacgcactcaacatctccgagaagcagcat gaggtgtattggaaggtctcagaagacaaaaaagcaaatgtgcagaaaaggggaaatcaaaacagacagagtgcctcaactac atccgggtgctgcagccgctcagcgccacttcccttttacgtgtgtgggaccaacgcattccagccggcctgtgaccacctgaactta acatcctttaagttctggggaaaaacgaagatggcaaaggaagatgtccctttgacccagcgcacagctacacatccgtcatggtt gatggagaactttattcagggacgtcgtataatttttttgggaagtgaacccatcatctcccgaaattcttcccacagtcctctgaggac ggaatacgcaatcccttggctgaacgagcctagttttgtgtttgccgacgtgattcgaaaaagcccagacagccccgacggcgagg atgacagggtctacttcttcttcacagaggtgtctgtggagtacgagtttgtgttcagggtgctgatcccacggatagcaagagtgtgc aaggggaccagggcggcctgaggaccttgcagaagaaatggacctccttcctgaaagcccgactcatctgctcccggccagac agcagcttggtcttcaatgtgctgcgggacgtcttcgtgctcaggtccccgggcctgaaggtgcctgtgttctacgcactcttcaccc cacagctgaacaacgtggggctgtcggcagtgtgcgcctacaacctgtccacagccgaggaggtcttctcccacgggaaatacat gcagagcgccacggtggagcagtcccacaccaagtgggtgcgctacaacggcccggtccccaagccgcggcctggagcgtgc atcgacagtgaggcacgggcagccaactacaccagctccttgaatttgccagacaagacgctgcagttcgtcaaagaccaccctt gatggatgactcggtgaccccaatagacaacaggcccaggttaatcaagaaagatgtgaactacacccagatcgtggtggaccgg acccaggccctggatgggactgtctatgatgtcatgtttgtcagcacagaccggggagctctgcacaaagccatcagcctcgagca tgctgttcacatcatcgaggagaccagctcttccaggactttgagccggtccagaccctgctgctgtcttcaaagaagggcaggag gttcgtctatgctggctctaactcgggcgtggtccaggcccctctggccttctgtgggaagcacggcacctgcgaggactgtgtgct ggctcgggacccctactgcgcctggagcccacccacagcgacgtgtgtgctctgtaccagactgagagcccccagcaggggttt ggttcaggagatgagcggcgatgcttctgtgtgcccggataaaagtaaaggaagttaccggcagcatttttttcaagcacggtggca cagcggaactgaaatgctcccaaaagtccaacctggcccgggtgttttggaagttccagaatggcgtgttgaaggctgagagcccc aagtacggtcttatgggcagaaaaaacttgctcatcttcaacttatcagaaggagacagtggggtgtaccagtgcctgtcagaggag agggttaagaacaagacggtcttccaagtagtcgccaagcacgtcctggaagtgaaggtggttccaaagcccgtggtggccccca ccttgtcagttgttcagacagaaggtagtaggattgccaccaaagtgttggtggcatccacccaagggtcttctccccgaccccag ccgtgcaggccacctcctccggggccatcacccttcctcccaagcctgtgccaccagcacatcctgtgaaccaaagattgtcatc aacacggtcccccagctccactcggagaaaaccatgtatgttaagtccagcgataaccgcctcctcatgtccctcttcctcttcttcttt gttctcttcctctgcctctttttctacaactgctataaggggatacctgcccagacagtgcttgaaattccgctcggccctactaattggga agaagaagcccaagtcagatttctgtgaccgtgagcagagcctgaaggagacgttagtagagccagggagcttctcccagcagaa -continued tggggagcaccccaagccagccctggacaccggctatgagaccgagcaagacaccatcaccagcaaagtccccacggatagg gaggactcacagaggatcgacgacctttctgccagggacaagccctttgacgtcaagtgtgagctgaagttcgctgactcagacgc agatggagactga Nucleotide Sequence of Full Length Mouse SEMA4D SEQ ID No. 433 atgaggatgtgtgcccccgttagggggctgttcttggccctggtggtagtgttgagaaccgcggtggcatttgcacctgtgcctcgg ctcacctgggaacatggagaggtaggtctggtgcagtttcacaagccaggcatctttaactactcggccttgctgatgagtgaggac aaagacactctgtatgtaggcgcccgggaagcagtctttgcagtgaatgcgctgaacatctctgagaagcaacatgaggtatattgg aaggtctctgaagacaaaaaatccaagtgtgcagagaaggggaaatcaaagcagacggaatgcctaaactacattcgagtactac agccactaagcagcacttccctctatgtgtgtgggaccaatgcgttccagcccacctgtgaccacctgaacttgacatccttcaagttt ctggggaaaagtgaagatggcaaggaagatgcccttcgacccgcccacagctacacatcagtcatggttgggggcgagctct actctgggacgtcctataatttcttgggcagtgaacccatcatctctcgaaactcttcccacagtcccttgaggacggagtatgccatc ccgtggctgaacgagcctagcttcgtctttgctgacgtgatccagaaaagcccagatggtccggagggtgaagatgacaaggtcta cttcttttttacggaggtatccgtggagtacgaattcgtcttcaagttgatgatcccgcgagttgccagggtgtgcaagggcgaccag ggcggcctgcggactttgcaaaaaaagtggacctccttcctaaaggccaggctgatctgctccaagccagacagtggcctggtctt caacatacttcaggatgtgtttgtgctgagggcccgggcctcaaggagcctgtgttctatgcggtcttcaccccacagctgaacaat gtgggtctgtcagcggtgtgcgcctacacactggccacggtggaggcagtcttctcccgtggaaagtacatgcagagtgccacagt ggagcagtctcacaccaagtgggtgcgctacaatggcccagtgcccactccccgacctggagcgtgtatcgacagtgaggcccg ggcagccaactacaccagctccttgaatctcccagacaaaacactgcagtttgtaaaagaccacccctttgatggatgactcagtgac cccgatagacaacagacccaagctgatcaaaaagatgtaaactacacccagatagtggtagacaggacccaggccctggatgg gactttctacgacgtcatgttcatcagcacagaccggggagctctgcataaagcagtcatcctcacaaaagaggtgcatgtcatcga ggagacccaactcttccgggactctgaaccggtcctaactctgctgctatcgtcaaagaaggggaggaagtttgtctatgcaggctc caactctggagtggtccaagcgcccctggcattctgcgaaaagcacggtagctgtgaagactgtgtgttagcacgggaccctact gtgcctggagcccagccatcaaggcctgtgttaccctgcaccaggaagaggcctccagcaggggctggattcaggacatgagcg gtgacacatcctcatgcctggataagagtaaagaaagtttcaaccagcattttttcaagcacggcggcacagcggaactcaaatgttt ccaaaagtccaacctagcccgggtggtatggaagttccagaatggcgagttgaaggccgcaagtcccaagtacggctttgtgggc aggaagcacctgctcatcttcaacctgtcggacggagacagcggcgtgtaccagtgcctgtcagaggaaagggtgaggaataaa acggtctcccagctgctggccaagcacgttctggaagtgaagatggtacctcggaccccccctcacctacctcagaggatgctca gacagaaggtagtaagatcacatccaaaatgccggttgcatctacccaggggtcctctcccccctaccccggctctgtgggcaacct cccccagagccgccaccctacctcccaagtcctcctccggcacatcctgtgaaccaaagatggtcatcaacacggtcccccagctc cactcagagaagacggtgtatctcaagtccagtgacaaccgcctgctcatgtctctcctcctcttcatctttgtcctcttcctctgcctctt ttcctacaactgctacaagggctacctgcccggacagtgcttaaaattccgctcagccctgctgcttggaaagaaaacacccaagtc agacttctctgacctggagcagagtgtgaaggagacactggtcgagcctgggagcttctcccagcagaacggcgaccaccccaa gccagccctggatacgggctatgaaacggagcaggacaccatcaccagcaaagtccccacggatcgtgaggactcgcaacgga tcgatgaactctctgcccgggacaaaccgtttgatgtcaagtgtgaactgaagtttgcagattcggatgctgacggggactga Nucleotide Sequence of Full Length of Human Plexin B1

SEQ ID No. 434 atgcctgctctgggcccagctcttctccaggctctctgggccggggggtcctcaccctccagccccttccaccaactgcattcactc caatgcacgtatctgcagcacctggcaagggaccccacctcaggcaccctctacctggggctaccaacttcctgttccagctg agccctgggctgcagctggaggccacagtgtccaccggccctgtgctagacagcagggactgcctgccacctgtgatgcctgatg agtgcccccaggcccagcctaccaacaacccgaatcagctgctcctggtgagcccaggggccctggtggtatgcgggagcgtgc accagggggtctgtgaacagcggcgcctggggcagctcgagcagctgctgctgcggccagagcggcctggggacacacaatat

```
gtggctgccaatgatcctgcggtcagcacggtggggctggtagcccagggcttggcaggggagcccctcctgtttgtggggcga ggatacaccagcaggggtgtgggggggcattccacccatcacaacccgggccctgtggccgcccgaccccaagctgccttc tcctatgaggagacagccaagctggcagtgggccgcctctccgagtacagccaccacttcgtgagtgcctttgcacgtggggcca gcgcctacttcctgttcctgcggcgggacctgcaggctcagtctagagcttttcgtgcctatgtatctcgagtgtgtctccgggacca gcactactactcctatgtggagttgcctctggcctgcgaaggtggccgctacgggctgatccaggctgcagctgtggccacgtcca gggaggtggcgcatggggaggtgctctttgcagctttctcctcggctgcaccccccactgtgggccggcccccatcggcggctgc tggggcatctggagcctctgccctctgtgccttcccctggatgaggtggaccggcttgctaatcgcacgcgagatgcctgctacac ccgggagggtcgtgctgaggatgggaccgaggtggcctacatcgagtatgatgtcaattctgactgtgcacagctgccagtggac accctggatgcttatccctgtggctcagaccacacgcccagcccatggccagccgggtcccgctggaagccacaccaattctgg agtggccagggattcagctaacagctgtggcagtcaccatggaagatggacacaccatcgctttcctgggtgatagtcaagggca gctgcacagggtctacttgggcccagggagcgatggccacccatactccacacagagcatccagcaggggtctgcagtgagcag agacctcacctttgatgggacctttgagcacctgtatgtcatgacccagagcacacttctgaaggttcctgtggcttcctgtgctcagc acctggactgtgcatcttgccttgctcacagggacccatactgtgggtggtgcgtgctccttggcaggtgcagtcgccgttctgagtg ctcgaggggccagggcccagagcagtggctatggagcttccagcctgagctgggctgtctgcaagtggcagccatgagtcctgc caacatcagccgagaggagacgagggaggttttcctatcagtgccagacctgccacccctgtggccaggggagtcatattcctgc cactttggggaacatcagagtcctgccctgctgactggttctggtgtgatgtgcccctcccagaccctagtgaggcccagtgctg ccgagaggagccgactacgtatccgtgagcgtggagctcagatttggcgctgttgtgatcgccaaaacttccctctctttctatgact gtgtggcggtcactgaactccgcccatctgcgcagtgccaggcctgtgtgagcagccgctgggggtgtaactggtgtgtctggca gcacctgtgcacccacaaggcctcgtgtgatgctgggcccatggttgcaagccatcagagcccgcttgtctcccccagaccctcctg caagaggtggacccagcccctccccacccacagcccccaaagccctggccacccctgctcctgacacccttcccgtggagcctg gggctccctccacagccacagcttcggacatctcacctggggctagtccttccctgctcagcccctgggggccatgggcaggttct ggctccatatcttcccctggctccacagggtcgcctctccatgaggagcccctccctcccagccccaaaatggacctggaaccgc tgtccctgcccccactgacttcagaccctcagccacacctgaggacctcttggcctccccgctgtcaccgtcagaggtagcagcag tgccccctgcagaccctggccccgaggctcttcatcccacagtgcccctggacctgcccctgccactgttcctgccaccactttcc caggggccatgggctccgtgaagcccgccctggactggctcacgagagaaggcggcgagctgcccgaggcggacgagtgga cgggggggtgacgcaccgccttctccacttccaccctcctctcaggtgatggagactcagcagagcttgagggccctcccgcccc cctcatcctcccgtccagcctcgactaccagtatgacaccccgggctctgggagctggaagaggcgacctttgggggcaagctcc tgcccctgtgtggagagcgttcagggctccacgttgatgccggtccatgtggagcgggaaatccggctgctaggcaggaacctgc acctttccaggatggcccaggagacaatgagtgtgtgatggagctggagggcctcgaggtggtggttgaggcccgggtcgagtg tgagccacctccagatacccagtgccatgtcacctgccagcagcaccagctcagctatgaggctctgcagccggagctccgtgtg gggctgtttctgcgtcgggccggccgtctgcgtgtggacagtgctgaggggctgcatgtggtactgtatgactgttccgtgggacat ggagactgcagccgctgccaaactgccatgccccagtatggctgtgtgtggtgtgaggggagcgtccacgttgtgtgacccggg aggcctgtggtgaggctgaggctgtggccacccagtgcccagcgcccctcatccactcggtggagccactgactgggcctgtaga cggaggcacccgtgtcaccatcaggggctccaacctgggccagcatgtgcaggatgtgctgggcatggtcacggtggctggagt gccctgtgctgtggatgccaggagtacgaggtctccagcagcctcgtgtgcatcaccggggccagtggggaggaggtggccg gcgccacagcggtggaggtgccggaagaggacgtggtgtctcagaacacgactttgcctaccaggatccgaaggtccattccat cttcccggcccgcggcccagagctggggcacccgtctcaccctgaatggctccaagctcctgactgggcggctggaggacat ccgagtggtggttggagaccagccttgtcacttgctgccggagcagcagtcagaacaactgcggtgtgagaccagcccacgccc cacgcctgccacgctccctgtggctgtgtggtttggggccacggagcggaggcttcaacgcggacagttcaagtataccttggacc ccaacatcacctctgctggccccaccaagagcttcctcagtggaggacgtgagatatgcgtccgtggccagaatctggacgtggta cagacgccaagaatccgggtgaccgtggtctcgagaatgctgcagcccagccaggggcttggacggaggcgtcgcgtggtccc
```

-continued

```
ggagacggcatgttcccttggaccctcctgcagtagccagcaatttgaggagccgtgccatgtcaactcctcccagctcatcacgtg
ccgcacacctgccctcccaggcctgcctgaggaccccctgggtccgggtggaatttatccttgacaacctggtctttgactttgcaaca
ctgaaccccacacctttctcctatgaggccgaccccaccctgcagccactcaaccctgaggaccccaccatgccattccggcacaa
gcctgggagtgtgttctccgtggaggggggagaacctggaccttgcaatgtccaaggaggaggtggtggctatgataggggatggc
ccctgtgtggtgaagacgctgacgcggcaccacctgtactgcgagccccccgtggagcagccctgccacggcaccatgccctc
cgagaggcacctgactctttgcctgagttcacggtgcagatggggaacttgcgcttctcctgggtcacgtgcagtatgacggcga
gagccctggggcttttcctgtggcagcccaggtgggcttggggggggcacctctcttctggctctgggtgtcatcatcattgtcctc
atgtacaggaggaagagcaagcaggccctgagggactataagaaggttcagatccagctggagaatctggagagcagtgtgcgg
gaccgctgcaagaaggaattcacagacctcatgactgagatgaccgatctcaccagtgacctcctgggcagcggcatccccttcct
cgactacaaggtgtatgcggagaggatcttcttccctgggcaccgcgagtcgcccttgcaccgggacctgggtgtgcctgagagc
agacggcccactgtggagcaagggctggggcagctctctaacctgctcaacagcaagctcttcctcaccaagttcatccacacgct
ggagagccagcgcacctttttcagctcgggaccgtgcctacgtggcatctctgctcaccgtggcactgcatgggaagcttgagtattt
cactgacatcctccgcactctgctcagtgacctggttgcccagtatgtggccaagaaccccaagctgatgctgcgcaggacagaga
ctgtggtggagaagctgctcaccaactggatgtccatctgtctgtataccttcgtgagggactccgtaggggagcctctgtacatgct
ctttcgagggattaagcaccaagtggataaggggccagtggacagtgtgacaggcaaggccaaatacaccttgaacgacaaccg
cctgctcagagaggatgtggagtaccgtcccctgaccttgaatgcactattggctgtggggcctggggcaggagaggcccaggg
cgtgcccgtgaaggtcctagactgtgacaccatctcccaggcaaaggagaagatgctggaccagctttataaaggagtgcctctca
cccagcggccagaccctcgcacccttgatgttgagtggcggtctggggtggccgggcacctcattctttctgacgaggatgtcactt
ctgaggtccagggtctgtggaggcgcctgaacacactgcagcattacaaggtcccagatggagcaactgtggccctcgtcccctg
cctcaccaagcatgtgctccgggaaaaccaggattatgtccctggagagcggaccccaatgctggaggatgtagatgaggggggg
catccggccctggcacctggtgaagccaagtgatgagccggagccgcccaggcctcggaggggcagccttcggggggggag
cgtgagcgcgccaaggccatccctgagatctacctgacccgcctgctgtccatgaagggcaccctgcagaagttcgtggatgacc
tgttccaggtgattctcagcaccagccgccccgtgccgctcgctgtgaagtacttctttgacctgctggatgagcaggcccagcagc
atggcatctccgaccaggacaccatccacatctggaagaccaacagcttgcctctgaggttctggatcaatataataaaaaacccgc
agtttgtgttcgacgtgcaaacatctgataacatggatgcggtgctccttgtcattgcacagaccttcatggacgcctgcaccctggcc
gaccacaagctgggccgggactccccgatcaacaaacttctgtatgcacgggacattccccggtacaagcggatggtggaaaggt
actatgcagacatcagacagactgtcccagccagcgaccaagagatgaactctgtcctggctgaactgtcctggaactactccgga
gacctcggggcgcgagtggccctgcatgaactctacaagtacatcaacaagtactatgaccagatcatcactgccctggaggagg
atggcacggcccagaagatgcagctgggctatcggctccagcagattgcagctgctgtgaaaacaaggtcacagatctatag
```

SEMA4D Point Mutation Antibody Amino Acid Sequences
5D8-h1/h3 Heavy Chain Variable Region SEQ ID No. 435

QVQLQESGAGLLKPSETLSLTCAVYGGSFSGYYWSIRQPPGKGLEWIGEIDHSGST

NYNPSLKSRVTISVDTSKNQFSLKLSSVTAADTAVYYCARTRYYGSGSWSLFDYWG

QGTLVTVSS

5D8-h1/h3 Heavy Chain CDR2

SEQ ID No. 436

EIDHSGSTNYNPSLKS

5D8-h1/h2 Light Chain Variable Region

SEQ ID No. 437

QPVLTQPPSASGAPGQTVTISCSGGNSNVGTNTVNWYQQLPGTAPKLLIYYDDLLAS

GVSDRFSGSKSGTSASLAISGLQAEEEADYYCAAWDDTLSGWVFGGGTKLTVL

5D8-h1/h2 Light Chain CDR3

SEQ ID No. 438

AAWDDTLSGWV

| | |
|---|---|
| 5D8-h2/h4 Heavy Chain Variable Region | SEQ ID No. 439 |

QVQLQESGAGLLKPSETLSLTCAVYGGSFSGYYWSWIRQPPGKGLEWIGEINHAGST
NYNPSLKSRVTISVDTSKNQFSLKLSSVTAADTAVYYCARTRYYGSGSWSLFDYWG
QGTLVTVSS

| | |
|---|---|
| 5D8-h2/h4 Heavy Chain CDR2 | SEQ ID No. 440 |

EINHAGSTNYNPSLKS

| | |
|---|---|
| 5D8-h3/h4 Light Chain Variable Region | SEQ ID No. 441 |

QPVLTQPPSASGAPGQTVTISCSGGNSNVGTNTVNWYQQLPGTAPKLLIYYDDLLAS
GVSDRFSGSKSGTSASLAISGLQAEEEADYYCAAWDDTLNAWVFGGGTKLTVL

| | |
|---|---|
| 5D8-h3/h4 Light Chain CDR3 | SEQ ID No. 442 |

AAWDDTLNAWV

Amino Acid Sequence Numbers of SEMA4D Framework Region Back-mutated Antibodies

| | |
|---|---|
| 2D5-b1 Heavy Chain Variable Region | SEQ ID No. 443 |

QVTLRESGPALVKPTQTLTLTCTFSGFSLTTTGVAVTWIRQPPGKALEWLALIDWDD
DKYYSTSLKTRLTISKDTSKNQVVLTMTNMDPVDTATYYCARIASGDSGGYFADWG
QGTLVTVSS

| | |
|---|---|
| 2D5-b1 Light Chain Variable Region | SEQ ID No. 444 |

SYELTQPPSVSVSPGQTASITCSGDKLDDKYVYWYQQKPGQSPVLVIYRDNKRPSGIP
ERFSGSNSGNTATLTISGTQAMDEADYYCQAWESSSDQYVFGTGTKVTVL

| | |
|---|---|
| 5D8-h2b4 Light Chain Variable Region (5D8-h2b4-L) | SEQ ID No. 445 |

QPVLTQPPSASGTPGQTVTISCSGGNSNVGTNTVNWYQQLPGTAPKLLIYYDDLLAS
GVPDRFSGSKSGTSASLAISGLQSEEEADYYCAAWDDTLSGWVFGGGTKLTVL

| | |
|---|---|
| 2D5-b1-3D9 Heavy Chain Variable Region | SEQ ID No. 446 |

QVTLRESGPALVKPTQTLTLTCTFSGFSLTTTGVAVTWIRQPPGKALEWLALIDWDD
DKYYSTSLKTRLTISKDTSKNQVVLTMTNMDPVDTATYYCARIASGDSGGYFADWG
QGTLVTVSS

| | |
|---|---|
| 2D5-b1-3D9 Heavy Chain CDR1 | SEQ ID No. 447 |

TTGVAVT

| | |
|---|---|
| 2D5-b1-3D9 Heavy Chain CDR2 | SEQ ID No. 448 |

LIDWDDDKYYSTSLKT

| | |
|---|---|
| 2D5-b1-3D9 Heavy Chain CDR3 | SEQ ID No. 449 |

IASGDSGGYFAD

| | |
|---|---|
| 2D5-b1-3D9 Light Chain Variable Region | SEQ ID No. 450 |

SYELTQPPSVSVSPGQTASITCSGDKLDDKYVYWYQQKPGQSPVLVIYMDNKRKSGI
PERFSGSNSGNTATLTISGTQAMDEADYYCQAWESSSDQYVFGTGTKVTVL

| | |
|---|---|
| 2D5-b1-3D9 Light Chain CDR1 | SEQ ID No. 451 |

SGDKLDDKYVY

| | |
|---|---|
| 2D5-b1-3D9 Light Chain CDR2 | SEQ ID No. 452 |

MDNKRKS

| | |
|---|---|
| 2D5-b1-3D9 Light Chain CDR3 | SEQ ID No. 453 |

QAWESSSDQYV

The invention claimed is:

1. An antibody, which binds to SEMA4D, wherein the antibody comprises: (1) heavy chain variable region comprising the following three complementary determining regions of CDRs: VH-CDR1 comprising SEQ ID NO: 322, VH-CDR2 comprising SEQ ID NO: 323, and VH-CDR3 comprising SEQ ID NO: 324; and (2) a light chain variable region comprising the following three complementary determining regions of CDRs: VL-CDR1 comprising SEQ ID NO: 326, VL-CDR2 comprising SEQ ID NO: 327, and VL-CDR3 comprising SEQ ID NO: 328.

2. The antibody of claim 1, wherein the antibody is an animal-derived antibody, chimeric antibody, or a humanized antibody.

3. The antibody of claim 1, wherein the heavy chain variable region of the antibody comprises the amino acid sequence SEQ ID NO: 443; and the light chain variable region comprises the amino acid sequence SEQ ID NO: 444.

4. A recombinant protein, wherein the recombinant protein comprises: (i) the antibody of claim 1; and (ii) a tag sequence to assist expression and/or purification.

5. A polynucleotide, wherein the polynucleotide encodes a recombinant protein comprising the antibody of claim 1.

6. A vector, wherein the vector comprises the polynucleotide according to claim 5.

7. A genetically engineered host cell, wherein the host cell contains the vector of claim 6.

8. A pharmaceutical composition, wherein the pharmaceutical composition comprises the antibody of claim 1 and a pharmaceutically acceptable carrier.

9. A method for detecting SEMA4D protein in a sample in vitro, comprising providing a sample; applying the antibody of claim 1 at a concentration of 10 μg/mL, 100 μg/mL, or 500 μg/mL to the sample; and determining the presence of SEMA4D protein.

* * * * *